United States Patent
Aoki et al.

(10) Patent No.: US 6,376,491 B1
(45) Date of Patent: Apr. 23, 2002

(54) BICYCLIC COMPOUNDS

(75) Inventors: Yuhko Aoki; Hirosato Ebiike, both of Chigasaki; Toshihiko Fujii, Yokohama; Kenichi Kawasaki, Fujisawa, all of (JP); Pingli Liu, Wilmington, DE (US); Miyako Masubuchi, Yokohama (JP); Tatsuo Ohtsuka; Shinji Tsujii, both of Kamakura (JP)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/464,240

(22) Filed: Dec. 15, 1999

(30) Foreign Application Priority Data

Dec. 18, 1998 (EP) ............................................ 98124120

(51) Int. Cl.$^7$ ...................... A61K 31/535; A61K 31/44; A61K 31/34; C07D 413/00; C07D 405/00
(52) U.S. Cl. .................... 514/235.5; 514/337; 514/469; 544/125; 546/284.1; 549/467
(58) Field of Search ...................... 544/125; 514/235.5, 514/337, 469; 546/284.1; 549/467

(56) References Cited

U.S. PATENT DOCUMENTS

| | | | |
|---|---|---|---|
| 4,056,626 A | 11/1977 | Ito et al. |
| 5,082,967 A | 1/1992 | Heuckeroth et al. |
| 5,266,576 A | 11/1993 | Vincent et al. |

FOREIGN PATENT DOCUMENTS

| | | |
|---|---|---|
| DE | 22 23 184 | 11/1972 |
| DE | 26 35 064 | 4/1977 |
| EP | 146 243 | 6/1985 |
| EP | 499 521 | 8/1992 |
| GB | 1129072 | 10/1968 |
| GB | 1256.735 | 12/1971 |
| RU | 671256 | 11/1986 |

OTHER PUBLICATIONS

K. J. Lodge et al., Proc. Natl. Acad. Sci., vol. 91, pp. 12008–12012 (1994).
D. R. Johnson et al., Annual Rev. Biochem., vol. 63, pp. 869–914 (1994).
T. Stearns et al., Mol. Cell. Biol., vol. 10, pp. 6690–6699 (1990).
P. K. Herman et al., Cell, vol. 64, pp. 425–443 (1991).
R. J. Duronio et al., Proc. Natl. Acad. Sci., vol. 89, pp. 4129–4133 (1992).
R. A. Weiberg et al., Molecular Microbiology, vol. 16, pp. 241–250 (1995).
Abstract of Japanese Patent No. 07215940 (Aug. 19, 1995).
Kumar, et al., Indian Journal of Chmistry, vol.25, pp. 106–110 (Jan. 1986).
Howard Tucker, J. Med. Chem., vol. 24, No. 11, pp. 1364–1368 (1981).
Areschka etal., Chimie Therapeutique, No. 6, pp. 613–620 (Nov.–Dec. 1973).
Abstract of Japanese Patent No. 57040479 (Mar. 6, 1982).
Goldenberg et al., Chimie Therapeutique, No. 4, pp. 285–289 (1970).
Descamps etal., L'ingenieur Chimiste, vol. 49, pp. 34–38 (1967).
Sangwan et al., Eur. J. Med.Chem.. vol. 22, pp. 153–156 (1987).
Crowther et al., J. of Medicinal Chemistry., vol. 15, No. 3, pp. 260–266 (1972).
Grinev etal., Khim.Farm. ZH., vol. 21, No. 11, pp. 1318–1320 (1987).
Abstract of Japanese Patent No. 08198826 (Sep. 6, 1996).

*Primary Examiner*—Deborah C. Lambkin
(74) *Attorney, Agent, or Firm*—George W. Johnston; Dennis P. Tramaloni

(57) ABSTRACT

The present invention is directed to new bicyclic compounds of the formula [I],

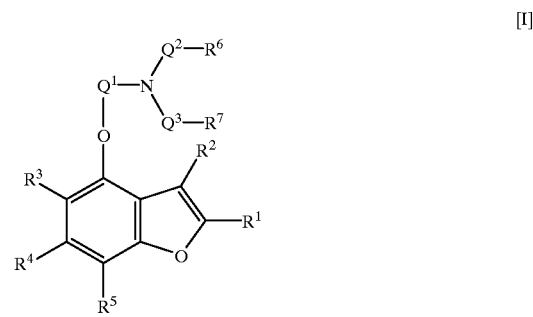

and pharmaceutically acceptable salts thereof wherein $R^1$, $R^2$, $R^3$, $R^4$, $R^5$, $R^6$, $R^7$, $Q^1$ $Q^2$ and $Q^3$ are as defined in the claims. The compounds have N-myristoyltransferase inhibitory and antifungal activity.

44 Claims, No Drawings

BICYCLIC COMPOUNDS

BACKGROUND OF THE INVENTION

N-myristoyltransferase (hereinafter referred to as NMT) is an enzyme that transfers cellular fatty acid myristate from myristoyl CoA to the N-terminal glycine of eukaryotic cellular proteins. N-myristoylation of several G-proteins, Gpa1, Arf1, Arf2 and Vps15, which are essential for fungal growth, have been reported to be indispensable for their function in *Saccharomyces cerevisiae* (K. J. Lodge el al., Proc. Natl. Acad. Sci., Vol. 91, PP. 12008–12012, 1994; D. R. Johnson et al., Annu. Rev. Biochem., Vol. 63, PP. 869–914, 1994; Stearns T. et al., Mol. Cell Biol., Vol.10, PP. 6690–6699, 1990; P. K. Harman et al., Cell, Vol. 64, PP. 425–437, 1991). Genetic studies have also demonstrated that this enzyme is essential for the viability of the fungi including medically important pathogenic fungi. For example, the essentiality of the enzyme in *S. cerevisiae* has been reported by Robert J. Duronio et al. (Proc. Natl. Acad. Sci., Vol. 89, pp. 4129–4133, 1992), the essentiality in *Candida albicans* has been reported by Robin A. Weiberg et al. (Molecular Microbiology, Vol. 16, PP. 241–250, 1995), and the essentiality in *Cryptococcus neoformans* has been reported by K. J. Lodge et al. (Proc. Natl. Acad. Sci., Vol. 91, pp. 12008–12012, 1994). Therefore, NMT has been believed to be a target for the development of fungicidal drugs.

SUMMARY OF THE INVENTION

In accordance with the present invention it has been found that the novel bicyclic compounds show NMT inhibitory activity and antifungal activity. The present invention relates to these novel bicyclic compounds having NMT inhibitory activity and antifungal activity, processes for producing the same, the use in the medical therapy of said compounds and pharmaceutical compositions containing said compounds.

DETAILED DESCRIPTION OF THE INVENTION

The present invention relates to novel bicyclic compounds of the formula [I],

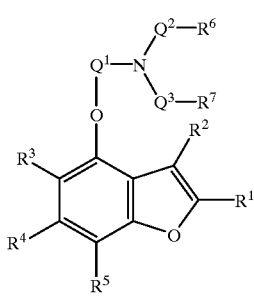

[I]

wherein $R^1$ is hydrogen, an unsubstituted or substituted heterocyclic ring,

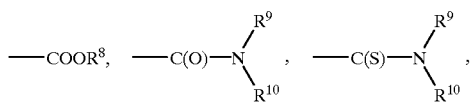

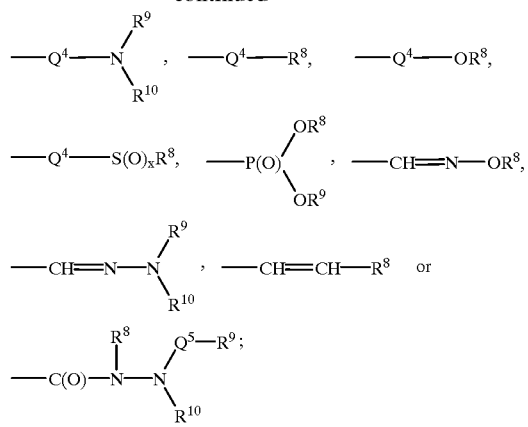

$R^2$ is hydrogen, unsubstituted or substituted lower alkyl, aralkyl, cycloalkyl or cycloalkylalkyl;

$R^3$, $R^4$ and $R^5$ are independently hydrogen or halogen;

$R^6$ and $R^7$ are independently hydrogen, unsubstituted or substituted lower alkyl, an aromatic ring or aliphatic ring which may contain heteroatom(s); or $R^6$ and $R^7$ form an aliphatic ring which may contain further heteroatom(s) together with the adjacent $Q^2$, N and $Q^3$; or $Q^1$ and $R^6$ form an aliphatic ring which may contain further heteroatom(s) together with the adjacent N and $Q^2$;

$R^8$, $R^9$ and $R^{10}$ are independently hydrogen, unsubstituted or substituted lower alkyl, aralkyl, cycloalkyl, cycloalkylalkyl, an aromatic ring or aliphatic ring which may contain heteroatom(s); or $R^9$ and $R^{10}$ form an aliphatic ring which may contain further heteroatom(s) together with the adjacent nitrogen;

$Q^1$ is unsubstituted or substituted lower alkylene other than unsubstituted or substituted methylene;

$Q^2$ and $Q^3$ are each independently a single bond, unsubstituted or substituted lower alkylene;

$Q^4$ is a single bond, carbonyl, oxime, oxime O-ether which has a substituted or unsubstituted lower alkyl, lower alkenyl, aralkyl or aryl radical on the oxygen atom, or unsubstituted or substituted lower alkylene;

Q5 is a single bond or carbonyl; and x is an integer of 0 to 2;

with the proviso that when $R^1$ is $-COOC_2H_5$, then

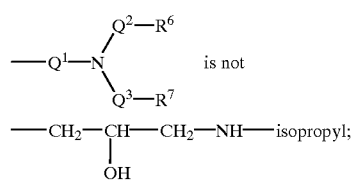

is not $-CH_2-\underset{\underset{OH}{|}}{CH}-CH_2-NH-$ isopropyl;

and pharmaceutically acceptable salts thereof.

Unless otherwise indicated, the following definitions are set forth to illustrate and defined the meaning and scope of the various terms used to describe the invention herein.

In this specification the term "heterocyclic ring" is used to mean a radical of a 3 to 10 membered ring containing one or more heteroatom(s), such as N, S and O.

The term "lower" is used to mean a radical consisting of 1 to 5, preferably 1 to 4 carbon atom(s), unless otherwise indicated.

The term "alkyl" refers to a branched or straight chain monovalent saturated aliphatic hydrocarbon radical of 1 to 5, preferably 1 to 4 carbon atom(s).

The term "alkenyl" refers to a branched or straight chain monovalent unsaturated aliphatic hydrocarbon radical of 3 to 5 carbon atom(s).

The term "aralkyl" refers to a branched or straight chain monovalent saturated aliphatic hydrocarbon radical of 1 to 5, preferably 1 to 3 carbon atom(s) having a monovalent carbocyclic aromatic radical such as phenyl, naphthyl optionally mono-, di-, tri- or tetra-substituted, independently, with lower alkyl, trifluoromethyl, halogen and the like.

The term "cycloalkyl" refers to a monovalent carbocyclic radical of 3 to 10 carbon atom(s), preferably 3 to 6 carbon atoms.

The term "cycloalkylalkyl" refers to a branched or straight chain monovalent saturated aliphatic carbon radical of 1 to 5, preferably 1 to 4 carbon atom(s) having a monovalent carbocyclic radical of 3 to 10 carbon atom(s), preferably 3 to 6 carbon atoms.

The term "aromatic ring" refers to a monovalent 5 to 10 membered aromatic hydrocarbon radical, i.e. "aryl", or heteroaromatic radical.

The term "aliphatic ring" refers to a monovalent carbocyclic radical of 3 to 10 carbon atom(s), preferably 3 to 6 carbon atoms.

The term "heteroatom" refers to N, O and S.

The term "lower alkylene" refers to a branched or straight chain aliphatic hydrocarbon radical of 1 to 5, preferably 1 to 4 carbon atom(s).

The term "halogen" refers to fluoro, chloro, bromo and iodo.

The term "acyl" refers to a monovalent carbonyl radical having a hydrogen, heterocyclic ring defined above, lower alkyl defined above, aralkyl defined above, cycloalkyl defined above, cycloalkylalkyl defined above or aromatic ring defined above.

The term "acyloxy" refers to a monovalent oxy-radical having an acyl radical defined above.

The term "alkoxy" refers to the group —O—R', where R' is an alkyl.

The present invention also relates to the use of the compounds of formula [I] in the prophylaxis and/or treatment of mycoses. Furthermore, the present invention relates to a pharmaceutical composition comprising a compound of formula [I] as an active ingredient and a pharmaceutically acceptable carrier.

The respective groups in the formula [I], which are defined above, are explained in more detail as follows:

In a preferred embodiment, $R^1$ is hydrogen, unsubstituted or substituted heterocyclic ring,

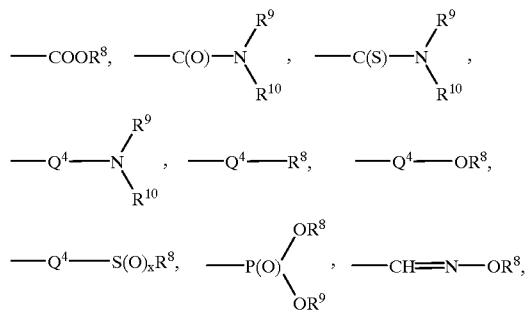

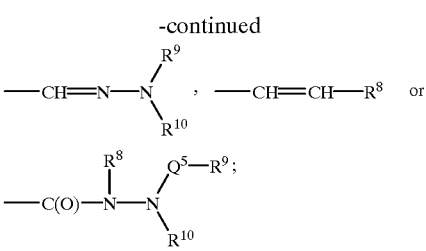

wherein $R^8$, $R^9$ and $R^{10}$ are independently hydrogen, unsubstituted or substituted lower alkyl, aralkyl, cycloalkyl, cycloalkylalkyl or an aromatic ring or aliphatic ring which may contain heteroatom(s); or $R^9$ and $R^{10}$ form an aliphatic ring which may contain further heteroatom(s) together with the adjacent nitrogen; and $Q^4$ is a single bond, carbonyl, oxime, oxime O-ether which has a substituted or unsubstituted lower alkyl, lower alkenyl, aralkyl or aryl radical on the oxygen atom, or unsubstituted or substituted lower alkylene; $Q^5$ is a single bond or carbonyl; and x is an integer of 0 to 2.

In the above definitions of $R^1$, the term "heterocyclic ring" means a 3 to 10 membered ring containing one or more heteroatom(s) such as N, S and O, preferably 1 to 4. More preferably, "unsubstituted heterocyclic ring" means oxazolyl, thiazolyl, 4,5-dihydro-oxazolyl, 4,5-dihydro-thiazolyl, furyl, pyrrolyl, thienyl, imidazolyl, triazolyl, tetrazolyl, pyrazinyl, pyrimidinyl, triazinyl, oxadiazolyl, thiadiazolyl and the like, more preferably oxazolyl, thiazolyl, 4,5-dihydro-oxazolyl and 4,5-dihydro-thiazolyl.

"Substituted heterocyclic ring" means a heterocyclic ring as defined above having one or more substituents such as F, Cl, Br, I, hydroxy, hydroxymethyl, nitro, cyano and unsubstituted or substituted amino, lower alkoxycarbonyl, lower alkyl, lower alkoxy, cycloalkylalkyl, aralkyl, carbamoyl, acyl, acyloxy, (heterocyclic ring)-carbonyl and heterocyclic ring. The preferred heterocyclic ring substituents are unsubstituted or substituted lower alkyl, lower alkoxy, lower alkoxycarbonyl, (lower alkyl)carbamoyl, arylcarbamoyl, heterocyclic ring, cycloalkylalkyl, (heterocyclic ring) carbonyl, optionally substituted with lower alkyl, heterocyclic ring, halogen, lower alkoxycarbonyl. The term "(heterocyclic ring)carbonyl" refers to a monovalent carbonyl radical attached to a nitrogen atom in a heterocyclic ring, having at least one nitrogen atom in the ring, preferably unsubstituted or substituted piperazinylcarbonyl, piperidinylcarbonyl, thiazolidinylcarbonyl, morpholinocarbonyl, oxazolidinylcarbonyl, optionally substituted with lower alkyl, lower alkoxy, aralkyl, lower alkoxycarbonyl, halogen, nitro, cyanocarbamoyl, hydroxy, or amino. "Substituted heterocyclic ring" preferably means lower alkoxycarbonyl-oxazolyl, lower alkoxycarbonyl-thiazolyl, cycloalkylalkyl-lower-alkoxy-carbonyl-oxazolyl, (lower-alkyl-piperazine-carbonyl)-oxazolyl, (lower-alkylcarbamoyl)-oxazolyl, (lower-alkoxycarbonyl-piperidine-carbonyl)-oxazolyl, {(tetrahydro-furan-2-ylmethyl)-carbamoyl}-oxazolyl, (difluorophenyl-carbamoyl)-oxazolyl, (lower-alkoxycarbonyl-thiazolyl)-oxazolyl, cycloalkylalkyl-lower-alkoxycarbonyl-dihydro-oxazolyl, cycloalkylalkyl-(lower-alkyl-piperazine-carbonyl)-dihydro-oxazolyl, (difluoro-benzyl)-(lower-alkyl-piperazine-carbonyl-dihydro-oxazolyl and more preferably 4-ethoxycarbonyl-oxazolyl, 4-ethoxycarbonyl-thiazolyl, 5-cyclohexylmethyl-4-ethoxycarbonyl-oxazolyl, 4-(4-methyl-piperazine-1-carbonyl)-oxazolyl, 4-(isopropylcarbamoyl)-oxazolyl, 4-(3-ethoxycarbonyl-1- piperidine-1-carbonyl)-oxazolyl, 4-{(tetrahydro-furan-2-ylmethyl)-carbamoyl}-oxazolyl, 4-(2,4-difluorophenyl-carbamoyl)-oxazolyl, 4-(4-ethoxycarbonyl-thiazol-2-yl)-oxazolyl, 5-cyclohexylmethyl-4-ethoxycarbonyl-4,5-dihydro-oxazolyl, 5-cyclohexylmethyl-4-(4-methyl-piperazine-1-carbonyl)-4,5-dihydro-oxazolyl, 5-(difluoro-benzyl)-4-(4-methyl-piperazine-1-carbonyl)-4,5-dihydro-oxazolyl and the like, and most preferably 5-cyclohexylmethyl-4-(4-methyl-piperazine-1-carbonyl)-4,5-dihydro-oxazolyl, and 5-(difluoro-benzyl)-4-(4-methyl-piperazine-1-carbonyl)-4,5-dihydro-oxazolyl.

"Unsubstituted or substituted amino" means —NH$_2$, mono-lower-alkyl-amino, mono-aryl-amino, mono-aralkyl-amino, mono-cycloalkyl-amino, mono-cycloalkylalkyl-amino and di-lower-alkyl-amino.

$R^8$, $R^9$ and $R^{10}$ in the radical $R^1$ have the meanings mentioned above, wherein "Unsubstituted lower alkyl" means a branched or straight chain monovalent saturated aliphatic hydrocarbon radical of 1 to 5, preferably 1 to 4 carbon atom(s), e.g. methyl, ethyl, propyl, isopropyl, isobutyl, tert-butyl and sec-butyl. "Unsubstituted lower alkyl" preferably means methyl, ethyl, propyl, isopropyl, tert-butyl and the like.

"Substituted lower alkyl" means a lower alkyl as defined above substituted independently with one or more radicals such as F; Cl; Br; I; hydroxy; nitro; cyano; hydroxymethyl; unsubstituted or substituted lower alkoxy substituted with one or more radical(s) such as halogen, hydroxy, nitro, cyano and unsubstituted or substituted amino; unsubstituted or substituted lower alkoxycarbonyl substituted with one or more radical(s) such as halogen, hydroxy, nitro, cyano, lower alkoxy, lower alkyl, lower alkoxycarbonyl and unsubstituted or substituted amino; unsubstituted or substituted amino substituted with one or more radical(s) such as lower alkyl, cycloalkyl, cycloalkylalkyl and aryl; unsubstituted or substituted carbamoyl substituted with one or more radical(s) such as lower alkyl, cycloalkyl, cycloalkylalkyl and aryl; unsubstituted or substituted acyl substituted with one or more radical(s) such as halogen, hydroxy, nitro, cyano, lower alkoxy, lower alkyl, lower alkoxycarbonyl and unsubstituted or substituted amino; unsubstituted or substituted acyloxy substituted with one or more radical(s) such as halogen, hydroxy, nitro, cyano, lower alkoxy, lower alkyl, lower alkoxycarbonyl and unsubstituted or substituted amino; unsubstituted or substituted heterocyclic ring substituted with one or more radical(s) such as halogen, hydroxy, nitro, cyano, lower alkoxy, lower alkyl, lower alkoxycarbonyl and unsubstituted or substituted amino; unsubstituted or substituted imino substituted with lower alkyl, cycloalkyl, cycloalkylalkyl and aryl; unsubstituted or substituted amindino substituted with lower alkyl, cycloalkyl, cycloalkylalkyl and aryl and unsubstituted or substituted guanidino substituted with lower alkyl, cycloalkyl, cycloalkylalkyl and aryl, preferably hydroxy, amino, pyridyl, Cl, F, lower alkoxycarbonyl, mono-(lower alkyl)-amino, di-(lower alkyl)-amino, imidazolyl, carboxy, lower alkoxy and amidino, most preferably hydroxy and F. Most preferably "substituted lower alkyl" means hydroxymethyl, 2-hydroxy-1,1-dimethyl-ethyl, 3-amino-2,2-dimethyl-ethyl, 2-pyridyl-ethyl, 2,2,2-trifluoroethyl, 2,2,3,3-tetrafluoropropyl, 2,2,3,3,3-pentafluoropropyl, 2-methoxycarbonyl-ethyl, 2-dimethylamino-ethyl, pyridylmethyl, 3-(imidazolyl)propyl, 2-(imidazolyl)ethyl, carboxylmethyl, ethoxylcarbonylmethyl, amidino and the like, more preferably hydroxymethyl and 2,2,2-trifluoroethyl.

"Unsubstituted or substituted aralkyl" means a branched or straight chain monovalent saturated aliphatic hydrocarbon, radical, i.e. lower alkyl radical, of 1 to 5, preferably 1 to 3 carbon atom(s) having a monovalent carbocyclic aromatic radical. The aromatic radical, such as phenyl, naphthyl, is optionally substituted with one or more substituents independently selected from lower alkyl, lower alkoxy, halogen, hydroxy, amino, nitro, carbonyl, cyano, acyl, acyloxy, carbamoyl, or methylenedioxy, preferably lower alkyl, halogen, lower alkoxy, hydroxy or methylenedioxy, such as phenyl, naphthyl, benzo[1,3]dioxol-5-yl, mono- and di-(lower alkyl)phenyl, lower alkoxyphenyl, nitrophenyl, aminophenyl, cyanophenyl, lower alkoxycarbonylphenyl, carbamoylphenyl, hydroxyphenyl, acylphenyl, acyloxyphenyl, mono-, di- and tri-fluorophenyl, mono- and di-chlorophenyl, bromophenyl and iodophenyl. "Unsubstituted or substituted aralkyl" preferably means benzyl, 2-phenethyl, 3-phenylpropyl, 4-phenylbutyl, fluorobenzyl, difluorobenzyl, chlorobenzyl, dichlorobenzyl, methoxybenzyl, ethoxybenzyl, methylbenzyl, dimethylbenzyl, dimethoxybenzyl, benzo[1,3]dioxol-5-ylmethyl, (hydroxyphenyl)ethyl, dihydroxybenzyl, (dihydroxyphenyl)ethyl, dimethylaminobenzyl, trifluorobenzyl and the like, more preferably 2-phenethyl and benzo[1,3]dioxol-5-ylmethyl, fluorobenzyl, difluorobenzyl and trifluorobenzyl.

"Unsubstituted or substituted cycloalkyl" means 3 to 7 membered ring, which do not contain any heteroatoms in the ring. The cycloalkyl radical, such as cyclopropyl, cyclobutyl, cyclopentyl, cyclohexyl and cycloheptyl is optionally substituted with one or more substituents independently selected from lower alkyl, lower alkoxy, halogen, hydroxy, amino, nitro, carbonyl, cyano, acyl, acyloxy or carbamoyl, preferably lower alkyl, halogen, lower alkoxy and hydroxy. "Unsubstituted or substituted cycloalkyl" preferably means cyclopropyl, cyclobutyl, cyclopentyl, cyclohexyl, hydroxycyclohexyl and the like, more preferably cyclohexyl."Unsubstituted or substituted cycloalkylalkyl" means lower alkyl substituted by cycloalkyl. The cycloalkyl, such as cyclopropyl, cyclobutyl, cyclopentyl, cyclohexyl and cycloheptyl, is optionally substituted with one or more substituents independently selected from lower alkyl, lower alkoxy, halogen, hydroxy, amino, nitro, carbonyl, cyano, acyl, acyloxy or carbamoyl, preferably lower alkyl, halogen, lower alkoxy and hydroxy.

"Unsubstituted cycoalkylalkyl", preferably means 2-cyclohexylethyl, cyclohexylmethyl, cyclopentylmethyl, cyclopropylmethyl, cyclobutylmethyl, 3-cyclohexylpropyl, (2-methylcyclopropyl)methyl and the like, more preferably 2-cyclohexylethyl.

"Unsubstituted aromatic ring" means monocyclic aromatic ring such as phenyl, furyl, thienyl, pyrimidinyl, and pyridyl, thiazolyl, imidazolyl, pyrazolyl, and fused aromatic ring such as naphthyl, benzofuranyl, benzothiophenyl, benzimidazolyl, indolyl, benzoxazolyl and benzothiazolyl. "Unsubstituted aromatic ring" preferably means pyridyl, phenyl, naphthyl, thienyl, furyl, thiazolyl, imidazolyl, pyrazolyl, and the like, more preferably phenyl, imidazolyl and pyridyl.

"Substituted aromatic ring" means aromatic ring as defined above having one or more radical(s) independently selected from F, Cl, Br, I, nitro, cyano, hydroxy, hydroxymethyl, and unsubstituted or substituted lower alkyl as defined above, lower alkoxy, amino, lower alkoxycarbonyl, carbamoyl, methylenedioxy, acyl and acyloxy. "Substituted aromatic ring" preferably means mono-, di- or trichlorophenyl, mono-, di-, tri-, tetra- or pentafluorophenyl, bromofluorophenyl, lower alkoxycarbonylphenyl, morpholinophenyl, benzo[1,3]

dioxol-5-yl, lower-alkoxyphenyl, lower-dialkoxyphenyl, cyanophenyl, nitrophenyl, lower-alkyl-imidazolyl, lower-alkoxycarbonyl-benzofuranyl, lower-alkoxy-lower-alkylbenzofuranyl, carbamoyl-benzofuranyl, phenylimidazolyl, lower-alkylnitrophenyl and (lower-alkyl)-(lower-haloalkyl)pyrazole, more preferably chlorophenyl, dichlorophenyl, trichlorophenyl, fluorophenyl, difluorophenyl, trifluorophenyl, tetrafluorophenyl, pentafluorophenyl, ethoxycarbonylphenyl, morpholinophenyl, benzo[1,3]dioxol-5-yl, methoxyphenyl, dimethoxyphenyl, cyanophenyl, nitrophenyl, triflurorophenyl, 5-methyl-imidazol-4-yl, 2-ethoxycarbonyl-benzofuran-5-yl, 2-ethoxymethyl-benzofuran-5-yl, 2-carbamoy-benzofuran-5-yl, 2-phenylimidazol-4-yl, 4-methyl-2-nitrophenyl, 4-methyl-3-nitrophenyl, 1-methyl-5-(trifluoromethyl)pyrazol-3-yl and the like, and most preferably fluorophenyl, difluorophenyl, trifluorophenyl, bromofluorophenyl, cyanophenyl, nitrophenyl 1-methyl-5-(trifluoromethyl)pyrazol-3-yl and chlorophenyl.

"Unsubstituted or substituted aliphatic ring which may contain further heteroatom(s)" preferably means pyrrolidinyl, tetrahydrothienyl, tetrahydrofuryl, morpholinyl, piperidyl, piperazinyl, 1-methylpiperazinyl and the like.

"Aliphatic ring which may contain further heteroatom(s) together with the adjacent nitrogen" formed by $R^9$ and $R^{10}$ preferably means a ring with 1 to 3 heteroatoms independently selected from N, S and O, e.g. pyrrolidine, piperidine, piperazine, lower-alkyl-piperazine, e.g. 4-methylpiperazine, morpholine, thiomorpholine and the like, more preferably piperidine, 4-methylpiperazine and morpholine.

"Unsubstituted lower alkylene" means lower alkylene as defined above, such as methylene, ethylene, trimethylene, tetramethylene and pentamethylene.

"Substituted lower alkylene" means unsubstituted lower alkylene as defined above having one or more radical(s) independently selected from F, Cl, Br, I, nitro, hydroxy, hydroxymethyl, cyano, and unsubstituted or substituted lower alkyl, lower alkoxy, amino, lower alkoxycarbonyl, carbamoyl, carboxyl, acyl and acyloxy, preferably hydroxyl, unsubstituted lower alkyl.

In a further preferred embodiment, the invention comprises compounds of formula [I], wherein $R^1$ is an unsubstituted or substituted heterocyclic ring.

In a further preferred embodiment, the invention comprises compounds of formula [I], wherein $R^1$ is "—COOR$^8$" with $R^8$ being hydrogen, unsubstituted or substituted lower alkyl, aralkyl, cycloalkyl, cycloalkylalkyl, an aromatic ring or an aliphatic ring which may contain heteroatom(s), preferably 1 to 3. More preferably, $R^8$ is unsubstituted or substituted lower-alkyl or cycloalkyl, and more preferably $R^1$ means methoxycarbonyl, ethoxycarbonyl, propoxycarbonyl, isopropoxycarbonyl, butoxycarbonyl, isobutoxycarbonyl, tert-butoxycarbonyl, 2-cyclohexylethyloxycarbonyl and the like, and most preferably ethoxycarbonyl and 2-cyclohexylethyloxycarbonyl.

In a further preferred embodiment, the invention comprises compounds of formula [I], wherein $R^1$ is

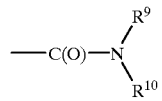

with $R^9$ and $R^{10}$ independently being hydrogen, unsubstituted or substituted lower alkyl, aralkyl, cycloalkyl, cycloalkylalkyl, an aromatic ring or an aliphatic ring which may contain heteroatom(s), preferably 1 to 3, or with $R^9$ and $R^{10}$ forming an aliphatic ring which may contain further heteroatom(s), preferably 1 to 3, together with the adjacent nitrogen. Preferably

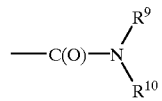

means substituted or unsubstituted aralkylcarbamoyl, cycloalkylcarbamoyl, lower alkylcarbamoyl, cycloalkylalkylcarbamoyl or arylcarbamoyl, optionally substituted with one or more substituents selected from lower alkyl, lower alkoxy, cyano, nitro, lower alkoxycarbonyl, halogen, methylenedioxy, morpholino, unsubstituted or substituted amino and the like; more preferably the above group means methylcarbamoyl, ethylcarbamoyl, propylcarbamoyl, isopropylcarbamoyl, butylcarbamoyl, isobutylcarbamoyl, tert-butylcarbamoyl, phenylcarbamoyl, cyanophenylcarbamoyl, nitrophenylcarbamoyl, ethoxycarbonylphenylcarbamoyl, fluorophenylcarbamoyl, chlorophenylcarbamoyl, difluorophenylcarbamoyl, trifluorophenylcarbamoyl, 2-cylohexylethylcarbamoyl, (benzo [1,3]dioxol-5-yl)carbamoyl, morpholinophenylcarbamoyl, dimethoxylphenylcarbamoyl and the like, more preferably ethoxycarbonylphenylcarbamoyl, fluorophenylcarbamoyl, chlorophenylcarbamoyl, difluorophenylcarbamoyl and trifluorophenylcarbamoyl.

In a further preferred embodiment, the invention comprises compounds of formula [I], wherein $R^1$ is

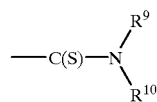

with $R^9$ and $R^{10}$ independently being hydrogen, unsubstituted or substituted lower alkyl, aralkyl, cycloalkyl, cycloalkylalkyl, an aromatic ring or an aliphatic ring which may contain heteroatom(s), preferably 1 to 3, or $R^9$ and $R^{10}$ may form an aliphatic ring together with the adjacent nitrogen, which may contain further heteroatom(s), preferably 1 to 3; more preferably

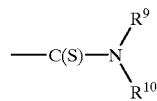

means unsubstituted or substituted aralkylthiocarbamoyl, cycloalkylthiocarbamoyl, lower alkylthiocarbamoyl, cycloalkylalkylthiocarbamoyl or arylthiocarbamoyl, optionally substituted with one or more substituent(s) independently selected from cyano, nitro, lower alkyl, lower alkoxy, halogen, lower alkoxylcarbonyl, methylenedioxy, morpholino, unsubstituted or substituted amino and the like; most preferably the group means methylthiocarbamoyl, ethylthiocarbamoyl, propylthiocarbamoyl, isopropylthiocarbamoyl, butylthiocarbamoyl, isobutylthiocarbamoyl, tert-butylthiocarbamoyl, phenylthiocarbamoyl, cyanophenylthiocarbamoyl, nitrophenylthiocarbamoyl, ethoxycarbonylphenylthiocarbamoyl, fluorophenylthiocarbamoyl, chlorophenylthiocarbamoyl, difluorophenylthiocarbamoyl, trifluorophenylthiocarbamoyl, 2-cylohexylethythiocarbamoyl, (benzo[1,3]dioxol-5-yl)thiocarbamoyl, morpholinophenylthiocarbamoyl, dimethoxylphenylthiocarbamoyl and the like, more preferably ethoxycarbonylphenylthiocarbamoyl, fluorophenylthiocarbamoyl, chlorophenylthiocarbamoyl, difluorophenylthiocarbamoyl and trifluorophenylthiocarbamoyl.

In a further preferred embodiment, the invention comprises compounds of formula [I], wherein $R^1$ is

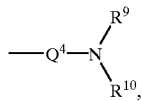

wherein $R^9$ and $R^{10}$ are independently hydrogen, unsubstituted or substituted lower alkyl, aralkyl, cycloalkyl, cycloalkylalkyl; or $R^9$ and $R^{10}$ may form an aliphatic ring together with the adjacent nitrogen, which may contain further heteroatom(s), preferably 1 to 3; and $Q^4$ is a single bond, carbonyl, unsubstituted or substituted lower alkylene. Preferably,

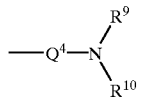

means unsubstituted or substituted lower alkylaminomethyl, cycloalkylaminomethyl or arylaminomethyl, optionally substituted with amino, hydroxy, cyano, nitro, lower alkyl, lower alkoxy, lower alkoxycarbonyl, halogen, methylenedioxy, morpholino and the like. More preferably the above group means N-methylaminomethyl, N-ethylaminomethyl, N-propylaminomethyl, N-isopropylaminomethyl, N-butylaminomethyl, N-isobutylaminomethyl, N-(tert-butylamino)methyl, N-phenylaminomethyl, N-(ethoxycarbonylphenylamino)methyl, N-(fluorophenylamino)methyl, N-(chlorophenylamino)methyl, N-(difluorophenylamino)methyl, N-(trifluorophenylamino)methyl, N-(2-cylohexylethylamino)methyl, N-(benzo[1,3]dioxol-5-ylamino)methyl, (morpholinophenylamino)methyl, N-(dimethoxylphenylamino)methyl and the like, more preferably N-(ethoxycarbonylphenylamino)methyl, N-(fluorophenylamino)methyl, N-(chlorophenylamino)methyl, N-(difluorophenylamino)methyl and N-(trifluorophenylamino)methyl.

In a further preferred embodiment, the invention comprises compounds of formula [I], wherein $R^1$ is "—$Q^4$—$R^8$" with $R^8$ being hydrogen, unsubstituted or substituted lower alkyl, aralkyl, cycloalkyl, cycloalkylalkyl, an aromatic ring or an aliphatic ring which may contain heteroatom(s), preferably 1 to 3; and $Q^4$ is a single bond, carbonyl, oxime, oxime O-ether which has a substituted or unsubstituted lower alkyl, lower alkenyl, aralkyl or aryl radical on the oxygen atom, or unsubstituted or substituted lower alkylene. Preferably, "—$Q^4$—$R^8$" means hydrogen, formyl, unsubstituted or substituted lower alkyl, lower alkylcarbonyl, oxime bearing an aromatic ring, oxime O-ether bearing an aromatic ring, carbonyl bearing an aromatic ring or lower alkyl bearing an aromatic ring, optionally substituted with one or more substituent(s) independently selected from hydroxy, halogen, cyano, nitro, morpholino, or unsubstituted or substituted lower alkyl, lower alkoxy, lower alkoxycarbonyl, lower (lower alkylamino)alkyl or lower (arylmethylamino)alkyl. The substituent on the oxygen atom of oxime O-ether bearing an aromatic ring, optionally substituted with one or more substituent(s) independently selected from hydroxy; halogen; cyano; nitro; morpholino; or unsubstituted or substituted lower alkyl, lower alkenyl, lower alkoxy, lower alkoxycarbonyl, lower (lower alkylamino)alkyl or lower (arylmethylamino)alkyl is preferably lower alkyl, lower alkenyl, aralkyl or aryl group. More preferably, "—$Q^4$—$R^8$" means hydrogen, methyl, ethyl, propyl, isopropyl, butyl, isobutyl, pentyl, phenyl, 2-methoxyphenyl, formyl, acetyl, propanoyl, butanoyl, benzoyl, imidazolecarbonyl, methylimidazolecarbonyl, methylpyridinecarbonyl, pyridinecarbonyl, (4,5-dimethyl-thiazol-2-yl)-carbonyl, (5,6-difluoro-1-methyl-1H-benzoimidazol-2-yl)-carbonyl, [1-(2-morpholin-4-yl-ethyl)-1H-benzoimidazol-2-yl]-carbonyl, [1-(2-pyridyl-ethyl)-1H-benzoimidazol-2-yl]-carbonyl, hydroxyimino-(5-methyl-pyridin-2-methyl), ethoxyimino-(5-methyl-pyridin-2-yl)-methyl, (4,5-dimethyl-thiazol-2-yl)-hydroxyimino-methyl, (4,5-dimethyl-thiazol-2-yl)-(4-nitro-benzyloxyimino)-methyl, (4,5-dimethyl-thiazol-2-yl)-phenoxyimino-methyl, allyloxyimino-(4,5-dimethyl-thiazol-2-yl)-methyl, (4,5-dimethyl-thiazol-2-yl)-ethoxyimino-methyl, 2-ethoxycarbonylethyl, 2-phenylethyl, 2-(chlorophenyl)ethyl, 2-(nitrophenyl)ethyl, 2-(cyanophenyl)ethyl, 2-(trifluoromethylphenyl)ethyl, 2-(morpholinophenyl)ethyl, 2-(fluorophenyl)ethyl, 2-(difluorophenyl)ethyl, 2-(trifluorophenyl)ethyl, 2-(tetrafluorophenyl)ethyl, 2-(bromofluorophenyl)ethyl, benzyl, 5-ethoxycarbonyl-2-hydroxybenzyl, (difluorophenyl)-hydroxy-methyl, phenyl-hydroxy-methyl, 1-hydroxypropyl, 4-(3-tert-butylaminopropyl)-3-methylbenzofuran-2-yl, 3-methyl-4-{3-(pyridin-3-ylmethyl)amino]propyl}benzofuran-2-yl and the like, more preferably 2-(chlorophenyl)ethyl, 2-(nitrophenyl)ethyl, 2-(cyanophenyl)ethyl, 2-phenylethyl, 2-(fluorophenyl)ethyl, 2-(difluorophenyl)ethyl, (5,6-difluoro-1-methyl-1H-benzoimidazol-2-yl)-carbonyl, [1-(2-morpholin-4-yl-ethyl)-1H-benzoimidazol-2-yl]-carbonyl, [1-(2-pyridyl-ethyl)-1H-benzoimidazol-2-yl]-carbonyl, methylimidazolecarbonyl, methylpyridinecarbonyl and pyridinecarbonyl.

In a further preferred embodiment, the invention comprises compounds of formula [I], wherein $R^1$ is "—$Q^4$—$OR^8$" with $R^8$ being hydrogen, unsubstituted or substituted lower alkyl, aralkyl, cycloalkyl, cycloalkylalkyl, an aromatic ring or an aliphatic ring which may contain heteroatom(s), preferably 1 to 3; and $Q^4$ is a single bond, carbonyl, unsubstituted or substituted lower alkylene. Preferably, "—$Q^4$—$OR^8$" means unsubstituted or substituted lower (lower alkoxy)alkyl, lower (aryloxy)alkyl or lower (arylalkoxy)alkyl, optionally substituted with one or more substituents independently selected from hydroxy, hydroxymethyl, aminoalkyl, lower alkoxy, lower (lower alkoxy)alkyl, halogen, cyano, nitro, morpholino, lower alkyl, lower alkoxycarbonyl, lower alkylcarbonyl, lower (lower haloalkyl)alkyl, lower (lower haloalkoxy)alkyl or methylenedioxy. More preferably, "—$Q^4$—$OR^8$" means (2,2,2-trifluoroethoxy)methyl, hydroxymethyl, methoxymethyl, ethoxymethyl, propoxymethyl, isopropoxymethyl, butoxymethyl, isobutoxymethyl, tert-butoxymethyl, phenyloxymethyl, (chlorophenyl)oxymethyl, (2-(ethoxymethyl)benzofuran-5-yl)oxymethyl, (2-(hydroxymethyl)benzofuran-5-yl)oxymethyl, (2-(aminomethyl)benzofuran-5-yl)oxymethyl, (2-

(ethoxycarbonyl)benzofuran-5-yl)oxymethyl, (2-(2,2,2-trifluoroethoxymethyl)benzofuran-5-yl)oxymethyl, (2-acetylbenzofuran-4-yl)oxymethyl, (trifluoromethylphenyl)oxymethyl, (morpholinophenyl)oxymethyl, (fluorophenyl)oxymethyl, (difluorophenyl)oxymethyl, (trifluorophenyl)oxymethyl, (tetrafluorophenyl)oxymethyl, (bromofluorophenyl)oxymethyl, (nitrophenyl)oxymethyl, (cyanophenyl)oxymethyl, 3-(fluorophenyl)oxypropyl, 3-(difluorophenyl)oxypropyl, 3-(trifluorophenyl)oxypropyl, 3-(cyanophenyl)oxypropyl, 3-(fluorophenyl)methyloxy)propyl, 3-(difluorophenyl)methyloxypropyl and the like, more preferably (fluorophenyl)oxymethyl, (difluorophenyl)oxymethyl, (trifluorophenyl)oxymethyl, (bromofluorophenyl)oxymethyl, (nitrophenyl)oxymethyl, (cyanophenyl)oxymethyl and (chlorophenyl)oxymethyl.

In a further preferred embodiment, the invention comprises compounds of formula [I], wherein $R^1$ is "—$Q^4$—S(O)$_x$$R^8$" with $R^8$ being hydrogen, unsubstituted or substituted lower alkyl, aralkyl, cycloalkyl, cycloalkylalkyl, an aromatic ring or an aliphatic ring which may contain heteroatom(s), preferably 1 to 3; $Q^4$ is a single bond, carbonyl, unsubstituted or substituted lower alkylene and x is an integer of 0 to 2. Preferably, "—$Q^4$—S(O)$_x$$R^8$" means unsubstituted or substituted lower (lower alkylthio)alkyl, lower (arylthio)alkyl, lower (aralkyltl-lio)alkyl, (cycloalkylthio)alkyl, (cycloalkylalkylthio)alkyl, lower (lower alkylsulfinyl)alkyl, lower (arylsulfinyl)alkyl, lower (aralkylfulfinyl)alkyl, (cycloalkylsulfinyl)alkyl, (cycloalkylalkylsulufinyl)alkyl, lower (lower alkylsulfonyl)alkyl, lower (arylsulfonyl)alkyl, lower (aralkylsulfonyl)alkyl, (cycloalkylsulfonyl)alkyl or (cycloalkylalkylsulfonyl)alkyl, optionally substituted with one or more substituents independently selected from haloalkyl, lower alkyl, lower alkoxy, lower alkoxycarbonyl, hydroxy, halogen, cyano, nitro and morpholino. More preferably, "—$Q^4$—S(O)$_x$$R^8$" means methylthiomethyl, ethylthiomethyl, propylthiomethyl, isopropylthiomethyl, butylthiomethyl, isobutylthiomethyl, tert-butylthiomethyl, (2-phenylethyl)thiomethyl, phenylthiomethyl, (chlorophenyl)thiomethyl, (trifluoromethylphenyl)thiomethyl, (morpholinophenyl)thiomethyl, (fluorophenyl)thiomethyl, (difluorophenyl)thiomethyl, (trifluorophenyl)thiomethyl, (tetrafluorophenyl)thiomethyl, (bromofluorophenyl)thiomethyl, (nitrophenyl)thiomethyl, (cyanophenyl)thiomethyl, methylsulfinylmethyl, ethylsulfinylmethyl, propylsulfinylmethyl, isopropylsulfinylmethyl, butylsulfinylmethyl, isobutylsulfinylmethyl, tert-butylsulfinylmethyl, (2-phenylethyl)sulfinylmethyl, phenylsulfinylmethyl, (chlorophenyl)sulfinylmethyl, (trifluoromethylphenyl)sulfinylmethyl, (morpholinophenyl)sulfinylmethyl, (fluorophenyl)sulfinylmethyl, (difluorophenyl)sulfinylmethyl, (trifluorophenyl)sulfinylmethyl, (tetrafluorophenyl)sulfinylmethyl, (bromofluorophenyl)sulfinylmethyl, (nitrophenyl)sulfinylmethyl, (cyanophenyl)sulfinylmethyl, methylsulfonylmethyl, ethylsulfonylmethyl, propylsulfonylmethyl, isopropylsulfonylmethyl, butylsulfonylmethyl, isobutylsulfonylmethyl, tert-butylsulfonylmethyl, (2-phenylethyl)sulfonylmethyl, phenylsulfonylmethyl, (chlorophenyl)sulfonylmethyl, (trifluoromethylphenyl)sulfonylmethyl, (morpholinophenyl)sulfonylmethyl, (fluorophenyl)sulfonylmethyl, (difluorophenyl)sulfonylmethyl, (trifluorophenyl)sulfonylmethyl, (tetrafluorophenyl)sulfonylmethyl, (bromofluorophenyl)sulfonylmethyl, (nitrophenyl)sulfonylmethyl, (cyanophenyl)sulfonylmethyl and the like, more preferably ethylthiomethyl, propylthiomethyl, tert-butylthiomethyl, isopropylthiomethyl, (fluorophenyl)thiomethyl, (difluorophenyl)thiomethyl, (trifluorophenyl)thiomethyl, (bromofluorophenyl)thiomethyl, (nitrophenyl)thiomethyl, (cyanophenyl)thiomethyl, (chlorophenyl)thiomethyl, ethylsulfinylmethyl, propylsulfinylmethyl, tert-butylsulfinylmethyl, isopropylsulfinylmethyl, (fluorophenyl)sulfinylmethyl, (difluorophenyl)sulfinylmethyl, (trifluorophenyl)sulfinylmethyl, (bromofluorophenyl)sulfinylmethyl, (nitrophenyl)sulfinylmethyl, (cyanophenyl)sulfinylmethyl, (chlorophenyl)sulfinylmethyl, ethylsulfonylmethyl, propylsulfonylmethyl, tert-butylsulfonylomethyl, isopropylsulfonylmethyl, (fluorophenyl)sulfonylmethyl, (difluorophenyl)sulfonylmethyl, (trifluorophenyl)sulfonylmethyl, (bromofluorophenyl)sulfonylmethyl, (nitrophenyl)sulfonylmethyl, (cyanophenyl)sulfonylmethyl and (chlorophenyl)sulfonylmethyl.

In a further preferred embodiment, the invention comprises compounds of formula [I], wherein $R^1$ is

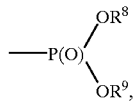

wherein $R^8$ and $R^9$ are independently hydrogen, unsubstituted lower alkyl, aralkyl, cycloalkyl, cycloalkylalkyl or an aromatic ring or aliphatic ring which may contain heteroatom(S), preferably 1 to 3. Preferably,

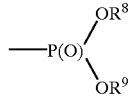

means di-(lower alkoxy)phosporyl or di-(aryloxy)phosphoryl. More preferably the group means dimethoxyphosphoryl, diethoxyphosphoryl, diisopropoxyphosphoryl, dipropoxyphosphoryl, dibutoxyphosphoryl, diphenyloxyphosphoryl and the like, more preferably diethoxyphosphoryl and diisopropoxyphosphoryl.

In a further preferred embodiment, the invention comprises compounds of formula [I], wherein $R^1$ is "—CH=N—OR$^8$" wherein $R^8$ is hydrogen, unsubstituted or substituted lower alkyl, aralkyl, cycloalkyl, cycloalkylalkyl or an aromatic ring or aliphatic ring which may contain heteroatom(s), preferably 1 to 3. Preferably, "—CH=N—OR$^8$" means unsubstituted or substituted lower (hydroxyimino)alkyl, lower (lower alkoxyimino)alkyl, lower (aralkyloxyimino)alkyl or lower (aryloxyimino)alkyl. More preferably the group means (hydroxyimino)methyl (methyoxyimino)methyl, (ethoxyimino)methyl, (propoxyimino)methyl, (isopropoxyimino)methyl, (butoxyimino)methyl, (isobutoxyimino)methyl, (tert-butoxyimino)methyl, {(2-phenylethyl)oxyimino}methyl, (benzyloxyimino)methyl, and the like, more preferably (methyloxyimino)methyl, (ethyloxyimino)methyl, (tert-butoxyimino)methyl and (benzyloxyimino)methyl.

In a further preferred embodiment, the invention comprises compounds of formula [I], wherein $R^1$ is

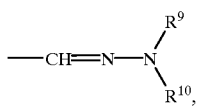

wherein $R^9$ and $R^{10}$ are independently hydrogen, unsubstituted or substituted lower alkyl, aralkyl, cycloalkyl, cycloalkylalkyl; or $R^9$ and $R^{10}$ may form an aliphatic ring together with the adjacent nitrogen, which may contain further heteroatom(s), preferably 1 to 3. Preferably,

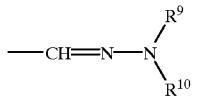

means (formylhydrazono)methyl, unsubstituted or substituted {(lower alkyl)hydrazono}methyl or (arylhydrazono) methyl, optionally substituted with one or more substituents independently selected from halogen, lower alkyl or lower haloalkyl, or iminomethyl substituted with a heterocyclic ring which is optionally substituted with lower alkyl. Preferably, the group means (dimethylhydrazono)methyl, (pyrrolidinylimino)methyl, {4-(1,2,4-triazolyl) imino}methyl, {(4-methylpiperazinyl)imino}methyl, (morpholinylimino)methyl, (formylhydrazono)methyl, (phenylhydrazono)methyl, (fluorophenylhydrazono)methyl, (difluorophenylhydrazono)methyl, (trifluorophenylhydrazono)methyl and the like, more preferably (pyrrolidinylimino)methyl, {(4-methylpiperazinyl) imino}methyl and (morpholinylimino)methyl.

In a further preferred embodiment, the invention comprises compounds of formula [I], wherein $R^1$ is "—CH=CH—$R^8$" wherein $R^8$ is hydrogen, unsubstituted or substituted lower alkyl, aralkyl, cycloalkyl, cycloalkylalkyl or an aromatic ring or aliphatic ring which may contain heteroatom(s), preferably 1 to 3. Preferably, "—CH=CH—$R^8$" means lower alkoxyvinyl, lower alkylvinyl or arylvinyl, optionally substituted with one or more substituents independently selected from lower alkyl, halogen, cyano, lower halomethyl, morpholino or nitro. More preferably the group means 2-ethoxycarbonylvinyl, 2-methylvinyl, 2-ethylvinyl, 2-propylvinyl, 2-isopropylvinyl, 2-butylvinyl, 2-isobutylvinyl, 2-(tert-butyl)vinyl, 2-phenylvinyl, 2-(chlorophenyl)vinyl, 2-(cyanophenyl)vinyl, 2-(trifluoromethylphenyl)vinyl, 2-(morpholinophenyl)vinyl, 2-(fluorophenyl)vinyl, 2-(difluorophenyl)vinyl, 2-(trifluorophenyl)vinyl, 2-(tetrafluorophenyl)vinyl, 2-(bromofluorophenyl)vinyl, 2-(nitrophenyl)vinyl, 2-(cyanophenyl)vinyl and the like, more preferably 2-(fluorophenyl)vinyl, 2-(difluorophenyl)vinyl and 2-phenylvinyl.

In a further preferred embodiment, the invention comprises compounds of formula [I], wherein $R^1$ is

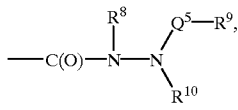

wherein $R^8$, $R^9$ and $R^{10}$ are independently hydrogen, unsubstituted or substituted lower alkyl, aralkyl, cycloalkyl, an aromatic ring or an aliphateic ring which may contain heteroatom(s), preferably 1 to 3, or with $R^9$ and $R^{10}$ forming an aliphatic ring which may contain further hetroatom(s), preferably 1 to 3, together with the adjacent nitrogen; and $Q^5$ is a single bond or carbonyl. Preferably,

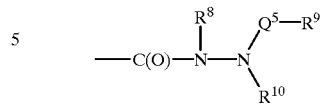

means unsubstituted or substituted N'-arylhydrazinocarbonyl, N-arylhydrazinocarbonyl, N'-benzoyl-hydrazinocarbony, N'-(4-morpholin-4-ylcarbamoyl) or N'-(pyridinecarbonyl)-hydrazinocarbonyl. More preferably the above group means N'-(nitropheny) hydrozinocarbonyl, N'-(fluorophenyl)-hydrazinocarbonyl, N-(fluorophenyl)hydrazinocarbonyl.

$R^2$ is hydrogen, unsubstituted or substituted lower alkyl, aralkyl, cycloalkyl or cycloalkylalkyl, more preferably unsubstituted lower alkyl or cycloalkyl.

In the above, the term "unsubstituted lower alkyl" preferably means methyl, ethyl, propyl, butyl and isopropyl and the like, more preferably methyl and ethyl.

"Substituted lower alkyl" preferably means hydroxymethyl, ethoxymethyl, aminomethyl and the like, more preferably aminomethyl.

"Cycloalkyl" preferably means cyclopropyl and the like.
"Cycloalkylalkyl" preferably means cyclopentylmethyl and the like.

$R^6$ and $R^7$ are independently hydrogen, unsubstituted or substituted lower alkyl, an aromatic ring or 3 to 7 membered aliphatic ring which may contain heteroatom(s), preferably 1 to 3; or $R^6$ and $R^7$ form an aliphatic ring which may contain further heteroatom(s) together with the adjacent $Q^2$, N and $Q^3$; or $Q^1$ and $R^6$ form an aliphatic ring which may contain further heteroatom(s) together with the adjacent N and $Q^2$.

In the above, "unsubstituted lower alkyl" preferably means methyl, ethyl, propyl, isopropyl, isobutyl, tert-butyl and sec-butyl and the like, more preferably methyl, ethyl, isopropyl and tert-butyl.

"Substituted lower alkyl" preferably means an "unsubstituted lower alkyl" as defined above optionally substituted with one or more substituents independently selected from lower-alkyl, hydroxy, amino, lower alkoxy, e.g. 1,1-dimethyl-2-hydroxyethyl, 3-amino-2,2-dimethylpropyl, hydroxypropyl, hydroxyethyl, aminopropyl, aminoethyl, methoxyethyl, ethoxyethyl and the like, more preferably 1,1-dimethyl-2-hydroxyethyl.

"Unsubstituted aromatic ring" preferably means phenyl, pyrazinyl, pyrimidinyl, pyridazinyl, pyridyl, imidazolyl, triazolyl, thienyl, furyl, pyrrolyl, pyrazolyl, thiazolyl, indolyl, benzoimidazolyl and the like, more preferably pyridyl.

"Substituted aromatic ring" means an "unsubstituted aromatic ring" as defined above, substituted with one or more substituents independently selected from methylenedioxy, lower-alkyl, lower alkoxy, halogen, and aryl, unsubstituted or substituted amino. Most preferably the term means benzo[1,3]dioxol-5-yl, 4-N,N-dimethylaminophenyl, chloropyridyl, 5-methyl-4-imidazolyl, N-methyl-2-pyrrolyl, 2-phenyl-4-imidazolyl, 5-methyl-2-pyrazinyl and the like.

"Unsubstituted 3 to 7 membered ring which may contain heteroatom(s)" preferably means cycloalkyl, piperidyl, pyrrolidinyl, more preferably cyclopropyl, cyclobutyl, cyclopentyl, cyclohexyl, cycloheptyl, 4-piperidyl, 3-pyrrolidinyl and the like, and most preferably cyclohexyl.

"Substituted 3 to 7 membered ring which may contain heteroatom(s)" preferably means 1-ethyl-4-piperidinyl, 1-(3-pyridylmethyl)-4-piperidyl, 1-indanyl, 4-methyl-1-piperazinyl, tetrahydrofuran-2-one-3-yl, 1-benzyl-3-pyrrolidinyl and the like.

"unsubstituted aliphatic ring formed by $R^6$ and $R^7$ together with the adjacent $Q^2$, N and $Q^3$ ring which may contain further heteroatom(s)" preferably means piperidine, morpholine, thiomorpholine piperazine, pyrrolidine and the like. "Substituted aliphatic ring formed by $R^6$ and $R^7$ together with the adjacent $Q^2$, N and $Q^3$ which may contain further heteroatom(s)" preferably means 4-aminomethylpiperidine, 2-methylpiperidine, 3-aminopyrrolidine and the like.

"Aliphatic ring" formed by $Q^1$ and $R^6$ together with adjacent N and $Q^2$ which may contain further heteroatom (s) preferably means a piperidine ring. And thus, when $Q^1$ and $R^6$ form an aliphatic ring which may contain further heteroatom(s) together with adjacent N and $Q^2$, the radical

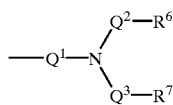

in the formula [I] preferably means

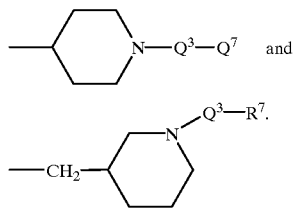

In a preferred embodiment the invention comprises compounds of formula [I], wherein $R^6$ is hydrogen and $R^7$ is unsubstituted or substituted lower alkyl.

In a further preferred embodiment the invention comprises compounds of formula [I], wherein $R^6$ is hydrogen and $R^7$ is an aromatic ring or a 3 to 7 membered aliphatic ring which may contain heteroatoms.

In a further preferred embodiment the invention comprises compounds of formula [I], wherein $R^6$ is unsubstituted or substituted lower alkyl and $R^7$ is unsubstituted or substituted lower alkyl.

In a further preferred embodiment the invention comprises compounds of formula [I], wherein $R^6$ is unsubstituted or substituted lower alkyl and $R^7$ is an aromatic ring or a 3 to 7 membered aliphatic ring which may contain heteroatoms.

In a further preferred embodiment the invention comprises compounds of formula [I], wherein $R^3$, $R^4$ and $R^5$ are hydrogen and the structure $Q^1N(Q^2R^6)(Q^3R^7)$ is

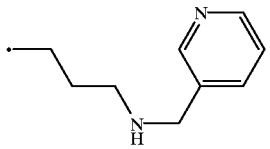

In a further preferred embodiment the invention comprises compounds of formula [I], wherein $R^3$, $R^4$ and $R^5$ are hydrogen, $R^2$ is methyl and the structure $Q^1N(Q^2R^6)(Q^3R^7)$ is

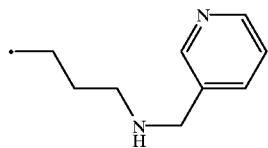

$Q^1$ is unsubstituted or substituted lower alkylene other than unsubstituted or substituted methylene;

In the above, "unsubstituted lower alkylene" preferably means ethylene, trimethylene, tetramethylene and pentamethylene and the like, more preferably trimethylene and tetramethylene.

"Substituted lower alkylene" preferably means —CH$_2$CH(OH)CH$_2$—, —CH(CH$_3$)CH$_2$CH$_2$—, —CH$_2$CH$_2$CH(CH$_3$)—, —CH$_2$CH(NHCH$_2$CH$_3$)CH$_2$— and the like, more preferably —CH$_2$CH(OH)CH$_2$—.

$Q^2$ and $Q^3$ are a single bond, or unsubstituted or substituted lower alkylene; In the above, "unsubstituted lower alkylene" preferably means methylene, ethylene, trimethylene, tetramethylene and pentamethylene and the like, more preferably methylene and ethylene.

"Substituted lower alkylene" preferably means —CH(CH$_3$)— and the like.

In a preferred embodiment the invention comprises compounds of formula [I], wherein $Q^2$ and $Q^3$ are each a single bond.

In a further preferred embodiment the invention comprises compounds of formula [I], wherein $Q^2$ is a single bond and $Q^3$ is a single bond or unsubstituted or substituted lower alkylene.

In another preferred embodiment the invention comprises compounds of formula [I], wherein $R^1$ is —$Q^4$—$R^8$ [where $Q^4$ is carbonyl and $R^8$ is an unsubstituted or substituted, preferably substituted aromatic ring which may contain heteroatom(s), e.g. benzoimidazolyl preferably substituted with halogen, such as fluoro, lower alkyl, such as methyl, pyridinyl-lower alkyl, such as pyridinyl-ethyl and/or morpholinyl-lower alkyl, such as morpholinyl-ethyl]; $R^2$ is lower alkyl, e.g. methyl; $Q^1$ is lower alkylene, e.g. propylene; $Q^2$ is a single bond; $Q^3$ is unsubstituted lower alkylene, e.g. methylene; $Q^4$ is carbonyl; $R^3$, $R^4$, $R^5$ and $R^6$ are hydrogen; and $R^7$ is an aromatic ring which may contain heteroatoms, e.g. phenyl, pyridyl, pyrimidinyl and the like, preferably pyridyl.

Preferred bicyclic compounds in accordance with the present invention are as follows (Each compound No. coincides with the compounds in each Example described hereinafter):

1. 3-cyclopropyl-4-{3-[(pyridin-3-ylmethyl)-amino]-propoxy}-benzofuran-2-carboxylic acid ethyl ester
2. 3-isopropyl-4-{3-[(pyridin-3-ylmethyl)-amino]-propoxy}-benzofuran-2-carboxylic acid ethyl ester
3. 3-ethyl-4-{3-[(pyridin-3-ylmethyl)-amino]-propoxy}-benzofuran-2-carboxylic acid ethyl ester
4. 4-{3-[(pyridin-3-ylmethyl)-amino]-propoxy}-benzofuran-2-carboxylic acid ethyl ester
5. 4-(3-tert-butylamino-propoxy)-3-propyl-benzofuran-2-carboxylic acid ethyl ester
6. 3-butyl-4-(3-tert-butylamino-propoxy)-benzofuran-2-carboxylic acid ethyl ester
7. 3-aminomethyl-4-{3-[(pyridin-3-ylmethyl)-amino]-propoxy}-benzofuran-2-carboxylic acid ethyl ester
8. 4-(3-tert-butylamino-propoxy)-3-hydroxymethyl-benzofuran-2-carboxylic acid methyl ester 9. 4-(3-tert-butylamino-propoxy)-3-ethoxymethyl-benzofuran-2-carboxylic acid ethyl ester
10. (3-cyclopropyl-4-{3-[(pyridin-3-ylmethyl)-amino]-propoxy}-benzofuran-2-yl)-methanol
11. (3-methyl-4-{3-[(pyridin-3-ylmethyl)-amino]-propoxy}-benzofuran-2-yl)-methanol
12. {3-[2-(2,4-difluorophenoxymethyl)-3-methyl-benzofuran-4-yloxy]-propyl}-pyridin-3-ylmethyl-amine
13. {3-[2-(3-trifluoromethylphenoxymethyl)-3-methyl-benzofuran-4-yloxy]-propyl}-pyridin-3-ylmethyl-amine
14. [3-(2-phenoxymethyl-3-methyl-benzofuran-4-yloxy-propyl]-pyridin-3-ylmethyl-amine
15. {3-[2-(2-fluorophenoxymethyl)-3-methyl-benzofuran-4-yloxy]-propyl}-pyridin-3-ylmethyl-amine
16. {3-[2-(3-fluorophenoxymethyl)-3-methyl-benzofuran-4-yloxy]-propyl}-pyridin-3-ylmethyl-amine
17. {3-[2-(4-fluorophenoxymethyl)-3-methyl-benzofuran-4-yloxy]-propyl}-pyridin-3-ylmethyl-amine
18. (3-[2-(2,3-difluorophenoxymethyl)-3-methyl-benzofuran-4-yloxy]-propyl}-pyridin-3-ylmethyl-amine
19. {3-[2-(2,5-difluorophenoxymethyl)-3-methyl-benzofuran-4-yloxy]-propyl}-pyridin-3-ylmethyl-amine
20. {3-[2-(2,6-difluorophenoxymethyl)-3-methyl-benzofuran-4-yloxy]-propyl}-pyridin-3-ylmethyl-amine
21. {3-[2-(2,3,4-trifluorophenoxymethyl)-3-methyl-benzofuran-4-yloxy]-propyl}-pyridin-3-ylmethyl-amine
22. {3-[2-(2,3,5-trifluorophenoxymethyl)-3-methyl-benzofuran-4-yloxy]-propyl}-pyridin-3-ylmethyl-amine
23. {3-[2-(2,4,5-trifluorophenoxymethyl)-3-methyl-benzofuran-4-yloxy]-propyl}-pyridin-3-ylmethyl-amine
24. {3-[2-(2,3,6-trifluorophenoxymethyl)-3-methyl-benzofuran-4-yloxy]-propyl}-pyridin-3-ylmethyl-amine
25. {3-[2-(2,4,6-trifluorophenoxymethyl)-3-methyl-benzofuran-4-yloxy]-propyl}-pyridin-3-ylmethyl-amine
26. {3-[2-(2,3,4,5,6-pentafluorophenoxymethyl)-3-methyl-benzofuran-4-yloxy]-propyl}-pyridin-3-ylmethyl-amine
27. {3-[2-(3,5,-bistrifluoromethylphenoxymethyl)-3-methyl-benzofuran-4-yloxy]-propyl}-pyridin-3-ylmethyl-amine
28. {3-[2-(3-morpholin-phenoxymethyl)-3-methyl-benzofuran-4-yloxy]-propyl}-pyridin-3-ylmethyl-amine
29. {3-[2-(4-morpholin-phenoxymethyl)-3-methyl-benzofuran-4-yloxy]-propyl}-pyridin-3-ylmethyl-amine
30. {3-[2-(4-chlorophenoxymethyl)-3-methyl-benzofuran-4-yloxy]-propyl}-pyridin-3-ylmethyl-amine
31. {3-[3-methyl-2-(pyridin-3-yloxymethyl)-benzofuran-4-yloxy]-propyl}-pyridin-3-yimethyl-amine
32. 4-(3-methyl-4-{3-[(pyridin-3-ylmethyl)-amino]-propoxy}-benzofuran-2-ylmethoxy)-benzonitrile
33. {3-[3-methyl-2-(2,2,2-trifluoro-ethoxymethyl)-benzofuran-4-yloxy)-propyl}-pyridin-3-ylmethyl-amine
34. (4-hydroxy-piperidin-1-yl)-[5-(3-methyl-4-{3-[(pyridin-3-ylmethyl)-amino]-propoxy}-benzofuran-2-ylmethoxy)-benzofuran-2-yl]-methanone
35. [5-(3-methyl-4-{3-[(pyridin-3-ylmethyl)-amino]-propoxy}-benzofuran-2-ylmethoxy)-benzofuran-2-yl]-piperazin-1-yl-methanone
36. 5-[3-methyl-4-[3-[(pyridin-3-ylmethyl)-amino]-propoxyl]-benzofuran-2-ylmethoxy]-benzofuran-2-carboxylic acid ethyl ester
37. 7-[3-methyl-4-[3-[(pyridin-3-ylmethyl)-amino]-propoxyl]-benzofuran-2-ylmethoxyl]-benzofuran-2-carboxylic acid ethyl ester
38. 5-(3-cyclopropyl-4-{3-[(pyridin-3-ylmethyl)-amino]-propoxy}-benzofuran-2-ylmethoxy)-benzofuran-2-carboxylic acid ethyl ester
39. 5-[3-methyl-4-[3-[(pyridin-3-ylmethyl)-amino]-propoxyl]-benzofuran-2-ylmethoxyl]-benzofuran-2-carboxylic acid amide
40. [5-[3-methyl-4-[3-[(pyridin-3-ylmethyl)-amino]-propoxyl]-benzofuran-2-ylmethoxyl]-benzofuran-2-yl]-methanol
41. [3-[2-(2-aminomethyl-benzofuran-5-ylmethyl)-3-methyl-benzofuran-4-yloxy]-propyl]-pyridin-3-ylmethyl-amine
42. [3-[2-(2-ethoxymethyl-benzofuran-5-yloxymethyl)-3-methyl-benzofuran-4-yloxy]-propyl]-pyridin-3-ylmethyl-amine
43. [3-[3-methyl-2-[2-(2,2,2-trifluoro-ethoxymethyl)-benzofuran-5-yloxymethyl]-benzofuran-4-yloxy]-propyl]-pyridin-3-ylmethyl-amine
44-1. 1-[5-(3-methyl-4-{3-[(pyridin-3-ylmethyl)-amino]-propoxy}-benzofuran-2-ylmethoxy)-benzofuran-2-yl]-ethanone
44-2. 2-[5-(3-methyl-4-{3-[(pyridin-3-ylmethyl)-amino]-propoxy}-benzofuran-2-ylmethoxy)-benzofuran-2-yl]-propan-2-ol
45. {3-[2-(2-ethoxymethyl-benzofuran-5-yloxymethyl)-3-methyl-benzofuran-4-yloxy]-propyl}-methyl-pyridin-3-ylmethyl-amine
46. {3-[2-(2,4-difluoro-phenoxymethyl)-3-methyl-benzofuran-4-yloxy]-propyl}-methyl-pyridin-3-ylmethyl-amine
47. 5-(3-cyclopropyl-4-{3-[(pyridin-3-ylmethyl)-amino]-propoxy}-benzofuran-2-ylmethoxy)-benzofuran-2-carboxylic acid ethylamide
48. 5-(3-cyclopropyl-4-{3-[(pyridin-3-ylmethyl)-amino]-propoxy}-benzofuran-2-ylmethoxy)-benzofuran-2-carboxylic acid cyclopropylamide
49. 3-[4-[2-(2-ethoxymethyl-benzofuran-5-yloxymethyl)-3-methyl-benzofuran-4-yloxy]-piperidin-1-ylmethyl]-pyridine
50. [5-[3-methyl-4-(1-pyridin-3-ylmethyl-piperidin-3-ylmethoxy)-benzofuran-2-ylmethoxy]-benzofuran-2-yl]-methanol
51. acetic acid 5-[3-methyl-4-(1-pyridin-3-ylmethyl-piperidin-3-ylmethoxy)-benzofuran-2-ylmethoxy]-benzofuran-2-ylmethyl ester
52. [3-(2-ethoxymethyl-3-methyl-benzofuran-4-yloxy)-propyl]-pyridin-3-ylmethyl-amine 53. [3-[2-(2-cyclohexyl-ethoxymethyl)-3-methyl-benzofuran-4-yloxy]-propyl]-pyridin-3-ylmethyl-amine
54. [3-[2-(3,5-dimethoxy-benzyloxymethyl)-3-methyl-benzofuran-4-yloxy]-propyl]-pyridin-3-ylmethyl-amine
55. isopropyl-[3-(3-methyl-2-phenethylsulfanylmethyl-benzofuran-4-yloxy)-propyl]-amine
56. [3-(3-methyl-2-phenethylsulfanylmethyl-benzofuran-4-yloxy)-propyl]-pyridin-3-ylmethyl-amine
57. [3-(3-methyl-2-phenylsulfanylmethyl-benzofuran-4-yloxy)-propyl]-pyridin-3-ylmethyl-amine
58. {3-[2-(4-chloro-phenylsulfanylmethyl)-3-methyl-benzofuran-4-yloxy]-propyl}-pyridin-3-ylmethyl-amine
59. {3-[2-(4-chloro-benzylsulfanylmethyl)-3-methyl-benzofuran-4-yloxy]-propyl}-pyridin-3-ylmethyl-amine
60. [3-(2-ethylsulfanylmethyl-3-methyl-benzofuran-4-yloxy)-propyl]-pyridin-3-ylmethyl-amine
61. (RS)-[3-[3-methyl-2-(2-phenyl-ethylsulfinylmethyl)-benzofuran-4-yloxy]-propyl]-pyridin-3-ylmethyl-amine
62. 3-methyl-4-{3-[(pyridin-3-ylmethyl)-amino]-propoxy}-benzofuran-2-carboxylic acid (2-cyclohexyl-ethyl)-amide
63. 3-methyl-4-(3-pyrrolidin-1-yl-propoxy)-benzofuran-2-carboxylic acid 2-cyclohexyl-ethyl)-amide
64. 4-[[4-(3-tert-butylamino-propoxy)-3-methyl-benzofuran-2-carbonyl]-amino]-benzoic acid ethyl ester
65. 2-[[4-(3-tert-butylamino-propoxy)-3-methyl-benzofuran-2-carbonyl]-amino]-benzoic acid ethyl ester
66. 3-methyl-4-{3-[(pyridin-3-ylmethyl)-amino]-propoxy}-benzofuran-2-carboxylic acid (2,4-difluorophenyl)-amide
67. 3-methyl-4-{3-[(pyridin-3-ylmethyl)-amino]-propoxy}-benzofuran-2-carboxylic acid (2,3,4-trifluorophenyl)-amide
68. 3-methyl-4-{3-[(pyridin-3-ylmethyl)-amino]-propoxy}-benzofuran-2-carboxylic acid (2-fluorophenyl)-amide
69. 3-methyl-4-{3-[(pyridin-3-ylmethyl)-amino]-propoxy}-benzofuran-2-carboxylic acid (4-morpholin-4-yl-phenyl)-amide
70. 3-methyl-4-{3-[(pyridin-3-ylmethyl)-amino]-propoxy}-benzofuran-2-carboxylic acid benzo[1,3]dioxol-5-yl amide
71. 3-methyl-4-{3-[(pyridin-3-ylmethyl)-amino]-propoxy}-benzofuran-2-carboxylic acid (3,5-dimethoxy-phenyl)-amide
72. 3-methyl-4-{3-[(pyridin-3-ylmethyl)-amino]-propoxy}-benzofuran-2-carboxylic acid phenyl-amide
73. 3-methyl-4-{3-[(pyridin-3-ylmethyl)-amino]-propoxy}-benzofuran-2-carboxylic acid (4-chloro-phenyl)-amide
74. 3-methyl-4-{3-[(pyridin-3-ylmethyl)-amino]-propoxy}-benzofuran-2-carboxylic acid (2-chloro-phenyl)-amide
75. (3-methyl-4-{3-[pyridin-3-ylmethyl)-amino]-propoxy}-benzofuran-2-yl phosphonic acid diethyl ester
76. (3-methyl-4-{3-[pyridin-3-ylmethyl)-amino]-propoxy}-benzofuran-2-yl phosphonic acid diisopropyl ester
77. 2-{4-[3-(tert-butylamino)-propoxy]-3-methyl-benzofuran-2-yl}-oxazole-4-carboxylic acid ethyl ester
78. 2-(3-methyl-4-{3-[(pyridin-3-ylmethyl)-amino]-propoxy}-benzofuran-2-yl)-oxazole-4-carboxylic acid ethyl ester
79. (4-methyl-piperazin-1-yl)-[2-(3-methyl-4-{3-[(pyridin-3-ylmethyl)-amino]propoxy}-benzofuran-2-yl)-oxazol-4-yl]-methanone
80. 2-(3-methyl-4-{3-[(pyridin-3-ylmethyl)-amino]-propoxy}-benzofuran-2-yl)-oxazole-4-carboxylic acid isopropylamide
81. (RS)-2-[3-methyl-4-[3-[(pyridin-3-ylmethyl)-amino]-propoxy]-benzofuran-2-yl]-oxazole-4-carboxylic acid (tetrahydro-furan-2-ylmethyl)-amide
82. (RS)-1-[2-[3-methyl-4-[3-[(pyridin-3-ylmethyl)-amino]-propoxy]-benzofuran-2-yl]-oxazole-4-carbonyl]-piperidine-3-carboxylic acid ethyl ester
83. [2-(3-methyl-4-{3-[(pyridin-3-ylmethyl)-amino]-propoxy}-benzofuran-2-yl)-oxazol-4-yl]-thiazolidin-3-yl-methanone
84. 2-(3-methyl-4-{3-[(pyridin-3-ylmethyl)-amino]-propoxy}-benzofuran-2-yl)-oxazole-4-carboxylic acid (3,5-difluoro-phenyl)-amide
85. 2-(3-methyl-4-{3-[(pyridin-3-ylmethyl)-amino]-propoxy}-benzofuran-2-yl)-thiazole-4-carboxylic acid ethyl ester
86. 2-[2-[3-methyl-4-[3-[(pyridin-3-ylmethyl)-amino]-propoxy]-benzofuran-2-yl]-oxazol-4-yl]-thiazole-4-carboxylic acid ethyl ester
87. dl-5-cyclohexylmethyl-2-(3-methyl-4-{-3-[(pyridin-3-ylmethyl)-amino]-propoxy}-benzofuran-2-yl)-trans-4,5-dihydro-oxazole-4-carboxylic acid ethyl ester
88. dl-[5-cyclohexylmethyl-2-(3-methyl-4-{3)-[(pyridin-3-ylmethyl)-amino]-propoxy}-benzofuran-2-yl)-trans-4,5-dihydro-oxazol-4-yl]-(4-methyl-piperazin-1-yl)-methanone
89. dl-[5-(2,4-difluoro-benzyl)-2-(3-methyl-4-{3-[(pyridin-3-ylmethyl)-amino]-propoxy}-benzofuran-2-yl)-trans-4,5-dihydro-oxazol-4-yl]-(4-methyl-piperazin-1-yl)-methanone
90. 5-cyclohexylmethyl-2-(3-methyl-4-{3-[(pyridin-3-ylmethyl)-amino]-propoxy}-benzofuran-2-yl)-oxazole-4-carboxylic acid ethyl ester
91. 4-[2-hydroxy-3-[(pyridin-3-ylmethyl)-amino]-propoxy]-3-methyl-benzofuran-2-carboxylic acid ethyl ester
92. 4-(2-hydroxy-3-isopropylamino-propoxy)-3-methyl-benzofuran-2-carboxylic acid cyclohexylamide
93. [4-(2-hydroxy-3-isopropylamino-propoxy)-3-methyl-benzofuran-2-yl]-piperidin-1-yl-methanone
94. 4-(2-hydroxy-3-isopropylamino-propoxy)-3-methyl-benzofuran-2-carboxylic acid ethylamide
95. 4-(2-hydroxy-3-isopropylamino-propoxy)-3-methyl-benzofuran-2-carboxylic acid 2-cyclohexyl-ethyl ester
96. 3-methyl-4-{3-[(pyridin-3-ylmethyl)-amino]-propoxy}-benzofuran-2-carboxylic acid ethyl ester
97. 3-methyl-4-(3-(2-pyridin-3-yl -ethylamino)-propoxy)-benzofuran-2-carboxylic acid ethyl ester
98. 4-(3-benzylamino-propoxy)-3-methyl-benzofuran-2-carboxylic acid ethyl ester 99. 4-(3-(4-dimethylamino-benzylamino)-propoxy)-3-methyl-benzofuran-2-carboxylic acid ethyl ester
100. 4-(3-(1-benzyl-piperidin-4-ylamino)-propoxy)-3-methyl-benzofuran-2-carboxylic acid ethyl ester
101. 4-(3-(indan-1-ylamino)-propoxy)-3-methyl-benzofuran-2-carboxylic acid ethyl ester
102. 4-[3-(1-ethyl-piperidin-4-ylamino)-propoxy]-3-methyl-benzofuran-2-carboxylic acid ethyl ester
103. 3-methyl-4-[3-(1-pyridin-3-ylmethyl-piperidin-4-ylamino)-propoxy]-benzofuran-2-carboxylic acid ethyl ester
104. 4-(4-tert-butylamino-butoxy)-3-methyl-benzofuran-2-carboxylic acid ethyl ester
105. 4-(5-tert(-butylamino-pentyloxy)-3-methyl-benzofuran-2-carboxylic acid ethyl ester
106-1. 3-methyl-4-[1-methyl-3-[(pyridin-3-ylmethyl)-amino]-propoxy]-benzofuran-2-carboxylic acid ethyl ester
106-2. 3-methyl-4-[3-[(pyridin-3-ylmethyl)-amino]-butoxy]-benzofuran-2-carboxylic acid ethyl ester
107. 4-(2-tert-butylamino-ethoxy)-3-methyl-benzofuran-2-carboxylic acid ethyl ester
108. 3-methyl-4-(1-pyridin-3-ylmethyl-piperidin-4-yloxy)-benzofuran-2-carboxylic acid ethyl ester
109. 3-methyl-4-[3-(1-pyridin-3-yl-ethylamino)-propoxy]-benzofuran-2-carboxylic acid ethyl ester
110. 4-(3-guanidino-propoxy)-3-methyl-benzofuran-2-carboxylic acid ethyl ester hydrochloride
111. 3-methyl-4-(1-pyridin-3-ylmethyl-piperidin-3-ylmethoxy)-benzofuran-2-carboxylic acid ethyl ester
112. 4-[3-(1-benzyl-piperidin-4-ylamino)-propoxy]-3-methyl-benzofuran-2-carboxylic acid phenethyl-amide
113. 5-bromo-4-(3-tert-butylamino-propoxy)-3-methyl-benzofuran-2-carboxylic acid ethyl ester
114. 3-methyl-4-{3-[(pyridin-3-ylmethyl)-amino]-propoxy}-benzofuran-2-carbothioic acid (2,4-difluoro-phenyl)-amide
115. (5-methyl-isoxazol-3-yl)-{3-methyl-4-[3-(methyl-pyridin-3-ylmethyl-amino)-propoxy]-benzofuran-2-ylmethyl}-amine
116. (E)-[3-(3-methyl-2-styryl-benzofuran-4-yloxy)-propyl]-pyridin-3-ylmethyl-amine
117. [3-(3-methyl-2-phenethyl-benzofuran-4-yloxy)-propyl]-pyridin-3-ylmethyl-amine
118. 1-(3-methyl-4-{3-[(pyridin-3-ylmethyl)-amino]-propoxy}-benzofuran-2-yl)-butan-1-one
119. (3-{2-[3-(3-fluoro-phenoxy)-propyl]-3-methyl-benzofuran-4-yloxy}-propyl)-pyridin-3-ylmethyl-amine
120. (3-{2-[3-(3-fluoro-benzyloxy)-propyl]-3-methyl-benzofuran-4-yloxy}-propyl)-pyridin-3-ylmethyl-amine
121. {3-[2-(4-fluoro-phenylsulfanylmethyl)-3-methyl-benzofuran-4-yloxy]-propyl}-pyridin-3-ylmethyl-amine
122-1. {3-[2-(4-fluoro-benzenesulfinylmethyl)-3-methyl-benzofuran-4-yloxy]-propyl}-pyridin-3-ylmethyl-amine
122-2. {3-[2-(4-fluoro-benzenesulfonylmethyl)-3-methyl-benzofuran-4-yloxy]-propyl}-pyridin-3-ylmethyl-amine
123. 3-methyl-4-[3-(methyl-pyridin-3-ylmethyl-amino)-propoxy]-benzofuran-2-carbaldehyde O-ethyl-oxime
124. {3-methyl-4-[3-(methyl-pyridin-3-ylmethyl-amino)-propoxy]-benzofuran-2-ylmethylene}-morpholin-4-yl-amine
125. {3-methyl-4-[3-(methyl-pyridin-3-ylmethyl-amino)-propoxy]-benzofuran-2-ylmethylene}-(4-methyl-piperazin-1-yl)-amine
126. 5-fluoro-3-methyl-4-{3-[(pyridin-3-ylmethyl)-amino]-propoxy}-benzofuran-2-carboxylic acid ethyl ester
127. 7-fluoro-3-methyl-4-{3-[(pyridin-3-ylmethyl)-amino]-propoxy}-benzofuran-2-carboxylic acid ethyl ester
128. (3-methyl-4-{3-[(pyridin-3-ylmethyl)-amino]-propoxy}-benzofuran-2-yl-pyridin-2-yl-methanone
129. (5,6-difluoro-1-methyl-1H-benzoimidazol-2-yl)-(3-methyl-4-{3-[(pyridin-3-ylmethyl)-amino]-propoxy}-benzofuran-2-yl)-methanone
130. (3-methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone
131. (3-methyl-4-{3-[(pyridin-3-ylmethyl)-amino]-propoxy}-benzofuran-2-yl)-[1-(2-pyridin-2-yl-ethyl)-1H-benzoimidazol-2-yl]-methanone
132. (4,5-dimethyl-thiazol-2-yl)-(3-methyl-4-{3-[(pyridin-3-ylmethyl)-amino]-propoxy}-benzofuran-2-yl)-methanone
133-1. (4,5-dimethyl-thiazol-2-yl)-(3-methyl-4-{3-[(pyridin-3-ylmethyl)-amino]-propoxy}-benzofuran-2-yl)-methanone oxime
133-2. (4,5-dimethyl-thiazol-2-yl)-(3-methyl-4-{3-[(pyridin-3-ylmethyl)-amino]-propoxy}-benzofuran-2-yl)-methanone oxime
134 (4,5-dimethyl-thiazol-2-yl)-(3-methyl-4-{3-[(pyridin-3-ylmethyl)-amino]-propoxy}-benzofuran-2-yl)-methanone O-ethyl-oxime
135. (4,5-dimethyl-thiazol-2-yl)-(3-methyl-4-{3-[(pyridin-3-ylmethyl)-amino]-propoxy}-benzofuran-2-yl)-methanone O-(4-nitro-benzyl)-oxime
136. (4,5-dimethyl-thiazol-2-yl)-(3-methyl-4-{3-[(pyridin-3-ylmethyl)-amino]-propoxy}-benzofuran-2-yl)-methanone O-phenyl-oxime
137. (4,5-dimethyl-thiazol-2-yl)-(3-methyl-4-{3-[(pyridin-3-ylmethyl)-amino]-propoxy}-benzofuran-2-yl)-methanone O-allyl-oxime
138. {3-[2-(2-methoxy-phenyl)-3-methyl-benzofuran-4-yloxy]-propyl}-pyridin-3-ylmethyl-amine
139-1. 3-methyl-4-{3-[(pyridin-3-ylmethyl)-amino]-propoxy}-benzofuran-2-carboxylic acid N'-(4-fluoro-phenyl)-hydrazide
139-2. 3-methyl-4-{3-[(pyridin-3-ylmethyl)-amino]-propoxy}-benzofuran-2-carboxylic acid N-(4-fluoro-phenyl)-hydrazide
140. 3-methyl-4-{3-[(pyridin-3-ylmethyl)-amino]-propoxy}-benzofuran-2-carboxylic acid N'-(3-nitro-phenyl)-hydrazide
141. isonicotinic acid N'-(3-methyl-4-{3-[(pyridin-3-ylmethyl)-amino]-propoxy}-benzofuran-2-carbonyl)-hydrazide Further preferred bicyclic compounds in accordance with the present invention are as follows:

(5,6-difluoro-1-methyl-1H-benzoimidazol-2-yl)-(3-methyl-4-{3-[(pyridin-3-ylmethyl)-amino]-propoxy}-benzofuran-2-yl)-methanone, (3-methyl-4-{3-[(pyridin-3-ylmethyl)-amino]-propoxy}-benzofuran-2-yl)-[1-(2-pyridin-2-yl-ethyl)-1H-benzoimidazol-2-yl]-methanone, and (3-methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone.

In summary, bicyclic compounds of the formula [I] of the present invention can be produced by either one or more of the following methods:

A process for producing bicyclic compounds of the formula [IV],

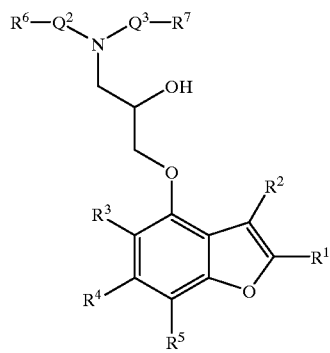

[IV]

wherein $R^1$, $R^2$, $R^3$, $R^4$, $R^5$, $R^6$, $R^7$, $Q^2$ and $Q^3$ are the same as defined above, may comprise alkylating a compound of the formula [V],

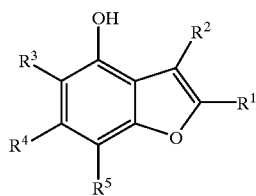

[V]

wherein $R^1$, $R^2$, $R^3$, $R^4$ and $R^5$ are the same as defined above, with an alkylating agent of the formula [VI]

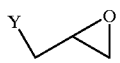

[VI]

wherein Y is chloro, bromo, iodo, tosyloxy or mesyloxy, and aminating the resulting compound of the formula [VII],

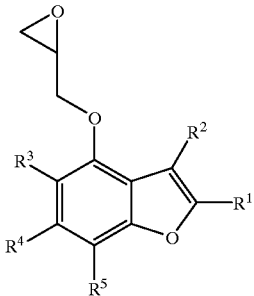

[VII]

wherein $R^1$, $R^2$, $R^3$, $R^4$ and $R^5$ are the same as defined above, with an aminating agent of the formula [VIII],

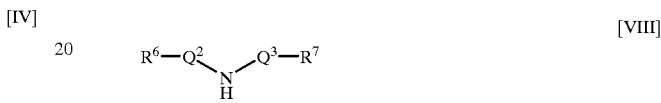

[VIII]

wherein $R^6$, $R^7$, $Q^2$ and $Q^3$ are the same as defined above.

A further embodiment of the present invention comprises a process for producing bicyclic compounds of the formula [I] as defined above which comprises alkylating a compound of the formula [V],

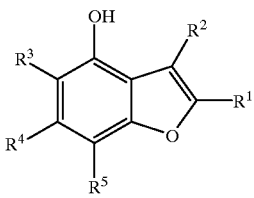

[V]

wherein $R^1$, $R^2$, $R^3$, $R^4$ and $R^5$ are the same as defined above, with a dihalogenated alkane, and aminating the resulting compound of the formula [IX],

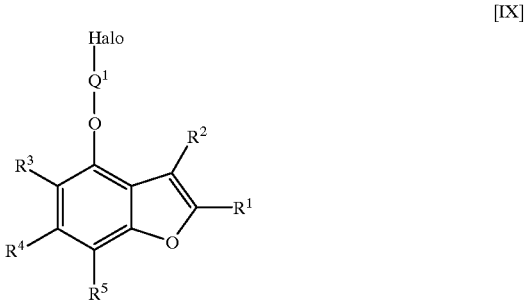

[IX]

wherein Halo is halogen, and $R^1$, $R^2$, $R^3$, $R^4$, $R^5$ and $Q^1$ are the same as defined above,
with an aminating agent of the formula [VIII]

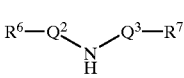

[VIII]

wherein $R^6$, $R^7$ $Q^2$ and $Q^3$ are the same as defined above. A further process of the present invention comprises a process for producing bicyclic compounds of the formula [I] as defined above which comprises alkylating a compound of the formula [V],

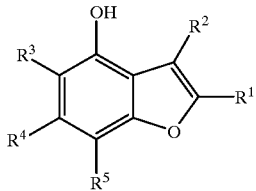

[V]

wherein $R^1$, $R^2$, $R^3$, $R^4$, and $R^5$ are the same as defined in claim 1, with an alkylating agent of the formula [X],

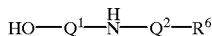

[X]

wherein $Q^1$, $Q^2$ and $R^6$ are the same as defined above, and alkylating the resulting compound of the formula [XI]

[XI]

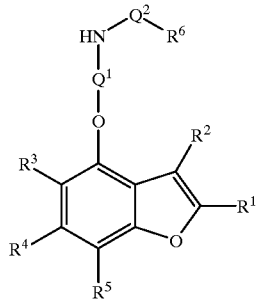

wherein $R^1$, $R^2$, $R^3$, $R^4$, $R^5$, $R^6$ and $Q^1$ are the same as above, with an alkylating agent of formula [XII],

[XII]

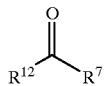

wherein $R^{12}$ is hydrogen or lower alkyl, and $R^7$ is the same as defined above, or with an alkylating agent [XIII]

Halo-$R^{92}$ [XIII]

wherein Halo is halogen and $R^{92}$ is unsubstituted or substituted lower alkyl, aralkyl, cycloalkyl or cycloalkylalkyl.

In more detail, the compound of the present invention may be prepared as follows:

Process 1

Compounds of the following formula [II] (in which $R^{11}$ is hydrogen, unsubstituted lower alkyl, aralkyl, cycloalkyl or cycloalkylalkyl) and of the formula [III] (in which $R^{11}$ is hydrogen, unsubstituted lower alkyl, aralkyl, cycloalkyl or cycloalkylalkyl, and one of $R^3$, $R^4$ and $R^5$ is halogen) can be the starting materials for the synthesis of compounds of the formula [I] defined as above.

Compounds of the formula [II] (in which $R^{11}$ is hydrogen) can be prepared by the method reported by S. Yamaguchi et al., Bull. Chem. Soc. Jpn., Vol. 62, 4066–4068 (1989). Compounds of the formula [II] (in which $R^{11}$ is hydrogen, unsubstituted lower alkyl, aralkyl, cycloalkyl or cycloalkylalkyl) and of the formula [III] (in which $R^{11}$ is hydrogen, unsubstituted lower alkyl, aralkyl, cycloalkyl or cycloalkylalkyl, and one of $R^3$, $R^4$ and $R^5$ is halogen) can be prepared according to the following Flow Chart 1:

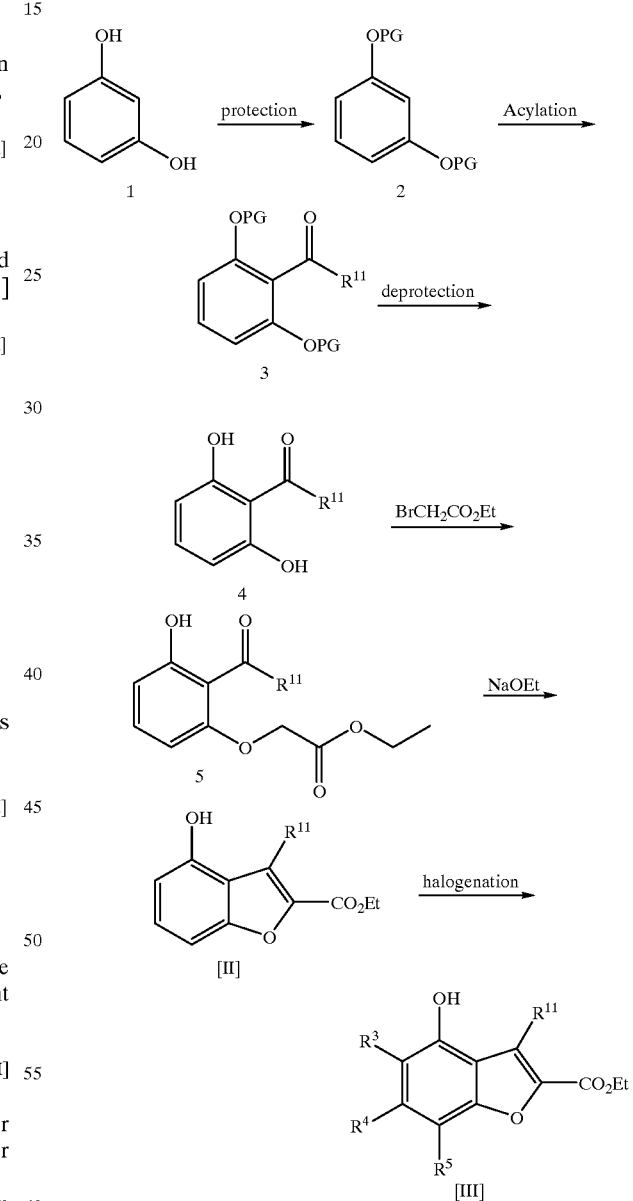

Flow Chart 1

PG in Flow Chart 1 means a protective group such as methoxymethyl.

Compound of the formula [II] (in which $R^{11}$ is hydrogen, unsubstituted lower alkyl, aralkyl, cycloalkyl or cycloalkylalkyl) can be prepared from compound 4 by practically the same method as described in EP 0146243 (J.

G. Atkinson et al.,). When $R^{11}$ is methyl, compound 4 is commercially available (e.g. Wako Pure Chemical Industries, Ltd.). When $R^{11}$ is not hydrogen or methyl, compound 4 can be prepared from resorcinol 1 via compounds 2 and 3. Resorcinol 1 is commercially available (e.g. Wako Pure Chemical Industries, Ltd.). For example, compound 1 is converted into compound 2 by treating compound 1 with a base such as NaH and then methoxymethyl chloride in an inert solvent such as N,N-dimethylformamide. Compound 2 is acylated by a similar method to the literature (V. Snieckus et al, Chem. Rev. Vol. 90, pp. 879–933 (1990)). Compound 2 is then treated with a base such as butyl lithium and then the obtained anion is treated with various acyl halides to give compound 3. The treatment of compound 3 with an acid such as hydrochloric acid gives compound 4.

Compound of the formula [II] (in which $R^{11}$ is hydrogen, unsubstituted lower alkyl, aralkyl, cycloalkyl or cycloalkylalkyl) can be converted into compound of the formula [III] (in which $R^{11}$ is hydrogen, unsubstituted lower alkyl, aralkyl, cycloalkyl or cycloalkylalkyl, and one of $R^3$, $R^4$ and $R^5$ is halogen) by known methods per se. For example, when bromine is used as a reagent (J. G. Atkinson et al., EP 0146243), bromination occurs at position 5 to give compound of the formula [III] (in which $R^{11}$ is hydrogen, unsubstituted lower alkyl, aralkyl, cycloalkyl or cycloalkylalkyl, $R^3$ is bromo, and $R^4$ and $R^5$ are hydrogen). When N-fluoro-2,5-dichloropyridinium tetrafluoroborate is used as a reagent (T. Umemoto et al, J. Org. Chem. Rev. Vol. 60, pp. 6563–6570 (1995)), fluorination occurs at position 5 or position 7 to give compound of the formula [III] (in which $R^{11}$ is hydrogen, unsubstituted lower alkyl, aralkyl, cycloalkyl or cycloalkylalkyl, $R^3$ is fluoro, and $R^4$ and $R^5$ are hydrogen) and compound of the formula [III] (in which $R^{11}$ is hydrogen, unsubstituted lower alkyl, aralkyl, cycloalkyl or cycloalkylalkyl, $R^5$ is fluoro, and $R^3$ and $R^4$ are hydrogen).

Process 2

Compounds of the formula [I] (in which $R^2$ is unsubstituted or substituted lower alkyl such as ethyl, propyl, butyl, $CH_2OH$, $CH_2OEt$ or $CH_2NH_2$) can be prepared according to the following Flow Chart 2:

Flow Chart 2

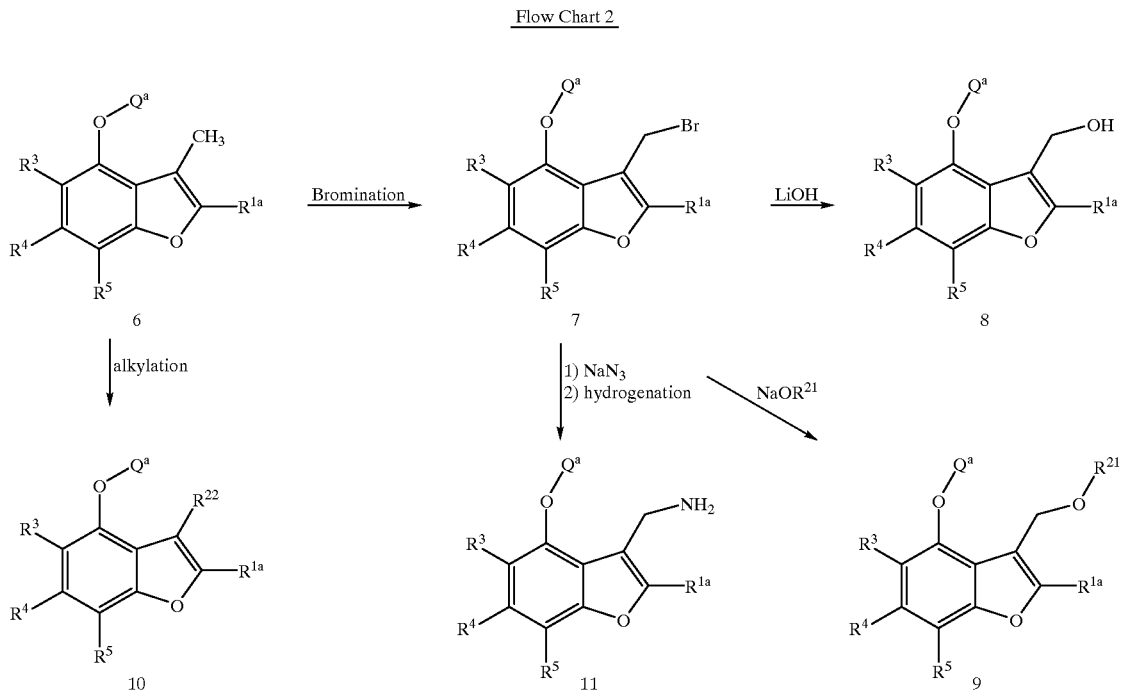

$Q^a$ in Flow Chart 2 is

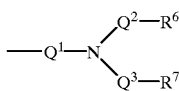

as defined above or a radical that can be converted into

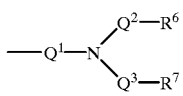

by known methods per se or one of the methods selected from Flow Chart 7, Flow Chart 8 and Flow Chart 9 hereinafter. $R^{1a}$ is the same as $R^1$ defined above or a radical that can be converted into $R^1$ by known methods per se or one of the methods selected from Flow Chart 3, Flow Chart 4, Flow Chart 5, Flow Chart 6 and Flow Chart 10 hereinafter. $R^{21}$ is unsubstituted lower alkyl, aralkyl, cycloalkyl or cycloalkylalkyl. $R^{22}$ is unsubstituted lower alkyl, aralkyl, cycloalkyl or cycloalkylalkyl. $Q^1$, $Q^2$, $Q^3$, $R^3$, $R^4$, $R^5$, $R^6$ and $R^7$, are the same as defined above.

Alkylation of compound 6 to obtain compound 10 can be carried out as follows:
1) Compound 6 is treated with a base such as lithium diisopropylamide in an inert solvent such as tetrahydrofuran,
2) and then the obtained anion is treated with lower alkyl halide such as methyl iodide, ethyl bromide and n-propyl bromide.

Bromination of compound 6 to obtain compound 7 can be carried out by reacting compound 6 with N-bromosuccinimide in an inert solvent such as carbon tetrachloride. Compound 7 is converted into an azide derivative by the reaction with sodium azide in an inert solvent such as N,N-dimethylformamide. Hydrogenolysis of the azide gives amine 11. Hydrogenolysis can be carried out under standard conditions known in the art, for example Pd on carbon is used as a catalyst.

Hydrolysis and alcoholysis of compound 7 gave hydroxy derivative 8 and alkoxy derivative 9, respectively.

$R^1$ in the formula [I] can be modified by one of the methods described in the following Flow Chart 3, Flow Chart 4, Flow Chart 5, Flow Chart 6 and Flow Chart 10 hereinafter.

Process 3

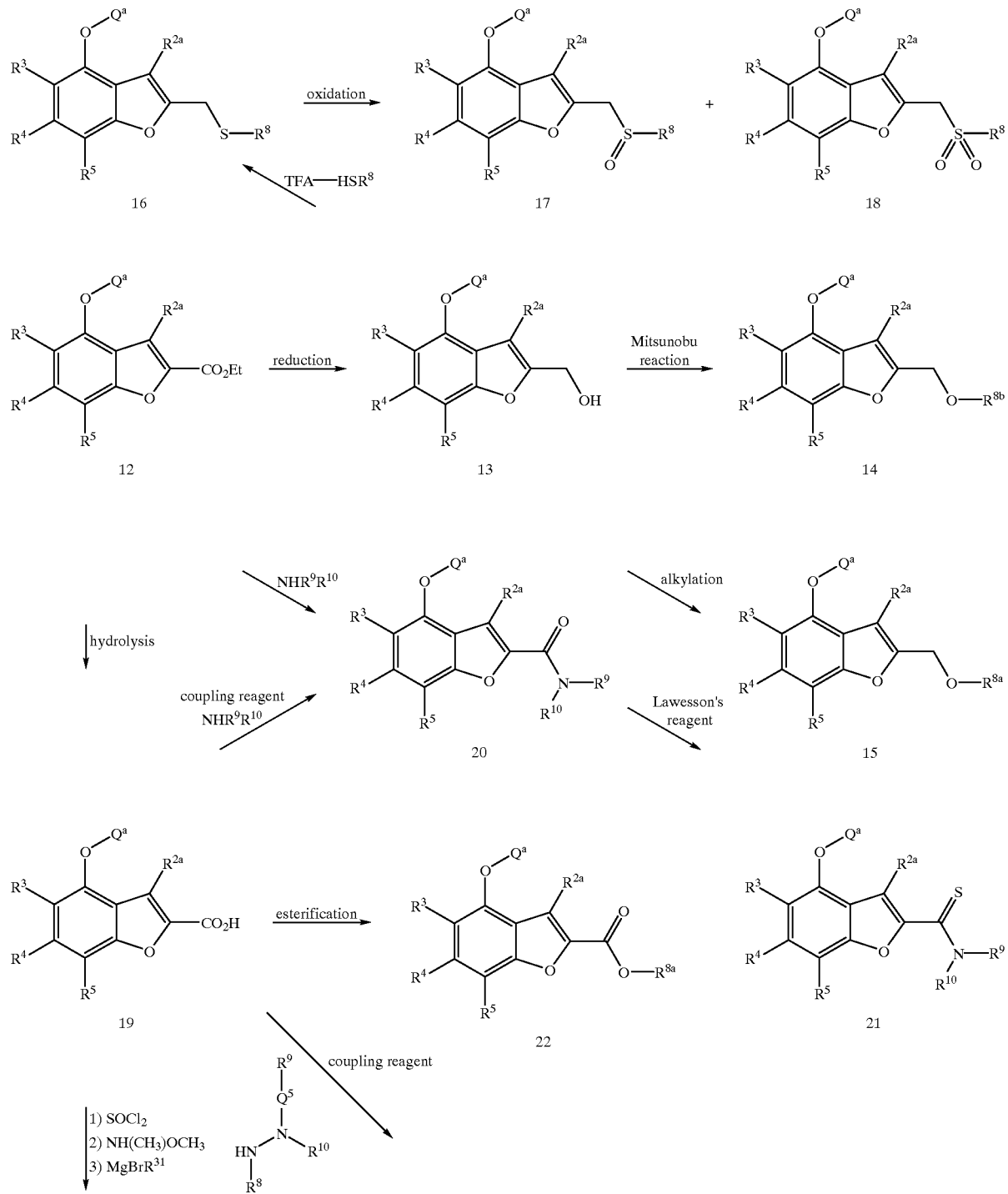

Flow Chart 3

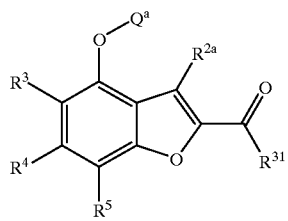
23

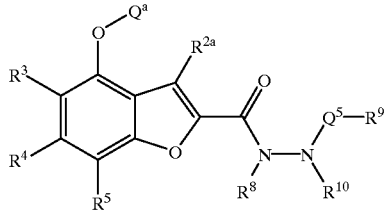
56a

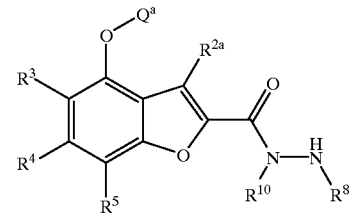
56b

In Flow Chart 3, $Q^a$ is

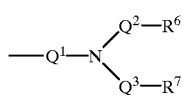

or a radical which can be converted into

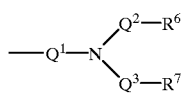

by known methods per se or by one of the methods described in Flow Chart 7, Flow Chart 8 and Flow Chart 9 hereinafter. $R^{2a}$ is $R^2$ or a radical which can be converted into $R^2$ by known methods per se or by one of the methods described in Flow Chart 2.

$R^{8a}$ is unsubstituted or substituted lower alkyl, aralkyl, cycloalkyl, cycloalkylalkyl. $R^{8b}$ is unsubstituted or substituted aromatic ring, or lower alkyl substituted by fluorine atoms such as 2,2,2-trifluoroethyl. $R^{31}$ is lower alkyl, aralkyl, cycloalkyl, cycloalkylalkyl or an aromatic ring which can be further substituted by fluoro, chloro, lower alkyl and lower alkoxy. TFA is trifluoroacetic acid. $Q^1$, $Q^2$, $Q^3$, $Q^5$, $R^3$, $R^4$, $R^5$, $R^6$, $R^7$, $R^8$, $R^9$ and $R^{10}$ are the same as defined above.

Compound 12 is reduced by a known reducing agent such as lithium aluminium hydride to give an alcohol derivative 13. Various amide derivatives can be prepared by the standard methods per se. For example, compound 12 is directly aminated to give amide 20 by heating the compound 12 together with an appropriate amine, $NHR^9R^{10}$. Amide 20 can also be prepared by the coupling of acid 19, which is obtained from ester 12 by alkaline hydrolysis, with desired amine $NHR^9R^{10}$. Various coupling reagents such as thionyl chloride and water soluble carbodiimide can be used for the coupling (for example, refer to E. Gross el al. "The peptides", Academic Press, 1979). Amide 20 can be converted into thioamide 21 by Lawesson's reagent (M. P. Cava et al. Vol. 41, PP.5061–5087, 1985). The compound 13 is further converted into ether 15 by the reaction with 1) a base such as NaH and 2) halogen-$R^{8a}$ (in which $R^{8a}$ is unsubstituted or substituted lower alkyl, aralkyl, cycloalkyl, cycloalkylalkyl) in an inert solvent such as tetrahydrofuran. Compound 13 is also converted into ether derivative 14 (wherein $R^{8b}$ is unsubstituted or substituted aromatic ring, or lower alkyl substituted by fluorine atoms such as 2,2,2-trifluoroethyl) by Mitsunobu reaction (for example, O. Mitsunobu, Synthesis PP. 1–28, 1981 and J. R. Falck et al., Tetrahedron Letters, Vol. 35, PP. 5997–6000, 1994) in an inert solvent such as tetrahydrofuran and benzene. Various phosphines such as trimethylphosphine, tributylphosphine and triphenylphosphine and various azodicarbonyl compounds such as azodicarboxylic acid diethyl ester, 1,1'-(azodicarbonyl)dipiperidine and 1,1'-azobis(N,N-dimethylformamide) can be used for Mitsunobu reaction. Compound 13 is also converted into thioether derivative 16 by the treatment of compound 13 with desired thiol, $HSR^8$, in the presence of acid such as trifluoroacetic acid. Thioether 16 is oxidised to give sulfoxide 17 by bis(2,4-pentanedionato)vanadium oxide or per acid such as m-chloroperbenzoic acid. Sulfone 18 can be obtained by oxidising thioether 16 with bis(2,4-pentanedionato) vanadium oxide (C. Bolm et al., Angew. Chem., Int. Ed. Engl. Vol. 34, PP. 2640–2642, 1995). Esterification of compound 19 to compound 22 can be carried out by the treatment of compound 19 with a base such as potassium carbonate and alkyl halide, $R^{8a}$-halogen, or the condensation of compound 19 and alcohol, $R^{8a}OH$, in the presence of a coupling reagent such as water-soluble carbodiimide. Compound 19 can be converted into ketone 23 by practically the same method as that reported by S. Nahm and S. M. Weinreb (Tetrahedron Letters, Vol. 22, PP 3815–3813, 1981). Hydrazides 56a and 56b are prepared from acid 19 by the reaction with hydrazine or hydrazide,

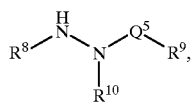

in the presence of a coupling reagent such as water soluble carbodiimide. When $Q^5$ is a single bond and $R^9$ is hydrogen, both 56a and 56b can be prepared by this method. When $Q^5$ is carbonyl, only 56a is prepared by the method. When neither $Q^5$—$R^9$ nor $R^{10}$ is hydrogen, only 56a is prepared by the method.

Process 4

Flow Chart 4

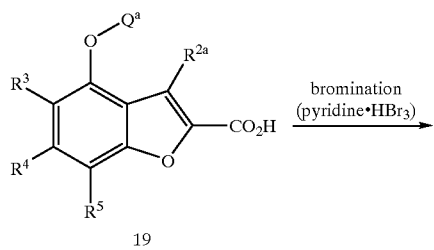
19

-continued

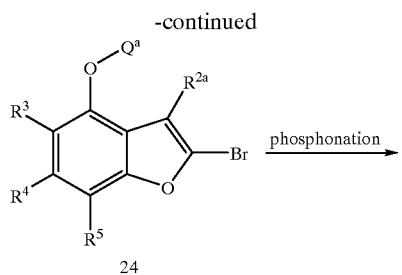

phosphonation

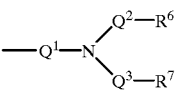

In Flow Chart 4, $Q^2$ is

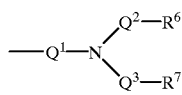

or a radical which can be converted into

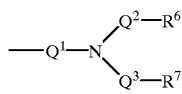

by known methods per se or by one of the methods described in Flow Chart 7, Flow Chart 8 and Flow Chart 9 hereinafter. $R^{2a}$ is $R^2$ or a radical which can be converted into $R^2$ by known methods per se or by one of the methods described in Flow Chart 2.

$Q^1$, $Q^2$, $Q^3$, $R^3$, $R^4$, $R^5$, $R^6$, $R^7$, $R^8$ and $R^9$ are the same as defined above.

Compound 19 can be converted into compound 24 by the reaction with a bromination reagent such as pyridinium tribromide (O. H. Hankovszky et al., Synthesis, P91, 1991). The obtained bromide 24 is phosphonated by the reaction with trialkylphosphite in the presence of palladium catalyst such as tetrakis(triphenylphosphine)palladium and with tertiary amine such as triethylamine in an inert solvent such as toluene to give compound 25.

Process 5

Introduction of heterocyclic ring at position 2 of the benzofuran ring can be carried out by various methods. For example, oxazole, dihydrooxasole and thiazole can be introduced by the methods described in Flow Chart 5.

In Flow Chart 5, $Q^a$ is or a radical which can be converted into by known methods per se or by one of the methods described in Flow Chart 7, Flow Chart 8 and Flow Chart 9 hereinafter. $R^{2a}$ is $R^2$ or a radical which can be converted into $R^2$ by known methods per se or by one of the methods described in Flow Chart 2.

T is O or S. $R^{51}$ is lower alkyl. $R^{52}$ and $R^{53}$ are independently hydrogen, unsubstituted or substituted lower alkyl, aralkyl, cycloalkyl, cycloalkylalkyl or aromatic ring; in which $R^{52}$ and $R^{53}$ may form aliphatic ring which may contain further heteroatom(s) together with the adjacent nitrogen. $R^{54}$ means unsubstituted or substituted lower alkyl, aralkyl, cycloalkyl, cycloalkylalkyl or aromatic ring. $Q^1$, $Q^2$, $Q^3$, $R^3$, $R^4$, $R^5$, $R^6$ and $R^7$ are the same as defined above.

Flow Chart 5

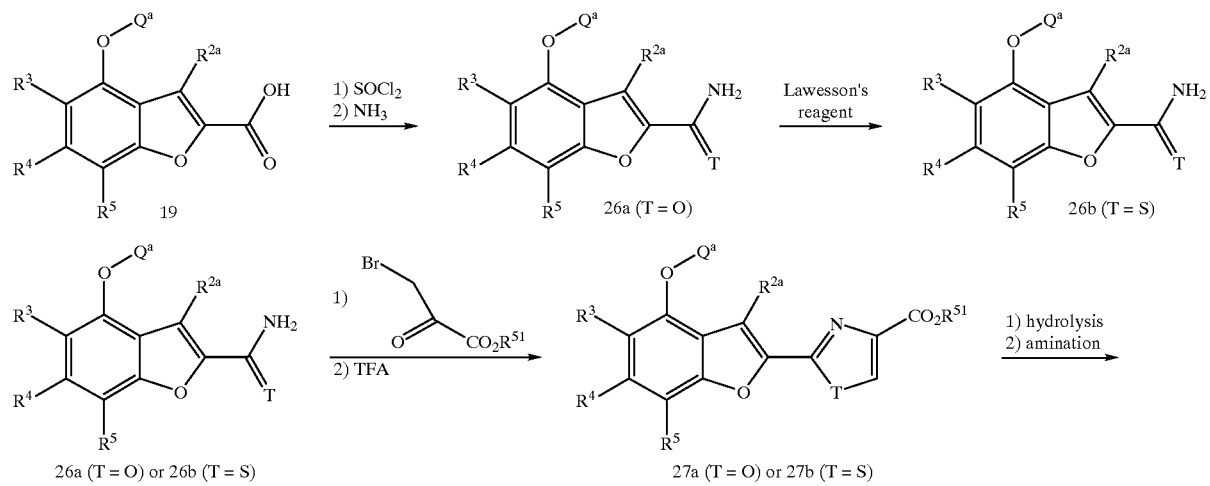

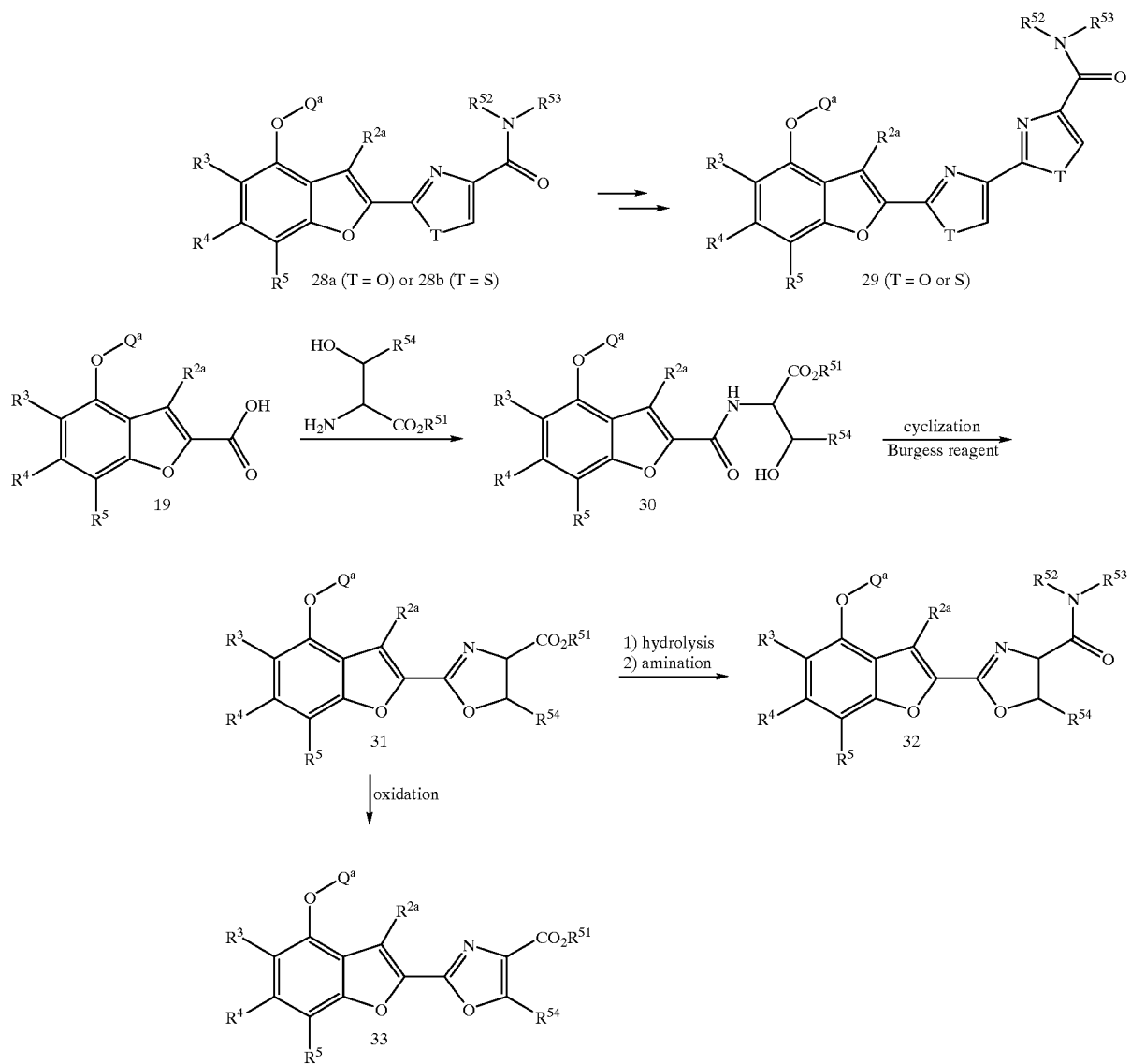

Amide 26a is obtained from carboxylic acid 19 by treating 19 with thionyl chloride and ammonia, and then amide 26a is converted into thioamide 26b by using Lawesson's reagent (M. P. Cava and M. I. Levinson, Tetrahedron Vol. 41, PP.5061–5087, 1985). Oxazole derivative 27a (T=O) and thiazole derivative 27b (T=S) are obtained from amide 26a and thioamide 26b (T=S), respectively, by the method reported by J. S. Panek el al. (J. Org. Chem., Vol. 61, PP. 6496–6497, 1996). Esters 27a and 27b can be converted into amide 28a and 28b, respectively, as follows: 1) Base catalyzed hydrolysis of each of 27a and 27b and 2) coupling of the resulted acid and an appropriate amine, $HNR^{52}R^{53}$, in the presence of a coupling agents such as 2-(1H-benzotriazole-1-yl)-1,1,3,3-tetramethyluronium hexafluorophosphate (HBTU) (E. Atherton et al. 'Solid phase peptide synthesis—a practical approach', IRL Press, P 85, 1989). When $R^{52}$ and $R^{53}$ are hydrogen, compound 28a and 28b can be converted into compounds 29 by repeating practically the same procedures as the procedures from compound 26a or 26b to compound 28a or 28b.

Carboxylic acid 19 can be aminated to give amide derivative 30 by known method per se. Cyclization from compound 30 to compound 31 is carried out according to the reported procedures (G. Li et al., J. Org. Chem. Vol. 61, pp.778–780, 1996). Compound 31 can be further modified to amide derivative 32 by the standard methods known in the art per se and also it can be oxidized to give oxazole derivative 33 by treating compound 31 with an oxidizing reagent such as $NiO_2$ (D. L. Evans et al., J. Org. Chem., Vol. 44, PP. 497–501, 1979).

Process 6

$R^1$ can also be modified according to Flow Chart 6.

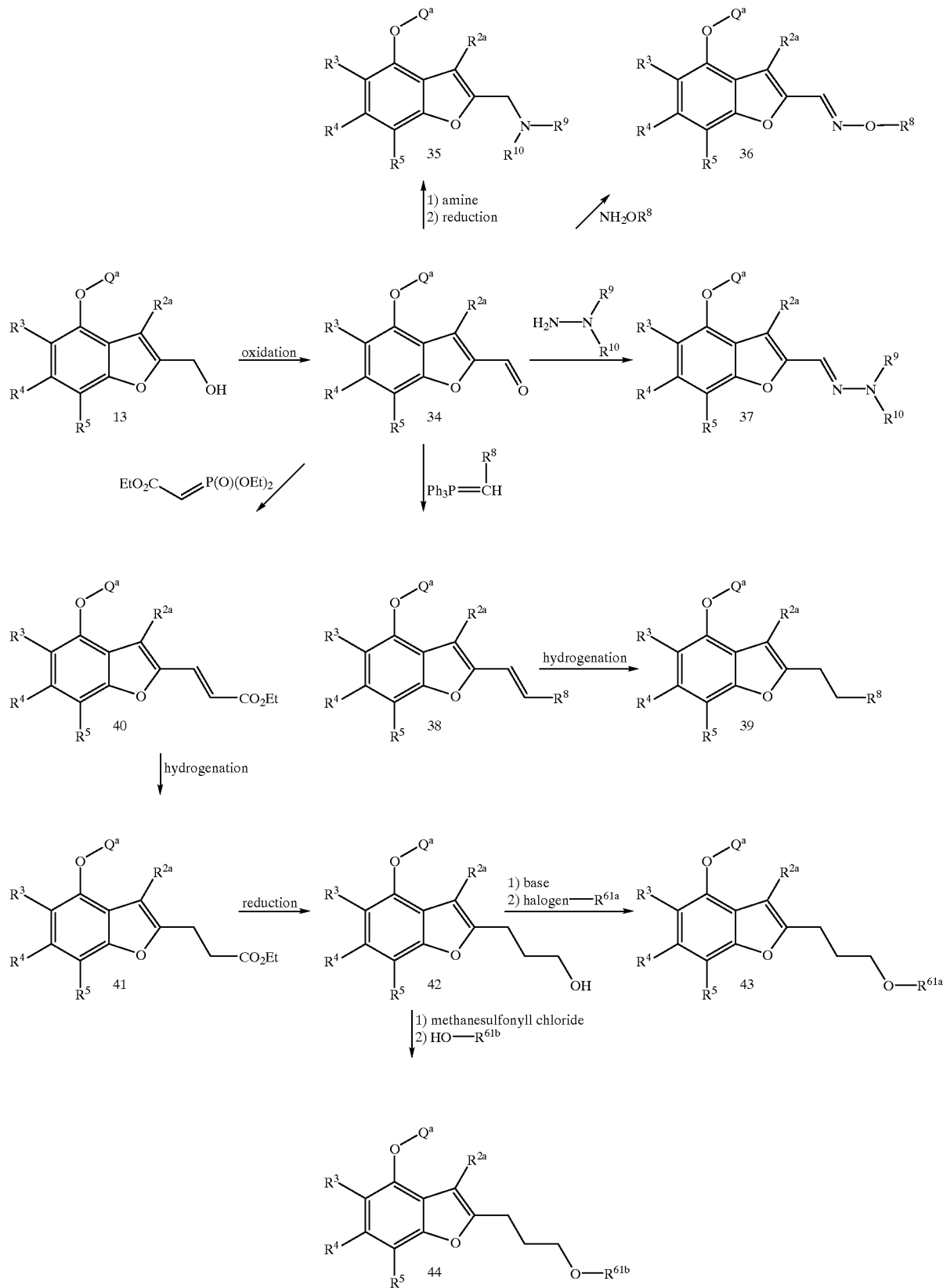
Flow Chart 6

In Flow Chart 6, $Q^a$ is

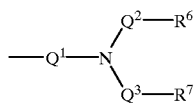

or a radical which can be converted into

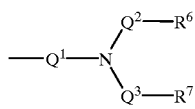

by known methods per se or by one of the methods described in Flow Chart 7, Flow Chart 8 and Flow Chart 9 hereinafter. $R^{2a}$ is $R^2$ or a radical which can be converted into $R^2$ by known methods per se or by one of the methods described in Flow Chart 2. $R^{61a}$ means unsubstituted or substituted lower alkyl, lower alkyl substituted by an unsubstituted or substituted aromatic ring, cycloalkyl or cycloalkylalkyl. $R^{16}b$ means an unsubstituted or substituted aromatic ring. $Q^1$, $Q^2$, $Q^3$, $R^3$, $R^4$, $R^5$, $R^6$, $R^7$, $R^8$, $R^9$ and $R^{10}$ are the same as defined above.

Aldehyde 34 can be obtained from compound 13 by the reaction using an oxidizing agent such as manganese dioxide. Aldehyde 34 can be the starting material for compounds 35, 36, 37, 38, 39, 40, 41, 42, 43 and 44. Amine 35 can be prepared by the reaction of compound 34 with an amine followed by reduction with a reducing agent such as sodium borohydride and sodium cyanoborohydride. Compounds 36 and 37 can be prepared by the reaction of compound 34 and a hydroxylamine derivative ($NH_2OR^8$) and a hydrazine derivative ($NH_2NR^9R^{10}$) respectively. Wittig reaction (A. Maercker, Organic Reactions. Vol. 14, PP. 270–490) of compound 34 gives compound 38 and the hydrogenation of compound 38 gives compound 39. Wittig-Honor reaction (J. Boutagy and R. Thomas, Chem. Rev. Vol. 74, PP. 87–99, 1974) of compound 34 gives compound 40. Compound 40 can be converted into compound 41 by hydrogenation over a catalyst such as Palladium on carbon. Compound 41 can be converted into alcohol 42 by reducing compound 41 with a reducing agent such as lithium aluminium hydride. When compound 42 is treated with a base such as sodium hydride and halogen-$R^{61a}$, compound 43 is obtained. When methanesulfonyl derivative of compound 42, which can be obtained by the reaction of compound 42 and methanesulfonyl chloride in the presence of a base such as triethylamine, is treated with HO—$R^{61b}$ in the presence of a base such as cesium carbonate, compound 44 is prepared.

The radical

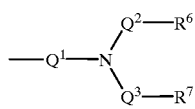

can be modified by one of the methods described in Flow Chart 7 Flow Chart 8 and Flow Chart 9.

Process 7

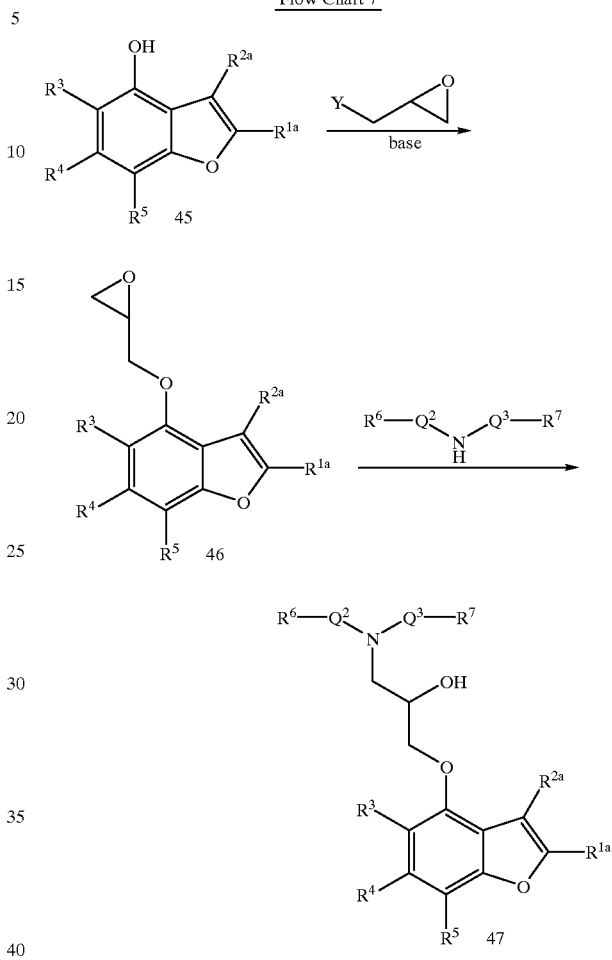

$R^{1a}$ is the same as $R^1$ defined above or a radical which can be converted into $R^1$ by known methods per se or by one of the methods described in Flow Chart 3, Flow Chart 4, Flow Chart 5, Flow Chart 6 and Flow Chart 10. $R^{2a}$ is the same as $R^2$ or a radical which can be converted into $R^2$ by known methods per se or by one of the methods described in Flow Chart 2. Y is chloro, bromo, iodo, tosyloxy or mesyloxy. $Q^2$, $Q^3$, $R^3$, $R^4$, $R^5$, $R^6$ and $R^7$ are the as defined above.

Phenol 45 is reacted with an oxirane compound such as epibromhydrin, epichlorohydrin, glycidyl tosylate and glycidyl mesylate in a solvent such as acetone, 2-butanone, acetonitrile and N,N-dimethylformamide (DMF) in the presence of a base such as sodium hydride, potassium carbonate and cesium carbonate at a temperature between –20° C. and 100° C., preferably at 20° C. to 85° C., to give epoxide 46. The epoxide is reacted with amine, $NH(Q^2R^6)(Q^3R^7)$, in the absence or in the presence of a solvent such as EtOH, DMF and N-methyl-2-pyrrolidone at a temperature between 0° C. and 150° C., preferably at 20° C. to 130° C., to give amino derivative 47.

41
Process 8
Flow Chart 8

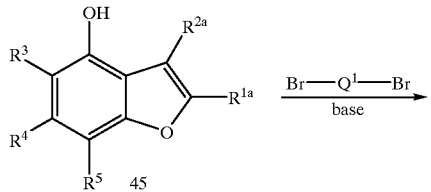

45

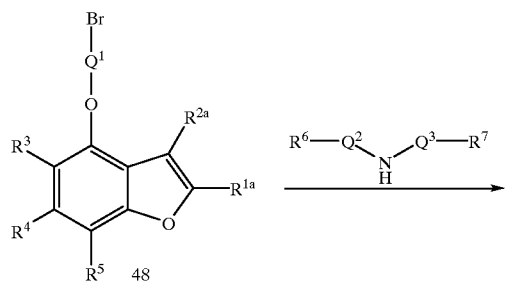

48

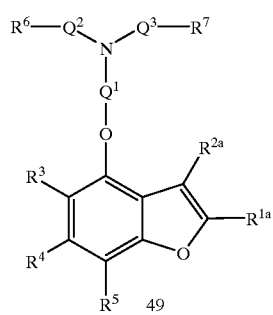

49

$R^{1a}$ is the same as $R^1$ defined above or a radical which can be converted into $R^1$ by known methods per se or by one of the methods described in Flow Chart 3, Flow Chart 4, Flow Chart 5, Flow Chart 6 and Flow Chart 10. $R^{2a}$ is the same as $R^2$ or a radical which can be converted into $R^2$ by known methods per se or by one of the methods described in Flow Chart 2. $Q^1$, $Q^2$, $Q^3$, $R^3$, $R^4$, $R^5$, $R^6$ and $R^7$ are the same as defined above.

Phenol 45 is reacted with Br—$Q^1$—Br in a solvent such as acetone, 2-butanone, acetonitrile and N,N-dimethylformamide (DMF) in the presence of a base such as sodium hydride, potassium carbonate and cesium carbonate at a temperature between –20° C. and 100° C., preferably at 20° C. to 85° C. to give bromide 48. Bromide 48 can be reacted with amine, NH($Q^2R^6$)($Q^3R^7$), in the absence or in the presence of a solvent such as EtOH, DMF and N-methyl-2-pyrrolidone at a temperature between 0° C. and 150° C., preferably at 20° C. to 130° C., to give an amino derivative 49.

42
Process 9
Flow Chart 9

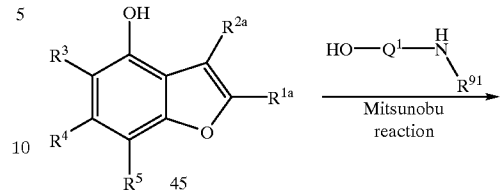

45

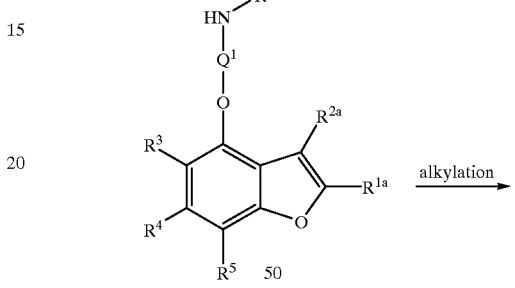

50

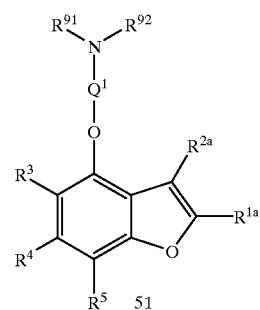

51

$R^{1a}$ is the same as $R^1$ defined above or a radical which can be converted into $R^1$ by known methods per se or by one of the methods described in Flow Chart 3, Flow Chart 4, Flow Chart 5, Flow Chart 6 and Flow Chart 10. $R^{2a}$ is the same as $R^2$ or a radical which can be converted into $R^2$ by known methods per se or by one of the methods described in Flow Chart 2. $R^{91}$ and $R^{92}$ are independently hydrogen, unsubstituted lower alkyl or lower alkyl substituted by unsubstituted or substituted aromatic ring. $Q^1$ $R^3$, $R^4$, $R^5$ are the same as defined above.

Phenol 45 can be alkylated to give amine 50 by Mitsunobu reaction in an inert solvent such as tetrahydrofuran, toluene and benzene at a temperature between –50° C. and 100° C., preferably –40° C. to 80° C. Various phosphines such as trimethylphosphine, tributylphosphine and triphenylphosphine and various azodicarbonyl compounds such as azodicarboxylic acid diethyl ester, 1,1'-(azodicarbonyl) dipiperidine and 1,1'-azobis(N,N-dimethylformamide) can be used for Mitsunobu reaction. Compound 51 can be obtained from amine 50 by reductive alkylation with various aldehydes or ketones or by alkylation with halide, halogen-$R^{92}$ (in which $R^{92}$ is unsubstituted or substituted lower alkyl, aralkyl, cycloalkyl or cycloalkylalkyl). Various reducing-agents such as sodium cyanoborohydride and sodium triacetoxyborohydride can be used for the reductive alkylation. The reductive alkylation can be carried out in a solvent such as methanol, ethanol and tetrahydrofuran at a temperature between −20° C. and 60° C., preferably 0° C. to 30° C. The solvent usually contain acid such as acetic acid and hydrochloric acid. The alkylation with halide, halogen-$R^{92}$ can be carried out in the presence or in the absence of a solvent such as EtOH, DMF and N-methyl-2-pyrrolidone at a temperature between 0° C. and 150° C., preferably at 20° C. to 130° C.

$R^1$ in the formula [I] can also be modified by one of the methods described in Flow Chart 10 hereinafter.

Process 10

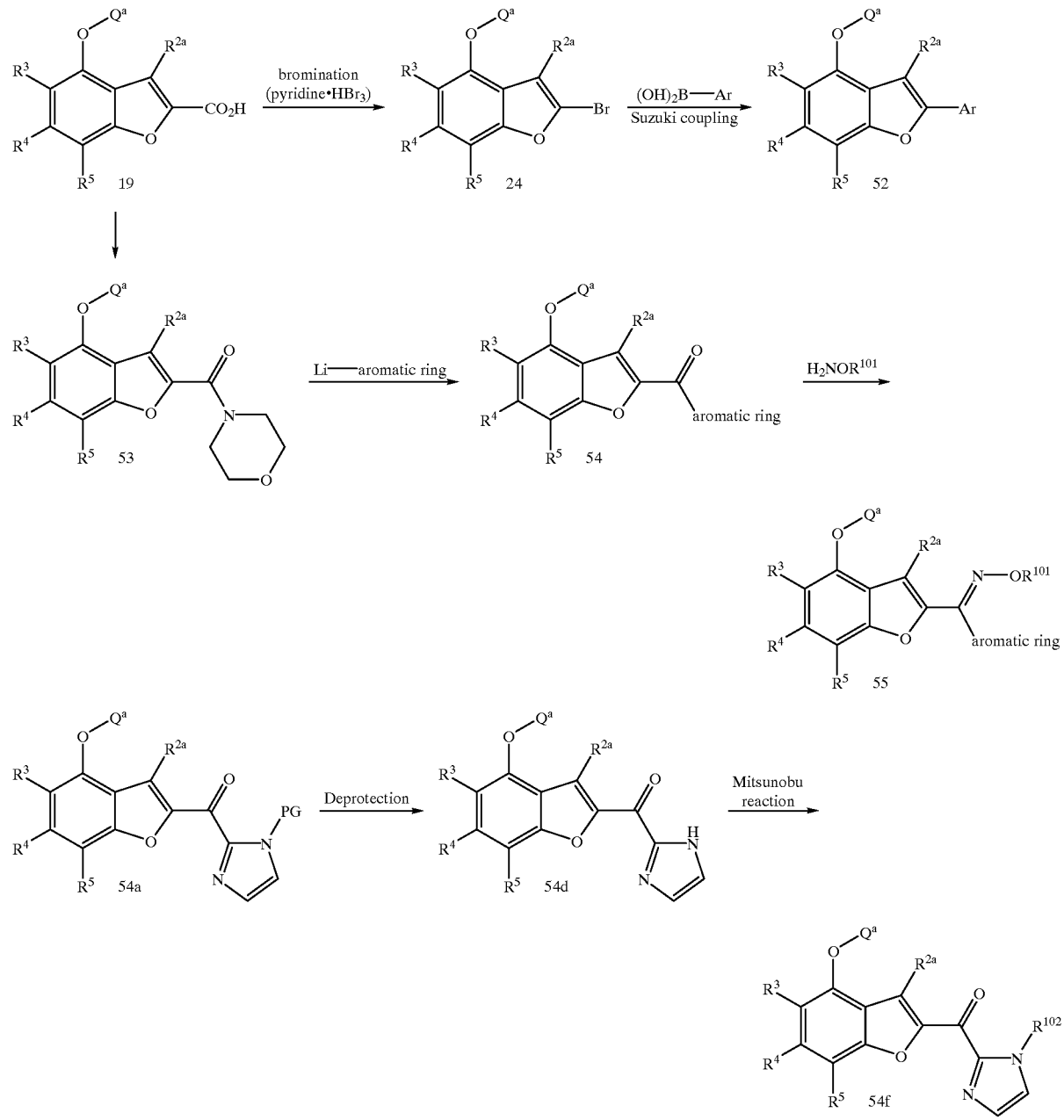

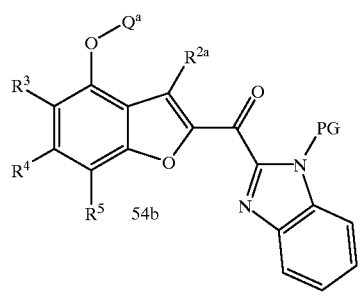
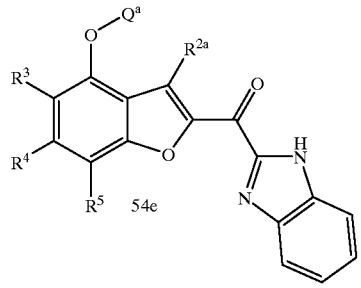
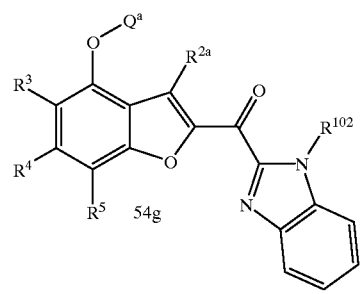

PG in Flow Chart 10 means a protective group such as methoxymethyl.

In Flow Chart 10, $Q^a$ is

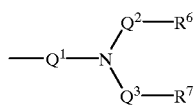

or a radical which can be converted into

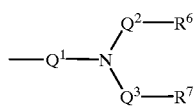

by known methods per se or by one of the methods described in Flow Chart 7, Flow Chart 8 and Flow Chart 9. $R^{2a}$ is $R^2$ or a radical which can be converted into $R^2$ by known methods per se or by one of the methods described in Flow Chart 2.

$Q^1$, $Q^2$, $Q^3$, $R^3$, $R^4$, $R^5$, $R^6$ and $R^7$ are the same as defined above. $R^{101}$ is hydrogen or substitute or unsubstituted lower alkyl, lower alkenyl, aralkyl or aryl. $R^{102}$ is substituted or unsubstituted lower alkyl, lower alkenyl or aralkyl.

Compound 19 can be converted into compound 24 by reaction with a bromination reagent such as pyridinium tribromide (O. H. Hankovszky et al., Synthesis, P91, 1991). Bromide 24 can be coupled with various Ary-boronic acids at elevated temperature in the presence of a base such as sodium tert-butoxide and palladium catalyst such as tetrakis (triphenylphosphine)-palladium in an inert solvent such as N,N-dimethylformamide to give compound 52. Amide 53 can be prepared from acid 19 by reaction with thionyl chloride followed by reaction with morpholine. The morpholine group can be replaced with various aromatic rings by reaction with amide 53 and lithium-aromatic compound in an inert solvent such as ether and tetrahydrofuran to give compound 54. Unsubstituted imidazole, 54d, and benzoimidazole, 54e, can be prepared by the same reaction followed by deprotecting the protective group as shown Flow Chart 10. When the protective group is methoxymethyl, it can be cleaved under acidic conditions. Unsubstituted imidazole, 54d, and benzimidazole, 54e, can further be alkylated by Mitsunobu reaction to give 54f or 54g, respectively. Various phosphines such as trimethylphosphine, tributylphosphine and triphenylphosphine and various azodicarbonyl compounds such as azodicarboxylic acid diethyl ester, 1,1'-(azodicarbonyl) dipiperidine and 1,1'-azobis(N,N-dimethylformamide) can be used for Mitsunobu reaction. Compound 55 can be obtained from ketone 54 by reaction with hydroxylamine hydrochloride or hydroxylamine O-ether hydrochloride in pyridine at a temperature between room temperature and 115° C. This reaction gives a mixture of E and Z oximes.

The manufacture of the pharmaceutically acceptable acid addition salts of the compound of the formula [I] can be carried out by treating a free base of the compound represented by the formula [I] with an acid in a per se conventional procedure for the salt formation. Examples of therapeutically acceptable acids useful in the above process are inorganic acids (e.g. hydrochloric acid, hydrobromic acid, phosphoric acid, nitric acid, sulfuric acid) and organic acids (e. g. oxalic acid, acetic acid, formic acid, trifluoroacetic acid, maleic acid, succinic acid, fumaric acid, tartaric acid, citric acid, salicylic acid, sorbic acid, lactic acid, methanesulfonic acid). Moreover, the compounds of the formula [I] can be converted into hydrates or solvates and their salts by various methods known to those skilled in the art.

The bicyclic compounds of the formula [I] are strong NMT inhibitors. This inhibitory activity indicates that the compounds of the formula [I] and pharmaceutically acceptable salts thereof can be antimycotic agents.

The bicyclic compounds of the formula [I] and pharmaceutically acceptable salts thereof are very active antimycotic agents. They are active against a variety of fungal species including *Candida albicans, Cryptococcus neoformans, Aspergillus fumigatus*, Trichophyton spp., Microsporum spp., Exophiala spp., *Blastomyces dermatitidis*, and *Histoplasma capsulatum*.

Thus, the bicyclic compounds of the present invention are useful for topical and systemic treatment of mycoses in animals as well as in human. Accordingly, the present invention comprises the use of the above compounds for the manufacture of medicaments for the prophylaxis and treatment of mycoses and the corresponding pharmaceutical compositions which comprise a bicyclic compound as defined above and a pharmaceutically acceptable carrier.

For example, they are useful in treating topical and mucous Trichophyton, or Microsporum. They may also be used in the treatment of systemic fungal infections caused by, for example, Candida, Cryptococcus, Aspergillus, Paracoccidiodes, Sporotric, Exophiala, Blastomyces or Histoplasma.

The inhibitory activity of the bicyclic compounds of the present invention can be demonstrated as follows:

Determination of the NMT Inhibitory Activity

*Candida albicans* NMT inhibitory activity was measured using the method reported by David A. Rudnick et al. (J. Biol. Chem. Vol. 267, PP. 23852–23861, 1992).

The inhibitory activity of the compounds of the general formula [I] on Candida NMT ranged from 0.002 $\mu$g/ml to 100 $\mu$g/ml.

Determination of In vitro Antifungal Activity

In vitro antifungal activity of the bicyclic compounds was determined using the *Cryptococcus neoformans* (*Cr. neoformans*) cells (strain MTU13001) according to the broth micro-dilution procedure (National Committee for Clinical Laboratory Standard (1992). Document M27-P). $10^4$ cells in 100 ml of YNBPB medium (YNB (Difco), 1% (w/v) dextrose (Wako), 0.25% $K_2HPO_4$ (Wako)) containing various concentrations of compounds were dispensed in 96-well plates and incubated at 35° C. for 24 hours. The turbidity of the cell suspension was measured using a Microplate leader (WL320, Bio-Tek Instrument) at 600 nm. Antifungal activity of each compound was indicated as 50% inhibition concentration ($IC_{50}$) values that was determined by calculation the minimum concentration of the compound required for the 50% reduction of the turbidity (OD600) of cells compared to untreated control cells.

The inhibitory activity of bicyclic compounds of the formula [I] against in vitro growth of *Cr. neoformans* is summarized in Table 1.

TABLE 1

| | Inhibition against in vitro cell growth |
|---|---|
| Compound No. | *Cr. neoformans* (MTU13001) $IC_{50}$ ($\mu$g/ml) |
| 12 | 4.4 |
| 21 | 5.8 |
| 31 | 19 |
| 32 | 69 |
| 42 | 2.5 |
| 44-2 | 6.1 |
| 52 | 2.6 |
| 55 | 1.8 |
| 64 | 2.1 |
| 69 | 57 |
| 88 | 5.3 |
| 99 | 1.9 |
| 100 | 2.1 |
| 112 | 3.1 |

The acute toxicity ($LD_{50}$) of the representative bicycle compound (Example 42) of the present invention was examined by intravenous administration in mice. The $LD_{50}$ value of the compound obtained in Example 42 as mentioned below was more than 50 mg/Kg.

For clinical use, the bicycle compounds of the formula [I] or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and /or ointment base. The admixture can be used for oral, injectable, rectal or topical administration.

In more detail, as mentioned earlier, medicaments containing a compound of formula [I] are also an object of the present invention, as is a process for the manufacture of such medicaments, which process comprises bringing one or more compounds of formula [I] and, if desired, one or more other therapeutically valuable substances into a galenical administration form.

The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, table, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The antifungal can also be administered in the form of a suppository or pessary, or they may be applied topically in the form of a lotion, solution, cream, ointment or dusting powder.

The daily dosage level of the antifungal compounds of the formula [I] is from 0.1 to 100 mg/Kg when administered by either the oral or parenteral route. Thus tablets or capsules can contain from 5 mg to 1000 mg of active compound for administration singly or two or more at a time as appropriate. In any event the actual dosage can be weight and response of the particular patient.

The bicycle compounds of the formula [I] and salts thereof have activity against a variety of plant pathogenic fungi, including for example *Pyricularia oryzae, Pythium aphanidermatum*, Alternaria spp., and *Paecilomyces variotii*.

Thus, they can be applied for agricultural and horticultural purposed preferably in the form of a composition formulated as dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compound having herbicidal or insecticidal, or additional antifungal compositions can be applied in a number of ways, for example they can be applied directly to the plant foliage, stems, branches, seeds or roots or to the soil or other growing medium, and they may be used not only to eradicate disease, but also prophylactically to protect the plants or seeds from fungal attack.

The following examples illustrate the preferred methods for the preparation of the compounds of the present invention, which are not intended to limit the scope of the invention thereto.

EXAMPLE 1

Preparation of 3-Cyclopropyl-4-{3-[(pyridin-3-ylmethyl)-amino]-propoxy}-benzofuran-2-carboxylic Acid Ethyl Ester a) Preparation of 1,3-bis-methoxymethoxy-benzene:

To a solution of resorcinol (10.22 g) in N,N-dimethylformamide (DMF) (100 ml) was added sodium hydride (7.96 g, 60% in paraffin liquid) at 0° C. followed by the addition of methoxymethyl chloride (14.1 ml). After 1 hour the reaction mixture was diluted with ethyl acetate and washed with saturated aqueous $NH_4Cl$ solution (100 ml), water (100 ml) and brine (100 ml), then dried over anhydrous magnesium sulfate. The filtrate was concentrated in vacuo and purified by silica gel column chromatography to give the desired compound as a colorless oil (17.8 g). EI-MS: m/z 198 ($M^+$); $^1$H-NMR ($CDCl_3$): δ 3.48 (6H, s), 5.16 (4H, s), 6.68–6.75 (3H, m), 7.19 (1H, t, J=8.6 Hz).

b) Preparation of (2,6-bis-methoxymethoxy-phenyl)-cyclopropyl-methanone:

To a solution of 1,3-bis-methoxymethoxy-benzene (1 g) in dry hexane (10 ml) was added n-buthyl lithium (1.6M in hexane, 4 ml) at room temperature. After 30 minutes the mixture was cooled to −78° C. followed by the addition of tetrahydrofuran (THF) solution of cyclopropylcarbonyl chloride (1.4 ml) and gradually warmed to room temperature and stirred for 1 hour. The mixture was diluted with ethyl acetate (50 ml) and washed with saturated aqueous $NH_4Cl$ solution (50 ml) then, dried over anhydrous magnesium sulfate and evaporated. The residue was purified by silica gel column chromatography developed by hexane-ethyl acetate. The desired product was obtained as a pale yellow oil (771 mg). EI-MS: m/z 266 ($M^+$); $^1$H-NMR ($CDCl_3$): δ 0.97–1.03 (2H, m), 1.19–1.25 (2H, m), 2.25 (1H, m), 3.47 (6H, s), 5.16 (4H, s), 6.78 (2H, d, J=8.3 Hz), 7.23 (1H, t, J=8.3 Hz).

c) Preparation of cyclopropyl-(2,6-dihydroxy-phenyl)-methanone:

To a solution of 1-(2,6-bis-methoxymethoxy-phenyl)-propan-1-one (770 mg) in methanol (12 ml) and 1,4-dioxane (12 ml) was added 4N-HCl (2 ml) at room temperature, then the mixture was heated to 50° C. and stirred for 2 hours. The mixture was diluted with ethyl acetate and washed with water (20 ml) and brine (20 ml). The separated organic layer was dried over anhydrous magnesium sulfate and evaporated. The residue was purified by silica gel column chromatography developed by hexane-ethyl acetate. 1-(2,6-dihydroxyphenyl)-propan-1-one was obtained as a yellow solid (398 mg). EI-MS: m/z 178 ($M^+$); $^1$H-NMR ($CDCl_3$): δ 1.03–1.08 (2H, m), 1.29–1.35 (2H, m), 2.21–2.31 (1H, m), 6.41 (2H, d, J=8.3 Hz), 7.23 (1H, t, J=8.3 Hz) 9.24 (2H, brs).

d) Preparation of (2-cyclopropanecarbonyl-3-hydroxy-phenoxy)-acetic acid ethyl ester:

To a mixture of cyclopropyl-(2,6-dihydroxy-phenyl)-methanone (398 mg) and potassium carbonate (500 mg) in acetone (5 ml) was added bromoacetic acid ethyl ester (300 μl) at room temperature. The suspension was heated to reflux for 1.5 hours and diluted with ethyl acetate (10 ml), washed with diluted hydrochloric acid (5 ml) and brine (5 ml), dried over anhydrous sodium sulfate, then concentrated in vacuo. The mixture was purified by silica gel column chromatography developed by hexane-ethyl acetate to give (2-cyclopropanecarbonyl-3-hydroxy-phenoxy)-acetic acid ethyl ester as a pale yellow solid (382 mg). EI-MS: m/z 264 ($M^+$); $^1$H-NMR ($CDCl_3$): δ 1.04–1.09 (2H, m), 1.23–1.29 (2H, m), 1.28 (3H, t, J=7.26 Hz), 2.26–2.35 (1H, m), 4.29 (2H, q, J=7.26 Hz), 4.70 (2H, s), 6.27 (1H, dd J=0.99 Hz, 8.25 Hz), 6.62 (1H, dd, J=0.99 Hz, 8.25 Hz), 6.41 (2H, d, J=8.25 Hz), 7.31 (1H, dd, J=8.25 Hz, 8.25 Hz), 12.89 (1H, s).

e) Preparation of 3-cyclopropyl-4-hydroxy-benzofuran-2-carboxylic acid ethyl ester:

To an anhydrous ethanol (2 ml) was added sodium (50 mg) at 0° C. under argon atmosphere. After 10 minutes, (2-cyclopropanecarbonyl-3-hydroxy-phenoxy)-acetic acid ethyl ester (380 mg) was added to the reaction mixture and the reaction mixture was stirred overnight at 0° C. The reaction was quenched with 2 N hydrochloric acid (5 ml) and stirred for 30 minutes yielding a white precipitate. The mixture was diluted with ethyl acetate (10 ml), washed with water (5 ml) and brine (5 ml), dried over anhydrous sodium sulfate, concentrated in vacuo. The residue was purified by silica gel column chromatography developed by hexane-ethyl acetate yielding 3-cyclopropyl-4-hydroxy-benzofuran-2-carboxylic acid ethyl ester (298 mg) as a white solid. FAB-MS: m/z 246 ($M^+$); $^1$H-NMR ($CDCl_3$): δ 0.99–1.05 (2H, m), 1.17–1.24 (2H, m), 1.45 (3H, t, J=7.26 Hz), 2.26–2.35 (1H, m), 4.45 (2H, q, J=7.26 Hz), 6.27 (1H, s), 6.71 (1H, dd, J=0.99 Hz, 8.25 Hz), 7.09 (1H, dd, J=0.99 Hz, 8.25 Hz), 6.41 (2H, d, J=8.25 Hz), 7.29 (1H, dd, J=8.25 Hz, 8.25 Hz).

f) Preparation of 4-(3-bromo-propoxy)-3-cyclopropyl-benzofuran-2-carboxylic acid ethyl ester:

To a mixture of 3-cyclopropyl-4-hydroxy-benzofuran-2-carboxylic acid ethyl ester (92 mg) and potassium carbonate (62 mg) in N,N-dimethylformamide (1.5 ml) was added 1,3-dibromopropane (190 μl) and the reaction mixture was stirred for 2 hours at room temperature. The reaction was quenched with saturated aqueous ammonium chloride solution (5 ml) and diluted with ethyl acetate (8 ml). The organic layer was washed with water (5 ml twice) and brine, dried over anhydrous sodium sulfate, then concentrated in vacuo to dryness. The residue was purified by silica gel column chromatography developed by hexane-ethyl acetate to give 4-(3-bromo-propoxy)-3-cyclopropyl-benzofuran-2-carboxylic acid ethyl ester (120 mg) as a white solid. EI-MS: m/z 368 ($M^+$); $^1$H-NMR ($CDCl_3$): δ 0.91–0.95 (4H, m), 1.37

(3H, t, J=7.26 Hz), 2.36 (2H, quintet, J=7.26 Hz), 2.47–2.51 (1H, m), 3.60 (2H, t, J=7.26 Hz), 4.16 (2H, t, J=7.26 Hz), 4.37 (2H, q, J=7.26 Hz), 6.58 (1H, d, J=8.25 Hz), 7.07 (1H, d, J=8.25 Hz), 7.24 (1H, dd, J=8.25 Hz, 8.25 Hz).

g) Preparation of 3-cyclopropyl-4-{3-[(pyridin-3-ylmethyl)-amino]-propoxy}-benzofuran-2-carboxylic acid ethyl ester:

To a solution of 4-(3-bromo-propoxy)-3-cyclopropyl-benzofuran-2-carboxylic acid ethyl ester (92 mg) in ethanol (4 ml) was added 3-aminomethylpyridine (500 μl) and heated at 70° C. overnight. The mixture was diluted with ethyl acetate (10 ml) and washed with saturated aqueous ammonium chloride solution (5 ml) and water (5 ml), then dried over anhydrous sodium sulfate, concentrated in vacuo to dryness. The residue was purified by silica gel column chromatography developed by dichloromethane-methanol to give 3-cyclopropyl-4-{3-[(pyridin-3-ylmethyl)-amino]-propoxy}-benzofuran-2-carboxylic acid ethyl ester as a pale yellow oil (108 mg). ESI-MS: m/z 395 (MH$^+$); $^1$H-NMR (CDCl$_3$): δ 0.95–1.08 (4H, m), 1.44 (3H, t, J=7.3 Hz), 2.10 (2H, quintet, J=6.3 Hz), 2.54–2.60 (1H, m), 2.89 (2H, t, J=6.3 Hz), 3.85 (2H, s), 4.17 (2H, t, J=6.3 Hz), 4.45 (2H, q, J=7.3 Hz), 6.63 (1H, d, J=7.9 Hz), 7.13 (1H, d, J=7.9 Hz), 7.21–7.34 (2H, m), 7.68 (1H, d, J=7.9 Hz), 8.48 (1H, dd, J=1.7 Hz, 4.9 Hz), 8.56 (1H, d, J=1.7 Hz).

Following compounds in Example 2, Example 3 and Example 4 were prepared from resorcinol in a similar manner to Example 1.

EXAMPLE 2

Preparation of 3-Isopropyl-4-{3-[(pyridin-3-ylmethyl)-amino]-propoxy}-benzofuran-2-carboxylic Acid Ethyl Ester ESI-MS: m/z 397 (MH$^+$); $^1$H-NMR (CDCl$_3$): δ 1.36 (6H, d, J=6.9 Hz), 1.44 (3H, t, J=7.3 Hz), 2.14 (2H, quintet, J=6.3 Hz), 2.91 (2H, t, J=6.3 Hz), 3.85 (2H, s), 4.20–4.35 (3H, m), 4.45 (2H, q, J=7.3 Hz), 6.67 (1H, d, J=7.9 Hz), 7.14 (1H, d, J=7.9 Hz), 7.22–7.36 (2H, m), 7.68 (1H, d, J=7.9 Hz), 8.48 (1H, dd, J=1.7 Hz, 4.9 Hz), 8.56 (1H, d, J=1.7 Hz).

EXAMPLE 3

Preparation of 3-Ethyl-4-{3-[(pyridin-3-ylmethyl)-amino]-propoxy}-benzofuran-2-carboxylic Acid Ethyl Ester ESI-MS: m/z 383 (MH$^+$); $^1$H-NMR (CDCl$_3$): δ 1.23 (3H, t, J=7.3 Hz), 1.45 (3H, t, J=7.3 Hz), 2.12 (2H, quintet, J=6.3 Hz), 2.90 (2H, t, J=6.6 Hz), 3.17 (2H, q, J=7.3 Hz), 3.85 (2H, s), 4.24 (2H, t, J=6.3 Hz), 4.31 (2H, s), 4.45 (2H, q, J=7.3 Hz), 6.68 (1H, d, J=8.3 Hz), 7.16 (1H, d, J=8.3 Hz), 7.21 (1H, dd, J=4.9 Hz, 7.9 Hz), 7.35 (1H, t, J=8.3 Hz), 7.68 (1H, d, J=7.9 Hz, 8.48 (1H, dd, J=1.7 Hz, 4.9 Hz), 8.56 (1H, d, J=1.7 Hz).

EXAMPLE 4

Preparation of 4-{3-[(Pyridin-3-ylmethyl)-amino]-propoxy}-benzofuran-2-carboxylic Acid Ethyl Ester FAB-MS: m/z 355 (MH$^+$); $^1$H-NMR (CDCl$_3$): δ 1.46 (3H, t, J=7.3 Hz), 2.11 (2H, quintet, J=6.3 Hz), 2.91 (2H, t, J=6.9 Hz), 3.87 (2H, s), 4.22 (2H, t, J=6.3 Hz), 4.48 (2H, q, J=7.3 Hz), 6.65 (1H, s), 6.70 (1H, d, J=8.3 Hz), 7.18 (1H, d, J=8.6 Hz), 7.24 (1H, dd, J=3.9 Hz, 7.9 Hz), 7.37 (1H, dd, J=8.3 Hz, 8.6 Hz), 7.70 (1H, d, J=7.9 Hz), 8.49 (1H, d, J=3.9 Hz), 8.58 (1H, s).

EXAMPLE 5

Preparation of 4-(3-tert-Butylamino-propoxy)-3-propyl-benzofuran-2-carboxylic Acid Ethyl Ester a) Preparation of 4-(3-bromo-propoxy)-3-methyl-benzofuran-2-carboxylic acid ethyl ester:

4-Hydroxy-3-methyl-benzofuran-2-carboxylic acid ethyl ester (22 g) (Joseph G. Atkinson et al., European patent application 0146243 (1985)), potassium carbonate (13.8 g) and 1,3-dibromopropane were suspended in 2-butanone (400 ml). The mixture was refluxed overnight. Inorganic salt was filtered out and the mother solution was evaporated to dryness. The residue was dissolved in ethyl acetate (800 ml), washed with water, dried over anhydrous sodium sulfate and evaporated to dryness. The residue was separated by silica gel column chromatography developed by ethyl acetate-hexane. 4-(3-Bromo-propoxy)-3-methyl-benzofuran-2-carboxylic acid ethyl ester was crystallized from hexane (28 g) as colorless needles. ESI-MS: m/z 341 (MH$^+$); $^1$H-NMR (CDCl$_3$): δ 1.43 (3H, t, J=7 Hz), 2.41 (2H, quintet, J=6.5 Hz), 2.74 (3H, s), 3.65 (2H, t, J=6.5 Hz), 4.23 (2H, t, J=6.5 Hz), 4.45 (2H, q, J=7 Hz), 6.65 (1H, d, J=8 Hz), 7.13 (1H, d, J=8 Hz), 7.31 (1H, t, J=8 Hz).

b) Preparation of 4-(3-tert-butylamino-propoxy)-3-methyl-benzofuran-2-carboxylic acid ethyl ester:

The compound in Example 5-a was heated with tert-butylamine to 70° C. overnight. The reaction mixture was evaporated to dryness and purified by silica gel column chromatography.

c) Preparation of 4-[3-(tert-butoxycarbonyl-tert-butyl-amino)-propoxy]-3-methyl-benzofuran-2-carboxylic acid ethyl ester:

To a solution of 4-(3-tert-butylamino-propoxy)-3-methyl-benzofuran-2-carboxylic acid ethyl ester (1.0 g) in dichloromethane (20 ml) was added di-tert-butyl dicarbonate (730 μl) at room temperature. The reaction mixture was stirred overnight and quenched with saturated ammonium chloride solution (10 ml) and washed with water (10 ml). The separated organic layer was dried over anhydrous sodium sulfate, then concentrated in vacuo to dryness. The residue was purified by silica gel column chromatography developed by dichloromethane-methanol to give 4-[3-(tert-butoxycarbonyl-tert-butyl-amino)-propoxy]-3-metliyl-benzofuran-2-carboxylic acid ethyl ester as white crystals (520 mg). FAB-MS: m/z 434 (MH$^+$); $^1$H-NMR (CDCl$_3$): δ 1.12–1.54 (21H, m), 2.09 (2H, m), 2.75 (3H, s), 3.52 (2H, dd, J=7.6 Hz, 9.9 Hz), 4.09 (2H, t, J=5.9 Hz), 4.43 (2H, q, J=7.3 Hz), 6.61 (1H, d, J=7.9 Hz), 7.12 (1H, d, J=8.6 Hz), 7.31 (1H, dd, J=8.6 Hz, 7.9 Hz).

d) Preparation of 4-[3-(tert-butoxycarbonyl-tert-butyl-amino)-propoxy]-3-propyl-benzofuran-2-carboxylic acid ethyl ester:

To a dry tetrahydrofuran (3 ml) solution of 4-[3-(tert-butoxycarbonyl-tert-butyl-amino)-propoxy]-3-methyl-benzofuran-2-carboxylic acid ethyl ester (50 mg) was added lithium diisopropylamide (1.2 ml, 0.5N in THF) at −78° C. After 30 minutes ethyl iodide (160 μl) was added at the same temperature. Then reaction mixture was allowed to warm to ambient temperature and stirred overnight. The reaction mixture was diluted with ethyl acetate and washed with saturated ammonium chloride solution and dried over anhydrous sodium sulfate then concentrated in vacuo to dryness. The residue was purified by silica gel column chromatography developed by dichloromethane-methanol to give 4-[3-(tert-butoxycarbonyl-tert-butyl-amino)-propoxy]-3-propyl-benzofuran-2-carboxylic acid ethyl ester as a pale yellow oil (5.1 mg). FAB-MS: m/z 462 (MH$^+$); $^1$H-NMR (CDCl$_3$): δ 1.12–1.54 (21H, m), 2.09 (2H, m), 2.75 (3H, s), 3.52 (2H, dd, J=7.6 Hz, 9.9 Hz), 4.09 (2H, t, J=5.9 Hz), 4.43 (2H, q, J=7.3 Hz), 6.61 (1H, d, J=7.9 Hz), 7.12 (1H, d, J=8.6 Hz), 7.31 (1H, dd, J=8.6 Hz, 7.9 Hz).

e) Preparation of 4-(3-tert-butylamino-propoxy)-3-propyl-benzofuran-2-carboxylic acid ethyl ester:

To a dichloromethane (0.5 ml) solution of 4-[3-(tert-butoxycarbonyl-tert-butyl-amino)-propoxy]-3-propyl-benzofuran-2-carboxylic acid ethyl ester (5.0 mg) was added trifluoroacetic acid (0.5 ml) at room temperature. After stirring overnight, the reaction mixture was concentrated in vacuo to dryness. The residue was purified by silica gel column chromatography developed by dichloromethane-methanol to give 4-(3-tert-butylamino-propoxy)-3-propyl-benzofuran-2-carboxylic acid ethyl ester (2.4 mg) as a pale yellow oil. FAB-MS: m/z 362 (MH$^+$); $^1$H-NMR (CDCl$_3$): δ 0.91 (3H, t, J=7.3 Hz), 1.34 (s, 9H), 1.25–1.45 (5H, m), 1.64 (2H, quintet, J=7.3 Hz), 2.23 (2H, quintet, J=7.3 Hz), 3.07 (2H, t, J=7.3 Hz), 3.16 (2H, t, J=7.3 Hz), 4.09 (2H, t, J=5.9 Hz), 4.42 (2H, q, J=6.9 Hz), 6.52 (1H, d, J=8.3 Hz), 7.12 (1H, d, J=8.3 Hz), 7.28 (1H, dd, J=8.3 Hz, 8.3 Hz).

EXAMPLE 6

Preparation of 3-Butyl-4-(3-tert-butylamino-propoxy)-benzofuran-2-carboxylic Acid Ethyl Ester This compound was prepared in a similar manner to Example 5.

FAB-MS: m/z 376 (MH$^+$); $^1$H-NMR (CDCl$_3$): δ 0.91 (3H, t, J=7.3 Hz), 1.34 (s, 9H), 1.25–1.45 (7H, m), 1.64 (2H, quintet, J=7.3 Hz), 2.23 (2H, quintet, J=7.3 Hz), 3.07 (2H, t, J=7.3 Hz), 3.16 (2H, t, J=7.3 Hz), 4.09 (2H, t, J=5.9 Hz), 4.42 (2H, q, J=6.9 Hz), 6.52 (1H, d, J=8.3 Hz), 7.12 (1H, d, J=8.3 Hz), 7.28 (1H, dd, J=8.3 Hz, 8.3 Hz).

EXAMPLE 7

Preparation of 3-Aminomethyl-4-{3-[(pyridin-3-ylmethyl)-amino]-propoxy}-benzofuran-2-carboxylic Acid Ethyl Ester a) Preparation of 4-(tert-butyl-dimethyl-silanyloxy)-3-methyl-benzofuran-2-carboxylic acid ethyl ester:

To a mixture of 4-hydroxy-3-methyl-benzofuran-2-carboxylic acid ethyl ester (Joseph G. Atkinson et al., European patent application 0146243 (1985)) (69 mg) and imidazole (26 mg) in DMF (2 ml) was added t-butyldimethylsilyl chloride (50 mg) and the mixture was stirred overnight. To the reaction flask was added saturated NH$_4$Cl solution (3 ml) and the product was extracted with ethyl acetate (6 ml). The organic layer was washed with water and brine, dried over anhydrous magnesium sulfate and evaporated to dryness. The residue was purified by silica gel column chromatography developed by ethyl acetate-hexane giving the desired compound as a white solid (100 mg). EI-MS: m/z 334 (M$^+$); $^1$H-NMR (CDCl$_3$): δ 0.34 (6H, s), 1.05 (9H, s), 1.44 (3H, t, J=7.3 Hz), 2.76 (3H, s), 4.45 (2H, q, J=7.3 Hz), 6.64 (1H, d, J=7.9 Hz), 7.12 (1H, d, J=8.2 Hz), 7.25 (1H, dd, J=7.9 Hz, 8.2 Hz).

b) Preparation of 3-bromomethyl-4-(tert-butyl-dimethyl-silanyloxy)-benzofuran-2-carboxylic acid ethyl ester:

4-(tert-Butyl-dimethyl-silanyloxy)-3-methyl-benzofuran-2-carboxylic acid ethyl ester (100 mg) was dissolved in benzene (10 ml) followed by the addition of N-bromosuccinimide (59 mg) and wet benzoylperoxide (10 mg). The mixture was refluxed overnight and evaporated to dryness. The obtained solid was suspended in hexane (10 ml) and filtered off. The filtrate was concentrated in vacuo to give the desired compound (128 mg) as a yellow oil. EI-MS: m/z 412 (M$^+$); $^1$H-NMR (CDCl$_3$): δ 0.37 (6H, s), 1.65 (9H, s), 1.46 (3H, t, J=7.3 Hz), 4.48 (2H, q, J=7.3 Hz), 4.95 (2H, s), 6.69 (1H, d, J=7.6 Hz), 7.17 (1H, d, J=8.3 Hz), 7.31 (1H, dd, J=7.6 Hz, 8.3 Hz).

c) Preparation of 3-azidomethyl-4-(tert-butyl-dimethyl-silanyloxy)-benzofuran-2-carboxylic acid ethyl ester:

4-(tert-Butyl-dimethyl-silanyloxy)-3-methyl-benzofuran-2-carboxylic acid ethyl ester (128 mg) and sodium azide (120 mg) were suspended in acetonitrile (4 ml) and refluxed. After 4 hours the reaction mixture was cooled to room temperature and diluted with ethyl acetate (10 ml) and washed with water (6 ml) and brine (6 ml) successively. The organic layer was dried over anhydrous magnesium sulfate and concentrated in vacuo. The residue was purified by silica gel chromatography developed by hexane-ethyl acetate giving the desired compound as a colorless oil (66 mg). FAB-MS: m/z 376 (MH$^+$); $^1$H-NMR (CDCl$_3$): δ 0.40 (6H, s), 1.08 (9H, s), 1.47 (3H, t, J=6.9 Hz), 4.49 (2H, q, J=6.9 Hz), 5.14 (2H, s), 6.69 (1H, d, J=7.9 Hz), 7.14 (1H, d, J=8.6 Hz), 7.30 (1H, dd, J=7.9 Hz, 8.6 Hz).

d) Preparation of 3-azidomethyl-4-hydroxy-benzofuran-2-carboxylic acid ethyl ester:

3-Azidomethyl-4-(tert-butyl-dimethyl-silanyloxy)-benzofuran-2-carboxylic acid ethyl ester (66 mg) was dissolved in anhydrous THF (2 ml) followed by the addition of tetrabutylammonium fluoride (1 M THF solution, 200 μl) at room temperature. After 10 minutes, the reaction was quenched with saturated ammonium chloride solution (3 ml), extracted with ethyl acetate (5 ml), dried over anhydrous magnesium sulfate, and then concentrated in vacuo. The residue was purified by silica gel column chromatography developed by hexane-ethyl acetate to give the desired compound (45 mg) as white crystals. EI-MS: m/z 261 (M$^+$); $^1$H-NMR (CDCl$_3$): δ 1.46 (3H, t, J=7.3 Hz), 4.48 (2H, q, J=7.3 Hz), 5.12 (2H, s), 6.78 (1H, d, J=7.9 Hz), 7.13 (1H, dd, J=0.7, 8.3 Hz), 7.35 (1H, dd, J=7.3, 7.9 Hz).

e) Preparation of 3-aminomethyl-4-{3-[(pyridin-3-ylmethyl)-amino]-propoxy}-benzofuran-2-carboxylic acid ethyl ester:

3-Azidomethyl-4-{3-[(pyridin-3-ylmethyl)-amino]-propoxy}-benzofuran-2-carboxylic acid ethyl ester (49 mg) and triphenylphosphine (50 mg) were dissolved in THF (2.5 ml). To the solution was added water (0.3 ml) and the mixture was heated to 70° C. overnight. The reaction mixture was diluted with ethyl acetate (5 ml) and washed with brine (5 ml), then dried over anhydrous sodium sulfate. The filtrate was concentrated in vacuo and the residue was purified by silica gel chromatography developed by dichloromethane-methanol giving 3-aminomethyl-4-{3-[(pyridin-3-ylmethyl)-amino]-propoxy}-benzofuran-2-carboxylic acid ethyl ester as a colorless oil (15 mg). FAB-MS: m/z 384 (MH$^+$); $^1$H-NMR (CDCl$_3$): δ 1.45 (3H, t, J=7.3 Hz), 2.12 (2H, quintet, J=6.3 Hz), 2.90 (2H, t, J=6.6 Hz), 3.85 (2H, s), 4.24 (2H, t, J=6.3 Hz), 4.31 (2H, s), 4.45 (2H, q, J=7.3 Hz), 6.68 (1H, d, J=8.3 Hz), 7.16 (1H, d, J=8.3 Hz), 7.21 (1H, dd, J=4.9 Hz, 7.9 Hz), 7.35 (1H, t, J=8.3 Hz), 7.68 (1H, d, J=7.9 Hz), 8.48 (1H, dd, J=1.7 Hz, 4.9 Hz), 8.56 (1H, d, J=1.7 Hz).

EXAMPLE 8

Preparation of 4-(3-tert-Butylamino-propoxy)-3-hydroxymethyl-benzofuran-2-carboxylic Acid Methyl Ester a) Preparation of 4-[3-(tert-butoxycarbonyl-tert-butyl-amino)-propoxy]-3-hydroxymethyl-benzofuran-2-carboxylic acid: 3-Bromomethyl-4-[3-(tert-butoxycarbonyl-tert-butyl-amino)-propoxy]-benzofuran-2-carboxylic acid ethyl ester was prepared from the compound in Example 5-b by the same method as Example 7-b. To a solution of 3-bromomethyl-4-[3-(tert-butoxycarbonyl-tert-butyl-amino)-propoxy]-benzofuran-2-carboxylic acid ethyl ester (23 mg) in THF (1 ml) was added 1N LiOH at room temperature and the mixture was stirred overnight. The reaction mixture was quenched by the addition of saturated ammonium chloride solution (10 ml) and water (10 ml) and extracted with ethyl acetate (10 ml) twice. The combined organic layer was dried over anhydrous sodium sulfate and concentrated in vacuo. The mixture was purified by reversed phase silica gel developed by methanol-$H_2O$ to give 4-[3-(tert-butoxycarbonyl-tert-butyl-amino)-propoxy]-3-hydroxymethyl-benzofuran-2-carboxylic acid (5.3 mg) as a white solid. FAB-MS: m/z 444 (MNa$^+$); $^1$H-NMR (CD$_3$OD): δ 1.35 (18H, s), 2.02 (2H, quintet, J=7.3 Hz), 3.47 (2H, t, J=7.3 Hz), 4.04 (2H, t, J=7.3 Hz), 5.07 (2H, s), 6.62 (1H, d, J=7.9 Hz), 6.99 (1H, d, J=7.9 Hz), 7.18 (1H, dd, J=7.9 Hz, 7.9 Hz).

b) Preparation of 4-[3-(tert-butoxycarbonyl-tert-butyl-amino)-propoxy]-3-hydroxymethyl-benzofuran-2-carboxylic acid methyl ester:

To a suspension of potassium carbonate (4.0 mg) and 4-[3-(tert-butoxycarbonyl-tert-butyl-amino)-propoxy]-3-hydroxymethyl-benzofuran-2-carboxylic acid (5.0 mg) in dry DMF (0.8 ml) was added methyl iodide (48 μl) at room temperature and the mixture was stirred overnight. The solvent was evaporated in vacuo to give the crude material as a white heavy syrup, which was then treated with 0.1N HCl (10 ml). The product was extracted with ethyl acetate (10 ml) three times and washed with saturated sodium hydrogen carbonate solution and dried over anhydrous sodium sulfate. The residue was purified by silica gel column chromatography developed by hexane-ethyl acetate to give 4-[3-(tert-butoxycarbonyl-tert-butyl-amino)-propoxy]-3-hydroxymethyl-benzofuran-2-carboxylic acid methyl ester (3.7 mg) as a white solid. FAB-MS: m/z 436 (MH$^+$); $^1$H-NMR (CDCl$_3$): δ 1.42–1.48 (18H, m), 2.11 (2H, quintet, J=7.3 Hz), 3.54 (2H, t, J=7.3 Hz), 4.07 (1H, t, J=6.9 Hz), 4.12 (2H, t, J=7.3 Hz), 4.48 (3H, s), 5.22 (2H, d, J=6.9 Hz), 6.68 (1H, d, J=7.9 Hz), 7.18 (1H, d, J=7.9 Hz), 7.40 (1H, dd, J=7.9 Hz, 7.9 Hz).

c) Preparation of 4-(3-tert-butylamino-propoxy)-3-hydroxymethyl-benzofuran-2-carboxylic acid methyl ester:

Treatment of 4-[3-(tert-butoxycarbonyl-tert-butyl-amino)-propoxy]-3-hydroxymethyl-benzofuran-2-carboxylic acid methyl ester obtained above with trifluoroacetic acid gave 4-(3-tert-butylamino-propoxy)-3-hydroxymethyl-benzofuran-2-carboxylic acid methyl ester as a yellow syrup.

FAB-MS: m/z 336 (MH$^+$); $^1$H-NMR (CDCl$_3$): δ 1.17 (9H, s), 2.14 (2H, quintet, J=7.3 Hz), 2.89 (2H, t, J=7.3 Hz), 3.99 (3H, s), 4.26 (2H, t, J=7.3 Hz), 5.19 (2H, s), 6.71 (1H, d, J=7.9 Hz), 7.18 (1H, d, J=7.9 Hz), 7.40 (1H, dd, J=7.9 Hz, 7.9 Hz).

EXAMPLE 9

Preparation of 4-(3-tert-Butylamino-propoxy)-3-ethoxymethyl-benzofuran-2-carboxylic Acid Ethyl Ester a) Preparation of 4-[3-(tert-butoxycarbonyl-tert-butyl-amino)-propoxy]-3-ethoxymethyl-benzofuran-2-carboxylic acid ethyl ester:

To ethanol (2.0 ml) was added sodium metal (15 mg) at room temperature. After 25 minutes, 3-bromomethyl-4-[3-(tert-butoxycarbonyl-tert-butyl-amino)-propoxy]-benzofuran-2-carboxylic acid ethyl ester (98 mg) was added to the reaction mixture. The reaction was quenched by the addition of saturated aqueous ammonium chloride solution (10 ml) and water (20 ml). The product was extracted with ethyl acetate (10 ml) 3 times. Organic layer was combined and dried over anhydrous sodium sulfate, concentrated in vacuo to dryness. The residue was purified by silica gel column chromatography developed by hexane-ethyl acetate to give 4-[3-(tert-butoxycarbonyl-tert-butyl-amino)-propoxy]-3-ethoxymethyl-benzofuran-2-carboxylic acid ethyl ester (70 mg) as a pale yellow oil. FAB-MS: m/z 478 (MH$^+$); $^1$H-NMR (CDCl$_3$): δ 1.22 (3H, t, J=6.9 Hz), 1.37–1.47 (21H, m), 2.09 (2H, quintet, J=7.3 Hz), 3.54 (2H, t, J=7.3 Hz), 3.62 (2H, q, J=6.9 Hz), 4.12 (2H, t, J=7.3 Hz), 4.45 (2H, q, J=7.3 Hz), 5.06 (2H, s), 6.65 (1H, d, J=7.9 Hz), 7.14 (1H, d, J=7.9 Hz), 7.33 (1H, dd, J=7.9 Hz, 7.9 Hz).

b) Preparation of 4-(3-tert-butylamino-propoxy)-3-ethoxymethyl-benzofuran-2-carboxylic acid ethyl ester:

Treatment of 4-[3-(tert-butoxycarbonyl-tert-butyl-amino)-propoxy]-3-ethoxymethyl-benzofuran-2-carboxylic acid ethyl ester with trifluoroacetic acid gave 4-(3-tert-butylamino-propoxy)-3-ethoxymethyl-benzofuran-2-carboxylic acid ethyl ester as a white solid.

FAB-MS: m/z 378 (MH$^+$); $^1$H-NMR (CDCl$_3$): δ 1.18–1.22 (12H, m), 1.44 (3H, t, J=6.9 Hz), 2.13 (2H, quintet, J=7.3 Hz), 2.97 (2H, t, J=7.3 Hz), 3.61 (2H, q, J=7.3 Hz), 4.17 (2H, t, J=7.3 Hz), 4.45 (2H, q, J=6.9 Hz), 5.05 (2H, s), 6.65 (1H, d, J=7.9 Hz), 7.14 (1H, d, J=7.9 Hz), 7.33 (1H, dd, J=7.9 Hz, 7.9 Hz).

EXAMPLE 10

Preparation of (3-Cyclopropyl-4-{3-[(pyridin-3-ylmethyl)-amino]-propoxy}-benzofuran-2-yl)-methanol To a solution of the compound of Example 1 (146 mg) in dry tetrahydrofuran was added LiAlH$_4$ (14 mg) at 0° C. The mixture was stirred for 30 minutes at 0° C. To the reaction mixture was added a little water containing KF. To the mixture was added anhydrous sodium sulfate with stirring. Inorganic salt was removed by filtration and the mother solution was evaporated to dryness. The residue was purified by silica gel column chromatography to give a colorless solid (120 mg). FAB-MS: m/z 353 (MH$^+$); $^1$H-NMR (CDCl$_3$): δ 0.67–0.86 (4H, m), 1.67–1.73 (1H, m), 2.07 (2H, quintet, J=6.3 Hz), 2.89 (2H, t, J=6.3 Hz), 3.81 (2H, s), 4.18 (2H, t, J=6.3 Hz), 4.78 (2H, s), 6.62 (1H, d, J=7.9 Hz), 7.03 (1H, d, J=7.9 Hz), 7.21–7.34 (2H, m), 7.68 (1H, d, J=7.9 Hz), 8.48–8.52 (2H, m).

EXAMPLE 11

Preparation of (3-Methyl-4-{3-[(pyridin-3-ylmethyl)-amino]-propoxy}-benzofuran-2-yl)-methanol Starting from the compound in Example 96, (3-methyl-4-{3-[(pyridin-3-ylmethyl)-amino]-propoxy}-benzofuran-2-yl)-methanol was obtained by the same method as the method in Example 10. ESI-MS: m/z 327 (MH$^+$), $^1$H-NMR (CDCl$_3$): δ 2.00 (2H, quintet, J=6.5 Hz), 2.22 (3H, s), 2.83 (2H, t, J=7 Hz), 3.77 (2H, s), 4.10 (2H, t, J=6 Hz), 4.66 (3H, s), 6.55 (1H, d, J=8 Hz), 7.00 (1H, d, J=8 Hz), 7.12 (1H, t, J=8 Hz), 7.17 (1H, m), 7.63 (1H, brd, J=5 Hz), 8.42 (2H, m).

EXAMPLE 12

Preparation of {3-[2-(2,4-Difluorophenoxymethyl)-3-methyl-benzofuran-4-yloxy]-propyl}-pyridin-3-ylmethyl-amine To a solution of the compound in Example 11 (65 mg), tributylphosphine (61 mg) and 2,4-difluorophenol (26 mg) in THF (1 ml) was added bispiperidine azodicarboxyl amide (76 mg) in THF (0.5 ml) at −45° C. under argon atmosphere, and the mixture was slowly warmed up to room temperature over 18 hoursi period. The mixture was poured into sat. NaHCO$_3$ solution and extracted with ethyl acetate. The organic layer was washed with brine and dried over Na$_2$SO$_4$. After filtration, the solvent was removed under reduced pressure and the residue was chromatographed on silica gel (dichloromethane/methanol) to give a yellow oil (35 mg, 40%). ESIMS: m/z 439 (MH$^+$); $^1$H-NMR (CDCl$_3$): δ 2.07 (2H, tt, J=6.9 Hz, 5.9 Hz, CH2), 2.27 (3H, s, CH3), 2.89 (2H, t, J=6.9 Hz, NCH2), 3.83 (2H, s, NCH2), 4.13 (2H, t, J=5.9 Hz, OCH2), 5.10 (2H, s, OCH2), 6.59 (1H, d, J=7.9 Hz, Ar—H), 6.71–7.23 (6H, m, 6×Ar—H), 7.66 (1H, dd, J=1.7 Hz, 7.9 Hz, Ar—H), 8.49 (1H, d, J=4.9 Hz, Ar—H), 8.56 (1H, s, Ar—H).

Following compounds in Example 13 to Example 37 were prepared in a similar manner to Example 12.

EXAMPLE 13

Preparation of {3-[2-(3-Trifluoromethylphenoxymethyl)-3-methyl-benzofuran-4-yloxy]-propyl}-pyridin-3-ylmethyl-amine Yellow oil. ESI-MS: m/z 471 (MH$^+$); $^1$H-NMR (CDCl$_3$): δ 2.05 (2H, tt, J=6.9 Hz, 5.9 Hz, CH2), 2.36 (3H, s, CH3), 2.88 (2H, t, J=6.9 Hz, NCH2), 3.84 (2H, s, NCH2), 4.15 (2H, t J=5.9 Hz, OCH2), 5.12 (2H, s, OCH2), 6.61 (1H, d, J=7.9 Hz, Ar—H), 7.06 (1H, d, J=8.2 Hz, Ar—H), 7.15–7.23 (5H, m, 5×Ar—H), 7.66 (1H, dt, J=2.0 Hz, 7.6 Hz, Ar—H), 8.49 (1H, dt, J=1.6 Hz, 4.7 Hz, Ar—H), 8.57 (1H, d, J=1.6 Hz, Ar—H).

EXAMPLE 14

Preparation of [3-(2-Phenoxymethyl-3-methyl-benzofuran-4-yloxy-propyl]-pyridin-3-ylmethyl-amine Yellow oil. FAB-MS: m/z 403 (MH$^+$); $^1$H-NMR (CDCl$_3$): δ 2.05 (2H, tt, J=6.9 Hz, 5.9 Hz, CH2), 2.34 (3H, s, CH3), 2.88 (2H, t, J=6.9 Hz, NCH2), 3.84 (2H, s, NCH2), 4.15 (2H, t J=5.9 Hz, OCH2), 5.08 (2H, s, OCH2), 6.60 (1H, d, J=7.9 Hz, Ar—H), 6.96–7.07 (2H, m, 2×Ar—H), 7.15 (1H, d, J=7.9 Hz, Ar—H), 7.18–7.23 (1H, m, Ar—H), 7.28–7.34 (2H, m, 2×Ar—H), 7.43–7.55 (2H, m, 2×Ar—H), 7.66 (1H, d, J=7.6 Hz, Ar—H), 8.49 (1H, d, J=4.2 Hz, Ar—H), 8.57 (1H, s, Ar—H).

EXAMPLE 15

Preparation of {3-[2-(2-Fluorophenoxymethyl)-3-methyl-benzofuran-4-yloxy]-propyl}-pyridin-3-ylmethyl-amine Yellow oil. ESI-MS: m/z 422 (MH$^+$); $^1$H-NMR (CDCl$_3$): δ 2.04 (2H, tt, J=6.6 Hz, 5.9 Hz, CH2), 2.30 (3H, s, CH3), 2.87 (2H, t, J=6.6 Hz, NCH2), 3.83 (2H, s, NCH2), 4.13 (2H, t J=5.9 Hz, OCH2), 5.15 (2H, s, OCH2), 6.59 (1H, d, J=8.1 Hz, Ar—H), 6.91–6.96 (1H, m, Ar—H), 7.03–7.10 (4H, m, 4×Ar—H), 7.16 (1H, t, J=8.1 Hz, Ar—H), 7.20 (1H, dd, J=8.1 Hz, 7.3 Hz, Ar—H), 7.66 (1H, d, J=7.3 Hz, Ar—H), 8.47 (1H, d, J=3.7 Hz, Ar—H), 8.56 (1H, s, Ar—H).

EXAMPLE 16

Preparation of {3-[2-(3-Fluorophenoxymethyl)-3-methyl-benzofuran-4-yloxy]-propyl}-pyridin-3-ylmethyl-amine Pale yellow oil. ESI-MS: m/z 422 (MH$^+$); $^1$H-NMR (CDCl$_3$): δ 2.05 (2H, tt, J=6.6 Hz, 5.9 Hz, CH2), 2.35 (3H, s, CH3), 2.88 (2H, t, J=6.6 Hz, NCH2), 3.83 (2H, s, NCH2), 4.15 (2H, t, J=5.9 Hz, OCH2), 5.06 (2H, s, OCH2), 6.60 (1H, d, J=8.1 Hz, Ar—H), 6.67–6.81 (3H, m, 3×Ar—H), 7.05 (1H, d, J=8.1 Hz, Ar—H), 7.15–7.24 (3H, m, 3×Ar—H), 7.66 (1H, d, J=7.3 Hz, Ar—H), 8.49 (1H, d, J=3.7 Hz, Ar—H), 8.56 (1H, s, Ar—H).

EXAMPLE 17

Preparation of {3-[2-(4-Fluorophenoxymethyl)-3-methyl-benzofuran-4-yloxy]-propyl}-pyridin-3-ylmethyl-amine Yellow oil. ESI-MS: m/z 421 (MH$^+$); $^1$H-NMR (CDCl$_3$): δ 2.06 (2H, tt, J=6.6 Hz, 5.8 Hz, CH2), 2.31 (3H, s, CH3), 2.88 (2H, t, J=5.8 Hz, NCH2), 3.85 (2H, s, NCH2), 4.14 (2H, t, J=6.6 Hz, OCH2), 5.03 (2H, s, OCH2), 6.58 (1H, d, J=8.1 Hz, Ar—H), 6.95–7.00 (4H, m, 4×Ar—H), 7.04 (1H, d, J=8.8 Hz, Ar—H), 7.13 (1H, d, J=8.3 Hz, Ar—H), 7.19–7.22 (1H, m, Ar—H), 7.68 (1H, d, J=8.1 Hz, Ar—H), 8.48 (1H, d, J=3.7 Hz, Ar—H), 8.57 (1H, s, Ar—H).

EXAMPLE 18

Preparation of {3-[2-(2,3-Difluorophenoxymethyl)-3-methyl-benzofuran-4-yloxy]-propyl}-pyridin-3-ylmethyl-amine 5 Pale yellow oil. ESI-MS: m/z 439 (MH$^+$); $^1$H-NMR (CDCl$_3$): δ 2.04 (2H, tt, J=6.6 Hz, 5.9 Hz, CH2), 2.32 (3H, s, CH3), 2.87 (2H, t, J=6.6 Hz, NCH2), 3.83 (2H, s, NCH2), 4.14 (2H, t, J=5.9 Hz, OCH2), 5.16 (2H, s, OCH2), 6.59 (1H, d, J=7.3 Hz, Ar—H), 6.80 (1H, dq, J=1.5 Hz, 8.1 Hz, Ar—H), 6.88 (1H, dt, J=1.5 Hz, 6.6 Hz, Ar—H), 6.90–7.00 (1H, m, Ar—H), 7.04 (1H, d, J=8.1 Hz, Ar—H), 7.16 (1H, d, J=8.1 Hz, Ar—H), 7.19–7.22 (1H, m, Ar—H), 7.65 (1H, d, J=8.1 Hz, Ar—H), 8.47 (1H, d, J=3.7 Hz, Ar—H), 8.56 (1H, s, Ar—H).

EXAMPLE 19

Preparation of {3-[2-(2,5-Difluorophenoxymethyl)-3-methyl-benzofuran-4-yloxy]-propyl}-pyridin-3-ylmethyl-amine Pale yellow oil. ESI-MS: m/z 439 (MH$^+$); $^1$H-NMR (CDCl$_3$): δ 2.04 (2H, tt, J=6.6 Hz, 5.9 Hz, CH2), 2.33 (3H, s, CH3), 2.87 (2H, t, J=6.6 Hz, NCH2), 3.85 (2H, s, NCH2), 4.13 (2H, t, J=5.9 Hz, OCH2), 5.13 (2H, s, OCH2), 6.59 (1H, d, J=8.1 Hz, Ar—H), 6.60–6.64 (1H, m, Ar—H), 6.86 (1H, dq, J=3.7 Hz, 2.9 Hz, Ar—H), 6.98–7.04 (1H, m, Ar—H), 7.05 (1H, d, J=8.1 Hz, Ar—H), 7.16 (1H, d, J=8.1 Hz, Ar—H), 7.20 (1H, q, J=4.4 Hz, Ar—H), 7.68 (1H, d, J=8.1 Hz, Ar—H), 8.48 (1H, d, J=3.7 Hz, Ar—H), 8.56 (1H, d, J=1.5 Hz, Ar—H).

EXAMPLE 20

Preparation of {3-[2-(2,6-Difluorophenoxymethyl)-3-methyl-benzofuran-4-yloxy]-propyl}-pyridin-3-ylmethyl-amine Yellow oil. ESI-MS: m/z 439 (MH$^+$); $^1$H-NMR (CDCl$_3$): δ 2.03 (2H, tt, J=6.6 Hz, 5.9 Hz, CH2), 2.22 (3H, s, CH3), 2.85 (2H, t, J=6.6 Hz, NCH2), 3.82 (2H, s, NCH2), 4.12 (2H, t, J=5.9 Hz, OCH2), 5.19 (2H, s, OCH2), 6.57 (1H, d, J=7.3 Hz, Ar—H), 6.82–6.84 (1, m, Ar—H), 6.86 (1H, d, J=7.3 Hz, Ar—H), 6.92–6.99 (1H, m, Ar—H), 7.04 (1H, d, J=8.1 Hz, Ar—H), 7.15 (1H, d, J=8.1 Hz, Ar—H), 7.19 (1H, dd, J=2.9 Hz, 4.4 Hz, Ar—H), 7.64 (1H, d, J=8.7 Hz, Ar—H), 8.48 (1H, d, J=3.7 Hz, Ar—H), 8.55 (1H, s, Ar—H).

EXAMPLE 21

Preparation of {3-[2-(2,3,4-Trifluorophenoxymethyl)-3-methyl-benzofuran-4-yloxy]-propyl}-pyridin-3-ylmethyl-amine Pale yellow oil. ESI-MS: m/z 457 (MH$^+$); $^1$H-NMR (CDCl$_3$): δ 2.08 (2H, t, J=6.3 Hz, CH2), 2.29 (3H, s, CH3), 2.88 (2H, t, J=6.9 Hz, NCH2), 3.84 (2H, s, NCH2), 4.14 (2H, t, J=5.9 Hz, OCH2), 5.13 (2H, s, OCH2), 6.60 (1H, d, J=7.9 Hz, Ar—H), 6.75–6.91 (2H, m, 2×Ar—H), 7.04 (1H, d, J=8.4 Hz, Ar—H), 7.15–7.27 (2H, m, 2×Ar—H), 7.68 (1H, d, J=7.6 Hz, Ar—H), 8.49 (1H, d, J=4.0 Hz, Ar—H), 8.57 (1H, s, Ar—H).

EXAMPLE 22

Preparation of {3-[2-(2,3,5-Trifluorophenoxymethyl)-3-methyl-benzofuran-4-yloxy]-propyl}-pyridin-3-ylmethyl-amine Pale yellow oil. ESI-MS: m/z 457 (MH$^+$); $^1$H-NMR (CDCl$_3$): δ 2.07 (2H, t, J=6.3 Hz, CH2), 2.33 (3H, s, CH3), 2.89 (2H, t, J=6.9 Hz, NCH2), 3.72 (2H, s, NCH2), 4.15 (2H, t, J=5.9 Hz, OCH2), 5.14 (2H, s, OCH2), 6.51–6.73 (3H, m, 3×Ar—H), 7.05 (1H, d, J=7.9 Hz, Ar—H), 7.69 (1H, d, J=7.9 Hz, Ar—H), 8.50 (1H, dd, J=4.6 Hz, 1.7 Hz, Ar—H), 8.57 (1H, d, J=2.2 Hz, Ar—H).

EXAMPLE 23

Preparation of {3-[2-(2,4,5-Trifluorophenoxymethyl)-3-methyl-benzofuran-4-yloxy]-propyl}-pyridin-3-ylmethyl-amine Pale yellow oil. ESI-MS: m/z 457 (MH$^+$); $^1$H-NMR (CDCl$_3$): δ 2.07 (2H, tt, J=6.9 Hz, 5.9 Hz, CH2), 2.30 (3H, s, CH3), 2.89 (2H, t, J=6.9 Hz, NCH2), 3.86 (2H, s, NCH2), 4.14 (2H, t, J=5.9 Hz, OCH2), 5.11 (2H, s, OCH2), 6.60 (1H, d, J=7.9 Hz, Ar—H), 6.92–7.07 (3H, m, 3×Ar—H), 7.13–7.22 (2H, m, 2×Ar—H), 7.68–7.73 (1H, m, Ar—H), 8.50 (1H, d, J=3.6 Hz, Ar—H), 8.58 (1H, s, Ar—H).

EXAMPLE 24

Preparation of {3-[2-(2,3,6-Trifluorophenoxymethyl)-3-methyl-benzofuran-4-yloxy]-propyl}-pyridin-3-ylmethyl-amine Orange oil. ESI-MS: m/z 457 (M H$^+$); $^1$H-NMR (CDCl$_3$): δ 2.07 (2H, tt, J=6.9 Hz, 5.9 Hz, CH2), 2.27 (3H, s, CH3), 2.89 (2H, t, J=6.9 Hz, NCH2), 3.86 (2H, s, NCH2), 4.12 (2H, t, J=5.9 Hz, OCH2), 5.24 (2H, s, OCH2), 6.57 (1H, d, J=8.0 Hz, Ar—H), 6.75–6.90 (2H, m, 2×Ar—H), 7.04 (1H, d, J=8.2 Hz, Ar—H), 7.17 (1H, t, J=8.2 Hz, Ar—H), 7.22–7.24 (1H, m, Ar—H), 7.71 (1H, dt, J=2.0 Hz, 7.9 Hz, Ar—H), 8.50 (1H, dd, J=5.0 Hz, 1.7 Hz, Ar—H), 8.57 (1H, d, J=1.7 Hz, Ar—H).

EXAMPLE 25

Preparation of {3-[2-(2,4,6-Trifluorophenoxymethyl)-3-methyl-benzofuran-4-yloxy]-propyl}-pyridin-3-ylmethyl-amine Yellow oil. ESIMS: m/z 457 (MH$^+$); $^1$H-NMR (CDCl$_3$): δ 2.07 (2H, t, J=6.6 Hz, CH2), 2.28 (3H, s, CH3), 2.87 (2H, t, J=6.9 Hz, NCH2), 3.84 (2H, s, NCH2), 4.13 (2H, t, J=5.9 Hz, OCH2), 5.14 (2H, s, OCH2), 6.58 (1H, d, J=7.9 Hz, Ar—H), 6.61–6.71 (2H, m, 2×Ar—H), 7.04 (1H, d, J=8.2 Hz, Ar—H), 7.16 (1H, d, J=7.9 Hz, Ar—H), 7.20–7.24 (1H, m, Ar—H), 7.68 (1H, d, J=7.6 Hz, Ar—H), 8.49 (1H, d, J=3.6 Hz, Ar—H), 8.56 (1H, s, Ar—H).

EXAMPLE 26

Preparation of {3-[2-(2,3,4,5,6-Pentafluorophenoxymethyl)-3-methyl-benzofuran-4-yloxy]-propyl}-pyridin-3-ylmethyl-amine Yellow oil. ESI-MS: m/z 493 (MH$^+$); $^1$H-NMR (CDCl$_3$): δ 2.06 (2H, t, J=5.9 Hz, CH2), 2.26 (3H, s, CH3), 2.93 (2H, t, J=6.9 Hz, NCH2), 3.87 (2H, s, NCH2), 4.10 (2H, t, J=5.9 Hz, OCH2), 5.23 (2H, s, OCH2), 6.55 (1H, d, J=7.9 Hz, Ar—H), 7.04 (1H, d, J=8.2 Hz, Ar—H), 7.18 (1H, t, J=8.2 Hz, Ar—H), 7.22–7.25 (1H, m, Ar—H), 7.71 (1H, d, J=7.6 Hz, Ar—H), 8.50 (1H, d, J=5.0 Hz, Ar—H), 8.58 (1H, d, J=2.0 Hz, Ar—H).

EXAMPLE 27

Preparation of {3-[2-(3,5,-Bistrifluoromethylphenoxymethyl)-3-methyl-benzofuran-4-yloxy]-propyl}-pyridin-3-ylmethyl-amine Yellow oil. ESI-MS: m/z 539 (MH$^+$); $^1$H-NMR (CDCl$_3$): δ 2.07 (2H, t, J=6.3 Hz, CH2), 2.37 (3H, s, CH3), 2.89 (2H, t, J=6.9 Hz, NCH2), 3.86 (2H, s, NCH2), 4.17 (2H, t, J32 5.9 Hz, OCH2), 5.17 (2H, s, OCH2), 6.61 (1H, d, J=7.9 Hz, Ar—H), 7.05 (1H, d, J=8.2 Hz, Ar—H), 7.20 (1H, t, J=7.9 Hz, Ar—H), 7.2 (1H, d, J=7.9 Hz, Ar—H), 7.45 (2H, s, 2×Ar—H), 7.49 (1H, s, Ar—H), 7.68 (1H, dt, J=7.6 Hz, 2.0 Hz, Ar—H), 8.49 (1H, dd, J=2.0 Hz, 4.6 Hz, Ar—H), 8.57 (1H, d, J=2.0 Hz, Ar—H).

EXAMPLE 28

Preparation of {3-[2-(3-Morpholin-phenoxymethyl)-3-methyl-benzofuran-4-yloxy]-propyl}-pyridin-3-ylmethyl-amine Yellow oil. ESI-MS: m/z 488 (MH$^+$); $^1$H-NMR (CDCl$_3$): δ 2.08 (2H, t, J=6.6 Hz, CH2), 2.32 (3H, s, CH3), 2.92 (2H, t, J=6.9 Hz, NCH2), 3.15 (4H, t, J=4.6 Hz, 2×NCH2), 3.98 (4H, t, J=4.6 Hz, 2×OCH2), 3.89 (2H, s, NCH2), 4.14 (2H, t, J=5.9 Hz, OCH2), 5.06 (2H, s, OCH2), 6.55–6.60 (4H, m, 4×Ar—H), 7.04 (1H, d, J=8.2 Hz, Ar—H), 7.15 (1H, d, J=7.9 Hz, Ar—H), 7.18–7.24 (2H, m, 2×Ar—H), 7.75 (1H, d, J=7.9 Hz, Ar—H), 8.51 (1H, d, J=3.3 Hz, Ar—H), 8.59 (1H, d, J=1.7 Hz, Ar—H).

EXAMPLE 29

Preparation of {3-[2-(4-Morpholin-phenoxymethyl)-3-methyl-benzofuran-4-yloxy]-propyl}-pyridin-3-ylmethyl-amine Yellow oil. ESI-MS: m/z 488 (MH$^+$); $^1$H-NMR (CDCl$_3$): δ 2.08 (2H, tt, J=5.9 Hz, 6.9 Hz, CH2), 2.31 (3H, s, CH3), 2.90 (2H, t, J=6.9 Hz, NCH2), 3.07 (4H, t, J=4.6 Hz, 2×NCH2), 3.84 (4H, t, J=5.9 Hz, 2×OCH2), 3.88 (2H, s, NCH2), 4.14 (2H, t, J=5.9 Hz, OCH2), 5.03 (2H, s, OCH2), 6.59 (1H, d, J=7.6 Hz, Ar—H), 6.87–7.25 (7H, m, 7×Ar—H), 8.50 (1H, dd, J=1.7 Hz, 5.0 Hz, Ar—H), 8.58 (1H, d, J=1.7 Hz, Ar—H).

EXAMPLE 30

Preparation of {3-[2-(4-Chlorophenoxymethyl)-3-methyl-benzofuran-4-yloxy]-propyl}-pyridin-3-ylmethyl-amine Yellow oil. FABMS: m/z 539 (MH$^+$); $^1$H-NMR (CDCl$_3$): δ 2.08 (2H, tt, J=6.9 Hz, 6.3 Hz, CH2), 2.33 (3H, s, CH3), 2.88 (2H, t, J=6.9 Hz, NCH2), 3.84 (2H, s, NCH2), 4.15 (2H, t, J=6.3 Hz, OCH2), 5.05 (2H, s, OCH2), 6.60 (1H, d, J=7.9 Hz, Ar—H), 6.95 (1H, d, J=6.9 Hz, Ar—H), 7.05 (1H, d, J=8.2 Hz, Ar—H), 7.16 (1H, d, J=7.9 Hz, Ar—H), 7.18–7.24 (4H, m 4×Ar—H), 7.67 (1H, d, J=7.9 Hz, Ar—H), 8.49 (1H, d, J=4.6 Hz, Ar—H), 8.57 (1H, s, Ar—H).

EXAMPLE 31

Preparation of {3-[3-Methyl-2-(pyridin-3-yloxymethyl)-benzofuran-4-yloxy]-propyl}-pyridin-3-ylmethyl-amine Colorless oil. FAB-MS: m/z 404 (MH$^+$); $^1$H-NMR (CDCl$_3$): δ 2.06 (2H, quintet, J=6.5 Hz), 2.35 (3H, s), 2.88 (2H, t, J=7 Hz), 3.84 (2H, s), 4.15 (2H, t, J=6 Hz), 5.13 (2H, s), 6.61 (1H, d, J=8 Hz), 7.05 (1H, d, J=8 Hz), 7.18 (1H, t, J=8 Hz), 7.25 (2H, m), 7.33 (1H, ddd, J1=8.5 Hz, J2=3 Hz, J3=1.5 Hz), 7.67 (1H, dd, J1=8 Hz, J2=2 Hz), 8.25 (1H, dd, J1=5 Hz, J2=1.5 Hz), 8.42 (1H, d, J=3 Hz), 8.49 (1H, dd, J1=5 Hz, J2=2 Hz), 8.56 (1H, d, J=2 Hz).

EXAMPLE 32

Preparation of 4-(3-Methyl-4-{3-[(pyridin-3-ylmethyl)-amino]-propoxy}-benzofuran-2-ylmethoxy)-benzonitrile White powder. ESI-MS: m/z 428 (MH$^+$); $^1$H-NMR (CDCl$_3$): δ 2.06 (2H, quintet, J=6.5 Hz), 2.35 (3H, s), 2.87 (2H, t, J=7 Hz), 3.84 (2H, s), 4.15 (2H, t, J=6 Hz), 5.13 (2H, s), 6.61 (1H, d, J=8 Hz), 7.05 (1H, d, J=8 Hz), 7.07 (2H, d, J=9 Hz), 7.19 (1H, t, J=8 Hz), 7.22 (1H, m), 7.61 (2H, d, J=9 Hz), 7.67 (1H, dd, J1=8 Hz, J2=2 Hz), 8.49 (1H, dd, J1=5 Hz, J2=2 Hz), 8.56 (1H, d, J=2 Hz).

EXAMPLE 33

Preparation of {3-[3-Methyl-2-(2,2,2-trifluoro-ethoxymethyl)-benzofuran-4-yloxy]-propyl}-pyridin-3-ylmethyl-amine Colorless oil. FAB-MS: m/z 409 (MH$^+$); $^1$H-NMR (CDCl$_3$): δ 2.06 (2H, quintet, J=6.5 Hz), 2.32 (3H, s), 2.88 (2H, t, J=7 Hz), 3.85 (2H, q, J=9 Hz), 3.85 (2H, s), 4.15 (2H, t, J32 6 Hz), 4.72 (2H, s), 6.61 (1H, d, J=8 Hz), 7.04 (1H, d, J=8 Hz), 7.18 (1H, t, J=8 Hz), 7.21 (1H, m), 7.67 (1H, br d, J=8 Hz), 8.49 (1H, dd, J1=5 Hz, J2=2 Hz), 8.57 (1H, d, J=2 Hz).

EXAMPLE 34

Preparation of (4-Hydroxy-piperidin-1-yl)-[5-(3-methyl-4-{3-[(pyridin-3-ylmethyl)-amino]propoxy}-benzofuran-2-ylmethoxy)-benzofuran-2-yl]-methanone Colorless oil. FAB-MS: m/z 570 (MH$^+$); $^1$H-NMR (CDCl$_3$): δ 1.65 (2H, m), 1.96 (2H, m), 2.06 (2H, quintet, J=6.5 Hz), 2.33 (3H, s), 2.88 (2H, t, J=7 Hz), 3.49 (2H, br s), 3.84 (2H, s), 4.03 (1H, m), 4.14 (2H, t, J=6 Hz), 4.16 (2H, m), 5.11 (2H, s), 6.60 (1H, d, J=8 Hz), 7.06 (1H, d, J=8 Hz), 7.08 (1H, dd, J1=9 Hz, J2=2.5 Hz), 7.20 (4H, m), 7.42 (1H, d, J=9 Hz), 7.68 (1H, br d, J=8 Hz), 8.48 (1H, br d, J=5 Hz), 8.56 (1H, br s).

EXAMPLE 35

Preparation of [5-(3-Methyl-4-{3-[(pyridin-3-ylmethyl)-amino]-propoxy}-benzofuran-2-ylmethoxy)-benzofuran-2-yl]piperazin-1-yl-methanone Colorless oil. FAB-MS: m/z 555 (MH$^+$); $^1$H-NMR (CDCl$_3$): δ 2.06 (2H, quintet, J=6.5 Hz), 2.33 (3H, s), 2.88 (2H, t, J=7 Hz), 2.96 (4H, m), 3.84 (6H, br s), 4.15 (2H, t, J=6 Hz), 5.12 (2H, s), 6.60 (1H, d, J=8 Hz), 7.06 (1H, d, J=8 Hz), 7.09 (1H, dd, J1=9 Hz, J2=2.5 Hz), 7.18 (1H, t, J=8 Hz), 7.25 (3H, m), 7.42 (1H, d, J=9 Hz), 7.66 (1H, br d, J=8 Hz), 8.49 (1H, br d, J=4 Hz), 8.56 (1H, br s).

EXAMPLE 36

Preparation of 5-[3-Methyl-4-[3-[(pyridin-3-ylmethyl)-amino]-propoxyl]-benzofuran-2-ylmethoxy]-benzofuran-2-carboxylic Acid Ethyl Ester Colorless oil. FAB-MS: m/z 515 (MH$^+$); $^1$H-NMR (CDCl$_3$): δ 1.35 (3H, t, J=6.9 Hz), 2.01 (2H, m); 2.32 (3H, s), 2.87 (2H, t, J=6.6 Hz), 3.81 (2H, s), 4.13 (2H, t, J=5.9 Hz), 4.45 (1H, q, J=6.9 Hz), 5.08 (2H, s), 6.60 (1H, d, J=7.6 Hz), 7.04 (1H, d, J=7.6 Hz), 7.11–7.20 (4H, m), 7.45–7.49 (2H, m), 7.64 (1H, d, J=7.8 Hz), 8.48 (1H, brd, J=4.5 Hz), 8.56 (1H, brs).

EXAMPLE 37

Preparation of 7-[3-Methyl-4-[3-[(pyridin-3-ylmethyl)-amino]-propoxyl]-benzofuran-2-ylmethoxyl]-benzofuran-2-carboxylic Acid Ethyl Ester FAB-MS: m/z 515 (MH$^+$); $^1$H-NMR (CDCl$_3$): δ 1.31 (3H, t, J=6.9 Hz), 1.98 (2H, m), 2.22 (3H, s), 2.81 (2H, t, J=6.9 Hz), 3.77 (2H, s), 4.08 (2H, t, J=5.9 Hz), 4.35 (2H, q, J=6.9 Hz), Hz), 5.28 (2H, s), 6.52 (1H, d, J=7.6 Hz), 6.98–7.20 (6H, m), 7.44 (1H, s), 7.58 (1H, d, J=7.8 Hz), 8.41 (1H, brd, J=4.5 Hz), 8.49 (1H, brs).

EXAMPLE 38

Preparation of 5-(3-Cyclopropyl-4-{3-[(pyridin-3-ylmethyl)-amino]-propoxy}-benzofuran-2-ylmethoxy)-benzofuran-2-carboxylic Acid Ethyl Ester Starting from the compound in Example 10 and 5-hydroxybenzofuran-2-carboxylic acid ethyl ester, the title compound was prepared in the same manner to Example 12. FAB-MS: m/z 451 (MH$^+$); $^1$H-NMR (CDCl$_3$): δ 0.67–0.86 (4H, m), 1.43 (2H, t, J=7.3 Hz), 1.67–1.73 (1H, m), 2.07 (2H, quintet, J=6.3 Hz), 2.89 (2H, t, J=6.3 Hz), 3.81 (2H, s), 4.18 (2H, t, J=6.3 Hz), 4.43 (2H, q, J=7.3 Hz), 5.17 (2H, s), 6.64 (1H, d, J=7.3 Hz), 7.07–7.28 (5H, m), 7.47 (1H, s), 7.48 (1H, d, J=9.6 Hz), 7.68 (1H, d, J=7.9 Hz), 8.50 (1H, dd, J=4.9 Hz, 1.6 Hz), 8.52 (1H, d, J=1.6 Hz).

EXAMPLE 39

Preparation of 5-[3-Methyl-4-[3-[(pyridin-3-ylmethyl)-amino]-propoxyl]-benzofuran-2-ylmethoxyl]-benzofuran-2-carboxylic Acid Amide The compound in Example 36 (12 mg, 0.022 mmol) and NaCN (1 mg) in saturated NH$_3$ anhydrous MeOH solution was heated at 70° C. in a sealed flask overnight. Silica gel column chromatography (CH$_2$Cl$_2$/MeOH=20/1 to 10/1) gave desired product (10 mg, 88%) as a colorless solid. FAB-MS: m/z 486 (MH$^+$); $^1$H-NMR (CD$_3$OD): δ 2.01 (2H, m); 2.26 (3H, s), 2.80 (1H, t, J=6.9 Hz), 3.78 (2H, s), 4.10 (1H, t, J=5.9 Hz), 5.04 (2H, s), 5.80 (1H, brs), 6.50 (1H, brs), 6.52 (1H, d, J=7.6 Hz), 7.04–7.20 (5H, m), 7.33 (1H, d, J=8.9 Hz), 7.39 (1H, s), 8.41 (1H, brd, J=4.5 Hz), 8.49 (1H, brs).

EXAMPLE 40

Preparation of [5-[3-Methyl-4-[3-[(pyridin-3-ylmethyl)-amino]-propoxyl]-benzofuran-2-ylmethoxyl]-benzofuran-2-yl]-methanol To a solution of the compound in Example 36 (10 mg, 0.02 mmol) in THF was added LiAlH$_4$ (1.5 mg) at 0° C. After stirring for 20 min., the reaction was quenched by adding H$_2$O. Silica gel column chromatography (CH$_2$Cl$_2$/MeOH=20/1) gave desired product as a colorless oil. (9 mg, 98%). FAB-MS: m/z 473 (MH$^+$); $^1$H-NMR (CDCl$_3$): δ 2.04 (2H, m), 2.28 (3H, s), 2.86 (2H, t, J=7.5 Hz), 3.82 (2H, s), 4.14 (2H, t, J=5.5 Hz), 4.75 (2H, s) 5.11 (2H, s), 6.59 (1H, d, J=8 Hz), 6.95(1H, d, J=2 Hz), 7.06 (1H, d, J=8 Hz), 7.12–7.19 (2H, m), 7.34 (1H, d, J=9 Hz), 7.66 (1H, d, J=8 Hz), 8.44 (1H, brd, J=4.5 Hz), 8.51 (1H, brs).

EXAMPLE 41

Preparation of [3-[2-(2-Aminomethyl-benzofuran-5-ylmethyl)-3-methyl-benzofuran-4-yloxy]-propyl]-pyridin-3-ylmethyl-amine To a solution of the compound in Example 39 (22 mg) in THF was added LiAlH4 (1 eq.) at 0° C. Silica gel column chromatography (CH$_2$Cl$_2$/MeOH=10/1 to 3/1) gave desired product (2 mg, 5%) as a colorless oil). FAB-MS: m/z 472 (MH$^+$); $^1$H-NMR (CDCl$_3$): δ 1.98 (2H, m), 2.25 (3H, s), 2.81 (2H, t, J=7.5 Hz), 3.76 (2H, s), 3.86 (2H, s), 4.02 (2H, t, J=5.3 Hz), 5.018 (2H, s), 6.41 (1H, s), 6.52 (1H, d, J=7.6 Hz), 6.88,(1H, dd, J=9 Hz, 2.5 Hz), 6.98–7.20 (5H, m), 7.60, (1H, d, J=8 Hz), 8.40 (1H, brd, J=4,5 Hz), 8.47 (1H, brs).

EXAMPLE 42

Preparation of [3-[2-(2-Ethoxymethyl-benzofuran-5-yloxymethyl)-3-methyl-benzofuran-4-yloxy]-propyl]-pyridin-3-ylmethyl-amine To a solution of the compound in Example 40 (15 mg, 0.03 mmol) in anhydrous THF/H$_2$O were added K$_2$CO$_3$ and benzyloxycarbonyl chloride (3 eq), the mixture was stirred for 3 hours. The crude mixture was purified over SiO$_2$ column. The product was dissolved in anhydrous DMF (2 ml), NaH (5 mg) was added. The mixture was stirred for 10 minutes. Ethyl bromide (excess) was added to the reaction flask. The mixture was stirred for one hour. The crude product was hydrogenated over 10% Pd/C in MeOH to give the desired product as a colorless oil. ESI-MS: m/z 501 (MH$^+$); $^1$H-NMR (CDCl$_3$): δ 1.36 (3H, t, J=6.9 Hz), 2.16 (2H, m), 2.43 (3H, s), 2.98 (2H, t, J=6.9 Hz), 3.72 (2H, q, J=6.9 Hz), 3.94 (2H, s), 4.25 (2H, t, J=5.9 Hz), 4.68 (2H, s), 5.20 (2H, s), 5.40 (2H, s), 6.69 (1H, d, J=7.9 Hz), 6.73 (1H, s), 7.08 (1H, dd, J=9 Hz, 2.5 Hz), 7.18 (1H, d, J=18 Hz), 7.25–7.32 (3H, m), 7.46 (1H, d, J=9 Hz), 7.75 (1H, d, J=7.9 Hz), 8.59 (1H, dd, J=5 Hz, 1.5 Hz), 8.66 (1H, d, J=1.5 Hz).

EXAMPLE 43

Preparation of [3-[3-Methyl-2-[2-(2,2,2-trifluoro-ethoxymethyl)-benzofuran-5-yloxymethyl]-benzofuran-4-yloxy]-propyl]-pyridin-3-ylmethyl-amine The compound of Example 40 (60 mg) and 1,1'-(azodicarbonyl)dipiperidine (64 mg) were suspended in dry benzene (2 ml). To the suspension was added tributylphosphine (63 μl) at room temperature. The mixture was stirred at room temperature for 15 minutes. To the mixture was added 2,2,2-trifluoroethanol (74 μl). The mixture was stirred at room temperature overnight. After removing the solvent the reaction mixture was separated by silica gel column chromatography developed by the solvent mixture of dichloromethane and methanol. The title compound (57 mg) was obtained as a colorless oil. ESI-MS: m/z 555 (MH$^+$); $^1$H-NMR (CDCl$_3$): δ 2.05 (2H, quintet, J=6.5 Hz), 2.33 (3H, s), 2.87 (2H, t, J=7 Hz), 3.83 (2H, s), 3.91 (2H, q, 8.5 Hz), 4.14 (2H, t, J=6 Hz), 4.74 (2H, s), 5.10 (2H, s), 6.60 (1H, d, J=7 Hz), 6.71 (1H,s), 6.95–7.25 (5H, m), 7.38 (1H, d, J=9 Hz), 7.66 (1H, dt, J=7.5 Hz, 2 Hz), 8.48 (1H, dd, J=1.5 Hz, 4.5 Hz), 8.56 (1H, d, J=1.5 Hz).

EXAMPLE 44

Preparation of 1-[5-(3-Methyl-4-{3-[(pyridin-3-ylmethyl)-amino]-propoxy}-benzofuran-2-ylmethoxy)-benzofuran-2-yl]ethanone (Example 44-1) and 2-[5-(3-methyl-4-{3-[(pyridin-3-ylmethyl)-amino]-propoxy}-benzofuran-2-ylmethoxy)-benzofuran-2-yl]-propan-2-ol (Example 44-2)

To a solution of the compound of Example 36 (122 mg) in dry tetrahydrofuran (10 ml) was added the solution of methylmagnesium bromide (0.74 ml: 1.4 mol/L in toluene-tetrahydrofuran=75:25) at 0° C. The solution was stirred at room temperature for 4.5 hours. The reaction mixture was poured onto a mixture of ice and ammonium chloride solution. The mixture was extracted with ethyl acetate. The organic layer was dried over anhydrous sodium sulfate. After the removal of the solvent the organic layer was separated by silica gel column chromatography developed by ethyl acetate/methanol. 1-[5-(3-Methyl-4-{3-[(pyridin-3-ylmethyl)-amino]-propoxy}-benzofuran-2-ylmethoxy)-benzofuran-2-yl]-ethanone was obtained as colorless oil (16 mg): FAB-MS: m/z 501 (MH$^+$); $^1$H-NMR (CDCl$_3$): δ 2.06 (2H, quintet, J=6.5 Hz), 2.34 (3H, s), 2.60 (3H, s), 2.88 (2H, t, J=7 Hz), 3.84 (2H, s), 4.15 (2H, t, J=6 Hz), 5.12 (2H, s), 6.60 (1H, d, J=8 Hz), 7.06 (1H, d, J=8 Hz), 7.1–7.3 (4H, m), 7.45 (1H, s), 7.48 (1H, d, J=9 Hz), 7.67 (1H, dt, J=8 Hz, 1.5 Hz), 8.48 (1H, dd, J=4.5 Hz, 1.5 Hz), 8.56 (1H, d, J=1.5 Hz). 2-[5-(3-Methyl-4-{3-[(pyridin-3-ylmethyl)-amino]-propoxy}-benzofuran-2-ylmethoxy)-benzofuran-2-yl]-propan-2-ol was obtained as a colorless oil (24 mg) FAB-MS m/z 555 (MH$^+$); $^1$H-NMR (CDCl$_3$): δ 1.66 (6H, s), 2.05 (2H, quintet, J=6.5 Hz), 2.30 (3H, s), 2.86 (2H, t, J=7 Hz), 3.83 (2H, s), 4.14 (2H, t, J=6 Hz), 5.10 (2H, s), 6.52 (1H, s), 6.59 (1H, d, J=7.5 Hz), 6.94 (1H, dd, J=9 Hz, 2.5 Hz), 7.05 (1H, d, J=8 Hz), 7.1–7.25 (3H, m), 7.34 (1H, d, J=9 Hz), 7.66 (1H, dt, J=8 Hz, 1.5 Hz), 8.46 (1H, brd, J=4.5 Hz), 8.56 (1H, brs).

EXAMPLE 45

Preparation of {3-[2-(2-Ethoxymethyl-benzofuran-5-yloxymethyl)-3-methyl-benzofuran-4-yloxy]-propyl}-methyl-pyridin-3-ylmethyl-amine A mixture of the compound of Example 42 (25.3 mg), formalin (37%, 5.7 μl), acetic acid (12 μl) and sodium cyanoborohydride (6.4 mg) was stirred in MeOH (2 ml) at room temperature for 1.5 hours. MeOH was evaporated to dryness, the residue was purified by silica gel TLC (dichloromethane-MeOH=10:1) to give the title compound as a colorless oil (23.4 mg). FAB-MS: m/z 515 (MH$^+$); $^1$H-NMR (CDCl$_3$): δ 1.26 (3H, t, J=7 Hz), 2.03 (2H, quintet, J=6.5 Hz), 2.25 (3H, s), 2.27 (3H, s), 2.61 (2H, t, J=7 Hz), 3.55 (2H, s), 3.61 (2H, q, J=7 Hz), 4.10 (2H, t, J=6 Hz), 4.57 (2H, s), 5.09 (2H, s), 6.58 (1H, d, J=8 Hz), 6.63 (1H, s), 6.97

(1H, dd, J=9 Hz, 2.5 Hz), 7.0–7.2 (4H, m), 7.37 (1H, d, J=9 Hz), 7.64 (1H, dt, 7.5 Hz, 1.5 Hz), 8.42 (1H, dd, J=5 Hz, 1.5 Hz), 8.51 (1H, d, J=1.5 Hz).

EXAMPLE 46

Preparation of {3-[2-(2,4-Difluoro-phenoxymethyl)-3-methyl-benzofuran-4-yloxy]-propyl}-methyl-pyridin-3-ylmethyl-amine The title compound was obtained starting from the compound of Example 12 by an analogous procedure to that of Example 45. FAB-MS: m/z 453 (MH$^+$); $^1$H-NMR (CDCl$_3$): δ 2.02 (2H, quintet, J=6.5 Hz), 2.20 (3H, s), 2.26 (3H, s), 2.59 (2H, t, J=7 Hz), 3.53 (2H, s), 4.09 (2H, t, J=6 Hz), 5.10 (2H, s), 6.58 (1H, d, J=8 Hz), 6.7–6.9 (2H, m), 6.95–7.25 (4H, m), 7.62 (1H, dt, 8 Hz, 1.5 Hz), 8.42 (1H, dd, J=5 Hz, 1.5 Hz), 8.51 (1H, d, J=1.5 Hz).

EXAMPLE 47

Preparation of 5-(3-Cyclopropyl-4-{3-[(pyridin-3-ylmethyl)-amino]-propoxy}-benzofuran-2-ylmethoxy)-benzofuran-2-carboxylic Acid Ethylamide The compound in Example 38 was aminated by an analogous procedure to that of Example 39. Ethylamine was used instead of ammonia. FAB-MS: m/z 540 (MH$^+$); $^1$H-NMR (CD$_3$OD): δ 0.64–0.83 (4H, m), 1.26 (2H, t, J=7.3 Hz), 1.77–1.82 (1H, m), 2.08 (2H, quintet, J=6.3 Hz), 2.85 (2H, t, J=6.3 Hz), 3.44 (2H, q, J=7.3 Hz), 3.84 (2H, s), 4.16 (2H, t, J=6.3 Hz), 5.17 (2H, s), 6.68 (1H, d, J=7.3 Hz), 6.99 (1H, dd, J=7.3 Hz, 0.7 Hz), 7.13 (1H, dd, J=8.9 Hz, 2.6 Hz), 7.16 (1H, dd, J=7.3 Hz, 7.3 Hz), 7.32–7.51 (4H, m), 7.83 (1H, J=7.9 Hz), 8.41 (1H, dd, J=4.9 Hz, 1.6 Hz), 8.51 (1H, d, J=1.6 Hz).

EXAMPLE 48

Preparation of 5-(3-Cyclopropyl-4-{3-[(pyridin-3-ylmethyl)-amino]-propoxy}-benzofuran-2-ylmethoxy)-benzofuran-2-carboxylic Acid Cyclopropylamide The compound in Example 38 was aminated by a analogous procedure to that of Example 39. Cyclopropylamine was used instead of ammonia. FAB-MS: m/z 552 (MH$^+$); $^1$H-NMR (CD$_3$OD): δ 0.64–0.83 (8H, m), 1.68–1.74 (1H, m), 1.99 (2H, quintet, J=6.3 Hz), 2.73–2.80 (3H, m), 3.75 (2H, s), 4.07 (2H, t, J=6.3 Hz), 5.08 (2H, s), 6.59 (1H, d, J=7.3 Hz), 6.90 (1H, dd, J=7.3 Hz, 0.7 Hz), 7.04 (1H, dd, J=8.9 Hz, 2.6 Hz), 7.07 (1H, dd, J=7.3 Hz, 7.3 Hz), 7.23–7.42 (4H, m), 7.74 (1H, J=7.9 Hz), 8.32 (1H, dd, J=4.9 Hz, 1.6 Hz), 8.42 (1H, d, J=1.6 Hz).

EXAMPLE 49

Preparation of 3-[4-[2-(2-Ethoxymethyl-benzofuran-5-yloxymethyl)-3-methyl-benzofuran-4-yloxy]-piperidin-1-ylmethyl]-pyridine a) Preparation of [3-methyl-4-(1-pyridin-3-ylmethyl-piperidin-4-yloxy)-benzofuran-2-yl]-methanol:

To a cooled (0° C.) suspension of LiAlH$_4$ (17 mg) in THF (1 ml) was added a solution of 3-methyl-4-(1-pyridin-3-ylmethyl-piperidin-4-yloxy)-benzofuran-2-carboxylic acid ethyl ester (44 mg), the compound in Example 108, in THF (0.5 ml) and the resulting suspension was stirred at 0° C. for one hour. To the suspension was dropwise added a solution of KF (122 mg) in H$_2$O (100 μl) at 0° C. over five minutes. The suspension was stirred at room temperature for 30 minutes and diluted with ethyl acetate, dried over anhydrous sodium sulfate and evaporated to dryness. The residue was purified by preparative thin layer chromatography (using dichloromethane:MeOH=10:1 as a developing solvent) to give [3-methyl-4-(1-pyridin-3-ylmethyl-piperidin-4-yloxy)-benzofuran-2-yl]-methanol (33 mg) as a colorless oil. FAB-MS: m/z 353 (MH$^+$); $^1$H-NMR (CDCl$_3$): δ 2.00 (4H, m), 2.38 (3H, s), 2.42 (2H, m), 2.68 (2H, m), 3.55 (2H, s), 4.51 (1H, m), 4.71 (2H, s), 6.59 (1H, d, J=8 Hz), 7.00 (1H, d, J=8 Hz), 7.13 (1H, t, J=8 Hz), 7.26 (1H, dd, J1=8 Hz, J2=5 Hz), 7.68 (1H, dt, J1=8 Hz, J2=2 Hz), 8.51 (1H, dd, J1=5 Hz, J2=2 Hz), 8.54 (1H, d, J=2 Hz).

b) Preparation of 3-[4-[2-(2-ethoxymethyl-benzofuran-5-yloxymethyl)-3-methyl-benzofuran-4-yloxy]-piperidin-1-ylmethyl]-pyridine:

To a cooled (−30° C.) solution of [3-methyl-4-(1-pyridin-3-ylmethyl-piperidin-4-yloxy)-benzofuran-2-yl]-methanol (30 mg), 2-ethoxymethyl-benzofuran-5-ol (16 mg) and 1,1'-azobis(N,N-dimethylformamide) (37 mg) in THF (1 ml) was added tributylphosphine (53 μl) and the resulting solution was stirred overnight at −30° C. The resulting suspension was diluted with ethyl acetate, washed with water and brine, dried over anhydrous sodium sulfate and evaporated to dryness. The residue was purified by preparative thin layer chromatography (using dichloromethane:MeOH=20:1 as a developing solvent) to give 3-[4-[2-(2-ethoxymethyl-benzofuran-5-yloxymethyl)-3-methyl-benzofuran-4-yloxy]-piperidin-1-ylmethyl]-pyridine (27 mg) as a colorless oil. FAB-MS: m/z 527 (MH$^+$); $^1$H-NMR (CDCl$_3$): δ 1.26 (3H, t, J=7 Hz), 1.99 (4H, m), 2.41 (3H, s), 2.42 (2H, m), 2.70 (2H, m), 3.55 (2H, s), 3.61(2H, q, J=7 Hz), 4.52 (1H, m), 4.58 (2H, s), 5.10 (2H, s), 6.60 (1H, d, J=8 Hz), 6.63 (1H, s), 6.97 (1H, dd, J1=9 Hz, J2=2.5 Hz), 7.03 (1H, d, J=8 Hz), 7.15 (1H, t, J=8 Hz), 7.15 (1H, d, J=2.5 Hz), 7.26 (1H, dd, J1=8 Hz, J2=5 Hz), 7.37 (1H, d, J=9 Hz), 7.68 (1H, dt, J1=8 Hz, J2=2 Hz),8.51 (1H, dd, J1=5 Hz, J2=2 Hz), 8.56 (1H, d, J=2 Hz).

EXAMPLE 50

Preparation of [5-[3-Methyl-4-(1-pyridin-3-ylmethyl-piperidin-3-ylmethoxy)-benzofuran-2-ylmethoxy]-benzofuran-2-yl]-methanol a) Preparation of [3-methyl-4-(1-pyridin-3-ylmethyl-piperidin-3-ylmethoxy)-benzofuran-2-yl]-methanol:

To a cooled (0° C.) suspension of LiAlH$_4$ (223 mg) in THF (30 ml) was dropwise added a solution of 3-methyl-4-(1-pyridin-3-ylmethyl-piperidin-3-ylmethoxy)-benzofuran-2-carboxylic acid ethyl ester (600 mg), the compound in Example 111, in THF (20 ml) and the resulting suspension was stirred at 0° C. for one hour. To the suspension was dropwise added a solution of KF (1 g) in H$_2$O (1.2 ml) at 0° C. over 15 minutes. The suspension was stirred at room temperature for 30 minutes, diluted with ethyl acetate, dried over anhydrous sodium sulfate and evaporated to give [3-methyl-4-(1-pyridin-3-ylmethyl-piperidin-3-ylmethoxy)-benzofuran-2-yl]-methanol (532 mg) as a colorless oil. FAB-MS: m/z 367 (MH$^+$); $^1$H-NMR (CDCl$_3$): δ 1.13–2.25 (7H, m), 2.17 (3H, s), 2.81 (1H, br d, J=11 Hz), 2.93 (1H, br d, J=11 Hz), 3.42 (1H, d, J=13 Hz), 3.56 (1H, d, J=13 Hz), 3.84 (1H, dd, J1=9 Hz, J2=8 Hz), 3.96 (1H, dd, J1=9 Hz, J2=5 Hz), 4.68 (2H, s), 6.54(1H, d, J=8 Hz), 7.00 (1H, d, J=8 Hz, 7.13 (1H, t, J=8 Hz), 7.19 (1H, dd, J1=8 Hz, J2=5 Hz), 7.66 (1H, dt, J1=8 Hz, J2=2 Hz), 8.47 (2H, br s).

b) Preparation of 5-[3-methyl-4-(1-pyridin-3-ylmethyl-piperidin-3-ylmethoxy)-benzofuran-2-ylmethoxy]-benzofuran-2-carboxylic acid ethyl ester:

[3-Methyl-4-(1-pyridin-3-ylmethyl-piperidin-3-ylmethoxy)-benzofuran-2-yl]-methanol (107 mg), 5-hydroxybenzofuran-2-carboxylic acid ethyl ester (60 mg), triphenylphosphine (100 mg) and azodicarboxylic acid diethyl ester (70 μl) were dissolved in THF (7 ml). The solution was stirred overnight at room temperature. A white precipitate separated out. The precipitate was filtered out and the filtrate was evaporated to dryness. The residue was separated by silica gel column chromatography developed by dichloromethane-methanol to give 5-[3-methyl-4-(1-pyridin-3-ylmethyl-piperidin-3-ylmethoxy)-benzofuran-2-ylmethoxy]-benzofuran-2-carboxylic acid ethyl ester (48 mg) as a colorless oil. FAB-MS: m/z 555 (MH$^+$); $^1$H-NMR (CDCl$_3$): δ 1.25–2.23 (7H, m), 1.43 (3H, t, J=7 Hz), 2.24 (3H, s), 2.78 (1H, m), 2.95 (1H, m), 3.47 (1H, d, J=13 Hz), 3.57 (1H, d, J=13 Hz), 3.89 (2H, m), 4.44 (2H, q, J=7 Hz), 5.10 (2H, s), 6.55 (1H, d, J=8 Hz), 7.04 (1H, d, J=8 Hz), 7.14 (1H, dd, J1=9 Hz, J2=2 Hz), 7.23 (3H, m), 7.47 (1H, m), 7.48 (1H, s), 7.66 (1H, br d, J=7 Hz), 8.48 (1H, br d, J=5 Hz), 8.53 (1H, br s).

c) Preparation of [5-[3-methyl-4-(1-pyridin-3-ylmethyl-piperidin-3-ylmethoxy)-benzofuran-2-ylmethoxy]-benzofuran-2-yl]methanol:

To a cooled (0° C.) suspension of LiAlH$_4$ (12 mg) in THF (5 ml) was dropwise added a solution of 5-[3-methyl-4-(1-pyridin-3-ylmethyl-piperidin-3-ylmethoxy)-benzofuran-2-ylmethoxy]-benzofuran-2-carboxylic acid ethyl ester (42 mg) in THF (3 ml) and the resulting suspension was stirred at 0° C. for two hours. To the suspension was added H$_2$O (100 μl) dropwise at 0° C. The suspension was stirred at room temperature for four hours, diluted with ethyl acetate, dried over anhydrous sodium sulfate and evaporated to dryness. The residue was purified by preparative thin layer chromatography (using dichloromethane:MeOH=10:1 as a developing solvent) to afford [5-[3-methyl-4-(1-pyridin-3-ylmethyl-piperidin-3-ylmethoxy)-benzofaran-2-ylmethoxy]-benzofuran-2-yl]-methanol (26 mg) as a colorless oil. FAB-MS: m/z 513 (MH$^+$); $^1$H-NMR (CDCl$_3$): δ 1.25–2.20 (7H, m), 2.15 (3H, s), 2.80 (1H, m), 2.95 (1H, br d, J=9 Hz), 3.44 (1H, d, J=14 Hz), 3.59 (1H, d, J=14 Hz), 3.85 (1H, dd, J1=9 Hz, J2=8 Hz), 3.93 (1H, dd, J1=9 Hz, J2=5 Hz), 4.76 (2H, s), 5.09 (2H, s), 6.54 (1H, d, J=8 Hz), 6.61 (1H, s), 6.95 (1H, dd, J1=9 Hz, J2=2.5 Hz), 7.04 (1H, d, J=8 Hz), 7.12 (1H, d, J=2.5 Hz), 7.15 (1H, t, J=8 Hz), 7.17 (1H, dd, J1=8 Hz, J2=5 Hz), 7.35 (1H, d, J=9 Hz), 7.67 (1H, br d, J=8 Hz), 8.43 (1H, dd, J1=5 Hz, J2=1.5 Hz), 8.49 (1H, br s).

EXAMPLE 51

Preparation of Acetic acid 5-[3-methyl-4-(1-pyridin-3-ylmethyl-piperidin-3-ylmethoxy)-benzofuran-2-ylmethoxy]-benzofuran-2-ylmethyl Ester A solution of [5-[3-methyl-4-(1-pyridin-3-ylmethyl-piperidin-3-ylmethoxy)-benzofuran-2-ylmethoxy]-benzofuran-2-yl]-methanol (Example 50, 21 mg), acetic anhydride (100 μl) and pyridine (300 μl) was stirred at room temperature for one hour. The reaction mixture was dissolved in ethyl acetate and washed with saturated sodium hydrogencarbonate solution and water. The organic layer was washed with saturated ammonium chloride solution, dried over anhydrous sodium sulfate and evaporated to dryness to give acetic acid 5-[3-methyl-4-(1-pyridin-3-ylmethyl-piperidin-3-ylmethoxy)-benzofuran-2-ylmethoxy]-benzofuran-2-ylmethyl ester (22 mg) as a colorless oil. FAB-MS: m/z 555 (MH$^+$); $^1$H-NMR (CDCl$_3$): δ 1.25–2.23 (7H, m), 2.12 (3H, s), 2.23 (3H, s), 2.78 (1H, m), 2.97 (1H, br d, J=11 Hz), 3.47 (1H, d, J=13 Hz), 3.57 (1H, d, J=13 Hz), 3.86 (1H, dd, J1=9 Hz, J2=7 Hz), 3.94 (1H, dd, J1=9 Hz, J2=5 Hz), 5.09 (2H, s), 5.18 (2H, s), 6.55 (1H, d, J=8 Hz), 6.72 (1H, s), 7.00 (1H, dd, J1=9 Hz, J2=2.5 Hz), 7.04 (1H, d, J=8 Hz), 7.15 (1H, t, J=8 Hz), 7.16 (1H, d, J=2.5 Hz), 7.20 (1H, dd, J1=8 Hz, J2=5 Hz), 7.38 (1H, d, J=9 Hz), 7.66 (1H, br d, J=8 Hz), 8.48 (1H, br d, J=5 Hz), 8.53 (1H, br s).

EXAMPLE 52

Preparation of [3-(2-Ethoxymethyl-3-methyl-benzofuran-4-yloxy)-propyl]-pyridin-3-ylmethyl-amine a) Preparation of [3-(2-ethoxymethyl-3-methyl-benzofuran-4-yloxy)-propyl]-pyridin-3-ylmethyl-carbamic acid benzyl ester:

A mixture of compound in Example 11 (100 mg), benzyloxycarbonyl chloride (48 μl) and triethylamine (85 μl) was stirred overnight. The reaction mixture was purified by silica gel column chromatography developed by dichloromethane-methanol=40:1. [3-(2-hydrooxymethyl-3-methyl-benzofuran-4-yloxy)-propyl]-pyridin-3-ylmethyl-carbamic acid benzyl ester was obtained as a colorless solid (102 mg). ESI-MS: m/z 461 (MH$^+$). To a suspension of the compound obtained above (26 mg) and NaH (60%, 5 mg) in DMF (1 ml) was added ethyl iodide (7 μl) and the resulting suspension was stirred overnight at room temperature. The reaction mixture was diluted with ethyl acetate and washed with water and brine. The organic solvent was dried over anhydrous sodium sulfate and evaporated to dryness. The residue was purified by preparative thin layer chromatography (using dichloromethane:MeOH=10:1 as a developing solvent) to give [3-(2-ethoxymethyl-3-methyl-benzofuran-4-yloxy)-propyl]-pyridin-3-ylmethyl-carbamic acid benzyl ester (19 mg) as a colorless oil. FAB-MS: m/z 489 (MH$^+$); $^1$H-NMR (CDCl$_3$): δ 1.23 (3H, t, J=7 Hz), 2.07 (2H, br s), 2.29 (3H, m), 3.52 (2H, m), 3.56 (2H, q, J=7 Hz), 4.01 (2H, br s), 4.53 (4H, s), 5.16 (2H, s), 6.48 (1H, br s), 7.04 (1H, d, J=8 Hz), 7.13 (1H, t, J=8 Hz), 7.06–7.59 (7H, m), 8.52 (2H, m).

b) Preparation of [3-(2-ethoxymethyl-3-methyl-benzofuran-4-yloxy)-propyl]-pyridin-3-ylmethyl-amine:

To a solution of [3-(2-ethoxymethyl-3-methyl-benzofuran-4-yloxy)-propyl]-pyridin-3-ylmethyl-carbamic acid benzyl ester (19 mg) in ethyl acetate (1 ml) was added 5% Pd on charcoal catalyst (10 mg) under N2. The nitrogen atmosphere was replaced by hydrogen (1 atom) and the resulting mixture was stirred overnight at room temperature. The reaction mixture was filtered through a pad of celite and washed with methanol and dichloromethane. The filtrate combined was concentrated in vacuo. The residue was purified by preparative thin layer chromatography (using dichloromethane : MeOH : ammonia solution (25–28%)= 10:1:0.2 as a developing solvent) to give [3-(2-ethoxymethyl-3-methyl-benzofuran-4-yloxy)-propyl]-pyridin-3-ylmethyl-amine (9 mg) as a colorless oil. ESI-MS: m/z 355 (MH$^+$); $^1$H-NMR (CDCl$_3$): δ 1.24 (3H, t, J=7 Hz), 2.06 (2H, quintet, J=6.5 Hz), 2.31 (3H, s), 2.89 (2H, t, J=7 Hz), 3.56 (2H, q, J=7 Hz), 3.85 (2H, s), 4.14 (2H, t, J=6 Hz), 4.54 (2H, s), 6.58 (1H, d, J=8 Hz), 7.04 (1H, d, J=8 Hz), 7.14 (1H, t, J=8 Hz), 7.21 (1H, dd, J1=8 Hz, J2=5 Hz), 7.68 (1H, dd, J1=8 Hz, J2=2 Hz), 8.49 (1H, dd, J1=5 Hz, J2=2 Hz), 8.57 (1H, d, J=2 Hz).

EXAMPLE 53

Preparation of [3-[2-(2-Cyclohexyl-ethoxymethyl)-3-methyl-benzofuran-4-yloxy]-propyl]-pyridin-3-ylmethyl-amine The title compound was prepared in a similar manner to Example 52 as a colorless oil. FAB-MS: m/z 437 (MH$^+$);

¹H-NMR (CDCl₃): δ 0.85 (2H, m), 1.18 (2H, m), 1.31 (1H, m), 1.49 (2H, m), 2.01 (2H, m), 2.31 (3H, s), 2.89 (2H, t, J=6.9 Hz), 3.51 (2H, t, J=6.9 Hz), 3.85 (2H, s), 4.14 (2H, t, J=6.9 Hz), 4.52 (2H, s), 6.58 (1H, d, J=7.6 Hz), 7.04 (1H, d, J=7.6 Hz), 7.11 (1H, d, J=7.6 Hz), 7.22 (1H, m), 7.68 (1H, d, J=7.8 Hz), 8.48 (1H, brd, J=4.5 Hz), 8.57 (1H, brs).

EXAMPLE 54

Preparation of [3-[2-(3,5-Dimethoxy-benzyloxymethyl)-3-methyl-benzofuran-4-yloxy]-propyl]-pyridin-3-ylmethyl-amine The title compound was obtained in a similar manner to Example 52 as a colorless oil. FAB-MS: m/z 477(MH⁺): ¹H-NMR (CDCl₃): δ 1.97 (2H, m), 2.22 (3H, s), 2.81 (1H, t, J=6.9 Hz), 3.72 (6H, s), 3.77 (3H, s), 4.08 (1H, t, J=5.9 Hz), 4,45 (2H, s), 4.50 (2H, s), 6.32 (1H, d, J=2.5 Hz), 6.46 (1H, s), 6.47 (s, 1H), 6.52 (1H, d, J=7.6 Hz); 6.97 (1H, d, J=7.6 Hz), 7.06 (1H, d, J=8.3 Hz), 7.15 (1H, m), 7.58 (1H, d, J=6.7 Hz), 8.41 (1H, dd, J=5 Hz, 0.5 Hz), 8.49 (1H, d, J=0.5 Hz).

EXAMPLE 55

Preparation of Isopropyl-[3-(3-methyl-2-phenethylsulfanylmethyl-benzofuran-4-yloxy)-propyl]-amine a) Preparation of 4-(3-isopropylamino-propoxy)-3-methyl-benzofuran-2-carboxylic acid ethyl ester:

Starting form 4-hydroxy-3-methylbenzofuran-2-carboxylic acid ethyl ester (Joseph G. Atkinson et al., European patent application 0146243 (1985)) 4-(3-isopropylamino-propoxy)-3-methyl-benzofuran-2-carboxylic acid ethyl ester was prepared in a similar manner to Examples 5-a and 5-b. MALDI-TOF-MS: 320 (MH⁺).

b) Preparation of [4-(3-isopropylamino-propoxy)-3-methyl-benzofuran-2-yl]-methanol:

This compound was obtained in a similar manner to Example 10 starting form the compound above. ESI-MS: m/z 278 (MH⁺).

c) Preparation of isopropyl-[3-(3-methyl-2-phenethylsulfanylmethyl-benzofuran-4-yloxy)-propyl]-amine:

To a solution of [4-(3-isopropylamino-propoxy)-3-methyl-benzofuran-2-yl]-methanol (14 mg, 0.05 mmol) and phenethyl mercaptan (10.3 mg, 0.075 mmol) in anhydrous CH₂Cl₂ (0.9 ml) was added TFA (0.2 ml). The Mixture was stirred at room temperature for 2.5 hours. The solvent was removed in vacuo. The residue was purified over preparative TLC (CH₂Cl₂/MeOH=100/1) to give desired compound (15 mg, 74%). FAB-MS: m/z 398 (MH⁺); ¹H-NMR (CDCl₃): δ 1.11 (6H, d, J=6.2 Hz), 2.05 (2H, m), 2.34 (3H, s), 2.61–2.96 (7H, m), 3.80 (2H, s), 4.11 (2H, m), 6.56 (1H, m), 6.95–7.28 (7H, m).

EXAMPLE 56

Preparation of [3-(3-Methyl-2-phenethylsulfanylmethyl-benzofuran-4-yloxy)-propyl]-pyridin-3-ylmethyl-amine To a solution of the compound in Example 11 (20 mg, 0.06 mmol) and phenethyl mercaptan (30 mg) in anhydrous CH₂Cl₂ (0.9 ml) was added trifluoroacetic acid (TFA, 0.2 ml). The mixture was stirred at room temperature for 2.5 hours. The solvent was removed under reduced pressure. The residue was purified over preparative TLC (CH₂Cl₂/MeOH=100/1) to give the desired compound (26 mg, 95%) as a colorless oil. FAB-MS: m/z 446 (MH⁺); ¹H-NMR (CDCl₃): δ 2.10 (2H, m), 2.32 (3H, s), 2.79–2.97 (6H, m), 3.54 (2H, s), 3.85 (2H, s), 3.90 (2H, s), 6.63 (1H, d, J=7.6 Hz), 7.09–7.30 (3H, m), 7.71 (1H, d, J=7.8 Hz), 8.55 (1H, d, J=2.0 Hz), 8.62 (1H, s).

Following compounds in Examples 57 to 60 were prepared in a similar manner to Examples 56.

EXAMPLE 57

Preparation of [3-(3-Methyl-2-phenylsulfanylmethyl-benzofuran-4-yloxy)-propyl]-pyridin-3-ylmethyl-amine ESI-MS: m/z 419 (MH⁺); ¹H-NMR (CDCl₃): δ 1.99 (3H, s), 2.03 (2H, q, J=6.3 Hz), 2.91 (2H, t, J=6.3 Hz), 3.87 (2H, s), 4.09 (2H, t, J=6.3 Hz), 4.13 (2H, s), 6.55 (1H, d, J=7.6 Hz), 7.02 (1H, dd, J=8.9 Hz, 0.7 Hz), 7.12 (1H, dd, J=7.6 Hz, 8.9 Hz), 7.20–7.40 (6H, m), 7.68 (1H, d, 7.6 Hz), 8.50 (1H, dd, J=1.7 Hz, 4.6 Hz), 8.57 (1H, d, J=1.7 Hz).

EXAMPLE 58

Preparation of {3-[2-(4-Chloro-phenylsulfanylmethyl)-3-methyl-benzofuran-4-yloxy]-propyl}-pyridin-3-ylmethyl-amine ESI-MS: m/z 453 (MH⁺); ¹H-NMR (CDCl₃): δ 1.98–2.09 (5H, m), 2.86 (2H, t, J=7.3 Hz), 3.83 (2H, s), 4.10 (2H, s), 4.12 (2H, t, J=7.3 Hz), 6.57 (1H, d, J=7.6 Hz), 7.01 (1H, dd, J=8.9 Hz, 0.7 Hz), 7.13 (1H, dd, J=7.6 Hz, 8.1 Hz), 7.20–7.31 (5H, m), 7.65 (1H, d, 7.6 Hz), 8.50 (1H, dd, J=1.7 Hz, 4.6 Hz), 8.56 (1H, d, J=1.7 Hz).

EXAMPLE 59

Preparation of {3-[2-(4-Chloro-benzylsulfanylmethyl)-3-methyl-benzofuran-4-yloxy]-propyl}-pyridin-3-ylmethyl-amine ESI-MS: m/z 467 (MH⁺); ¹H-NMR (CDCl₃): δ 2.05 (2H, quintet, J=6.3 Hz), 2.17 (3H, s), 2.88 (2H, t, J=7.3 Hz), 3.67 (2H, s), 3.69 (2H, s), 3.84 (2H, s), 3.69 (2H, t, J=7.3 Hz), 6.58 (1H, d, J=7.6 Hz), 7.02 (1H, dd, J=8.9 Hz, 0.7 Hz), 7.12–7.30 (6H, m), 7.65–7.69 (1H, m), 8.49 (1H, dd, J=1.7 Hz, 4.6 Hz), 8.56 (1H, d, J=1.7 Hz).

EXAMPLE 60

Preparation of [3-(2-Ethylsulfanylmethyl-3-methyl-benzofuran-4-yloxy)-propyl]-pyridin-3-ylmethyl-amine ESI-MS: m/z 371 (MH⁺); ¹H-NMR (CD₃OD): δ 1.20 (3H, t, J=7.58 Hz), 2.07 (2H, quintet, J=7.3 Hz), 2.12 (3H, s), 2.54 (2H, q, J=7.6 Hz), 2.87 (2H, t, J=7.3 Hz), 3.80 (2H, s), 3.87 (2H, s), 4.13 (2H, t, J=7.3 Hz), 6.64 (1H, d, J=7.6 Hz), 6.94 (1H, d, J=7.6 Hz), 7.11 (1H, dd, J=7.6 Hz, 7.6 Hz), 7.37 (1H, dd, J=5.28 Hz, 7.92 Hz), 7.82–7.85 (1H, m), 8.42 (1H, dd, J=1.7 Hz, 4.6 Hz), 8.52 (1H, d, J=1.7 Hz).

EXAMPLE 61

Preparation of (RS)-[3-[3-Methyl-2-(2-phenyl-ethylsulfinylmethyl)-benzofuran-4-yloxy]-propyl]-pyridin-3-ylmethyl-amine To a solution of the compound in Example 56 (20 mg, 0.04 mmol) in CH₂Cl₂/TFA (8/2) (1 ml) was added m-CPBA (14 mg, 80%, 0.06 mmol) at 0° C. The mixture was stirred for 2 hours at room temperature. The solvent was removed under reduced pressure. The residue was purified over preparative TLC (CH$_2$Cl$_2$/MeOH=100/1) to give the desired compound (7.5 mg, 36%) as a colorless oil. FAB-MS: m/z 463 (MH$^+$); $^1$H-NMR (CDCl$_3$): δ 1.97 (2H, m), 2.24 (3H, s), 2.81 (2H, t, J=6.9 Hz), 2.88–3.07 (4H, m), 3.77 (2H, s), 4.04–4.10 (4H, m), 6.52 (1H, d, J=7.6 Hz), 6.91 (1H, d, J=7.6 Hz), 7.05–7.22 (7H, m), 7.58 (1H, d, J=7.8 Hz) 8.41 (1H, brd, J=4.5 Hz), 8.48 (1H, brs).

EXAMPLE 62

Preparation of 3-Methyl-4-{3-[(pyridin-3-ylmethyl)-amino]-propoxy}-benzofuran-2-carboxylic Acid (2-cyclohexyl-ethyl)-amide a) Preparation of 4-(3-bromo-propoxy)-3-methyl-benzofuran-2-carboxylic acid:

4-(3-Bromo-propoxy)-3-methyl-benzofuran-2-carboxylic acid ethyl ester (27.3 g), the compound in Example 5-a, was dissolved in THF (546 ml) and cooled at 0° C. To the solution were added LiOH.H$_2$O (6.72 g), water (410 ml) and MeOH (135 ml). The mixture was stirred at room temperature for seven hours. To the reaction mixture was added 1N-HCl (133 ml). After evaporating the organic solvent, the mixture was mixed with ethyl acetate (1,400 ml). The organic layer was dried over anhydrous sodium sulfate and evaporated to give colorless needles. The colorless needles were washed with ethyl acetate-hexane (2:8) to obtain pure 4-(3-bromo-propoxy)-3-methyl-benzofuran-2-carboxylic acid (28.3 g). FAB-MS: m/z 312 (M$^+$); $^1$H-NMR (CDCl$_3$): δ 2.43 (2H, quintet, J=6.5 Hz), 2.78 (3H, s), 3.66 (2H, t, J=6.5 Hz), 4.25 (2H, t, J=6.5 Hz), 6.67 (1H, d, J=8 Hz), 7.17 (1H, d, J=8 Hz), 7.38 (1H, t, J=8 Hz).

b) Preparation of 4-(3-bromo-propoxy)-3-methyl-benzofuran-2-carboxylic acid (2-cyclohexyl-ethyl)-amide:

4-(3-Bromo-propoxy)-3-methyl-benzofuran-2-carboxylic acid (1 g) was refluxed in thionylchloride (10 ml) for three hours. Thionylchloride was evaporated to dryness and the residue was dissolved in dry dichloromethane (15 ml). To the solution was added 2-cyclohexylethylamine (405 mg) in dry dichloromethane (5 ml). The mixture was stirred at room temperature for one hour. The mixture was purified by silica gel column chromatography (dichloromethane). The main product was crystallized from hexane to give 4-(3-bromo-propoxy)-3-methyl-benzofuran-2-carboxylic acid (2-cyclohexyl-ethyl)-amide as colorless needles (930 mg). FAB-MS: m/z 442 (M$^+$); $^1$H-NMR (CDCl$_3$): δ 0.85–1.85 (13H, m), 2.41 (2H, quintet, J=6.5 Hz), 2.78 (3H, s), 3.45 (2H, m), 3.65 (2H, t, J=6.5 Hz), 4.22 (2H, t, J=6.5 Hz), 6.53 (1H, t, J=6 Hz), 6.65 (1H, d, J=8 Hz), 7.05 (1H, d, J=8 Hz), 7.29 (1H, t, J=8 Hz).

c) Preparation of 3-methyl-4-{3-[(pyridin-3-ylmethyl)-amino]-propoxy}-benzofuran-2-carboxylic acid (2-cyclohexyl-ethyl)-amide:

4-(3-Bromo-propoxy)-3-methyl-benzofuran-2-carboxylic acid (2-cyclohexyl-ethyl)-amide (100 mg) and 3-picolyl amine (250 µl) were dissolved in 1-methylpyrrolidone (2 ml) and heated at 100° C. for two hours. The reaction mixture was dissolved in ethyl acetate and washed with saturated ammonium chloride solution and water. The organic solvent was dried over anhydrous sodium sulfate and evaporated to dryness. The residue was purified by silica gel column chromatography (dichloromethane-MeOH) to afford 3-methyl-4-{3-[(pyridin-3-ylmethyl)-amino]-propoxy}-benzofuran-2-carboxylic acid (2-cyclohexyl-ethyl)-amide. ESI-MS: m/z 450 (MH$^+$); $^1$H-NMR (CDCl$_3$): δ 0.85–1.85 (13H, m), 2.05 (2H, quintet, J=6.5 Hz), 2.72 (3H, s), 2.90 (2H, t, J=6.5 Hz), 3.46 (2H, m), 3.85 (2H, s), 4.15 (2H, t, J=6.5 Hz), 6.53 (1H, t, J=6 Hz), 6.62 (1H, d, 8 Hz), 7.01 (1H, d, J=8 Hz), 7.26 (2H, m), 7.68 (1H, dd, J=1.5 Hz, 8 Hz), 8.49 (1H, br d, J=3.5 Hz), 8.56 (1H, br s).

EXAMPLE 63

Preparation of 3-Methyl-4-(3-pyrrolidin-1-yl-propoxy)-benzofuran-2-carboxylic Acid (2-cyclohexyl-ethyl)-amide This compound was obtained from 4-(3-bromo-propoxy)-3-methyl-benzofuran-2-carboxylic acid (2-cyclohexyl-ethyl)-amide according to a manner analogous to that of Example 62. ESI-MS: m/z 413 (MH$^+$); $^1$H-NMR (CDCl$_3$): δ 0.85–1.85 (17H, m), 2.12 (2H, quintet, J=6 Hz), 2.60 (4H, m), 2.73 (2H, t, J=6 Hz), 2.78 (3H, s), 3.47 (2H, m), 4.14 (2H, t, J=6 Hz), 6.53 (1H, t, J=6 Hz), 6.62 (1H, d, J=8 Hz), 7.00 (1H, d, J=8 Hz), 7.26 (1H, t, J=8 Hz).

EXAMPLE 64

Preparation of 4-[[4-(3-tert-Butylamino-propoxy)-3-methyl-benzofuran-2-carbonyl]-amino]-benzoic Acid Ethyl Ester To a stirred solution of 4-(3-tert-butylamino-propoxy)-3-methyl-benzofuran-2-carboxylic acid ethyl ester (1938 mg), the compound in Example 5-b, in methanol (15 ml) was added 1.0N aqueous sodium hydroxide (8.70 ml) at room temperature. After 5 hours the reaction mixture was neutralized by an addition of 1.0N aqueous hydrochloric acid (8.70 ml) and the solvent was evaporated under reduced pressure to give a white solid (2.33 g). To this solid were added dichloromethane (50 ml) and thionyl chloride (25 g). After 9 hours at reflux temperature the reaction mixture was concentrated to dryness to give a white solid (2.58 g) which was the mixture of 4-(3-tert-butylamino-propoxy)-3-methyl-benzofuran-2-carboxylic acid chloride hydrochloride and sodium chloride.

The mixture (50 mg) obtained above and ethyl 4-aminobenzoate (45.8 mg) were dissolved in N,N-dimethylformamide (2 ml) and stirred at 50° C. for 15 hours. To a mixture water (2 ml) and dichloromethane (2 ml)were added and the organic layer was separated. After evaporation of the solvent under reduced pressure, the crude product was purified by silica gel column chromatography (Fuji Silysia, DU-3050) using 3:2 mixture of n-hexane and ethyl acetate as an eluent to give 4-[[4-(3-tert-butylamino-propoxy)-3-methyl-benzofuran-2-carbonyl]-amino]-benzoic acid ethyl ester (20 mg) as colorless needles. EI-MS: m/z 452 (M$^+$); NMR (CDCl$_3$): δ 1.12 (9H, s), 1.40 (3H, t, J=7.26 Hz), 2.04 (2H, quintet, J=4.94 Hz), 2.83 (2H, t, J=7.25 Hz), 2.85 (3H, s), 4.18 (2H, t, J=5.93 Hz), 4.38 (2H, q, J=7.26 Hz), 6.67 (1H, d, J=7.92 Hz), 7.08 (1H, d, J=8.24 Hz), 7.34 (1H, t, J=8.25 Hz), 7.79 (2H, d, J=8.58 Hz), 8.06 (2H, d, J=8.58 Hz), 8.44 (1H, brs).

EXAMPLE 65

Preparation of 2-[[4-(3-tert-Butylamino-propoxy)-3-methyl-benzofuran-2-carbonyl]-amino]-benzoic Acid Ethyl Ester Using ethyl 2-aminobenzoate in the place of ethyl 4-aminobenzoate, the title compound was prepared in a manner analogous to Example 64. Colorless viscous oil. EI-MS: m/z 452 (M$^+$); NMR (CDCl$_3$): δ 1.12 (9H, s), 1.46 (3H, t, J=7.26 Hz), 2.04 (2H, quintet, J=6.60 Hz), 2.84 (2H, t, J=7.25 Hz), 2.86 (3H, s), 4.17 (2H, t, J=5.93 Hz), 4.47 (2H, q, J=6.92 Hz), 6.65 (1H, d, J=7.92 Hz), 7.12 (1H, t, J=6.63 Hz), 7.18 (1H, d, J=8.58 Hz), 7.32 (1H, t, J=8.25 Hz), 7.57 (1H, t, J=6.93 Hz), 8.10 (1H, d, J=6.60 Hz), 8.89 (1H, d, J=8.57 Hz), 12.07 (1H, brs).

EXAMPLE 66

Preparation of 3-Methyl-4-{3-[(pyridin-3-ylmethyl)-amino]-propoxy}-benzofuran-2-carboxylic Acid (2, 4-difluorophenyl)-amide 4-Bromopropoxy-3-methyl-benzofuran-2-carbonyl chloride was obtained by refluxing the carboxylic acid in Example 62-a in thionyl chloride. This acid chloride (166 mg), 2,4-difluoroaniline (71 mg) and triethylamine (61 mg) in dichloromethane were stirred for 2 hours at room temperature. The solvent was removed under reduced pressure, and the residue was dissolved in ethanol (5 ml). The solution was heated with 3-methylamino-pyridine (541 mg) at 80° C. for 18 hours. The mixture was quenched by saturated ammonium chloride solution, and extracted with ethyl acetate. The organic layer was washed with brine and dried over sodium sulfate. The solution was concentrated under reduced pressure, and the residue was purified on silica gel column chromatography (dichloromethane/methanol) to give a purple solid (142 mg, 63%): FAB-MS: m/z 452 (MH$^+$); $^1$H-NMR (CDCl$_3$): δ 2.09 (2H, t, J=6.3 Hz, CH2), 2.76 (3H, s, CH3), 2.90 (2H, t, J=6.3 Hz, NCH2), 3.86 (2H, s, NCH2), 4.18 (2H, t, J=6.3 Hz, OCH2), 6.65 (1H, d, J=8.3 Hz, Ar—H), 6.92 (2H, m, 2×Ar—H), 7.10 (1H, d, J=7.9 Hz, Ar—H), 7.22 (2H, m, 2×Ar—H), 7.33 (1H, t, J=8.3 Hz, Ar—H), 7.67 (1H, m, Ar—H), 8.48 (1H, m, Ar—H), 8.58 (1H, br, Ar—H).

Following compounds in Example 67 to Example 74 were prepared in a similar manner to Example 66.

EXAMPLE 67

Preparation of 3-Methyl-4-{3-[(pyridin-3-ylmethyl)-amino]-propoxy}-benzofuran-2-carboxylic Acid (2, 3,4-trifluorophenyl)-amide Colorless solid. FAB-MS: m/z 470 (MH$^+$); $^1$H-NMR (CDCl$_3$): δ 2.08 (2H, m, CH2), 2.76 (3H, s, CH3), 2.90 (2H, t, J=6.9 Hz, NCH2), 3.85 (2H, s, NCH2), 4.18 (2H, t, J=6.3 Hz, OCH2), 6.65 (1H, d, J=7.9 Hz, Ar—H), 6.96 (1H, m, Ar—H), 7.09 (1H, d, J=8.3 Hz, Ar—H), 7.22 (1H, m, Ar—H), 7.34 (1H, t, J=8.3 Hz, Ar—H), 7.68 (1H, m, Ar—H), 8.20 (1H, m, Ar—H), 8.40 (1H, br, Ar—H), 8.50 (1H, d, J=5.0 Hz, Ar—H), 8.57 (1H, br, Ar—H).

EXAMPLE 68

Preparation of 3-Methyl-4-{3-[(pyridin-3-ylmethyl)-amino]-propoxy}-benzofuran-2-carboxylic Acid (2-fluorophenyl)-amide Colorless needles. FAB-MS: m/z 434 (MH$^+$); $^1$H-NMR (CDCl$_3$): δ 2.09 (2H, tt, J=6.3 Hz, 5.9 Hz CH2), 2.77 (3H, s, CH3), 2.93 (2H, t, J=6.9 Hz, NCH2), 3.86 (2H, s, NCH2), 4.18 (2H, t, J=5.9 Hz, OCH2), 6.66 (1H, d, J=7.9 Hz, Ar—H), 7.04–7.25 (5H, m, 5×Ar—H), 7.33 (1H, t, J=8.3 Hz, Ar—H), 7.68 (1H, d, J=7.6 Hz, Ar—H), 8.46–8.57 (3H, m, 3×Ar—H).

EXAMPLE 69

Preparation of 3-Methyl-4-{3-[(pyridin-3-ylmethyl)-amino]-propoxy}-benzofuran-2-carboxylic Acid (4-morpholin-4-yl-phenyl)-amide Yellow oil. FAB-MS: m/z 501 (MH$^+$); $^1$H-NMR (CDCl$_3$): δ 2.05 (2H, tt, J=6.9 Hz, 5.9 Hz, CH2), 2.75 (3H, s, CH3), 2.89 (2H, t, J=6.9 Hz, NCH2), 3.14 (4H, t, J=4.6 Hz, 2×NCH2), 3.84 (2H, s, NCH2), 3.86 (4H, t, J=4.6 Hz, 2×OCH2), 4.16 (2H, t, J=5.9 Hz, OCH2), 6.64 (1H, d, J=7.9 Hz, Ar—H), 6.92 (2H, dt, J=2.0 Hz, 6.9 Hz, 2×Ar—H), 7.18–7.25 (1H, m, Ar—H), 7.30 (1H, t, J=8.3 Hz, Ar—H), 7.60 (2H, dd J=2.0 Hz, 7.6 Hz, 2×Ar—H), 7.69 (1H, dt, J=2.0 Hz, 7.6 Hz, Ar—H), 8.27 (1H, br, NH), 8.48 (1H, d, J=3.6 Hz, Ar—H), 8.55 (1H, br, Ar—H).

EXAMPLE 70

Preparation of 3-Methyl-4-{3-[(pyridin-3-ylmethyl)-amino]-propoxy}-benzofuran-2-carboxylic Acid benzo[1,3]dioxol-5-yl Amide Colorless oil. FAB-MS: m/z 460 (MH$^+$); $^1$H-NMR (CDCl$_3$): δ 2.07 (2H, tt, J=6.2 Hz, 6.6 Hz, CH2), 2.75 (3H, s, CH3), 2.89 (2H, t, J=6.6 Hz, NCH2), 3.85 (2H, s, NCH2), 4.17 (2H, t, J=6.2 Hz, OCH2), 5.97 (2H, s, OCH2O), 6.64 (1H, d, J=7.9 Hz, Ar—H), 6.79 (2H, d, J=8.3 Hz, 2×Ar—H), 6.99 (1H, dd, J=2.3 Hz, 8.3 Hz, Ar—H), 7.06 (1H, d, J=7.9 Hz, Ar—H), 7.13–7.25 (1H, m, Ar—H), 7.31 (1H, t, J=8.3 Hz, Ar—H), 7.42 (1H, d, J=2.3 Hz, Ar—H), 7.67 (1H, dt, J=2.0 Hz, 7.9 Hz, Ar—H), 8.23 (1H, br, NH), 8.49 (1H, dd, J=5.0 Hz, 1.7 Hz, Ar—H), 8.57 (1H, d, J=1.7 Hz, Ar—H).

EXAMPLE 71

Preparation of 3-Methyl-4-{3-[(pyridin-3-ylmethyl)-amino]-propoxy}-benzofuran-2-carboxylic Acid (3, 5-dimethoxy-phenyl)-amide Colorless oil. FAB-MS: m/z 476 (MH$^+$); $^1$H-NMR (CDCl$_3$): δ 2.06 (2H, tt, J=6.3 Hz, 6.6 Hz, CH2), 2.77 (3H, s, CH3), 2.90 (2H, t, J=6.9 Hz, NCH2), 3.83 (6H, s, OCH3), 3.85 (2H, s, NCH2), 4.18 (2H, t, J=6.3 Hz, OCH2), 6.28 (1H, t, J=2.3 Hz, Ar—H), 6.66 (1H, d, J=7.6 Hz, Ar—H), 6.96 (2H, d, J=2.3 Hz, 2×Ar—H), 7.08 (1H, d, J=7.9 Hz, Ar—H), 7.21–7.24 (1H, m, Ar—H), 7.23 (1H, t, J=8.3 Hz, Ar—H), 7.68 (1H, dt, J=8.3 Hz, 2.3 Hz, Ar—H), 8.27 (1H, br, NH), 8.49 (1H, dd, J=4.6 Hz, 1.6 Hz, Ar—H), 8.57 (1H, d, J=2.0 Hz, Ar—H).

EXAMPLE 72

Preparation of 3-Methyl-4-{3-[(pyridin-3-ylmethyl)-amino]-propoxy}-benzofuran-2-carboxylic Acid phenyl-amide Colorless oil. FAB-MS: m/z 416 (MH$^+$); $^1$H-NMR (CDCl$_3$): δ 2.10 (2H, tt, J=6.3 Hz, 6.6 Hz, CH2), 2.76 (3H, s, CH3), 2.91 (2H, t, J=6.6 Hz, NCH2), 3.86 (2H, s, NCH2), 4.17 (2H, t, J=5.9 Hz, OCH2), 6.64 (1H, d, J=8.3 Hz, Ar—H), 7.07 (1H, d, J=8.3 Hz, Ar—H), 7.15 (1H, t, J=7.3 Hz, Ar—H), 7.21–7.24 (1H, m, Ar—H), 7.30 (1H, d, J=8.3 Hz, Ar—H), 7.38 (2H, t, J=8.3 Hz, 2×Ar—H), 7.70 (3H, d, J=7.9 Hz, 3×Ar—H), 8.31 (1H, br, NH), 8.50 (1H, d, J=3.6 Hz, Ar—H), 8.58 (1H, br, Ar—H).

EXAMPLE 73

Preparation of 3-Methyl-4-{3-[(pyridin-3-ylmethyl)-amino]-propoxy}-benzofuran-2-carboxylic Acid (4-chloro-phenyl)-amide Colorless solid. FAB-MS: m/z 450 (MH$^+$); $^1$H-NMR (CDCl$_3$): δ 2.08 (2H, tt, J=6.6 Hz, 6.6 Hz, CH2), 2.74 (3H, s, CH3), 2.90 (2H, t, J=6.9 Hz, NCH2), 3.86 (2H, s, NCH2), 4.18 (2H, t, J=5.9 Hz, OCH2), 6.66 (1H, d, J=7.9 Hz, Ar—H), 7.08 (1H, d, J=8.3 Hz, Ar—H), 7.26–7.36 (4H, m, 4×Ar—H), 7.66 (2H, dt, J=8.6 Hz, 1.7 Hz, 2×Ar—H), 7.74 (1H, dd, J=7.9 Hz, 1.6 Hz, Ar—H), 8.46 (1H, d, J=4.3 Hz, Ar—H), 8.52 (1H, br, Ar—H).

EXAMPLE 74

Preparation of 3-Methyl-4-{3-[(pyridin-3-ylmethyl)-amino]-propoxy}-benzofuran-2-carboxylic Acid (2-chloro-phenyl)-amide Colorless solid. FAB-MS: m/z 450 (MH$^+$); $^1$H-NMR (CDCl$_3$): δ 2.11 (2H, tt, J=6.6 Hz, 6.6 Hz, CH2), 2.74 (3H, s, CH3), 2.91 (2H, t, J=6.6 Hz, NCH2), 3.86 (2H, s, NCH2), 4.19 (2H, t, J=5.9 Hz, OCH2), 6.67 (1H, d, J=7.9 Hz, Ar—H), 7.07–7.14 (2H, m, 2×Ar—H), 7.28–7.36 (4H, m, 4×Ar—H), 7.44 (1H, d, J=7.9 Hz, Ar—H), 7.75 (1H, d, J=7.9 Hz, Ar—H), 8.46–8.54 (2H, m, 2×Ar—H).

EXAMPLE 75

Preparation of (3-Methyl-4-{3-[pyridin-3-ylmethyl)-amino]-propoxy}-benzofuran-2-yl Phosphonic Acid Diethyl Ester a) Preparation of 2-bromo-4-(3-bromo-propoxy)-3-methyl-benzofuran:

To a solution of 4-(3-bromo-propoxy)-3-methyl-benzofuran-2-carboxylic acid (the compound in Example 62-a, 1.5 g) and triethylamine (0.756 g) in dichloromethane (4 ml) was added pyridinium bromoperbromide (1.95 g) at 0° C. After 3 hours, saturated NH$_4$Cl solution was added thereto and the mixture was extracted with ethyl acetate (twice). The organic layer was washed with brine and dried over Na$_2$SO$_4$. After filtration, the solvent was removed under reduced pressure and the residue was chromatographed on silica gel (hexane) to yield a pale yellow solid (1.41 g, 81%): EI-MS: m/z 348 (M$^+$); $^1$H-NMR (CDCl$_3$): δ 2.30 (3H, s, CH3), 2.38 (2H, tt, J=6.3 Hz, 5.9 Hz, CH2), 3.63 (2H, t, J=6.3 Hz, NCH2), 4.20 (2H, t, J=5.9 Hz, OCH2), 6.63 (1H, d, J=7.9 Hz, Ar—H), 7.02 (1H, dd, J=0.6 Hz, 8.3 Hz, Ar—H), 7.12 (1H, d, J=8.3 Hz, Ar—H).

b) Preparation of [3-(2-bromo-3-methyl-benzofuran-4-yloxy)-propyl]-pyridin-3-ylmethylamine:

2-Bromo-4-(3-bromo-propoxy)-3-methyl-benzofuran (348 mg) was treated with 10% 3-picolylamine ethanol solution (2 ml) at 70° C. for 18 hours. The solvent was removed under reduced pressure and the residue was diluted with ethyl acetate. The solution was washed with sat. NH$_4$Cl solution, brine and dried over Na$_2$SO$_4$. After filtration, the filtrate was concentrated in vacuo and the residue was purified on silica gel column chromatography by using dichloromethane-methanol as an eluent. A yellow oil (167 mg, 45%) was obtained. FAB-MS: m/z 375 (MH$^+$); $^1$H-NMR (CDCl$_3$): δ 2.01 (2H, tt, J=6.9 Hz, 5.9 Hz, CH2), 2.21 (3H, s, CH3), 2.84 (2H, t, J=6.9 Hz, NCH2), 3.80 (2H, s, NCH2), 4.09 (2H, t, J=5.9 Hz, OCH2), 6.57 (1H, d, J=8.3 Hz, Ar—H), 6.97 (1H, d, J=7.9 Hz, Ar—H), 7.09 (1H, t, J=7.9 Hz, Ar—H), 7.15–7.20 (1H, m, Ar—H), 7.65 (1H, d, J=7.9 Hz, Ar—H), 8.47 (1H, d, J=5.0 Hz, Ar—H), 8.54 (1H, s, Ar—H).

c) Preparation of (3-methyl-4-{3-[pyridin-3-ylmethyl)-amino]-propoxy}-benzofuran-2-yl phosphonic acid diethyl ester:

[3-(2-Bromo-3-methyl-benzofuran-4-yloxy)-propyl]-pyridin-3-ylmethyl-amine (7 mg), triethylphosphite (33 mg), tetrakis(triphenylphosphine)palladium (6 mg) and triethylamine (0.5 mg) in toluene (1 ml) were refluxed for 18 hours under argon atmosphere. The solvent was removed under reduced pressure, the residue was purified on preparative TLC on silica gel (dichloromethane/methanol/ammonia water=100/10/1) to give a pale yellow oil (3 mg, 35%). FAB-MS: m/z 433 (MH$^+$); $^1$H-NMR (CD$_3$OD): δ 1.34 (6H, t, J=6.8 Hz, 2×CH3), 2.12 (2H, t, J=7.3 Hz, CH2), 2.54 (3H, d, J=2.0 Hz, CH3), 2.90 (2H, t, J=7.3 Hz, NCH2), 4.11–4.16 (2H, m, OCH2), 4.18 (4H, q, J=6.8 Hz, 2×OCH2), 6.76 (1H, d, J=7.8 Hz, Ar—H), 7.08 (1H, d, J=8.3 Hz, Ar—H), 7.34 (1H, t, J=8.3 Hz, Ar—H), 7.37–7.40 (1H, m, Ar—H), 7.86 (1H, d, J=7.8 Hz, Ar—H), 8.45–8.55 (2H, m, 2×Ar—H).

EXAMPLE 76

Preparation of (3-Methyl-4-{3-[pyridin-3-ylmethyl)-amino]-propoxy}-benzofuran-2-yl phosphonic Acid Diisopropyl Ester This compounds was prepared in a similar manner to Example 75. Yellow oil. FAB-MS: m/z 461 (MH$^+$); $^1$H-NMR (CD$_3$OD): δ 1.24 (6H, d, J=6.1 Hz, 2×CH3), 1.27 (3H, d. J=6.4 Hz, CH3), 1.37 (3H, d, J=6.1 Hz, CH3), 2.08 (2H, m, CH2), 2.54 (3H, d, J=2.4 Hz, CH3), 2.84 (2H, t, J=5.9 Hz, CH2N), 3.84 (2H, s, NCH2), 4.17 (2H, t, J=5.9 Hz, CH2O), 4.38 (1H, m, >CHO—), 4.68 (1H, m, >CHO—), 6.74 (1H, d, J=8.1 Hz, Ar—H), 7.06 (1H, d, J=8.3 Hz, Ar—H), 7.33 (1H, t, J=7.8 Hz, Ar—H), 7.40 (1H, m, Ar—H), 7.83 (1H, m, Ar—H), 8.40 (1H, br, Ar—H), 8.55 (1H, br, Ar—H).

EXAMPLE 77

Preparation of 2-{4-[3-(tert-Butylamino)-propoxy]-3-methyl-benzofuran-2-yl}-oxazole-4-carboxylic Acid Ethyl Ester To a stirred solution of 3-methyl-4-[3-(tert-buthylamino)-propoxy]-benzofuran-2-carboxylic acid amide (134 mg) in dioxane (1 ml) were added 1.0 N aqueous sodium hydroxide (1 ml) and benzyl chloroformate (69 μl) at 0° C. and the mixture was stirred at room temperature for 20 hours. After evaporation of the solvent under reduced pressure the residue was purified by silica gel column chromatography using a 1:1 mixture of n-hexane and ethyl acetate as an eluent to give 4-[3-(benzyloxycarbonyl-tert-buthyl-amino)-propoxy]-3-methyl-benzofuran-2-carboxylic acid amide as a colorless plate (163 mg). FAB-MS: m/z 439 (MH$^+$).

4-[3-(Benzyloxycarbonyl-tert-buthyl-amino)-propoxy]-3-methyl-benzofuran-2-carboxylic acid amide (51 mg) in tetrahydrofuran (0.5 ml) was treated with sodium bicarbonate (49 mg) and ethyl bromopyruvate (21 μl) followed by trifluoroacetic anhydride (50 μl) as reported by J. S. Panek et al., J. Org. Chem., (1996), 61, 6496 to give 2-{4-[3-(benzyloxycarbonyl-tert-butyl-amino)-propoxy]-3-methyl-benzofuran-2-yl}-oxazole-4-carboxylic acid ethyl ester as a pale yellow viscous oil (54 mg). FAB-MS: m/z 535 (MH$^+$).

2-{4-[3-(Benzyloxycarbonyl-tert-butyl-amino)-propoxy]-3-methyl-benzofuran-2-yl}-oxazole-4-carboxylic acid ethyl ester (20 mg) in methanol (5 ml) was treated with catalytic amount of 10% palladium on carbon under hydrogen atmosphere at room temperature for 18 hours. After filtration, evaporation and purification by silica gel column chromatography using 10:1 mixture of dichloromethane and methanol as an eluent, 2-{4-[3-(tert-butylamino)-propoxy]-3-methyl-benzofuran-2-yl}-oxazole-4-carboxylic acid ethyl ester was obtained as a white solid (8 mg). FAB-MS: m/z 401.

(MH$^+$); NMR (DMSO-d$_6$): δ 1.29 (9H, s), 1.32 (3H, t, J=7.26 Hz), 2.15 (2H, m), 2.75 (3H, s, 3.09 (2H, t-like), 4.24 (2H, t, J=5.94 Hz), 4.34 (2H, q, J=7.26 Hz), 6.86 (1H, d, J=8.25 Hz), 7.26 (1H, d, J=8.25 Hz), 7.41 (1H, t, J=8.25 Hz).

EXAMPLE 78

Preparation of 2-(3-Methyl-4-{3-[(pyridin-3-ylmethyl)-amino]-propoxy}-benzofuran-2-yl)-oxazole-4-carboxylic Acid Ethyl Ester 4-Allyloxy-3-methyl-benzofuran-2-carboxylic acid amide (3370 mg) in tetrahydrofuran (60 ml) was treated with sodium bicarbonate (5.58 g) and ethyl bromopyruvate (2.20 ml) followed by trifluoroacetic anhydride (5.63 ml) to give 2-(4-allyloxy-3-methyl-benzofuran-2-yl)-oxazole-4-carboxylic acid ethyl ester as a white solid [2443 mg, EI-MS: m/z 327 (M$^+$)] as mentioned in Example 77.

2-(4-Allyloxy-3-methyl-benzofuran-2-yl)-oxazole-4-carboxylic acid ethyl ester (671 mg) in 80% aqueous ethanol (60 ml) was stirred in the presence of chlorotris(triphenylphosphine)rhodium (63 mg) and triethylenediamine (32 mg) at 90° C. for 6 hours. The reaction mixture was poured into 1N aqueous hydrochloric acid and extracted with ethyl acetate. The combined organic extracts were washed with brine and dried over magnesium sulfate. Evaporation of the solvent under reduced pressure gave 2-(4-hydroxy-3-methyl-benzofuran-2-yl)-oxazole-4-carboxylic acid ethyl ester as a white solid (480 mg). EI-MS: m/z 287 (M$^+$).

2-(4-Hydroxy-3-methyl-benzofuran-2-yl)-oxazole-4-carboxylic acid ethyl ester was then converted to the title compound in the same manner as described in Examples 1-f and 1-g. Pale yellow solid. FAB-MS: m/z 436 (MH$^+$); NMR (CDCl$_3$): δ 1.42 (3H, t, J=6.93, 2.08 (2H, quintet, J=6.60 Hz), 2.73 (3H, s), 2.89 (2H, t, J=6.93 Hz), 3.84 (2H, s), 4.18 (2H, t, J=5.94 Hz), 4.43 (2H, q, J=7.26 Hz), 6.64 (1H, d, J=7.92 Hz), 7.12 (1H, d, J=8.25 Hz), 7.15–7.35 (2H, m), 7.66 (1H, brd, J=7.92 Hz), 8.30 (1H, s), 8.48 (1H, dd, J=1.32 Hz, 4.62 Hz), 8.57 (1H, d, J=2.31 Hz).

EXAMPLE 79

Preparation of (4-Methyl-piperazin-1-yl)-[2-(3-methyl-4-{3-[(pyridin-3-ylmethyl)-amino]-propoxy}-benzofuran-2-yl)-oxazol-4-yl]-methanone 2-(3-Methyl-4-{3-[(pyridin-3-ylmethyl)-amino]-propoxy}-benzofuran-2-yl)-oxazole-4-carboxylic acid ethyl ester (397 mg) in N,N-dimethylformamide (5 ml) was added to the suspension of N-[4-(4-nitrophenoxycarbonyloxymethyl)phenoxyacetyl]-N-methyl-aminomethylated polystyrene (loading rate=0.58 mmol/g: 3025 mg) in N,N-dimethylformamide (20 ml) and triethylamine (0.3 ml) and the mixture was agitated at 65° C. for 2 days. The resulted resin was washed with N,N-dimethylformamide, dichloromethane and methanol successively and dried under reduced pressure (3254 mg: calculated loading rate of the substrate=0.23 mmol/g).

The yellow resin obtained above (3254 mg) was suspended in dioxane (30 ml) and treated with 1.0N aqueous sodium hydroxide at room temperature for 18 hours. The end point of the reaction was determined by liquid chromatography-mass spectrometry (LCMS) analysis of a product cleaved from an aliquot of the resin by 10% trifluoroacetic acid in dichloromethane. After hydrolysis was completed, the resin was washed successively with N,N-dimethylformamide, dichloromethane and methanol and dried under reduced pressure to give N-{3-[2-(4-carboxyoxazol-2-yl)-3-methyl-benzofuran-4-yloxy]-propyl}-3-picolylamine linked through nitrogen to N-(4-hydroxymethylphenoxyacetyl)-N-methyl-aminomethylated polystyrene by forming carbamoyl linkage. The product was obtained as a light orange solid (3142 mg).

To the suspension of the polymer linked carboxylic acid (60 mg) in 1-methyl-2-pyrrolidinone (500 µl) were added N-methyl-piperazine (12 µl), 2-(1H-benzotriazole-1-yl)-1,1,3,3-tetramethyluronium hexafluorophosphate (HBTU: 76 mg), 4-dimethylaminopyridine (20 mg) and pyridine (100 µl) and the mixture was agitated at room temperature for 5 days. After successive washing with N,N-dimethylformamide, dichloromethane and methanol and drying under reduced pressure, 10% trifluoroacetic acid in dichloromethane (1 ml) was added and the suspension was allowed to stand at room temperature for 1 hour. Filtration and evaporation of the filtrate gave a crude product (12.7 mg) which was then purified by silica gel column chromatography (Fuji Silysia, DU-3050) using 1000:10:1 mixture of dichloromethane, methanol and triethylamine as an eluent to give (4-methyl-piperazin-1-yl)-[2-(3-methyl-4-{3-[(pyridin-3-ylmethyl)-amino]-propoxy}-benzofuran-2-yl)-oxazol-4-yl]-methanone (2.6 mg) as a white solid. FAB-MS: m/z 490 (MH$^+$); NMR (CDCl$_3$): δ 2.09 (2H, quintet, J=6.27 Hz), 2.36 (3H, s), 2.52 (4H, t, J=4.95 Hz), 2.70 (3H, s), 2.91 (2H, t, J=6.93 Hz), 3.82 (2H, brs), 3.86 (2H, s), 4.20 (2H, t, J=5.94 Hz), 4.22 (2H, brs), 6.60 (1H, d, J=8.25 Hz), 7.14 (1H, d, J=8.25 Hz), 7.2–7.4 (2H, m), 7.68 (1H, brd, J=7.92 Hz), 8.25 (1H, s), 8.49 (1H, dd, J=1.32 Hz, 4.62 Hz), 8.58 (1H, d, J=1.98 Hz).

The procedure using the polymer linked carboxylic acid described in Example 79 was repeated in Example 80 to Example 84 using an appropriate amine.

EXAMPLE 80

Preparation of 2-(3-Methyl-4-{3-[(pyridin-3-ylmethyl)-amino]-propoxy}-benzofuran-2-yl)-oxazole-4-carboxylic Acid Isopropylamide White solid. FAB-MS: m/z 449 (MH$^+$); NMR (CDCl$_3$): δ 1.29 (6H, d, J=6.59 Hz), 2.09 (2H, quintet, J=6.6 Hz), 2.71 (3H, s), 2.91 (2H, t, J=6.93 Hz), 3.86 (2H, s), 4.20 (2H, t, J=5.94 Hz), 4.31 (1H, eight lines, J=6.60 Hz), 6.67 (1H, d, J=7.92 Hz), 6.90 (1H, d, J=8.24 Hz), 7.16 (1H, d, J=8.25 Hz), 7.1–7.4 (2H, m), 7.68 (1H, dt, J=7.59 Hz, 1.98 Hz), 8.28 (1H, s, 8.49 (1H, dd, J=1.65 Hz, 4.62 Hz), 8.58 (1H, d, J=1.98 Hz).

EXAMPLE 81

Preparation of (RS)-2-[3-Methyl-4-[3-[(pyridin-3-ylmethyl)-amino]-propoxy]-benzofuran-2-yl]-oxazole-4-carboxylic Acid (tetrahydro-furan-2-ylmethyl)-amide White solid. FAB-MS: m/z 491 (MH$^+$); NMR (CDCl$_3$): δ 1.5–1.7 (2H, m), 1.85–2.05 (2H, m), 2.09 (2H, quintet, J=6.27 Hz), 2.71 (3H, s), 2.91 (2H, t, J=6.93 Hz), 3.42 (1H, m), 3.7–4.0 (3H, m), 3.86 (2H, s), 4.10 (2H, m), 4.20 (2H, t, J=6.27 Hz), 6.66 (1H, d, J=7.92 Hz), 7.15 (1H, d, J=8.25 Hz), 7.2–7.4 (2H, m), 7.68 (1H, brd, J=7.92 Hz), 8.28 (1H, s), 8.50 (1H, dd, J=1.32 Hz, 4.62 Hz), 8.58 (1H, d, J=1.98 Hz).

EXAMPLE 82

Preparation of (RS)-1-[2-[3-ethyl-4-[3-[(pyridin-3-ylmethyl)-amino]-propoxy]-benzofuran-2-yl]-oxazole-4-carbonyl]-piperidine-3-carboxylic Acid Ethyl Ester White solid. FAB-MS: m/z 547 (MH$^+$); NMR (CDCl$_3$): δ 1.25 (3H, t, J=6.90 Hz), 1.5–1.9 (4H, m), 2.09 (2H, quintet, J=6.60 Hz), 2.65 (1H, m), 2.71 (3H, s), 2.91 (2H, t, J=6.93 Hz), 3.86 (2H, s), 4.15 (2H, q, J=6.9 Hz), 4.19 (2H, t, J=5.94 Hz), 6.66 (1H, d, J=7.92 Hz), 7.13 (1H, d, J=8.25 Hz), 7.15–7.3 (2H, m), 7.68 (1H, dt, J=7.92 Hz, 1.95 Hz), 8.23 (1H, s) 8.49 (1H, dd, J=1.65 Hz, 4.95 Hz), 8.58 (1H, d, J=1.98 Hz).

EXAMPLE 83

Preparation of [2-(3-Methyl-4-{3-[(pyridin-3-ylmethyl)-amino]-propoxy}-benzofuran-2-yl)-oxazol-4-yl]-thiazolidin-3-yl-methanone White solid. FAB-MS: m/z 479 (MH$^+$); NMR (CDCl$_3$): δ 2.09 (2H, quintet, J=6.35 Hz), 2.70 (3H, s), 2.91 (2H, t, J=6.60 Hz), 3.08 (1H, t-like), 3.16 (1H, t-like), 3.86 (2H, s), 4.04 (1H, t-like), 4.20 (2H, t, J=5.94 Hz), 4.47 (1H, t-like), 5.21 (1H, s), 6.66 (1H, d, J=7.92 Hz), 7.14 (1H, d, J=8.58 Hz), 7.2–7.35 (2H, m), 7.68 (1H, brd, J=7.59 Hz), 8.33 (1H, s), 8.49 (1H, dd, J=1.32 Hz, 4.95 Hz), 8.58 (1H, d, J=2.31 Hz).

EXAMPLE 84

Preparation of 2-(3-Methyl-4-{3-[(pyridin-3-ylmethyl)-amino]-propoxy}-benzofuran-2-yl-oxazole-4-carboxylic Acid (3,5-difluoro-phenyl)-amide White solid. FAB-MS: m/z 519 (MH$^+$); NMR (CDCl$_3$): δ 2.09 (2H, quintet, J=6.40 Hz), 2.73 (3H, s), 2.91 (2H, t, J=6.75 Hz), 3.86 (2H, s), 4.21 (2H, t, J=5.94 Hz), 6.62 (1H, d, J=8.91 Hz), 6.68 (1H, d, J=7.83 Hz), 7.17 (1H, d, J=8.37 Hz), 7.2–7.4 (5H, m), 7.68 (1H, dt, J=5.94 Hz, 2.97 Hz), 8.39 (1H, s), 8.49 (1H, dd, J=1.62 Hz, 5.13 Hz), 8.58 (1H, d, J=2.16 Hz), 8.87 (1H, brs).

EXAMPLE 85

Preparation of 2-(3-Methyl-4-{3-[(pyridin-3-ylmethyl)-amino]-propoxy}-benzofuran-2-yl)-thiazole-4-carboxylic Acid Ethyl Ester To a solution of 4-allyloxy-3-methyl-benzofuran-2-carboxylic acid amide (430 mg) in toluene (50 ml) and tetrahydrofuran (10 ml), was added Lawessonis reagent (752 mg). After heating at 60° C. for 5 hours, the reaction mixture was directly poured onto silica gel column chromatography and eluted by 5:1 mixture of n-hexane and ethyl acetate to give thioamide as a yellow solid (424 mg). This was then dissolved in acetonitrile (20 ml) and ethyl bromopyruvate (400 μl) was added. After stirring at room temperature for 29 hours the reaction mixture was evaporated and purified by silica gel column chromatography using 5:1 mixture of n-hexane and ethyl acetate as an eluent to give 2-(4-allyloxy-3-methyl-benzofuran-2-yl)-thiazole-4-carboxylic acid ethyl ester (156 mg). FAB-MS: m/z 343 (MH$^+$).

2-(4-Allyloxy-3-methyl-benzofuran-2-yl)-thiazole-4-carboxylic acid ethyl ester (28 mg) in 80% aqueous ethanol (6 ml) was stirred in the presence of chlorotris(triphenylphosphine)rhodium (3 mg) and triethylenediamine (2 mg) at 90° C. for 6 hours. The reaction mixture was poured into 1N aqueous hydrochloric acid and extracted with ethyl acetate. The combined organic extracts were washed with brine and dried over magnesium sulfate. Evaporation of the solvent under reduced pressure gave 2-(4-hydroxy-3-methyl-benzofuran-2-yl)-thiazole-4-carboxylic acid ethyl ester as a white solid (21 mg). FAB-MS: m/z 304 (MH$^+$).

2-(4-Hydroxy-3-methyl-benzofuran-2-yl)-thiazole-4-carboxylic acid ethyl ester was then converted to the title compound in the same manner as described in Example 1-f and 1-g. White solid. FAB-MS: m/z 452 (MH$^+$); NMR (CDCl$_3$): δ 1.44 (3H, t, J=7.26 Hz), 2.09 (2H, quintet, J=6.27 Hz), 2.80 (3H, s), 2.91 (2H, t, J=6.93 Hz), 3.85 (2H, s), 4.19 (2H, t, J=6.27 Hz), 4.46 (2H, q, J=6.92 Hz), 6.64 (1H, d, J=7.92 Hz), 7.10 (1H, d, J=8.25 Hz), 7.15–7.30 (2H, m), 7.68 (1H, dt, J=7.59 Hz, 1.98 Hz), 8.12 (1H, s), 8.49 (1H, dd, J=1.65 Hz, 4.95 Hz), 8.58 (1H, d, J=1.98 Hz).

EXAMPLE 86

Preparation of 2-[2-[3-Methyl-4-[3-[(pyridin-3-ylmethyl)-amino]-propoxy]-benzofuran-2-yl]oxazol-4-yl]-thiazole-4-carboxylic Acid Ethyl Ester A mixture of 2-(4-Allyloxy-3-methyl-benzofuran-2-yl)-oxazole-4-carboxylic acid ethyl ester (300 mg), methanol (20 ml) and 1.0 N aqueous sodium hydroxide (20 ml) was stirred at room temperature for 2 hours. The solution was neutralized by 1.0 N aqueous hydrochloric acid (20 ml) and extracted with dichloromethane. Evaporation of the solvent under reduced pressure gave a pale yellow solid (320 mg). To this solid were added chloroform (50 ml) and thionyl chloride (10 ml). After heating at 60° C. for 5.5 hours, the reagent and the solvent were removed under reduced pressure. The resulted acid chloride was then dissolved in chloroform (50 ml) and concentrated aqueous ammonia (10 ml) was added. After stirring at room temperature overnight the reaction mixture was poured into water and extracted with chloroform. The organic layer was dried over magnesium sulfate. Evaporation of the solvent under reduced pressure and purification of the product by silica gel column chromatography using 2:1 mixture of n-hexane and ethyl acetate as an eluent gave 2-(4-allyloxy-3-methyl-benzofuran-2-yl)-oxazole-4-carboxylic acid amide as a white solid (218 mg). 2-(4-Allyloxy-3-methyl-benzofuran-2-yl)-oxazole-4-carboxylic acid amide (100 mg) was converted to the title compound in the same manner as described in Example 85.

White solid. FAB-MS: m/z 519 (MH$^+$); NMR (CDCl$_3$): δ 1.44 (3H, t, J=6.93 Hz), 2.10 (2H, quintet, J=6.27 Hz), 2.75 (3H, s), 2.91 (2H, t, J=6.93 Hz), 3.86 (2H, s), 4.20 (2H, t, J=5.94 Hz), 4.47 (2H, q, J=7.26 Hz), 6.67 (1H, d, J=7.92 Hz), 7.17 (1H, d, J=7.92 Hz), 7.15–7.25 (2H, m), 7.68 (1H, dt, J=7.92 Hz, 1.98 Hz), 8.24 (1H, s), 8.48 (1H, s), 8.50 (1H, dd, J=1.65 Hz, 4.62 Hz), 8.58 (1H, d, J=1.65 Hz).

EXAMPLE 87

Preparation of dl-5-Cyclohexylmethyl-2-(3-methyl-4-{3-[(pyridin-3-ylmethyl)-amino]-propoxy}-benzofuran-2-yl)-trans-4,5-dihydro-oxazole-4-carboxylic Acid Ethyl Ester To a solution of 3-Methyl-4-{3-[(pyridin-3-ylmethyl)-amino]-propoxy}-benzofuran-2-carboxylic acid ethyl ester (1677 mg) in dichloromethane (30 ml) were added di-tert-butyl dicarbonate (1.75 g) and triethylamine (1.90 ml) at 0∞° C. and the mixture was stirred at room temperature for 15 hours. The organic solvent was removed under reduced pressure and the residue was purified by silica gel column chromatography using 1:1 mixture of n-hexane and ethyl acetate as an eluent to give 4-{3-[tert-butoxycarbonyl-(pyridin-3-ylmethyl)-amino]-propoxy}-3-methyl-benzofuran-2-carboxylic acid ethyl ester (1099 mg). FAB-MS: m/z 469 (MH$^+$).

To a solution of 4-{3-[tert-butoxycarbonyl-(pyridin-3-ylmethyl)-amino]-propoxy}-3-methyl-benzofuran-2-carboxylic acid ethyl ester (121 mg) in methanol (5 ml) was added 1.0 N aqueous sodium hydroxide (1.0 ml) and the mixture was stirred at room temperature for 15 hours. After addition of 1.0 N aqueous hydrochloric acid (1.0 ml) the solvent was removed under reduced pressure to give a white solid (174 mg) which contained a desired carboxylic acid and sodium chloride.

Whole white solid, dl-2-amino-4-cyclohexyl-3-hydroxy-butyric acid ethyl ester (74 mg), 2-(1H-benzotriazole-1-yl)-1,1,3,3-tetramethyluronium hexafluorophosphate (HBTU: 196 mg), 4-dimethylaminopyridine (200 mg), pyridine (1 ml) and 1-methyl-2-pyrrolidinone (4 ml) were mixed and stirred at room temperature for 6.5 hours. The resulted solution was poured into saturated aqueous ammonium chloride and extracted with ethyl acetate. The combined organic extracts were dried over magnesium sulfate. After filtration and removal of ethyl acetate, the crude product (317 mg) was purified by silica gel column chromatography using 3:2 mixture of n-hexane and ethyl acetate as an eluent to give dl-2-[(4-{3-[tert-butoxycarbonyl-(pyridin-3-ylmethyl)-amino]-propoxy}-3-methyl-benzofuran-2-carbonyl)-amino]-4-cyclohexyl-3-hydroxy-butyric acid ethyl ester (119 mg). FAB-MS: m/z 652 (MH$^+$).

To a solution of dl-2-[(4-{3-[tert-butoxycarbonyl-(pyridin-3-ylmethyl)-amino]-propoxy}-3-methyl-benzofuran-2-carbonyl)-amino]-4-cyclohexyl-3-hydroxy-butyric acid ethyl ester (40.0 mg) in tetrahydrofuran (0.5 ml) was added dropwise Burgess reagent (19 mg) in tetrahydrofuran (0.5 ml) over a period of 15 minutes at room temperature and the mixture was stirred another 25 minuets at room temperature and then heated at 90° C. for 2 hours. After cooling, the reaction mixture was directly poured onto silica gel column chromatography and eluted with 2:3 mixture of n-hexane and ethyl acetate to give dl-5-cyclohexylmethyl-2-(3-methyl-4-{3-[tert-butoxycarbonyl-(pyridin-3-ylmethyl)-amino]-propoxy}-benzofuran-2-yl)-trans-4,5-dihydro-oxazole-4-carboxylic acid ethyl ester (35.7 mg). FAB-MS: m/z 634 (MH$^+$).

To a solution of dl-5-cyclohexylmethyl-2-(3-methyl-4-{3-[tert-butoxycarbonyl-(pyridin-3-ylmethyl)-amino]-propoxy}-benzofuran-2-yl)-trans-4,5-dihydro-oxazole-4-carboxylic acid ethyl ester (5.0 mg) in dichloromethane was added trifluoroacetic acid (0.5 ml) and the mixture was allowed to stand at room temperature for 1 hour. The resulted solution was poured into cold saturated aqueous sodium bicarbonate and extracted with dichloromethane. The organic layer was dried over magnesium sulfate and filtered. After evaporation of the solvent the title compound (4.2 mg) was obtained as a pale yellow viscous oil. FAB-MS: m/z 534 (MH$^+$); NMR (CDCl$_3$): δ 1.32 (3H, t, J=6.60 Hz), 2.09 (2H, quintet, J=6.60 Hz), 2.59 (3H, s), 2.93 (2H, t, J=6.60 Hz), 3.89 (2H, s), 4.16 (2H, t, J=5.87 Hz), 4.26 (2H, m), 4.45 (1H, d, J=7.33 Hz), 4.97 (1H, m), 6.59 (1H, d, J=8.07 Hz), 7.09 (1H, d, J=8.07 Hz), 7.2–7.3 (2H, m), 7.70 (1H, d, J=7.33 Hz), 8.49 (1H, d, J=4.4 Hz), 8.57 (1H, brs).

EXAMPLE 88

Preparation of dl-[5-Cyclohexylmethyl-2-(3-methyl-4-{3-[(pyridin-3-ylmethyl)-amino]-propoxy}-benzofuran-2-yl)-trans-4,5-dihydro-oxazol-4-yl]-(4-methyl-piperazin-1-yl)-methanone To a solution of dl-5-cyclohexylmethyl-2-(3-methyl-4-{3-[tert-butoxycarbonyl-(pyridin-3-ylmethyl)-amino]-propoxy}-benzofuran-2-yl)-trans-4,5-dihydro-oxazole-4-carboxylic acid ethyl ester (15.0 mg) in methanol (1 ml) was added 1.0 N aqueous sodium hydroxide (1.0 ml) and the mixture was stirred at room temperature for 20 hours. After addition of 1.0 N aqueous hydrochloric acid (1.0 ml) the solvent was removed under reduced pressure to give a white solid. The solid was then dissolved in 1-methyl-2-pyrrolidinone (1.5 ml) and N-methyl-piperazine (14 μl), 2-(1H-benzotriazole-1-yl)-1,1,3,3-tetramethyluronium hexafluorophosphate (HBTU: 44 mg), 4-dimethylaminopyridine (15 mg) and pyridine (75 μl) were added. The solution was stirred at room temperature for 15 hours. The reaction mixture was concentrated under reduced pressure and the crude product was purified by silica gel column chromatography (Fuji Silysia, DU-3050) using 2:3 mixture of n-hexane and ethyl acetate as an eluent to give dl-[5-cyclohexylmethyl-2-(3-methyl-4-{3-[tert-butoxycarbonyl-(pyridin-3-ylmethyl)-amino]-propoxy}-benzofuran-2-yl)-trans-4,5-dihydro-oxazol-4-yl]-(4-methyl-piperazin-1-yl)-methanone (2.4 mg). FAB-MS: m/z 688 (MH$^+$).

dl-[5-Cyclohexylmethyl-2-(3-methyl-4-{3-[tert-butoxycarbonyl-(pyridin-3-ylmethyl)-amino]-propoxy}-benzofuran-2-yl)-trans-4,5-dihydro-oxazol-4-yl]-(4-methyl-piperazin-1-yl)-methanone (11.9 mg) was dissolved in 1:1 mixture of trifluoroacetic acid and dichloromethane (1 ml) and was allowed to stand at room temperature for 45 minutes. The resulted solution was poured into saturated aqueous sodium bicarbonate and extracted with dichloromethane. The organic layer was dried over magnesium sulfate and filtered. After evaporation of the solvent the crude product was purified by silica gel column chromatography (Fuji Silysia, DU-3050) using 1000:10:1 mixture of dichloromethane, methanol and triethylamine as an eluent to give the title compound (7.7 mg) as a white solid. FAB-MS: m/z 588 (MH$^+$); NMR (CDCl$_3$): δ 0.9–2.0 (13H, m), 2.06 (2H, quintet, J=6.27 Hz), 2.34 (3H, s), 2.43 (2H, t, J=4.95 Hz), 2.55 (2H, m), 2.62 (3H, s), 2.89 (2H, t, J=6.93 Hz), 3.70 (2H, m), 3.81 (1H, m), 3.84 (2H, s), 4.07 (1H, m), 4.16 (2H, t, J=5.93 Hz), 4.55 (1H, d, J=6.60 Hz), 5.54 (1H, m), 6.61 (1H, d, J=7.92 Hz), 7.10 (1H, d, J=8.25 Hz), 7.15–7.30 (2H, m), 7.67 (1H, dt, J=7.92 Hz, 1.98 Hz), 8.49 (1H, dd, J=1.65 Hz, 4.95 Hz), 8.57 (1H, d, J=1.98 Hz).

EXAMPLE 89

Preparation of dl-[5-(2,4-Difluoro-benzyl)-2-(3-methyl-4-{3-[(pyridin-3-ylmethyl)-amino]-propoxy}-benzofuran-2-yl)-trans-4,5-dihydro-oxazol-4-yl]-(4-methyl-piperazin-1-yl)-methanone The title compounds (3.4 mg) was prepared in the same procedures as disclosed in Example 87 and Example 88 using dl-2-amino-4-(2,4-difluoro-phenyl)-3-hydroxy-butyric acid ethyl ester. White solid. FAB-MS: m/z 618 (MH$^+$); NMR (CDCl$_3$): δ 2.08 (2H, quintet, J=6.0 Hz), 2.33 (3H, s), 2.40 (2H, t, J=5.2 Hz), 2.46 (1H, m), 2.54 (1H, m), 2.56 (3H, s), 2.89 (2H, t, J=7.6 Hz), 3.07 (2H, dd, J=7.2 Hz, 13.2 Hz), 3.6–3.8 (3H, m), 3.86 (2H, s), 4.01 (1H, m), 4.16 (2H, t, J=6.0 Hz), 4.68 (1H, d, J=6.0 Hz), 5.71 (1H, q, J=6.0 Hz), 6.61 (1H, d, J=8.0 Hz), 6.83 (2H, m), 7.09 (1H, d, J=8.4 Hz), 7.2–7.35 (2H, m), 7.69 (1H, brd, J=7.2 Hz), 8.49 (1H, dd, J=1.6 Hz, 5.2 Hz), 8.58 (1H, d, J=2.0 Hz).

EXAMPLE 90

Preparation of 5-Cyclohexylmethyl-2-(3-methyl-4-{3-[(pyridin-3-ylmethyl)-amino]-propoxy}-benzofuran-2-yl)-oxazole-4-carboxylic Acid Ethyl Ester 5-Cyclohexylmethyl-2-(3-methyl-4-{3-[tert-butoxycarbonyl-(pyridin-3-ylmethyl)-amino]-propoxy}- benzofuran-2-yl)-trans-4,5-dihydro-oxazole-4-carboxylic acid ethyl ester (10.0 mg) and nickel peroxide hydrate (22 mg) in toluene (2 ml) was heated at 80° C. under the atmosphere of argon for 23 hours. The reaction mixture was directly poured onto silica gel column chromatography and eluted with 2:3 mixture of n-hexane and ethyl acetate to give 5-cyclohexylmethyl-2-(3-methyl-4-{3-[tert-butoxycarbonyl-(pyridin-3-ylmethyl)-amino]-propoxy}-benzofuran-2-yl)-oxazole-4-carboxylic acid ethyl ester (2.2 mg). FAB-MS: m/z 632 (MH$^+$).

The compound (2.2 mg) was then dissolved in 1:1 mixture of trifluoroacetic acid and dichloromethane and was allowed to stand at room temperature for 1 hour. The resulted solution was poured into saturated aqueous sodium bicarbonate and extracted with dichloromethane. The dichloromethane extract was dried over magnesium sulfate and filtered. Evaporation of the solvent gave the title compound (1.8 mg) as colorless glassy mass. FAB-MS: m/z 532 (MH$^+$); NMR (CDCl$_3$): δ 0.8–1.9 (13H, m), 1.42 (3H, t, J=6.92 Hz), 2.11 (2H, quintet, J=6.27 Hz), 2.68 (3H, s), 2.97 (2H, t, J=6.27 Hz), 3.03 (2H, d, J=7.26 Hz), 3.91 (2H, s), 4.17 (2H, t, J=5.94 Hz), 4.42 (2H, q, J=7.26 Hz), 6.60 (1H, d, J=7.58 Hz), 7.13 (1H, d, J=8.25 Hz), 7.2–7.3 (2H, m), 7.72 (1H, brd, J=7.59 Hz), 8.49 (1H, brd, J=3.3 Hz), 8.57 (1H, brs).

EXAMPLE 91

Preparation of 4-[2-Hydroxy-3-[(pyridin-3-ylmethyl)-amino]-propoxy]-3-methyl-benzofuran-2-carboxylic Acid Ethyl Ester 3-Methyl-4-oxiranylmethoxy-benzofuran-2-carboxylic acid ethyl ester (500 mg) (Naresh K. Sangwan et al., Eur. J. Med. Chem. (1987), 22(2), 153–6) and 3-picolylamine (1 ml) were dissolved in ethanol (5 ml) and stirred at 70° C. for two hours. The reaction mixture was dissolved in ethyl acetate and washed with saturated ammonium chloride solution and water. The organic solvent was dried over anhydrous sodium sulfate and evaporated to dryness. The residue was purified by silica gel column chromatography (dichloromethane-MeOH) to afford 4-[2-hydroxy-3-[(pyridin-3-ylmethyl)-amino]-propoxy]-3-methyl-benzofuran-2-carboxylicacid ethyl ester (330 mg) as a white powder. FAB-MS: m/z 385 (MH$^+$); $^1$H-NMR (CDCl$_3$): δ 1.44 (3H, t, J=7 Hz), 2.70 (3H, s),2.86 (1H, dd, J1=12 Hz, J2=7 Hz),2.97 (1H, dd, J1=12 Hz, J2=3.5 Hz), 3.85 (1H, d, J=14 Hz), 3.91 (1H, d, J=14 Hz), 4.13 (3H, m), 4.44 (2H, q, J=7 Hz), 6.63 (1H, d, J=8 Hz), 7.14 (1H, d, J=8 Hz), 7.26 (1H, m), 7.28 (1H, t, J=8 Hz), 7.68 (1H, br d, J=8 Hz),8.52 (1H, dd, J1=5 Hz, J2=2 Hz), 8.58 (1H, d, J=2 Hz).

EXAMPLE 92

Preparation of 4-(2-Hydroxy-3-isopropylamino-propoxy)-3-methyl-benzofuran-2-carboxylic Acid Cyclohexylamide A mixture of 4-(2-hydroxy-3-isopropylamino-propoxy)-3-methyl-benzofuran-2-carboxylic acid ethyl ester (A. N. Grinev et al., Otkrytiya, Izobret. 1986, (43), 275) (10 mg) and cyclohexylamine (50 μl) was heated at 175° C. for 11 hours. The reaction mixture was dissolved in ethyl acetate and washed with 0.1 N HCl solution and water. The organic solvent was dried over anhydrous sodium sulfate and evaporated to dryness. The residue was purified by preparative thin layer chromatography (using dichloromethane:MeOH:ammonia solution (25–28%)=10:1:0.2 as a developing solvent) to give 4-(2-hydroxy-3-isopropylamino-propoxy)-3-methyl-benzofuran-2-carboxylic acid cyclohexylamide (7 mg) as a white powder. FAB-MS: m/z 389 (MH$^+$); $^1$H-NMR (CDCl$_3$): δ 1.10 (6H, d, J=6 Hz), 1.20–2.04 (10H, m), 2.78 (3H, s), 2.83 (1H, m), 2.87 (1H, dd, J1=12.5 Hz, J2=6 Hz), 2.97 (1H, dd, J1=12.5 Hz, J2=3 Hz), 3.97 (1H, m), 4.08 (3H, m), 6.45 (1H, br d, J=8 Hz), 6.64 (1H, d, J=8 Hz), 7.04 (1H, d, J=8 Hz), 7.27 (1H, t, J=8 Hz).

EXAMPLE 93

[4-(2-Hydroxy-3-isopropylamino-propoxy)-3-methyl-benzofuran-2-yl]-piperidin-1-yl-methanone This compound was prepared in a manner analogous to that of Example 92. Colorless oil. MALDI-TOF-MS: m/z 375 (MH$^+$); $^1$H-NMR (CDCl$_3$): δ 1.22 (6H, d, J=6 Hz), 1.20–2.10 (6H, m), 2.54 (3H, s), 2.91 (1H, dd, J1=12 Hz, J2=8.5 Hz), 3.04 (1H, m), 3.09 (1H, dd, J1=12 Hz, J2=3 Hz), 3.60 (4H, m), 4.06 (1H, dd, J1=10 Hz, J2=6 Hz), 4.16 (1H, dd, J1=10 Hz, J2=5.5 Hz), 4.26 (1H, m), 6.63 (1H, d, J=8 Hz), 7.06 (1H, d, J=8 Hz), 7.23 (1H, t, J=8 Hz.

EXAMPLE 94

Preparation of 4-(2-Hydroxy-3-isopropylamino-propoxy)-3-methyl-benzofuran-2-carboxylic Acid Ethylamide a) Preparation of 4-(2-hydroxy-3-isopropylamino-propoxy)-3-methyl-benzofuran-2-carboxylic acid:

A solution of 4-(2-hydroxy-3-isopropylamino-propoxy)-3-methyl-benzofuran-2-carboxylic acid ethyl ester (100 mg) in methanol (5 ml) was treated with 5 N NaOH solution (1 ml) at room temperature, and the resulting mixture was stirred overnight at the same temperature. The solution was acidified with 1N HCl solution (6 ml) and concentrated in vacuo. The residue was dissolved in H$_2$O and passed through Sep-Pak Cartridge (C18) which was developed with H$_2$O-MeOH. The fractions containing the target compound were collected and concentrated in vacuo to give 4-(2-hydroxy-3-isopropylamino-propoxy)-3-methyl-benzofuran-2-carboxylic acid (79 mg) as a white powder. FAB-MS: m/z 308 (MH$^+$); $^1$H-NMR (DMSO-d$_6$): δ 1.05 (6H, d, J=6 Hz), 2.65 (3H, s), 2.73 (1H, dd, J1=12 Hz, J2=7 Hz), 2.86 (2H, m), 3.99 (1H, m), 4.16 (2H, d, J=5 Hz), 6.68 (1H, d, J=8 Hz), 7.01 (1H, d, J=8 Hz), 7.17 (1H, t, J=8 Hz).

b) Preparation of 4-(2-hydroxy-3-isopropylamino-propoxy)-3-methyl-benzofuran-2-carboxylic acid ethylamide A solution of 4-(2-hydroxy-3-isopropylamino-propoxy)-3-methyl-benzofuran-2-carboxylic acid (5 mg), ethylamine hydrochloride (42 mg), water-soluble carbodiimide hydrochloride (10 mg), 1-hydroxybenzotriazole (8 mg) and triethylamine (100 μl) in DMF (1 ml) was stirred at room temperature for five hours. The solvent was removed under reduced pressure, and the residue was diluted with ethyl acetate and washed with water. The organic layer was dried over anhydrous sodium sulfate and evaporated. The residue was purified by preparative thin layer chromatography (using dichloromethane:MeOH:H$_2$O=65:30:5 as a developing solvent) to give 4-(2-hydroxy-3-isopropylamino-propoxy)-3-methyl-benzofuran-2-carboxylic acid ethylamide (2 mg) as a white powder. MALDI-TOF-MS: m/z 335 (MH$^+$); $^1$H-NMR (CDCl$_3$): δ 1.27 (3H, t, J=7 Hz), 1.34 (6H, d, J=6 Hz), 2.72 (3H, s), 3.13 (1H, dd, J1=12 Hz, J2=9 Hz), 3.32 (2H, m), 3.49 (2H, dq, J1=7 Hz, J2=6 Hz), 4.05 (1H, dd, J1=10 Hz, J2=6 Hz), 4.15 (1H, dd, J1=10 Hz, J2=5 Hz), 4.53 (1H, br s), 6.55 (1H, d, J=8 Hz), 6.56 (1H, m), 7.00 (1H, d, J=8 Hz), 7.22 (1H, t, J=8 Hz).

EXAMPLE 95

4-(2-Hydroxy-3-isopropylamino-propoxy)-3-methyl-benzofuran-2-carboxylic Acid 2-cyclohexyl-ethyl Ester This compound was prepared in a manner analogous to that of Example 94. Colorless oil. MALDI-TOF-MS: m/z 418 (MH$^+$); $^1$H-NMR (CDCl$_3$): δ 0.92–1.80 (13H, m), 1.28 (6H, d, J=6 Hz), 2.70 (3H, s), 3.03 (1H, dd, J1=12 Hz, J2=9 Hz), 3.20 (2H, m), 4.08 (1H, dd, J1=10 Hz, J2=6 Hz), 4.13 (1H, dd, J1=10 Hz, J2=5 Hz), 4.40 (3H, brt, J=7 Hz), 6.57 (1H, d, J=8 Hz), 7.12 (1H, d, J=8 Hz), 7.27 (1H, t, J=8 Hz).

EXAMPLE 96

Preparation of 3-Methyl-4-{3-[(pyridin-3-ylmethyl)-amino]-propoxy}-benzofuran-2-carboxylic Acid Ethyl Ester 4-(3-bromo-propoxy)-3-methyl-benzofuran-2-carboxylic acid ethyl ester (Example 5-a: 180 mg) and 3-picolylamine (500 μl) were dissolved in ethanol (2 ml) and heated at 50° C. for 16 hours. The reaction mixture was dissolved in ethyl acetate and washed with saturated ammonium chloride solution and water. The organic solvent was dried over anhydrous sodium sulfate and evaporated to dryness. The residue was purified by silica gel column chromatography (dichloromethane-MeOH) to afford 3-methyl-4-{3-[(pyridin-3-ylmethyl)-amino]-propoxy}-benzofuran-2-carboxylic acid ethyl ester (150 mg) as a colorless oil. EI-MS: m/z 368 (M$^+$); $^1$H-NMR (CDCl$_3$): δ 1.44 (3H, t, J=7 Hz), 2.07 (2H, quintet, J=6.5 Hz), 2.67 (3H, s), 2.89 (2H, t, J=7 Hz), 3.84 (2H, s), 4.17 (2H, t, J=6 Hz), 4.44 (2H, q, J=7 Hz), 6.62 (1H, d, 8 Hz), 7.12 (1H, d, J=8 Hz), 7.21 (1H, dd, J1=8 Hz, J2=5 Hz), 7.30 (1H, t, J=8 Hz), 7.66 (1H, dd, J1=8 Hz, J2=2 Hz), 8.49 (1H, dd, J1=5 Hz, J2=2 Hz), 8.57 (1H, d, J=2 Hz).

The following compounds in Examples 97–101 were obtained from 4-(3-bromo-propoxy)-3-methyl-benzofuran-2-carboxylic acid ethyl ester (Example 5-a) according to a manner analogous to that of Example 96.

EXAMPLE 97

Preparation of 3-Methyl-4-(3-(2-pyridin-3-yl-ethylamino)-propoxy)-benzofuran-2-carboxylic Acid Ethyl Ester Colorless oil. FAB-MS: m/z 383 (MH$^+$); $^1$H-NMR (CDCl$_3$): δ 1.43 (3H, t, J=7 Hz), 2.04 (2H, quintet, J=6.5 Hz), 2.73 (3H, s), 2.87 (6H, m), 4.14 (2H, t, J=6 Hz), 4.44 (2H, q, J=7 Hz), 6.61 (1H, d, J=8 Hz), 7.12 (1H, d, J=8 Hz), 7.18 (1H, dd, J1=8 Hz, J2=5 Hz), 7.30 (1H, t, J=8 Hz), 7.52 (1H, dd, J1=8 Hz, J2=2 Hz), 8.44 (1H, dd, J1=5 Hz, J2=2 Hz), 8.48 (1H, d, J=2 Hz).

EXAMPLE 98

Preparation of 4-(3-Benzylamino-propoxy)-3-methyl-benzofuran-2-carboxylic Acid Ethyl Ester Colorless oil. FAB-MS: m/z 368 (MH); $^1$H-NMR (CDCl$_3$): δ 1.44 (3H, t, J=7 Hz), 2.07 (2H, quintet, J=7 Hz), 2.67 (3H, s), 2.88 (2H, t, J=7 Hz), 3.83 (2H, s), 4.17 (2H, t, J=6 Hz), 4.43 (2H, q, J=7 Hz), 6.62 (1H, d, J=8 Hz), 7.11 (1H, d, J=8 Hz), 7.27 (6H, m).

EXAMPLE 99

Preparation of 4-(3-(4-Dimethylamino-benzylamino)-propoxy)-3-methyl-benzofuran-2-carboxylic Acid Ethyl Ester Light brown oil. EI-MS: m/z 410 (M$^+$); $^1$H-NMR (CDCl$_3$): δ 1.43 (3H, t, J=7 Hz), 2.11 (2H, quintet, J=6.5 Hz), 2.65 (3H, s), 2.90 (6H, s), 2.90 (2H, t, J=7 Hz), 3.76 (2H, s), 4.14 (2H, t, J=6 Hz), 4.43 (2H, q, J=7 Hz), 6.60 (1H, d, J=8 Hz), 6.66 (2H, d, J=9 Hz), 7.10 (1H, d, J=8 Hz), 7.21 (2H, d, J=9 Hz), 7.29 (1H, t, J=8 Hz).

EXAMPLE 100

Preparation of 4-(3-(1-Benzyl-piperidin-4-ylamino)-propoxy)-3-methyl-benzofuran-2-carboxylic Acid Ethyl Ester Colorless oil. FAB-MS: m/z 451 (MH$^+$); $^1$H-NMR (CDCl$_3$): δ 1.42 (2H, m), 1.43 (3H, t, J=7 Hz), 1.87–2.11 (6H, m), 2.51 (1H, m), 2.73 (3H, s), 2.88 (4H, m), 3.50 (2H, s), 4.15 (2H, t, J=6 Hz), 4.44 (2H, q, J=7 Hz), 6.62 (1H, d, J=8 Hz), 7.11 (1H, d, J=8 Hz), 7.28 (6H, m).

EXAMPLE 101

Preparation of 4-(3-(Indan-1-ylamino)-propoxy)-3-methyl-benzofuran-2-carboxylic Acid Ethyl Ester Light brown powder. FAB-MS: m/z 394 (MH$^+$); $^1$H-NMR (CDCl$_3$): δ 1.44 (3H, t, J=7 Hz), 1.86 (1H, m), 2.09 (2H, quintet, J=6.5 Hz), 2.42 (1H, m), 2.71 (3H, s), 2.82 (1H, m), 2.97 (2H, t, J=7 Hz), 3.00 (1H, m), 4.19 (2H, t, J=6 Hz), 4.30 (1H, t, J=7 Hz), 4.44 (2H, q, J=7 Hz), 6.63 (1H, d, J=8 Hz), 7.11 (1H, d, J=8 Hz), 7.14–7.36 (5H, m).

EXAMPLE 102

Preparation of 4-[3-(1-Ethyl-piperidin-4-ylamino)-propoxy]-3-methyl-benzofuran-2-carboxylic Acid Ethyl Ester To a solution of 4-(3-(1-benzyl-piperidin-4-ylamino)-propoxy)-3-methyl-benzofuran-2-carboxylic acid ethyl ester (the compound in Example 100, 14 mg) in ethanol (3 ml) was added 5% Pd on charcoal catalyst (10 mg) under N$_2$. The nitrogen atmosphere was replaced by hydrogen (1 atom) and the resulting mixture was stirred overnight at room temperature. The reaction mixture was filtered through a pad of celite and the pad of celite was rinsed with methanol and dichloromethane. The filtrate combined was concentrated in vacuo. The residue was purified by silica gel column chromatography (dichloromethane-MeOH) to give 4-[3-(1-ethyl-piperidin-4-ylamino)-propoxy]-3-methyl-benzofuran-2-carboxylic acid ethyl ester (5 mg) as a colorless oil. EI-MS: m/z 388 (M$^+$); $^1$H-NMR (CDCl$_3$): δ 1.13 (3H, t, J=7 Hz), 1.44 (3H, t, J=7 Hz), 1.54 (2H, m), 1.98–2.22 (6H, m), 2.53 (2H, q, J=7 Hz), 2.61 (1H, m), 2.74 (3H, s), 2.89 (2H, t, J=7 Hz), 3.02 (2H, m), 4.16 (2H, t, J=6 Hz), 4.44 (2H, q, J=7 Hz), 6.62 (1H, d, J=8 Hz), 7.12 (1H, d, J=8 Hz), 7.30 (1H, t, J=8 Hz).

EXAMPLE 103

Preparation of 3-Methyl-4-[3-(1-pyridin-3-ylmethyl-piperidin-4-ylamino)-propoxy]-benzofuran-2-carboxylic Acid Ethyl Ester a) Preparation of 3-methyl-4-[3-(piperidin-4-ylamino)-propoxy]-benzofuran-2-carboxylic acid ethyl ester:

To a solution of 4-(3-(1-benzyl-piperidin-4-ylamino)-propoxy)-3-methyl-benzofuran-2-carboxylic acid ethyl ester (the compound in Example 100, 100 mg) and acetic acid (2 ml) in ethyl acetate (6 ml) was added 10% Pd on charcoal catalyst (20 mg) under N$_2$. The nitrogen atmosphere was replaced by hydrogen (1 atom) and the resulting mixture was stirred overnight at room temperature. The reaction mixture was filtered through a pad of celite and the pad of celite was rinsed with methanol and dichloromethane. The filtrate combined was concentrated in vacuo. The residue was purified by silica gel column chromatography (dichloromethane-MeOH) to give 3-methyl-4-[3-(piperidin-4-ylamino)-propoxy]-benzofuran-2-carboxylic acid ethyl ester (48 mg) as a colorless oil. FAB-MS: m/z 361 (MH$^+$); $^1$H-NMR (CDCl$_3$): δ 1.36 (2H, m), 1.43 (3H, t, J=7 Hz), 1.97 (2H, m), 2.07 (2H, quintet, J=6.5 Hz), 2.68 (3H, m), 2.74 (3H, s), 2.89 (2H, t, J=7 Hz), 3.17 (2H, br d, J=12.5 Hz), 4.16 (2H, t, J=6 Hz), 4.44 (2H, q, J=7 Hz), 6.62 (1H, d, J=8 Hz), 7.11 (1H, d, J=8 Hz), 7.30 (1H, t, J=8 Hz).

b) Preparation of 3-methyl-4-[3-(1-pyridin-3-ylmethyl-piperidin-4-ylamino)-propoxy]-benzofuran-2-carboxylic acid ethyl ester:

A mixture of 3-methyl-4-[3-(piperidin-4-ylamino)-propoxy]-benzofuran-2-carboxylic acid ethyl ester (15 mg), 3-(chloromethyl)pyridine hydrochloride (8 mg) and N,N-diisopropylethylamine (22 μl) in ethanol (1.5 ml) was stirred overnight at 70° C. The reaction mixture was dissolved in ethyl acetate and washed with saturated ammonium chloride solution and water. The organic solvent was dried over anhydrous sodium sulfate and evaporated to dryness. The residue was purified by silica gel column chromatography (dichloromethane-MeOH) to afford 3-methyl-4-[3-(1-pyridin-3-ylmethyl-piperidin- 4-ylamino)-propoxy]-benzofuran-2-carboxylic acid ethyl ester (8 mg) as a colorless oil. FAB-MS: m/z 452 (MH$^+$); $^1$H-NMR (CDCl$_3$): δ 1.43 (3H, t, J=7 Hz), 1.60 (2H, m), 2.00 (4H, m), 2.20 (2H, quintet, J=6.5 Hz), 2.70 (1H, m), 2.72 (3H, s), 2.86 (2H, br d, J=12 Hz), 2.99 (2H, t, J=7 Hz), 3.49 (2H, s), 4.15 (2H, t, J=6 Hz), 4.43 (2H, q, J=7 Hz), 6.59 (1H, d, J=8 Hz), 7.11 (1H, d, J32 8 Hz), 7.22 (1H, m), 7.29 (1H, t, J=8 Hz), 7.66 (1H, brd, J=8 Hz), 8.48 (1H, m), 8.51 (1H, br s).

Following compounds in Examples 104 to 106 were prepared in a similar manner to Example 5-a and Example 96.

EXAMPLE 104

Preparation of 4-(4-tert-Butylamino-butoxy)-3-methyl-benzofuran-2-carboxylic Acid Ethyl Ester Colorless crystals. MALDI-TOF-MS: m/z 348 (MH$^+$); $^1$H-NMR (CDCl$_3$): δ 1.43 (3H, t, J=7 Hz), 1.46 (9H, s), 1.92 (2H, m), 2.29 (2H, m), 2.74 (3H, s), 3.02 (2H, brt, J=8 Hz), 4.02 (2H, t, J=6 Hz), 4.43 (2H, q, J=7 Hz), 6.51 (1H, d, J=8 Hz), 7.09 (1H, d, J=8 Hz), 7.25 (1H, t, J=8 Hz).

EXAMPLE 105

Preparation of 4-(5-tert-Butylamino-pentyloxy)-3-methyl-benzofuran-2-carboxylic Acid Ethyl Ester White powder. FAB-MS: m/z 362 (MH$^+$); $^1$H-NMR (CDCl$_3$): δ 1.43 (3H, t, J=7 Hz), 1.51 (9H, s), 1.60 (2H, m), 1.88 (2H, m), 2.18 (2H, m), 2.71 (3H, s), 2.95 (2H, brt, J=8 Hz), 4.02 (2H, t, J=6 Hz), 4.42 (2H, q, J=7 Hz), 6.57 (1H, d, J=8 Hz), 7.09 (1H, d, J=8 Hz), 7.28 (1H, t, J=8 Hz).

EXAMPLE 106

Preparation of 3-Methyl-4-[1-methyl-3-[(pyridin-3-ylmethyl)-amino]-propoxy]-benzofuran-2-carboxylic Acid Ethyl Ester and 3-Methyl-4-[3-[(pyridin-3-ylmethyl)-amino]-butoxy]-benzofuran-2-carboxylic Acid Ethyl Ester 1,3-Dibromobutane was used instead of 1,3-dibromopropane.

EXAMPLE 106-1

3-Methyl-4-[1-methyl-3-[(pyridin-3-ylmethyl)-amino]-propoxy]-benzofuran-2-carboxylic Acid Ethyl Ester A colorless oil. FAB-MS: m/z 383 (MH$^+$); $^1$H-NMR (CDCl$_3$): δ 1.38 (3H, d, J=6 Hz), 1.43 (3H, t, J=7 Hz), 1.90 (1H, m), 2.03 (1H, m), 2.67 (3H, s), 2.82 (2H, t, J=7 Hz), 3.80 (2H, s), 4.44 (2H, q, J=7 Hz), 4.69 (1H, m), 6.64 (1H, d, J=8 Hz), 7.09 (1H, d, J=8 Hz), 7.17 (1H, dd, J1=8 Hz, J2=5 Hz), 7.29 (1, t, J=8 Hz), 7.62 (1H, br d, J=8 Hz), 8.47 (1H, dd, J=5 Hz, 2 Hz), 8.53 (1H, br d, J=2 Hz).

Example 106-2

3-Methyl-4-[3-[(pyridin-3-ylmethyl)-amino]-butoxy]-benzofuran-2-carboxylic Acid Ethyl Ester A colorless oil. FAB-MS: m/z 383 (MH$^+$); $^1$H-NMR (CDCl$_3$): δ 1.21 (3H, d, J=6 Hz), 1.43 (3H, t, J=7 Hz), 1.97 (2H, m), 2.64 (3H, s), 3.00 (1H, tq, J=6 Hz, 6 Hz), 3.82 (1H, d, J=13.5 Hz), 3.87 (1H, d, J=13.5 Hz), 4.18 (2H, m), 4.43 (2H, q, J=7 Hz), 6.62 (1H, d, J=8 Hz), 7.12 (1H, d, J=8 Hz), 7.13 (1H, dd, J1=8 Hz, J2=5 Hz), 7.31 (1H, t, J=8 Hz), 7.64 (1H, br dd, J1 8 Hz, J2=2 Hz), 8.44 (1H, dd, J1=5 Hz, J2=2 Hz), 8.55 (1H, d, J=2 Hz). Hz).

EXAMPLE 107

Preparation of 4-(2-tert-Butylamino-ethoxy)-3-methyl-benzofuran-2-carboxylic Acid Ethyl Ester a) Preparation of 4-(2-hydroxy-ethoxy)-3-methyl-benzofuran-2-carboxylic acid ethyl ester:

4-Hydroxy-3-methyl-benzofuran-2-carboxylic acid ethyl ester (100 mg), potassium carbonate (500 mg) and 2-iodoethanol (195 μl) were suspended in acetonitrile (10 ml). The mixture was refluxed overnight. Inorganic salt was filtered out and the mother solution was evaporated to dryness. The residue was dissolved in ethyl acetate, washed with water, dried over anhydrous sodium sulfate and evaporated to dryness. The residue was purified by silica gel column chromatography developed by ethyl acetate-hexane to give 4-(2-hydroxy-ethoxy)-3-methyl-benzofuran-2-carboxylic acid ethyl ester (77 mg) as a white powder. FAB-MS: m/z 265 (MH$^+$).

b) Preparation of 4-(2-methanesulfonyloxy-ethoxy)-3-methyl-benzofuran-2-carboxylic acid ethyl ester:

To a cooled (0° C.) solution of 4-(2-hydroxy-ethoxy)-3-methyl-benzofuran-2-carboxylic acid ethyl ester (50 mg) and triethylamine (40 μl) in dichloromethane (5 ml) was dropwise added a solution of methanesulfonyl chloride(18 μl) in dichloromethane (1 ml) and the resulting solution was stirred at 0° C. for two hours. The solution was diluted with dichloromethane, washed with water and brine, dried over anhydrous sodium sulfate, and evaporated to give 4-(2-methanesulfonyloxy-ethoxy)-3-methyl-benzofuran-2-carboxylic acid ethyl ester (55 mg) as colorless crystals. FAB-MS: m/z 343 (MH$^+$).

c) Preparation of 4-(2-tert-butylamino-ethoxy)-3-methyl-benzofuran-2-carboxylic acid ethyl ester:

4-(2-Methanesulfonyloxy-ethoxy)-3-methyl-benzofuran-2-carboxylic acid ethyl ester (20 mg) and tert-butylamine (0.3 ml) were dissolved in THF (2 ml) and stirred overnight at 60° C. The reaction mixture was dissolved in ethyl acetate and washed with saturated ammonium chloride solution and water. The organic solvent was dried over anhydrous sodium sulfate and evaporated to dryness. The residue was purified by preparative thin layer chromatography (using dichloromethane:MeOH=10:1 as a developing solvent) to afford 4-(2-tert-butylamino-ethoxy)-3-methyl-benzofuran-2-carboxylic acid ethyl ester (11 mg) as a colorless oil. FAB-MS: m/z 320 (MH$^+$); $^1$H-NMR (CDCl$_3$): δ 1.20 (9H, s), 1.44 (3H, t, J=7 Hz), 2.75 (3H, s), 3.08 (2H, t, J=5 Hz), 4.23 (2H, t, J=5 Hz), 4.44 (2H, q, J=7 Hz), 6.62 (1H, d, J=8 Hz), 7.11 (1H, d, J=8 Hz), 7.29 (1H, t, J=8 Hz).

EXAMPLE 108

Preparation of 3-Methyl-4-(1-pyridin-3-ylmethyl-piperidin-4-yloxy)-benzofuran-2-carboxylic Acid Ethyl Ester a) Preparation of 3-methyl-4-(piperidin-4-yloxy)-benzofuran-2-carboxylic acid ethyl ester:

A mixture of 4-hydroxy-3-methyl-benzofuran-2-carboxylic acid ethyl ester (100 mg), 4-hydroxypiperidine (46 mg), tributylphosphine (170 μl) and 1,1'-azobis(N,N-dimethylformamide) (120 mg) in benzene (2 ml) was heated at 60° C. for one hour. The suspension was diluted with ethyl acetate, washed with water and brine, dried over anhydrous sodium sulfate and evaporated to dryness. The residue was separated by silica gel column chromatography developed by dichloromethane-methanol to give 3-methyl-4-(piperidin-4-yloxy)-benzofuran-2-carboxylic acid ethyl ester (24 mg) as a colorless oil.

EI-MS: m/z 303 (M$^+$); $^1$H-NMR (CDCl$_3$): δ 1.44 (3H, t, J=7 Hz), 1.87 (2H, m), 2.09 (2H, m), 2.77 (3H, s), 2.86 (2H, m), 3.18 (2H, m), 4.44 (2H, q, J=7 Hz), 4.61 (1H, m), 6.63 (1H, d, J=8 Hz), 7.10 (1H, d, J=8 Hz), 7.29 (1H, t, J=8 Hz).

b) Preparation of 3-methyl-4-(1-pyridin-3-ylmethyl-piperidin-4-yloxy)-benzofuran-2-carboxylic acid ethyl ester:

3-Methyl-4-(piperidin-4-yloxy)-benzofuran-2-carboxylic acid ethyl ester (44 mg), pyridine-3-aldehyde (41 μl) and acetic acid (50 μl) were dissolved in THF (2 ml). The solution was stirred at room temperature for one hour. To a solution was added NaB(OAc)$_3$H (160 mg) and the resulting suspension was stirred at room temperature for two hours. The reaction mixture was diluted with ethyl acetate and washed with saturated sodium hydrogencarbonate solution and water. The organic solvent was dried over anhydrous sodium sulfate and evaporated to dryness. The residue was purified by preparative thin layer chromatography (using dichloromethane:MeOH:ammonia solution (25–28%)=10:1:0.2 as a developing solvent) to give 3-methyl-4-(1-pyridin-3-ylmethyl-piperidin-4-yloxy)-benzofuran-2-carboxylic acid ethyl ester (44 mg) as a colorless oil. MALDI-TOF-MS: m/z 395 (MH$^+$); $^1$H-NMR (CDCl$_3$): δ 1.44 (3H, t, J=7 Hz), 2.02 (4H, m), 2.47 (2H, m), 2.72 (2H, m), 2.75 (3H, s). 3.56 (2H, s), 4.44 (2H, q, J=7 Hz), 4.58 (1H, m), 6.62 (1H, d, J=8 Hz), 7.09 (1H, d, J=8 Hz), 7.28 (1H, t, J=8 Hz), 7.29 (1H, m), 7.71 (1H, brd, J=8 Hz), 8.53 (1H, brd, J=4 Hz), 8.56 (1H, br s).

EXAMPLE 109

Preparation of 3-Methyl-4-[3-(1-pyridin-3-yl-ethylamino)-propoxy]-benzofuran-2-carboxylic Acid Ethyl Ester a) Preparation of 4-(3-amino-propoxy)-3-methyl-benzofuran-2-carboxylic acid ethyl ester:

To a solution of 4-(3-benzylamino-propoxy)-3-methyl-benzofuran-2-carboxylic acid ethyl ester (the compound in Example 98: 180 mg) in THF (10 ml) was added 20% Pd(OH)$_2$ on charcoal catalyst (40 mg) under N$_2$. The nitrogen atmosphere was replaced by hydrogen (1 atom) and the resulting mixture was stirred overnight at room temperature. The reaction mixture was filtered through a pad of celite and the pad of celite was rinsed with methanol and dichloromethane. The filtrate combined was concentrated in vacuo. The residue was purified by silica gel column chromatography (dichloromethane-MeOH) to give 4-(3-amino-propoxy)-3-methyl-benzofuran-2-carboxylic acid ethyl ester (125 mg) as a colorless oil. FAB-MS: m/z 278 (MH$^+$).

b) Preparation of 3-methyl-4-[3-(1-pyridin-3-yl-ethylamino)-propoxy]-benzofuran-2-carboxylic acid ethyl ester:

4-(3-Amino-propoxy)-3-methyl-benzofuran-2-carboxylic acid ethyl ester (40 mg), 3-acetylpyridine (19 mg) and acetic acid (100 μl) were dissolved in THF (5 ml). The solution was stirred at room temperature for one hour. To the solution was added NaB(OAc)$_3$H (100 mg) and the resulting suspension was stirred overnight at room temperature. The reaction mixture was diluted with ethyl acetate and washed with saturated sodium hydrogencarbonate solution and water. The organic solvent was dried over anhydrous sodium sulfate and evaporated to dryness. The residue was purified by preparative thin layer chromatography (using dichloromethane:MeOH:ammonia solution (25–28%)=10:1:0.2 as a developing solvent) to give 3-methyl-4-[3-(1-pyridin-3-yl-ethylamino)-propoxy]-benzofuran-2-carboxylic acid ethyl ester (9 mg) as a colorless oil. ESI-MS: m/z 383 (MH$^+$); $^1$H-NMR (CDCl$_3$): δ 1.40 (3H, d, J=6.5 Hz), 1.44 (3H, t, J=7 Hz), 2.03 (2H, m), 2.58 (3H, s), 2.66 (1H, dt, J1=12 Hz, J2=7 Hz), 2.80 (1H, dt, J1=12 Hz, J2=7 Hz), 3.87 (1H, q, J=6.5 Hz), 4.12 (2H, t, J=6 Hz), 4.43 (2H, q, J=7 Hz),6.59 (1H, d, J=8 Hz), 7.11 (1H, d, J=8 Hz), 7.17 (1H, dd, J1=8 Hz, J2=5 Hz), 7.29 (1H, t, J=8 Hz), 7.68 (1H, br d, J=8 Hz), 8.46 (1H, dd, J1=5 Hz, J2=2 Hz), 8.55 (1H, d, J=2 Hz).

EXAMPLE 110

Preparation of 4-(3-Guanidino-propoxy)-3-methyl-benzofuran-2-carboxylic Acid Ethyl Ester Hydrochloride A mixture of 4-(3-amino-propoxy)-3-methyl-benzofuran-2-carboxylic acid ethyl ester (the compound in Example 109-a: 10 mg), 3,5-dimethyl-1-guanylpyrazole nitrate (14 mg) and triethylamine (100 μl) in DMF (1 ml) was stirred at 40° C. for two days. The solvent was removed under a reduced pressure and the residue was purified by reversed phase column chromatography using Sep-Pak Cartridge C18 (Waters) (H$_2$O-MeOH) to give a white powder. The powder was dissolved in a solution of 1N HCl (0.3 ml) and ethanol (5 ml), and the solution was concentrated in vacuo to give 4-(3-guanidino-propoxy)-3-methyl-benzofuran-2-carboxylic acid ethyl ester hydrochloric acid salt (9 mg) as a white powder. FAB-MS: m/z 320 (MH$^+$); $^1$H-NMR (CD$_3$OD): δ 1.40 (3H, t, J=7 Hz), 2.18 (2H, quintet, J=6.5 Hz), 2.75 (3H, s), 3.46 (2H, t, J=7 Hz), 4.22 (2H, t, J=6 Hz), 4.39 (2H, q, J=7 Hz), 6.78 (1H, d, J=8 Hz), 7.10 (1H, d, J=8 Hz), 7.39 (1H, t, J=8 Hz).

EXAMPLE 111

Preparation of 3-Methyl-4-(1-pyridin-3-ylmethyl-piperidin-3-ylmethoxy)-benzofuran-2-carboxylic Acid Ethyl Ester a) Preparation of 3-methyl-4-(piperidin-3-ylmethoxy)-benzofuran-2-carboxylic acid ethyl ester:

A solution of 4-hydroxy-3-methyl-benzofuran-2-carboxylic acid ethyl ester (1 g), 3-(hydroxymethyl)piperidine (661 μl), triphenylphosphine (1.55 g) and azodicarboxylic acid diethyl ester (930 μl) in THF (20 ml) was stirred overnight at room temperature. A white precipitate separated out. The precipitate was filtered out and the filtrate was evaporated to dryness. The residue was separated by silica gel column chromatography developed by dichloromethane-methanol to give 3-methyl-4-(piperidin-3-ylmethoxy)-benzofuran- 2-carboxylic acid ethyl ester (1.1 g) as a colorless oil. FAB-MS: m/z 318 (MH$^+$); $^1$H-NMR (CDCl$_3$): δ 1.42–2.02 (4H, m), 1.43 (3H, t, J=7 Hz), 2.43 (1H, m), 2.74 (2H, m), 2.75 (3H, s), 3.34 (1H, br d, J=12 Hz), 3.49 (1H, br d, J=12 Hz), 3.96 (1H, dd, J1=9 Hz, J2=6 Hz), 4.02 (1H, dd, J1=9 Hz, J2=5 Hz), 4.43 (2H, q, J=7 Hz), 6.59 (1H, d, J=8 Hz), 7.13 (1H, d, J=8 Hz), 7.30 (1H, t, J=8 Hz).

b) Preparation of 3-methyl-4-(1-pyridin-3-ylmethyl-piperidin-3-ylmethoxy)-benzofuran-2-carboxylic acid ethyl ester:

3-Methyl-4-(piperidin-3-ylmethoxy)-benzofuran-2-carboxylic acid ethyl ester (700 mg), pyridine-3-aldehyde (700 µl) and acetic acid (1 ml) were dissolved in THF (20 ml). The solution was stirred at room temperature for four hours. To the solution was added NaB(OAc)$_3$H (1.4 g) and the resulting suspension was stirred overnight at room temperature. The reaction mixture was diluted with ethyl acetate and washed with saturated sodium hydrogencarbonate solution and brine. The organic solvent was dried over anhydrous sodium sulfate and evaporated to dryness. The residue was purified by silica gel column chromatography developed by dichloromethane-methanol to give 3-methyl-4-(1-pyridin-3-ylmethyl-piperidin-3-ylmethoxy)-benzofuran-2-carboxylic acid ethyl ester (777 mg) as a colorless oil. FAB-MS: m/z 409 (MH$^+$); $^1$H-NMR (CDCl$_3$): δ 1.15–2.30 (7H, m), 1.44 (3H, t, J=7 Hz), 2.58 (3H, s), 2.80 (1H, br d, J=11 Hz), 2.96 (1H, br d, J=8 Hz), 3.48 (1H, d, J=13.5 Hz), 3.57 (1H, d, J=13.5 Hz), 3.89 (1H, dd, J1=9 Hz, J2=8 Hz), 3.96 (1H, dd, J1=9 Hz, J2=5 Hz), 4.43 (2H, q, J=7 Hz), 6.57 (1H, d, J=8 Hz), 7.10 (1H, d, J=8 Hz), 7.21 (1H, dd, J1=8 Hz, J2=5 Hz), 7.28 (1H, t, J=8 Hz), 7.67 (1H, br d, J=8 Hz), 8.49 (1H, dd, J1=5 Hz, J2=1.5 Hz), 8.54 (1H, d, J=1.5 Hz).

EXAMPLE 112

Preparation of 4-[3-(1-Benzyl-piperidin-4-ylamino)-propoxy]-3-methyl-benzofuran-2-carboxylic Acid Phenethyl-amide A mixture of 4-(3-(1-benzyl-piperidin-4-ylamino)-propoxy)-3-methyl-benzofuran-2-carboxylic acid ethyl ester (the compound in Example 100, 15 mg) and phenethylamine (50 µl) was heated at 170° C. for four hours. The reaction mixture was dissolved in ethyl acetate and washed with saturated ammonium chloride solution and water. The organic solvent was dried over anhydrous sodium sulfate and evaporated to dryness. The residue was purified by preparative thin layer chromatography (using dichloromethane:MeOH:ammonia solution (25–28%)=10:1:0.2 as a developing solvent) to give 4-[3-(1-benzyl-piperidin-4-ylamino)-propoxy]-3-methyl-benzofuran-2-carboxylic acid phenethyl-amide (9 mg) as a colorless oil. EI-MS: m/z 525 (M$^+$); $^1$H-NMR (CDCl$_3$): δ 1.41 (2H, m), 1.85–2.09 (6H, m), 2.51 (1H, m), 2.78 (3H, s), 2.90 (6H, m),3.50 (2H, s), 3.70 (2H, q, J=7 Hz), 4.14 (2H, t, J=6 Hz), 6.61 (1H, d, J=8 Hz), 6.63 (1H, br s), 6.97 (1H, d, J=8 Hz), 7.28 (11H, m).

EXAMPLE 113

Preparation of 5-Bromo-4-(3-tert-butylamino-propoxy)-3-methyl-benzofuran-2-carboxylic Acid Ethyl Ester Starting from 5-bromo-4-hydroxy-3-methyl-benzofuran-2-carboxylic acid ethyl ester (Joseph G. Atkinson et al., European patent application 0146243 (1985)), the title compound was obtained in a similar manner to Example 5-a and 5-b.

FAB-MS: m/z 412 (MH$^+$); $^1$H-NMR (CDCl$_3$): δ 1.18 (9H, s), 1.44 (3H,t, J=7.3 Hz), 2.14 (2H, quintet, J=7.3 Hz), 2.73 (3H, s), 2.92 (2H, t, J=7.3 Hz), 4.13 (2H, t, J=7.3 Hz), 4.44 (2H, q, J=7.3 Hz), 7.22 (1H, d, J=7.9 Hz), 7.54 (1H, d, J=7.9 Hz).

EXAMPLE 114

Preparation of 3-Methyl-4-{3-[(pyridin-3-ylmethyl)-amino]-propoxy}-benzofuran-2-carbothioic Acid (2, 4-difluoro-phenyl)-amide 3-Methyl-4-{3-[(pyridin-3-ylmethyl)-amino]-propoxy}-benzofuran-2-carboxylic acid (2,4-difluorophenyl)-amide (the compound of Example 66: 42 mg) and Lawessonis reagent (88 mg) were heated at 100° C. in toluene for 24 hours. The reaction mixture was purified by silica gel TLC developed by dichloromethane-MeOH-28% ammonia water=200:10:1. The title compound was obtained as a yellow solid (10 mg). ESI-MS: m/z 468 (MH$^+$); $^1$H-NMR (CDCl$_3$): δ 2.10 (2H), 2.91 (2H), 2.92 (3H), 3.86 (2H), 4.19 (2H), 6.65 (1H), 6.9–8.4 (7H), 8.49 (1H), 8.58 (1H), 9.57 (1H).

EXAMPLE 115

Preparation of (5-Methyl-isoxazol-3-yl)-{3-methyl-4-[3-(methyl-pyridin-3-ylmethyl-amino)-propoxy]-benzofuran-2-ylmethyl}-amine a) Preparation of {3-methyl-4-[3-(methyl-pyridin-3-ylmethyl-amino)-propoxy]-benzofuran-2-yl}-methanol:

To a solution of (3-methyl-4-{3-[(pyridin-3-ylmethyl)-amino]-propoxy}-benzofuran-2-yl)-methanol (the compound of Example 11) (900 mg) and formalin (0.39 ml) in methanol (40 ml) and acetic acid (0.65 ml) was added sodium triacetoxyborohydride (1.16 g) at room temperature. After 2 hours the reaction mixture was concentrated under reduced pressure and diluted with ethyl acetate (100 ml). The mixture was washed with saturated sodium hydrogen carbonate solution (50 ml) and brine (100 ml), then dried over anhydrous sodium sulfate. The filtrate was concentrated in vacuo and purified by silica gel column chromatography developed by dichloromethane and methanol to give the desired compound as a white solid (890 mg). ESI-MS: m/z 341 (MH$^+$); $^1$H-NMR (CDCl$_3$): δ 1.96 (2H, quintet, J=6.6 Hz), 2.18 (3H, s), 2.28 (3H, s), 2.56 (2H, t, J=6.9 Hz), 3.48 (2H, s), 4.08 (2H, t, J=5.9 Hz), 4.69 (2H, s), 6.56 (1H, d, J=7.6 Hz), 6.99–7.03 (2H, m), 7.14 (1H, t, J=7.6 Hz), 7.57–7.61 (1H, m), 8.31–8.42 (2H, m).

b) Preparation of 3-methyl-4-[3-(methyl-pyridin-3-ylmethyl-amino)-propoxy]-benzofuran-2-carbaldehyde:

To a solution of {3-methyl-4-[3-(methyl-pyridin-3-ylmethyl-amino)-propoxy]-benzofuran-2-yl}-methanol (890 mg) in chloroform (50 ml) was added manganese(IV)-oxide (2.4 g) at room temperature. After stirring overnight the mixture was passed through a Celite pad and concentrated in vacuo. The residue was purified by silica gel column chromatography developed by the mixture of dichloromethane and methanol to give the title compound as a pale yellow oil (850 mg). ESI-MS: m/z 339 (MH$^+$); $^1$H-NMR (CDCl$_3$): δ 2.01–2.27 (2H, m), 2.33 (3H, s), 2.54–2.67 (5H, m), 3.56 (2H, s), 4.17 (2H, t, J=6.6 Hz), 6.62 (1H, d, J=7.6 Hz), 7.06–7.12 (2H, m), 7.41 (1H, t, J=7.6 Hz), 7.41–7.63 (1H, m), 8.35–8.58 (2H, m), 9.93 (1H, s).

c) Preparation of (5-methyl-isoxazol-3-yl)-{3-methyl-4-[3-(methyl-pyridin-3-ylmethyl-amino)-propoxy]-benzofuran-2-ylmethylene}-amine:

A solution of 3-methyl-4-[3-(methyl-pyridin-3-ylmethyl-amino)-propoxy]-benzofuran-2-carbaldehyde (55 mg) and 3-amino-5-methylisooxazole (160 mg) in toluene (4 ml) was refluxed overnight. The mixture was concentrated in vacuo and the residue was purified by silica gel column chromatography developed by ethyl acetate and methanol to give the titled compound as a pale yellow oil (46 mg). ESI-MS: m/z 419 (MH$^+$); $^1$H-NMR (CDCl$_3$): δ 2.00–2.09 (2H, m), 2.29 (3H, s), 2.44 (3H, s), 2.48 (2H, s), 2.68 (2H, t, J=10.2 Hz), 3.53 (2H, s), 4.14 (2H, t, J=5.9 Hz), 6.16 (1H, s), 6.62 (1H, d, J=7.9 Hz), 7.05–7.17 (2H, m), 7.32 (1H, s), J=7.9 Hz), 7.59–7.63 (1H, m), 8.41 (1H, dd, J=1.7 Hz, 4.9 Hz), 8.51 (1H, d, J=2.0 Hz), 8.82 (1H, s).

d) Preparation of (5-methyl-isoxazol-3-yl)-{3-methyl-4-[3-(methyl-pyridin-3-ylmethyl-amino)-propoxy]-benzofuran-2-ylmethyl}-amine:

To a solution of (5-methyl-isoxazol-3-yl)-{3-methyl-4-[3-(methyl-pyridin-3-ylmethyl-amino)-propoxy]-benzofuran-2-ylmethylene}-amine (46 mg) in methanol (2 ml) was added sodium borohydride (20 mg) at room temperature. After 1 hour the mixture was concentrated in vacuo and purified by silica gel column chromatography developed by dichloromethane and methanol to give the titled compound as white solids (28 mg). ESI-MS: m/z 421 (MH$^+$); $^1$H-NMR (CDCl$_3$): δ 1.97–2.06 (2H, m), 2.25 (3H, s), 2.27 (3H, s), 2.28 (3H, s), 2.59 (2H, t, J=6.9 Hz), 3.52 (2H, s), 4.09 (2H, t, J=5.94 Hz), 4.41 (2H, s), 5.53 (1H, s), 6.58 (1H, d, J=7.6 Hz), 7.00 (1H, d, J=7.6 Hz), 7.05–7.15 (2H, m), 7.59–7.63 (1H, m), 8.39 (1H, dd, J=1.7 Hz, 4.9 Hz), 8.49 (1H, d, J=2.0 Hz).

EXAMPLE 116

Preparation of (E)-[3-(3-Methyl-2-styryl-benzofuran-4-yloxy)-propyl]-pyridin-3-ylmethyl-amine a) Preparation of [3-(2-hydroxymethyl-3-methyl-benzofuran-4-yloxy)-propyl]-pyridin-3-ylmethyl-carbamic acid tert-butyl ester:

To an ice-cooled solution of (3-methyl-4-{3-[(pyridin-3-ylmethyl)-amino]-propoxy}-benzofuran-2-yl)-methanol (the compound of Example 11) (1.3 g) and diisopropylethylamine (620 mg) in dichloromethane (10 ml), di-tert-butyl dicarbonate (959 mg) in dichloromethane (10 ml) was added and the mixture was stirred at room temperature for 18 hours. After aqueous quenching, the mixture was extracted with ethyl acetate twice. The combined organic layers were washed with brine and dried over anhydrous sodium sulfate. After filtration, the solution was concentrated under reduced pressure and the residue was purified by silica gel column chromatography (dichloromethane-MeOH) to give a yellow solid (1.44 g, 84%). FAB-MS: m/z 427 (MH$^+$); $^1$H-NMR (CDCl$_3$): δ 1.46 (9H, s), 2.00 (2H, brs), 2.39 (3H, s), 3.39 (2H, brs), 4.07 (2H, t, J=5.6 Hz), 4.33 (2H, s), 4.68 (2H, s), 6.54 (1H, d, J=7.6 Hz), 7.01 (1H, d, J=8.3 Hz), 7.11 (1H, t, J=8.3 Hz), 7.18–7.32 (1H, m), 7.55 (1H, brs), 8.18 (1H, d, J=1.7 Hz), 8.43 (1H, d, J=3.6 Hz).

b) Preparation of 3-(2-formyl-3-methyl-benzofuran-4-yloxy)-propyl]-pyridin-3-ylmethyl-carbamic acid tert-butyl ester:

The mixture of [3-(2-hyroxymethyl-3-methyl-benzofuran-4-yloxy)-propyl]-pyridin-3-ylmethyl-carbamic acid tert-butyl ester (421 mg) and activated MnO$_2$ (Acros, 4 g) in carbon tetrachloride (10 ml) was stirred at room temperature for 18 hours. After filtration, the filtrate was concentrated and the residue was purified by silica gel column chromatography (dichloromethane-MeOH) to give a yellow solid (350 mg, 82%). FAB-MS: m/z 425 (MH$^+$); $^1$H-NMR (CDCl$_3$): δ 1.46 (9H, s), 2.11 (2H, brs), 2.67 (3H, s), 3.56 (2H, brs), 4.09 (2H, t, J=5.9 Hz), 4.49 (2H, s), 6.59 (1H, d, J=7.9 Hz), 7.09 (1H, d, J=8.6 Hz), 7.26 (1H, m), 7.37 (1H, t, J=8.3 Hz), 7.59 (1H, brs), 8.52 (2H, d, J=4.3 Hz), 9.99 (1H, s).

c) Preparation of [3-(3-methyl-2-styryl-benzofuran-4-yloxy)-propyl]-pyridin-3-ylmethyl-carbamic acid tert-butyl ester:

To the suspension of benzyl triphenylphosphonium bromide (48 mg) in THF (0.5 ml) was added n-butyl lithium (1.57 M in n-hexane, 64 μl) at –20° C. under Ar atmosphere. After 10 minutes, 3-(2-formyl-3-methyl-benzofuran-4-yloxy)-propyl]-pyridin-3-ylmethyl-carbamic acid tert-butyl ester (43 mg) in tetrahydrofuran (0.5 ml) was added thereto and the mixture was stirred at room temperature for 18 hours. The reaction mixture was quenched by saturated NH$_4$Cl solution, and extracted with ethyl acetate. The organic layer was washed with brine and dried over anhydrous sodium sulfate. After filtration, the filtrate was concentrated under reduced pressure and the residue was purified by silica gel column chromatography (dichloromethane-MeOH) to give a colorless oil (43 mg, 86%). The product was a mixture of E and Z (the ratio was 1/1 according to the analyses of LC and $^1$H-NMR). ESI-MS: m/z 499 (MH$^+$); $^1$H-NMR (CDCl$_3$): δ 1.45, 1.46 (9H, each s), 2.08 (2H, brs), 2.25, 2.40 (3H, each s), 3.44 (2H, brs), 4.05 (2H, brs), 4.47 (2H, brs), 6.39–7.55 (10H, m), 8.51 (2H, m).

d) Preparation of (E)-[3-(3-methyl-2-styryl-benzofuran-4-yloxy)-propyl]-pyridin-3-ylmethyl-amine To a solution of 10% trifluoroacetic acid in dichloromethane [3-(3-methyl-2-styryl-benzofuran-4-yloxy)-propyl]-pyridin-3-ylmethyl-carbamic acid tert-butyl ester (15 mg) in dichloromethane (1 ml) was added with ice-cooling. After 3 hours, the mixture was quenched with saturated sodium hydrogen carbonate solution and extracted with ethyl acetate. The organic layer was washed with brine and dried over anhydrous sodium sulfate. After filtration, the filtrate was concentrated under reduced pressure and the residue was purified by silica gel column chromatography (dichloromethane-MeOH) to give a colorless solid (7 mg, 58%). ESI-MS: m/z 399 (MH$^+$); $^1$H-NMR (CDCl$_3$): δ 2.12 (2H, s), 2.37 (3H, s), 2.94 (2H, t, J=6.9 Hz), 3.91 (2H, s), 4.14 (2H, t, J=5.9 Hz), 6.57 (1H, d, J=7.6 Hz), 7.02–7.28 (5H, m), 7.37 (2H, t, J=7.6 Hz), 7.53 (2H, d, J=7.6 Hz), 7.73 (2H, d, J=7.9 Hz), 8.52 (1H, d, J=4.6 Hz), 8.61 (1H, s).

EXAMPLE 117

Preparation of [3-(3-Methyl-2-phenethyl-benzofuran-4-yloxy)-propyl]-pyridin-3-ylmethyl-amine a) Preparation of [3-(3-methyl-2-phenethyl-benzofuran-4-yloxy)-propyl]-pyridin-3-ylmethyl-carbamic acid tert-butyl ester:

Ethanol solution (1 ml) of [3-(3-methyl-2-styryl-benzofuran-4-yloxy)-propyl]-pyridin-3-ylmethyl-carbamic acid tert-butyl ester (the compound of Example 116-c) (21 mg) was stirred with Pd—C (3 mg) under H$_2$ atmosphere. The catalyst was removed by filtration, and the filtrate was concentrated under reduced pressure and the residue was purified by silica gel column chromatography (dichloromethane-MeOH) to give a colorless oil (14 mg, 66%). FAB-MS: m/z 500 (MH$^+$); $^1$H-NMR (CDCl$_3$): δ 1.45 (9H, s), 2.07 (2H, brs) 2.08 (3H, s), 2.97 (4H, s), 3.41 (2H, brs), 4.03 (2H, t, J=5.6 Hz), 4.45 (2H, s), 6.53 (1H, d, J=7.6 Hz), 7.00–7.30 (8H, m), 7.53 (1H, brs), 8.48–8.52 (2H, m).

b) Preparation of [3-(3-methyl-2-phenethyl-benzofuran-4-yloxy)-propyl]-pyridin-3-ylmethyl-amine:

[3-(3-Methyl-2-phenethyl-benzofuran-4-yloxy)-propyl]-pyridin-3-ylmethyl-carbamic acid tert-butyl ester (14 mg) obtained above was treated with a 10% solution of trifluoroacetic acid in $CH_2Cl_2$ (1 ml) at 0° C. for 18 hours. The reaction mixture was quenched with saturated sodium hydrogen carbonate solution and the mixture was extracted with ethyl acetate. The organic layer was washed with brine and dried over anhydrous sodium sulfate. After filtration, the filtrate was concentrated under reduced pressure and the residue was purified by silica gel column chromatography (dichloromethane-MeOH) to give a colorless oil (10 mg, 89%). ESI-MS: m/z 401 (MH$^+$); $^1$H-NMR (CDCl$_3$): δ 2.04 (2H, t, J=6.9 Hz), 2.08 (3H, s), 2.87 (2H, t, J=6.9 Hz), 2.97 (4H, s), 3.83 (2H, s), 4.12 (2H, t, J=5.9 Hz), 6.58 (1H, d, J=6.9 Hz), 6.94–7.31 (8H, m), 7.66 (1H, d, J=7.9 Hz), 8.49 (1H, d, J=3.3 Hz), 8.56 (1H, s).

EXAMPLE 118

Preparation of 1-(3-Methyl-4-{3-[(pyridin-3-ylmethyl)-amino]-propoxy}-benzofuran-2-yl)-butan-1-one a) Preparation of 4-(3-bromo-propoxy)-3-methyl-benzofuran-2-carboxylic acid methoxy-methyl-amide:

4-(3-Bromo-propoxy)-3-methyl-benzofuran-2-carboxylic acid (the compound of Example 62-a) (90 mg) was refluxed in thionyl chloride (1 ml) for three hours. Thionyl chloride was evaporated to dryness and the residue was dissolved in dry dichloromethane (3 ml). To the solution was added N,O-dimethylhydroxylamine hydrochloride (32 mg) and triethylamine (0.1 ml). The mixture was stirred at room temperature for 4 hours. The mixture was purified by silica gel column chromatography (dichloromethane-MeOH). The title compound was obtained as a colorless solid (98 mg). ESI-MS: m/z 356 (MH$^+$); $^1$H-NMR (CDCl$_3$): δ 2.40 (2H, quintet, J=6.5 Hz.), 2.64 (3H, s), 3.36 (3H, s), 3.65 (2H, t, J=6.5 Hz), 3.85 (3H, s), 4.22 (2H, t, J=6 Hz), 6.64 (1H, d, J=8 Hz), 7.06 (1H, d, J=8 Hz), 7.28 (1H, t, J=8 Hz).

b) Preparation of 1-[4-(3-bromo-propoxy)-3-methyl-benzofuran-2-yl]-butan-1-one

To a solution of the compound obtained above in dry tetrahydrofuran was added propylmagnesium bromide in tetrahydrofuran (0.12 ml of the 2 ml/L solution) at 0° C. The mixture was stirred at room temperature for four hours and then treated with diluted hydrochloric acid. The product was extracted with ethyl acetate. The organic layer was washed with water, dried over anhydrous sodium sulfate and purified by silica gel column chromatography developed by hexane-ethyl acetate=10:1. The title compound was obtained as a colorless solid (14 mg). EI-MS: m/z 338 (M$^+$); $^1$H-NMR (CDCl$_3$): δ 1.02 (3H, t, J=7 Hz), 1.77 (2H, six-lines, J=7 Hz), 2.41 (2H, quintet, J=6 Hz), 2.76 (3H, s), 2.94 (2H, t, J=7 Hz), 3.67 (2H, t, J=6.5 Hz), 4.24 (2H, t, J=6 Hz), 6.65 (1H, d, J=8 Hz), 7.09 (1H, d, J=8 Hz), 7.34 (1H, t, J=8 Hz).

c) Preparation of 1-(3-methyl-4-{3-[(pyridin-3-ylmethyl)-amino]-propoxy}-benzofuran-2-yl)-butan-1-one 1-[4-(3-Bromo-propoxy)-3-methyl-benzofuran-2-yl] butan-1-one (13 mg) obtained above and 3-pyridylmethylamine (42 mg) were heated at 70° C. overnight in ethanol. The product was partitioned between ethyl acetate and sodium hydrogen carbonate solution. The organic layer was washed with water, dried over anhydrous sodium sulfate and purified by silica gel TLC developed by dichloromethane-methanol=10:1. The title compound was obtained as colorless oil. ESI-MS: m/z 367 (MH$^+$); $^1$H-NMR (CDCl$_3$): δ 1.02 (2H, t, J=7 Hz), 1.77 (2H, six-lines, J=7 Hz), 2.07 (2H, quintet, J=6.5 Hz), 2.70 (3H, s), 2.89 (2H, t, J=7 Hz), 2.94 (2H, t, J=7 Hz), 3.84 (2H, s), 4.17 (2H, t, J=6 Hz), 6.61 (1H, d, J=8 Hz), 7.07 (1H, d, J=8 Hz), 7.22 (1H, dd, J=8 Hz, 4.5 Hz), 7.33 (1H, t, J=8 Hz), 7.66 (1H, dt, J=8 Hz, 1.5 Hz), 8.49 (1H, dd, J=4.5 Hz, 1.5 Hz), 8.57 (1H, d, J=1.5 Hz).

EXAMPLE 119

Preparation of (3-{2-[3-(3-Fluoro-phenoxy)-propyl]-3-methyl-benzofuran-4-yloxy}-propyl)-pyridin-3-ylmethyl-amine a) Preparation of 3-methyl-4-(tetrahydro-pyran-2-yloxy)-benzofuran-2-carboxylic acid ethyl ester:

To a solution of 4-hydroxy-3-methylbenzofuran-2-carboxylic acid ethyl ester (1 g) and 3,4-dihydro 2H-pyran (1.1 g) in anhydrous dichloromethane (50 ml) was added pyridinum toluenesulfonate (200 mg). The mixture was stirred at room temperature overnight. The mixture was extracted with water, dried over anhydrous sodium sulfate and concentrated to afford the title compound (1.2 g) in 87% yield. $^1$H-NMR (CDCl$_3$): δ 1.43 (3H, t, J=7.2 Hz), 1.50–1.95 (6H, m), 2.76 (3H, s), 3.66 (1H, m), 3.90 (1H, m), 4.42 (2H, q, J=7.2 Hz), 5.61 (1H, m), 6.92 (1H, d, J=8.2 Hz), 7.15 (1H, d, J=8.2 Hz), 7.31 (1H, t, J=8.2 Hz).

b) Preparation of 3-[3-methyl-4-(tetrahydro-pyran-2-yloxy)-benzofuran-2-yl]-methanol:

To a solution of 3-methyl-4-(tetrahydro-pyran-2-yloxy)-benzofuran-2-carboxylic acid ethyl ester (1,2 g) in tetrahydrofuran (20 ml) was added LiAlH$_4$ (149 mg) at 0° C. After the addition, the reaction mixture was warmed to room temperature. The excess LiAlH$_4$ was hydrolyzed by slowly adding water to the reaction mixture at 0° C. Then the product was extracted with ethyl acetate and washed with water and brine. The organic layer was dried over anhydrous sodium sulfate, filtered and concentrated to give desired compound (1 g) as a colorless oil in 97% yield. ESI-MS: m/z 262 (M$^+$); $^1$H-NMR (CDCl$_3$): δ 1.52–2.01 (6H, m), 2.43 (3H, s), 3.62 (1H, m), 3.92 (1H, m), 4.73 (2H,d, J=5.6 Hz), 5.57 (1H, m), 6.90 (1H, d, J=7.9 Hz), 7.05 (1H, d, J=7.9 Hz), 7.18 (1H, t, J=7.91 Hz).

c) 3-Preparation of methyl-4-(tetrahydro-pyran-2-yloxy)-benzofuran-2-carbaldehyde:

To a solution of 3-[3-methyl-4-(tetrahydro-pyran-2-yloxy)-benzofuran-2-yl]-methanol (1 g) in CCl$_4$ (50 ml) was added manganese (IV) oxide (4 g). The mixture was stirred for 3 hours, filtered through Celite and concentrated to afford desired aldehyde (1 g) as a slightly yellow oil in quantitative yield. $^1$H-NMR (CDCl$_3$): δ 1.51–2.03 (6H, m), 2.81 (3H, s), 3.78 (1H, m), 3.89 (1H, m), 5.60 (1H, m), 6.90 (1H, d, J=7.9 Hz), 7.12 (1H, d, J=7.9 Hz), 7.41 (1H, t, J=7.9 Hz), 9.98 (1H, s).

d) Preparation of (E)-3-[3-methyl-4-(tetrahydro-pyran-2-yloxy)-benzofuran-2-yl]-acrylic acid ethyl ester:

To a solution of 3-methyl-4-(tetrahydro-pyran-2-yloxy)-benzofuran-2-carbaldehyde (1 g) and diethyl phosphonoacetic acid ethyl ester (1.7 g) in tetrahydrofuran (20 ml) was added LiOH monohydrate (0.3g). The mixture was stirred overnight. The solvent was removed and the residue was purified over silica gel (30% of ethyl acetate in hexane) to give desired compound as an oil (1.2 g) in 95% yield. ESI-MS: m/z 330 (M$^+$); $^1$H-NMR (CDCl$_3$): δ 1.34 (3H, t, 7.3 Hz), 1.53–2.03 (6H, m), 2.52 (3H, s), 3.62 (1H, m), 3.89 (1H, m), 4.22 (2H, q, J=7.3 Hz), 5.58 (1H, m), 6.45 (1H, d, J=15.5 Hz), 6.87 (1H, d, J=7.9 Hz), 7.03 (1H, d, J=7.9 Hz), 7.20 (1H, t, J=7.9 Hz), 7.65 (1H, d, J=15.5 Hz).

e) Preparation of 3-[3-methyl-4-(tetrahydro-pyran-2-yloxy)-benzofuran-2-yl]-propan-1-ol:

To a solution of (E)-3-[3-methyl-4-(tetrahydro-pyran-2-yloxy)-benzofuran-2-yl]-acrylic acid ethyl ester (1.2 g) in methanol (15 ml) was added 10% Pd—C (15 mg). The mixture was stirred under 1 atmosphere of hydrogen gas until the starting material was completely consumed. The mixture was filtered through Celite and concentrated to give an oil residue. The oil residue was dissolved in tetrahydrofuran and LiAlH$_4$ (150 mg) was added to the solution at 0° C. After the addition, the mixture was warmed to room temperature and stirred for 2 hours at room temperature. The excess LiAlH$_4$ was hydrolyzed by slowly adding water to the reaction mixture at 0° C. Then the product was extracted with ethyl acetate and washed with water and brine. The organic layer was dried over anhydrous sodium sulfate, filtered and concentrated to give desired compound (1 g) as a colorless oil in 95% yield. ESI-MS: m/z 291 (MH$^+$); $^1$H-NMR (CDCl$_3$): δ 1.54–2.01 (8H, m), 2.34 (3H, s), 2.81 (2H, t, J=6.9 Hz), 3.60–3.75 (3H, m), 3.93 (1H, m), 5.54 (1H, m), 6.86 (1H, d, J=7.9 Hz), 7.01 (1H, d, J=7.9 Hz), 7.04 (1H, t, J=7.9 Hz).

f) Preparation of (3-{2-[3-(3-fluoro-phenoxy)-propyl]-3-methyl-benzofuran-4-yloxy}-propyl)-pyridin-3-ylmethyl-amine:

To a solution of 3-[3-methyl-4-(tetrahydro-pyran-2-yloxy)-benzofuran-2-yl]-propan-1-ol (16 mg) in dichloromethane were added triethylamine (50mg) and methanesulfonyl chloride (10 mg) at 0° C. The mixture was stirred at 0° C. for 30 minutes. The mixture was filtered through a silica gel bed and concentrated to afford a slight yellow residue (22 mg).

The yellow residue was dissolved in anhydrous N,N-dimethylformamide (0.5 ml), 3-fluorophenol (20 mg) and cesium carbonate (100 mg) were added to the solution. After stirring at room temperature for 48 hours, the mixture was extracted with ethyl acetate and washed with water and brine. The organic layer was dried over anhydrous sodium sulfate, filtered and concentrated to give a yellow oil residue, which was used for next reaction without further purification.

The residue was dissolved in methanol (1 ml), pyridinum toluenesulfonate (5 mg) was added to the solution. After the starting material was consumed, the solvent was removed and the residue was dried in vacuo. The dried residue was dissolved in anhydrous N,N-dimethylformamide (0.5 ml). To the solution 1,3-dibromopropane (100 mg) and potassium carbonate (100 mg) were added. After stirring for 3 h, the mixture was extracted with ethyl acetate and washed with water and brine. The organic layer was dried over anhydrous sodium sulfate, filtered and concentrated to give a yellow oil residue, which was used for next reaction without further purification.

The residue was dissolved in anhydrous ethanol (0.5 ml) and 3-aminomethylpyridine (100 mg) was added to the solution. The solution was heated at 85° C. overnight. The desired product was purified by preparative TLC (dichloromethane-methanol=15:1) as a slightly yellow oil (12 mg) in 54% overall yield. ESI-MS: m/z 449 (MHz); $^1$H-NMR (CDCl$_3$): δ 204 (2H, m), 2.14 (2H, m), 2.15 (3H, s), 2.89 (4H, m), 3.82 (2H, s), 3.96 (2H, t, J=6.2 Hz), 4.11 (2H, t, J=6.2 Hz), 6.53–6.70 (4H, m), 6.97 (1H, d, J=7.9 Hz), 7.10 (1H, t, J=7.9 Hz), 7.20 (2H, m), 7.63 (1H, m), 8.46 (1H, m), 8.53 (1H, m).

EXAMPLE 120

Preparation of (3-{2-[3-(3-Fluoro-benzyloxy)-propyl]-3-methyl-benzofuran-4-yloxy}-propyl)-pyridin-3-ylmethyl-amine To a solution of 3-[3-methyl-4-(tetrahydro-pyran-2-yloxy)-benzofuran-2-yl]-propan-1-ol (15 mg) and 3-fluorobenzyl bromide (15 mg) in anhydrous N,N-dimethylformamide (0.5 ml), was added NaH (5 mg). After stirring at room temperature overnight, the mixture was extracted with ethyl acetate and washed with water and brine. The organic layer was dried over anhydrous sodium sulfate, filtered and concentrated to give a yellow oil residue, which was used for next reaction without further purification.

The residue was dissolved in methanol (1 ml), pyridinum toluenesulfonate (5 mg) was added to the solution. After the starting material was consumed, the solvent was removed in vacuo. The residue was dissolved in anhydrous N,N-dimethylformamide (0.5 ml). To the solution was added 1,3-dibromopropane (100 mg) and potassium carbonate (100 mg). After stirring for 3 hours, the mixture was extracted with ethyl acetate and washed with water and brine. The organic layer was dried over anhydrous sodium sulfate, filtered and concentrated to give a yellow oil residue, which was used for next reaction without further purification.

The residue was dissolved in anhydrous ethanol (0.5 ml). 3-Aminomethylpyridine (100 mg) was added to the solution and the solution was heated at 85° C. overnight. The desired product was purified by preparative TLC (dichloromethane-methanol=15:1) as a slightly yellow oil (7 mg) in 32% overall yield. ESI-MS: m/z 463 (MH$^+$); $^1$H-NMR (CDCl$_3$): δ 1.95–2.10 (4H, m), 2.21(3H, s), 2.78 (2H, t, J=7.3 Hz), 2.88 (2H, t, J=7.3 Hz), 3.48 (2H, t, J=7.3 Hz), 3.83 (2H, s), 4.13 (2H, t, J=7.3 Hz), 4.45 (2H, s), 6.58 (1H, d, J=7.9 Hz), 6.85–7.32 (7H, m), 7.63 (1H, m), 8.47 (1H, m), 8.54 (1H, m).

EXAMPLE 121

Preparation of {3-[2-(4-Fluoro-phenylsulfanylmethyl)-3-methyl-benzofuran-4-yloxy]-propyl}-pyridin-3-ylmethyl-amine Using 4-fluorothiophenol in place of phenethyl mercaptan, the title compound was prepared in a similar manner to Example 55-c. A colorless oil. ESI-MS: m/z 437 (MH$^+$); $^1$H-NMR (CDCl$_3$): δ 1.94 (3H, s), 2.02–2.09 (2H, m), 2.87 (2H, t, J=7.3 Hz), 3.85 (2H, s), 4.05 (2H, s), 4.12 (2H, t, J=5.9 Hz), 6.58 (1H, d, J=8.3 Hz), 6.92–7.37 (7H, m), 7.69 (1H, d, J=7.9 Hz), 8.49–8.59 (2H, m).

EXAMPLE 122

Preparation of {3-[2-(4-Fluoro-benzenesulfinylmethyl)-3-methyl-benzofuran-4-yloxy]-propyl}-pyridin-3-ylmethyl-amine (Example 122-1) and {3-[2-(4-fluoro-benzenesulfonylmethyl)-3-methyl-benzofuran-4-yloxy]-propyl}-pyridin-3-ylmethyl-amine (Example 122-2)

To a solution of {3-[2-(4-fluoro-phenylsulfanylmethyl)-3-methyl-benzofuran-4-yloxy]-propyl}-pyridin-3-ylmethyl-amine (16 mg) and bis(2,4-pentanedionato)-vanadium oxide (9.8 mg) in dichloromethane (2 ml) was added 30% hydrogenperoxide aqueous solution (20 μl) at room temperature and the mixture was stirred for 1 hour. After the addition of ammonia solution (2 ml) the whole mixture was vigorously stirred until the sticky precipitation disappeared, then extracted with ethyl acetate, washed with brine and dried over anhydrous sodium sulfate. The mixture was separated by silica gel column chromatography developed by dichloromethane and methanol. {3-[2-(4-fluoro-benzenesulfinylmethyl)-3-methyl-benzofuran-4-yloxy]- propyl}-pyridin-3-ylmethyl-amine (5 mg) was obtained as a white solid: ESI-MS: m/z 453 (MH$^+$); $^1$H-NMR (CDCl$_3$): δ 1.98 (3H, s), 2.00–2.09 (2H, m), 2.85 (2H, t, J=6.9 Hz), 4.01 (1H, d, J=13.5 Hz), 4.13 (2H, t, J=5.9 Hz), 4.32 (1H, d, J=13.5 Hz), 6.59 (1H, d, J=7.9 Hz), 6.94 (1H, d, J=8.2 Hz), 7.10–7.25 (4H, m), 7.44–7.49 (2H, m), 7.65–7.69 (1H, m), 8.49–8.59 (2H, m). {3-[2-(4-fluoro-benzenesulfonylmethyl)-3-methyl-benzofuran-4-yloxy]-propyl}-pyridin-3-ylmethyl-amine (11 mg) was obtained as a colorless oil:. ESI-MS: m/z 469 (MH$^+$); $^1$H-NMR (CDCl$_3$): δ 1.99–2.09 (2H, m), 2.12 (3H, s), 2.86 (2H, t, J=7.3 Hz), 3.84 (2H, s), 4.13 (2H, t, J=5.9 Hz), 4.50 (2H, s), 6.59 (1H, d, J=8.3 Hz), 6.89 (1H, d, J=8.2 Hz), 7.11–7.69 (7H, m), 7.69–8.57 (2H, m).

EXAMPLE 123

Preparation of 3-Methyl-4-[3-(methyl-pyridin-3-ylmethyl-amino)-propoxy]-benzofuran-2-carbaldehyde O-ethyl-oxime To a solution of 3-methyl-4-[3-(methyl-pyridin-3-ylmethyl-amino)-propoxy]-benzofuran-2-carbaldehyde (the compound of Example 115-b) (29 mg) in pyridine (5 ml) was added O-ethyl hydroxylamine hydrochloride (84 mg) at room temperature. After stirring for seven hours, the mixture was partitioned between ethyl acetate and NH$_4$Cl solution. The organic layer was dried over anhydrous sodium sulfate and evaporated under reduced pressure. The residue was purified by silica gel column chromatography developed by dichloromethane and methanol to give the title compound as a colorless oil (19 mg). ESI-MS: m/z 382 (MH$^+$); $^1$H-NMR (CDCl$_3$): δ 1.35 (3H, t, J=6.9 Hz), 2.03 (2H, m), 2.27 (3H, s), 2.29 (3H, s), 2.59 (2H, t, J=6.9 Hz), 3.52 (2H, s), 4.11 (2H, t, J=5.9 Hz), 4.32 (2H, q, J=6.9 Hz), 6.60 (1H, d, J=7.6 Hz), 7.05–7.11 (2H, m), 7.21 (1H, t, J=7.9 Hz), 7.58–7.63 (1H, m), 8.12 (1H, s), 8.42 (1H, dd, J=1.7 Hz, 4.9 Hz), 8.52 (1H, d, J=2.0 Hz).

EXAMPLE 124

Preparation of {3-Methyl-4-[3-(methyl-pyridin-3-ylmethyl-amino)-propoxy]-benzofuran-2-ylmethylene}-morpholin-4-yl-amine To a solution of 3-methyl-4-[3-(methyl-pyridin-3-ylmethyl-amino)-propoxy]-benzofuran-2-carbaldehyde (the compound of Example 115-b) (420 mg) in dichloromethane (50 ml) was added 4-aminomorpholine (380 mg) at room temperature. After stirring overnight, the mixture was washed with water (20 ml), NH$_4$Cl solution (20 ml) and dried over anhydrous sodium sulfate. The mixture was purified by silica gel column chromatography developed by dichloromethane and methanol to give the title compound as a colorless oil (340 mg). ESI-MS: m/z 423 (MH$^+$); $^1$H-NMR (CDCl$_3$): δ 1.98–2.07 (2H, m), 2.23 (3H, s), 2.30 (3H, s), 2.59 (2H, t, J=6.9 Hz), 3.21–3.26 (4H, m), 3.53 (2H, s), 3.88–3.92 (4H, m), 4.10 (2H, t, J=5.9 Hz), 6.58 (1H, d, J=7.6 Hz), 7.03–7.15 (3H, m), 7.58–7.63 (2H, m), 8.40–8.51 (2H, m).

EXAMPLE 125

Preparation of {3-Methyl-4-[3-(methyl-pyridin-3-ylmethyl-amino)-propoxy]-benzofuran-2-ylmethylene}-(4-methyl-piperazin-1-yl)-amine Using 1-amino-4-methylpiperazine dihydrochloride in place of 4-aminomorpholine, the title compound was prepared in a similar manner to the Example 124. A pale yellow oil. ESI-MS: m/z 436 (MH$^+$); $^1$H-NMR (CDCl$_3$): δ 2.01–2.08 (2H, m), 2.21 (3H, s), 2.28 (3H, s), 2.36 (3H, s), 2.56–2.65 (6H, m), 3.26–3.30 (4H, m), 3.53 (2H, s), 4.11 (2H, t, J=5.9 Hz), 6.57 (1H, d, J=6.6 Hz), 7.04–7.17 (3H, m), 7.52 (1H, s), 7.60–7.63 (1H, m), 8.40–8.51 (2H, m).

EXAMPLE 126

Preparation of 5-Fluoro-3-methyl-4-{3-[(pyridin-3-ylmethyl)-amino]-propoxy}-benzofuran-2-carboxylic Acid Ethyl Ester a) Preparation of 5-fluoro-4-hydroxy-3-methyl-benzofuran-2-carboxylic acid ethyl ester (Example 126-a-1) and 7-fluoro-4-hydroxy-3-methyl-benzofuran-2-carboxylic acid ethyl ester (Example 126-a-2):

To a solution of 4-hydroxy-3-methyl-benzofuran-2-carboxylic acid ethyl ester (Joseph G. Atkinson et al., European patent application 0146243 (1985)) (700 mg) in dichloromethane (20 ml) was added 1-fluoro-2,6-dichloropyridinium tetrafluoroborate (807 mg) at room temperature and the mixture was stirred overnight. The reaction was quenched by the addition of water (10 ml), extracted with ethyl acetate (20 ml), washed with brine and dried over anhydrous magnesium sulfate. The mixture was separated by silica gel column chromatography developed by dichloromethane and methanol. 5-fluoro-4-hydroxy-3-methyl-benzofuran-2-carboxylic acid ethyl ester (210 mg) was obtained as a white solid. EI-MS: m/z 238 (MH$^+$); $^1$H-NMR (CDCl$_3$): δ 1.50 (3H, t, J=7.3 Hz), 2.82 (3H, s), 4.46 (2H, q, J=7.3 Hz), 6.99 (1H, dd, J=3.3 Hz, 8.9 Hz), 7.15 (1H, dd, J=8.9 Hz, 10.6 Hz). And 7-fluoro-4-methyl-benzofuran-2-carboxylic acid ethyl ester was obtained as a colorless oil. EI-MS: m/z 238 (MH$^+$); $^1$H-NMR (CDCl$_3$): δ 1.44 (3H, t, J=7.3 Hz), 2.76 (3H, s), 4.46 (2H, q, J=7.3 Hz), 6.47 (1H, dd, J=3.0 Hz, 8.6 Hz), 6.97 (1H, dd, J=8.6 Hz, 10.2 Hz).

b) Preparation of 5-fluoro-3-methyl-4-{3-[(pyridin-3-ylmethyl)-amino]-propoxy}-benzofuran-2-carboxylic acid ethyl ester The title compound was prepared from 5-fluoro-4-hydroxy-3-methyl-benzofuran-2-carboxylic acid ethyl ester (Example 126-a-1) in a similar manner to Example 1-f and Example 1-g. Colorless oil. ESI-MS: m/z 387 (MH$^+$); $^1$H-NMR (CDCl$_3$): δ 1.44 (3H, t, J=6.9 Hz), 1.99–2.09 (2H, m), 2.69 (3H, s), 2.88 (2H, t, J=6.93 Hz), 3.84 (s, 2H), 4.35 (2H, dt, J=1.9 Hz, 6.3 Hz), 4.45 (2H, q, J=6.9 Hz), 7.12–7.27 (3H,m), 7.66–7.70 (1H, m), 8.50 (1H, dd, J=1.7 Hz, 4.6 Hz), 8.57 (1H, d, J=2.0 Hz).

EXAMPLE 127

Preparation of 7-Fluoro-3-methyl-4-{3-[(pyridin-3-ylmethyl)-amino]-propoxy}-benzofuran-2-carboxylic Acid Ethyl Ester The title compound was prepared from 7-fluoro-4-hydroxy-3-methyl-benzofuran-2-carboxylic acid ethyl ester (Example 126-a-2) in a similar manner to Example 1-f and Example 1-g. White solid. ESI-MS: m/z 387 (MH$^+$); $^1$H-NMR (CDCl$_3$): δ 1.44 (3H, t, J=6.9 Hz), 2.02–2.11 (2H, m), 2.68 (3H, s), 2.88 (2H, t, J=6.93 Hz), 3.85 (s, 2H), 4.17 (2H, t, J=6.3 Hz), 4.43 (2H, q, J=6.9 Hz), 6.49 (1H,dd, J=2.9 Hz, 8.9 Hz), 7.02 (1H, dd, J=8.9 Hz, 8.9 Hz), 7.19–7.25 (1H, m), 7.65–7.69 (1H, m), 8.49 (1H, dd, J=1.7 Hz, 4.9 Hz), 8.57 (1H, d, J=1.9 Hz).

EXAMPLE 128

Preparation of (3-Methyl-4-{3-[(pyridin-3-ylmethyl)-amino]-propoxy}-benzofuran-2-yl)-pyridin-2-yl-methanone a) Preparation of [4-(3-bromo-propoxy)-3-methyl-benzofuran-2-yl]-methanol:

To a solution of 4-(3-bromo-propoxy)-3-methyl-benzofuran-2-carboxylic acid ethyl ester (Example 5-a) (5.5 g) in dichloromethane (50 ml) was added diisobutylaluminium hydride (DIBAL-H) (1M in hexane, 34 ml) at 0° C. After 1 hour the reaction was quenched by the addition of saturated ammonium chloride solution (13 ml) and diluted with ether (50 ml) and the whole mixture was stirred overnight. The mixture was filtered through a pad of Celite after the addition of anhydrous magnesium sulfate and concentrated in vacuo. The titled compound (4.4 g) was obtained as a white solid after the purification by silica gel column chromatography developed by the mixture of hexane and ethyl acetate. EI-MS: m/z 299 (M$^+$); $^1$H-NMR (CDCl$_3$): δ 2.35–2.44 (5H, m), 3.64 (2H, t, J=6.6 Hz), 4.21 (2H, t, J=5.6 Hz), 4.71 (2H, s), 6.63 (1H, d, J=7.9 Hz), 7.05 (1H, d, J=8.2 Hz), 7.17 (1H, t, J=7.9 Hz).

b) Preparation of 4-(3-bromo-propoxy)-3-methyl-benzofuran-2-carbaldehyde

To a solution of [4-(3-bromo-propoxy)-3-methyl-benzofuran-2-yl]methanol (690 mg) in chloroform (10 ml) was added manganese(IV) oxide (1.2 g) at room temperature and the mixture was stirred vigorously overnight. The mixture was filtered through a pad of Celite and concentrated in vacuo. The titled compound (500 mg) was obtained as a white solid after the purification by silica gel column chromatography developed by the mixture of hexane and ethyl acetate. EI-MS: m/z 297 (M$^+$); $^1$H-NMR (CDCl$_3$): δ 2.38–2.47 (2H, m), 2.74 (3H, s), 3.65 (2H, t, J=6.6 Hz), 4.23 (2H, t, J=5.9 Hz), 6.68 (1H, d, J=7.9 Hz), 7.14 (1H, d, J=8.9 Hz), 7.40 (1H, t, J=8.3 Hz), 9.97 (1H, s).

c) Preparation of [4-(3-bromo-propoxy)-3-methyl-benzofuran-2-yl]pyridin-2-yl-methanol:

To a solution of 2-bromopyridine (20 μl) in dry THF (1.5 ml) was added n-butyl lithium (1.6 M in hexane, 125 μl) at −78° C. After 30 minutes, the solution of 4-(3-bromo-propoxy)-3-methyl-benzofuran-2-carbaldehyde (50 mg) in THF (2 ml) dropwise at the same temperature. The reaction was quenched by the addition of saturated ammonium chloride solution, extracted with ethyl acetate, dried over anhydrous sodium sulfate and then concentrated in vacuo. The mixture was purified by silica gel TLC developed by the mixture of dichloromethane and methanol yielding the titled compound (31 mg) as a colorless oil. ESI-MS: m/z 377 (MH$^+$); $^1$H-NMR (CDCl$_3$): δ 2.34–2.46 (5H, m), 3.65 (2H, t, J=6.6 Hz), 4.21 (2H, t, J=5.6 Hz), 5.98 (1H, s), 6.63 (1H, d, J=7.9 Hz), 6.97 (1H, d, J=8.3 Hz), 7.08–7.40 (3H, m), 7.65 (1H, dt, J=1.7 Hz, 7.6 Hz), 8.62 (1H, d, J=4.9 Hz).

d) Preparation of (3-methyl-4-{3-[(pyridin-3-ylmethyl)-amino]-propoxy}-benzofuran-2-yl)-pyridin-2-yl-methanol:

The title compound was obtained from [4-(3-bromo-propoxy)-3-methyl-benzofuran-2-yl]-pyridin-2-yl-methanol, the compound obtained above, as a pale yellow oil by a similar method to Example 1-g. ESI-MS: m/z 404 (MH$^+$); $^1$H-NMR (CDCl$_3$): δ 2.01–2.11 (2H, m), 2.38 (3H, s), 2.89 (2H, t, J=6.9 Hz), 3.92 (2H, s), 4.15 (2H, t, J=5.9 Hz), 5.98 (1H, s), 6.58 (1H, d, J=7.9 Hz), 6.96 (1H, d, J=8.3 Hz), 7.11 (1H, t, J=8.3 Hz), 7.19–7.25 (3H, m), 7.63–7.70 (2H, m), 8.47–8.62 (3H, m).

e) Preparation of {3-[2-(hydroxy-pyridin-2-yl-methyl)-3-methyl-benzofuran-4-yloxy]-propyl}-pyridin-3-ylmethyl-carbamic acid tert-butyl ester:

The title compound was obtained from (3-methyl-4-{3-[(pyridin-3-ylmethyl)-amino]-propoxy}-benzofuran-2-yl)-pyridin-2-yl-methanol, the compound obtained above, as a pale yellow oil by a similar method to Example 116-a. FAB-MS: m/z 504 (MH$^+$); $^1$H-NMR (CDCl$_3$): δ 1.46 (9H, s), 2.01–2.11 (2H, m), 2.36 (3H, s), 3.39 (2H, broad s), 4.01–4.11 (2H, m), 4.33 (1H, d, J=15.5 Hz), 4.48 (1H, d, J=15.5 Hz), 5.99 (1H, s), 6.55 (1H, d, J=7.9 Hz), 6.97 (1H, d, J=8.3 Hz), 7.11 (1H, t, J=7.9 Hz), 7.22–7.28 (3H, m), 7.55–7.70 (2H, m), 8.35 (1H, d, J=2.0 Hz), 8.51 (1H, dd, J=1.7 Hz, 4.6 Hz), 8.61 (1H, d, J=5.0 Hz).

f) Preparation of {3-[3-methyl-2-(pyridine-2-carbonyl)-benzofuran-4-yloxy]-propyl}-pyridin-3-ylmethyl-carbamic acid tert-butyl ester:

To a solution of {3-[2-(hydroxy-pyridin-2-yl-methyl)-3-methyl-benzofuran-4-yloxy]-propyl}-pyridin-3-ylmethyl-carbamic acid tert-butyl ester (30 mg) in chloroform (2 ml) was added manganese(IV) oxide (45 mg) at room temperature and the mixture was stirred vigorously overnight. The mixture was filtered through a pad of Celite and concentrated in vacuo. The titled compound (24 mg) was obtained as a pale yellow oil after the purification with silica gel TLC developed by the mixture of dichlormethane and methanol. FAB-MS: m/z 502 (MH$^+$); $^1$H-NMR (CDCl$_3$): δ 1.45 (9H, s), 2.10–2.15 (2H, m), 2.91 (3H, s), 3.40–3.50 (2H, m), 4.09 (2H, t, J=5.9 Hz), 4.48 (2H, broad s), 6.58 (1H, d, J=8.3 Hz), 7.10 (1H, d, J=8.3 Hz), 7.24 (1H, dd, J=5.3 Hz, 7.6 Hz), 7.34 (1H, t, J=8.3 Hz), 7.47–7.55 (2H, m), 7.87–7.98 (2H, m), 8.50–8.53 (2H, m), 8.77–8.80 (1H, m).

g) Preparation of (3-methyl-4-{3-[(pyridin-3-ylmethyl)-amino]-propoxy}-benzofuran-2-yl)-pyridin-2-yl-methanone:

The title compound was obtained from {3-[3-methyl-2-(pyridine-2-carbonyl)-benzofuran-4-yloxy]-propyl}-pyridin-3-ylmethyl-carbamic acid tert-butyl ester, the compound obtained above, as a light yellow oil by a similar method to Example 116-d. FAB-MS: m/z 402 (MH$^+$); $^1$H-NMR (CDCl$_3$): δ 2.04–2.13 (2H, m), 2.65 (3H, s), 2.91 (2H, t, J=6.6 Hz), 3.86 (2H, s), 4.19 (2H, t, J=5.9 Hz), 6.62 (1H, d, J=7.9 Hz), 7.09 (1H, d, J=8.3 Hz), 7.20–7.37 (2H, m), 7.47–7.52 (1H, m), 7.69 (1H, d, J=7.6 Hz), 7.87–7.97 (2H, m), 8.49 (1H, dd, J=1.3 Hz, 4.9 Hz), 8.57 (1H, d, J=2.0 Hz), 8.79 (1H, d, J=4.6 Hz).

EXAMPLE 129

Preparation of (5,6-Difluoro-1-methyl-1H-benzoimidazol-2-yl)-(3-methyl-4-{3-[(pyridin-3-ylmethyl)-amino]-propoxy}-benzofuran-2-yl)-methanone a) Preparation of (4,5-difluoro-2-nitro-phenyl)-methyl-amine:

To a solution of 4,5-difluoro-2-nitro-phenylamine (407 mg) in DMF (5 ml) was added NaH (60%, 95 mg) at room temperature. The mixture was stirred for ten minutes and then methyl iodide (0.15 ml) was added to the mixture. The mixture was further stirred at room temperature for 3 hours and was diluted with ethyl acetate. This solution was washed with water 3 times and brine, then it was dried over anhydrous sodium sulfate. Sodium sulfate was removed by filtration and the filtrate was evaporated to dryness. The residue was purified by silica gel column chromatography developed by hexane-ethyl acetate affording the titled compound as a yellow solid (120 mg). EI-MS: m/z 188 (M$^+$); $^1$H-NMR (CDCl$_3$): δ 3.01 (3H, d, J=5.3 Hz), 6.61 (1H, dd, J=6.9, 12.5 Hz), 8.07 (1H, dd, J=8.6, 10.6 Hz).

b) Preparation of 5,6-difluoro-1-methyl-1H-benzoimidazole:

To a solution of (4,5-difluoro-2-nitro-phenyl)-methylamine (120 mg) in ethanol (5 ml) was added 10% palladium on carbon (50 mg) and the mixture was stirred vigorously under hydrogen atmosphere at room temperature overnight. After celite filtration, the filtrate was evaporated to dryness. The residue was dissolved in trimethyl orthoformate (5 ml) and the solution was heated at reflux overnight and evaporated to dryness. The mixture was purified by silica gel thin layer chromatography developed by ethyl acetate affording the titled compound (86 mg) as a white solids. ESI-MS: m/z 169 (MH$^+$); $^1$H-NMR (CDCl$_3$): δ 3.82 (3H, s), 7.18 (1H, dd, J=6.6, 9.9 Hz), 7.57 (1H, dd, J=7.3, 10.6 Hz).

c) Preparation of [4-(3-bromo-propoxy)-3-methyl-benzofuran-2-yl]-morpholin-4-yl-methanone:

To a solution of 4-(3-bromo-propoxy)-3-methyl-benzofuran-2-carboxylic acid (1.84 g), the compound in Example 62-a, in dichloromethane (25 ml) were added oxalyl chloride (2.0 ml) and DMF (0.1 ml) at room temperature and the reaction mixture was stirred overnight. The solvent and excess of the reagent were removed under reduced pressure. The residue was dissolved in dichloromethane (50 ml). Morpholine (1.3 ml) was added to the solution at 0° C. and the mixture was warmed to room temperature. After 1 hour the reaction mixture was washed with water, aqueous NH$_4$Cl solution and brine (100 ml), and then it was dried over anhydrous sodium sulfate. Sodium sulfate was removed by filtration. The filtrate was concentrated to dryness and the residue was purified by silica gel column chromatography developed by hexane-ethyl acetate affording the titled compound as a colorless oil (2.02 g). FAB-MS: m/z 383 (MH$^+$); $^1$H-NMR (CDCl$_3$): δ 2.35–2.45 (2H, m), 2.59 (3H, s), 3.65 (2H, t, J=6.6 Hz), 3.76 (8H, s), 6.66 (1H, d, J=7.6 Hz), 7.06 (1H, d, J=7.6 Hz), 7.28 (1H, t, J=7.6 Hz).

d) Preparation of (3-methyl-4-{3-[(pyridin-3-ylmethyl)-amino]-propoxy}-benzofuran-2-yl)-morpholin-4-yl-methanone:

This compound was prepared in a similar manner to Example 1-g starting from the compound above. It was obtained as a pale yellow oil. FAB-MS: m/z 410 (MH$^+$); $^1$H-NMR (CDCl$_3$): δ 2.02–2.11 (2H, m), 2.52 (3H, s), 2.89 (2H, t, J=6.9 Hz), 3.76 (8H, s), 3.84 (2H, s), 4.16 (2H, t, J=6.9 Hz), 6.63 (1H, d, J=8.3 Hz), 7.04 (1H, d, J=8.2 Hz), 7.21–7.29 (2H, m), 7.68 (1H, d, J=7.9 Hz), 8.48–8.57 (2H, m).

e) Preparation of {3-[3-methyl-2-(morpholine-4-carbonyl)-benzofuran-4-yloxy]-propyl}-pyridin-3-ylmethyl-carbamic acid tert-butyl ester:

This compound was prepared in a similar manner to Example 5-c starting from the compound above. It was obtained as a white solid. FAB-MS: m/z 510 (MH$^+$); $^1$H-NMR (CDCl$_3$): δ 1.45 (9H, s), 2.08 (2H, broad singlet), 2.52 (3H, s), 3.43 (2H, broad singlet), 3.74 (8H, s), 4.05 (2H, t, J=5.6 Hz), 4.45 (2H, s), 6.56 (1H, d, J=7.9 Hz), 7.02 (1H, d, J=8.2 Hz), 7.20–7.26 (2H, m), 7.52–7.54 (1H, m), 8.46–8.50 (2H, m).

f) Preparation of {3-[2-(5,6-difluoro-1-methyl-1H-benzoimidazole-2-carbonyl)-3-methyl-benzofuran-4-yloxy]-propyl}-pyridin-3-ylmethyl-carbamic acid tert-butyl ester:

To a mixture of 5,6-difluoro-1-methyl-1H-benzoimidazole (20 mg), compound of Example 129-b, and N,N,N',N'-tetramethylethylenediamine (0.018 ml) in tetrahydrofuran (1 ml) was added 1.6N n-butyl lithium in hexane (0.075 ml) at −78° C. After 30 minutes {3-[3-methyl-2-(morpholine-4-carbonyl)-benzofuran-4-yloxy]-propyl}-pyridin-3-ylmethyl-carbamic acid tert-butyl ester (20 mg), compound of Example 129-e, in THF (1.5 ml) was dropwise added and the whole mixture was stirred for 30 minutes. The reaction was quenched with saturated aqueous NH$_4$Cl solution and extracted with ethyl acetate twice. The combined organic layer was washed with brine and dried over anhydrous sodium sulfate. Sodium sulfate was removed by filtration. The filtrate was evaporated to dryness and purified by silica gel thin layer chromatography developed by ethyl acetate affording the titled compound as a light yellow solid. ESI-MS: m/z 591 (MH$^+$); $^1$H-NMR (CDCl$_3$): δ 1.42 (9H, s), 2.02–2.15 (2H, m), 2.76 (3H, s), 3.33–3.50 (2H, m), 3.95–4.13 (5H, m), 4.48 (2H, s), 6.59 (1H, d, J=7.9 Hz), 7.16–7.76 (6H, m), 8.41–8.56 (2H, m).

g) Preparation of (5,6-difluoro-1-methyl-1H-benzoimidazol-2-yl)-(3-methyl-4-{3-[(pyridin-3-ylmethyl)-amino]-propoxy}-benzofuran-2-yl)-methanone:

To a solution of the compound above (19 mg) in dichloromethane (0.5 ml) was added trifluoroacetic acid (0.5 ml) and the mixture was stirred for 30 minutes at room temperature. The solution was diluted with ethyl acetate and washed with aqueous NaHCO$_3$ solution and brine, and dried over anhydrous sodium sulfate. Sodium sulfate was removed by filtration. The filtrate was evaporated to dryness and the residue was purified by silica gel thin layer chromatography developed by dichloromethane-methanol affording the titled compound as a light yellow oil (15 mg). ESI-MS: m/z 491 (MH$^+$); $^1$H-NMR (CDCl$_3$): δ 2.03–2.14 (2H, m), 2.74 (3H, s), 2.91 (2H, t, J=6.9 Hz), 3.86 (2H, s), 4.07 (3H, s), 4.20 (2H, t, J=6.3 Hz), 6.64 (1H, d, J=7.9 Hz), 7.17 (1H, d, J=8.3 Hz), 7.20–7.29 (2H, m), 7.39 (1H, t, J=8.3 Hz), 7.67–7.76 (2H, m), 8.49 (1H, dd, J=1.7, 4.6 Hz), 8.58 (1H, d, J=2.0).

EXAMPLE 130

Preparation of (3-Methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone a) Preparation of (2-morpholin-4-yl-ethyl)-(2-nitro-phenyl)-amine:

To a solution of 1-chloro-2-nitro-benzene (1.0 g) in ethanol (2 ml) was added N-(2-aminoethyl)morpholine (2.0 ml). The mixture was heated at 80° C. for 4 days and evaporated to dryness. The residue was purified by silica gel column chromatography developed by hexane-ethyl acetate affording the title compound as an orange oil (1.35 g). ESI-MS: m/z 252 (MH$^+$); $^1$H-NMR (CDCl$_3$): δ 2.50–2.54 (4H, m), 2.72 (2H, t, J=6.3 Hz), 3.33–3.39 (2H, m), 3.73–3.77 (4H, m), 6.59–6.66 (1H, m), 6.80 (1H, d, J=8.9 Hz), 7.38–7.44 (1H, m), 8.14–8.18 (1H, m), 8.46 (1H, broad singlet).

b) Preparation of 1-(2-morpholin-4-yl-ethyl)-1H-benzoimidazole:

This compound was prepared from the compound above in a similar manner to Example 129-b. It was obtained as a colorless needle. ESI-MS: m/z 232 (MH$^+$); $^1$H-NMR (CDCl$_3$): δ 2.48–2.51 (4H, m), 2.78 (2H, t, J=6.3 Hz), 3.68–3.72 (4H, m), 4.27 (2H, t, J=6.3 Hz), 7.28–7.35 (2H, m), 7.38–7.43 (1H, m), 7.80–7.84 (1H, m), 8.01 (1H, s).

c) Preparation of (3-methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone:

This compound was prepared from the compound above in a similar manner to Example 129-f and 129-g. It was obtained as a yellow solid. ESI-MS: m/z 554 (MH$^+$); $^1$H-NMR (CDCl$_3$): δ 2.02–2.15 (2H, m), 2.41–2.44 (4H, m), 2.65–2.69 (5H, m), 2.91 (2H, t, J=6.93 Hz), 3.35–3.39 (4H, m), 3.87 (2H, s), 4.20 (2H, t, J=5.94 Hz), 4.69 (2H, t, J=5.61 Hz), 6.64 (1H, d, J=7.92 Hz), 7.15 (1H, d, J=8.58 Hz), 7.21–7.26 (1H, m), 7.33–7.50 (4H, m), 7.71 (1H, d, J=7.59 Hz), 7.95 (1H, d, J=7.59 Hz), 8.48 (1H, dd, J=1.65, 4.95 Hz), 8.58 (1H, d, J=1.98 Hz).

EXAMPLE 131

Preparation of (3-Methyl-4-{3-[(pyridin-3-ylmethyl)-amino]-propoxy}-benzofuran-2-yl)-[1-(2-pyridin-2-yl-ethyl)-1H-benzoimidazol-2-yl]-methanone a) Preparation of 1-methoxymethyl-1H-benzoimidazole:

1H-Benzoimidazole (2.5 g) in DMF (10 ml) was stirred with NaH (60%, 850 mg) at 0° C. for ten minutes. To the solution was added methoxymethyl chloride (1.65 ml). The reaction mixture was stirred at the same temperature for 1 hour and then it was diluted with ethyl acetate. The solution was washed with water 3 times and brine, and dried over anhydrous sodium sulfate. Sodium sulfate was removed by filtration. The filtrate was purified by silica gel column chromatography developed by dichloromethane-methanol affording the titled compound as a pale yellow oil (2.6 g). ESI-MS: m/z 163 (MH$^+$); $^1$H-NMR (CDCl$_3$): δ 3.23 (3H, s), 5.51 (2H, s), 7.29–7.38 (2H, m), 7.50–7.57 (1H, m), 7.79–7.88 (1H, m),7.99(1H,s).

b) Preparation of {3-[2-(1-methoxymethyl-1H-benzoimidazole-2-carbonyl)-3-methyl-benzofuran-4-yloxy]-propyl}-pyridin-3-ylmethyl-carbamic acid tert-butyl ester:

This compound was prepared from the compound above in a similar manner to Example 129-f. It was obtained as a light yellow oil. ESI-MS: m/z 585 (MH$^+$); $^1$H-NMR (CDCl$_3$): δ 1.46 (9H, s), 2.05–2.01 (2H, m), 2.76 (2H, s), 3.28–3.67 (5H, m), 4.04–4.16 (2H, m), 4.50 (2H, s), 5.92 (2H, s), 6.61 (1H, d, J=6.3 Hz), 7.16–7.68 (7H, m), 7.97 (1H, d, J=7.6 Hz), 8.46–8.49 (2H, m).

c) Preparation of (1H-benzoimidazol-2-yl)-(3-methyl-4-{3-l(pyridin-3-ylmethyl)-amino]-propoxy}-benzofuran-2-yl)-methanone:

To a solution of the compound above (380 mg) in a mixture of methanol-THF (1:1, 10 ml) were added conc. HCl (3 ml) and water (3 ml). The resulted solution was heated at 70° C. overnight. The mixture was diluted with ethyl acetate and washed with NaHCO$_3$ aqueous solution and brine, then it was dried over anhydrous sodium sulfate. Sodium sulfate was removed by filtration. The filtrate was evaporated to dryness and the residue was purified by silica gel column chromatography developed by methanol-dichloromethane affording the titled compound as a yellow solid (271 mg). ESI-MS: m/z 441 (MH$^+$); $^1$H-NMR (CDCl$_3$): δ 2.12–2.23 (2H, m), 2.83 (3H, s), 3.05–3.17 (2H, m), 4.05 (2H, s), 4.14 (2H, t, J=5.9 Hz), 6.25–6.37 (1H, m), 7.06–7.80 (8H, m), 8.46 (1H, dd, J=1.3, 4.6 Hz), 8.57 (1H, d, J=1.7 Hz).

d) Preparation of (3-methyl-4-{3-[(pyridin-3-ylmethyl)-amino]-propoxy}-benzofuran-2-yl)-[1-(2-pyridin-2-yl-ethyl)-1H-benzoimidazol-2-yl]methanone:

To a solution of the compound above (10 mg), 2-pyridin-2-yl-ethanol (0.005 ml) and 1,1'-azobis(N,N-dimethylformamide) (12 mg) in THF (1 ml) was added tri n-butylphosphine (0.017 ml) and the mixture was stirred overnight at room temperature. The reaction mixture was evaporated to dryness and purified by silica gel thin layer chromatography developed by methanol-ethyl acetate affording the titled compound (11 mg) as a light yellow oil. ESI-MS: m/z 546 (MH$^+$); $^1$H-NMR (CDCl$_3$): δ 2.04–2.14 (2H, m), 2.70 (3H, s), 2.90 (2H, t, J=6.6 Hz), 3.42 (2H, t, J=6.9 Hz), 3.85 (2H, s), 4.20 (2H, t, J=5.9 Hz), 4.96 (2H, t, J=6.9 Hz), 6.64 (1H, d, J=8.3 Hz), 6.99–7.48 (9H, m), 7.66–7.70 (1H, m), 7.89–7.95 (1H, m), 8.48–8.58 (3H, m).

EXAMPLE 132

Preparation of (4,5-Dimethyl-thiazol-2-yl)-(3-methyl-4-{3-[(pyridin-3-ylmethyl)-amino]-propoxy}-benzofuran-2-yl)-methanone a) Preparation of {3-[2-(4,5-dimethyl-thiazole-2-carbonyl)-3-methyl-benzofuran-4-yloxy]-propyl}-pyridin-3-ylmethyl-carbamic acid tert-butyl ester:

This compound was prepared from {3-[3-methyl-2-(morpholine-4-carbonyl)-benzofuran-4-yloxy]-propyl}-pyridin-3-ylmethyl-carbamic acid tert-butyl ester, the compound of Example 129-e and 4,5-dimethylthiazole by the same method as Example 129-f. It was obtained as a yellow oil (93% yield) ESI-MS: m/z 536 (MH$^+$); $^1$H-NMR δ: 1.46 (9H, s), 2.01–2.18 (2H, m), 2.50 (6H, s), 2.79 (3H, s), 3.36–3.56 (2H, m), 4.06–4.13 (2H, m), 4.48 (2H, s), 6.59 (1H, d, J=7.9 Hz), 7.17–7.65 (4H, m), 8.49–8.53 (2H, m).

b) Preparation of (4,5-dimethyl-thiazol-2-yl)-(3-methyl-4-{3-[(pyridin-3-ylmethyl)-amino]-propoxy}-benzofuran-2-yl)-methanone:

This compound was prepared from the compound above by the same method as described in Example 129-f. This was obtained as a yellow oil (97%). ESI-MS: m/z 436 (MH$^+$); $^1$H-NMR δ: 2.05–2.15 (2H, m), 2.49 (6H, s), 2.79 (3H, s), 2.98–3.08 (2H, m), 3.89 (2H, s), 4.18 (2H, t, J=5.9 Hz), 6.60 (1H, d, J=7.6 Hz), 7.15–7.39 (3H, m), 7.72 (1H, d, J=7.6 Hz), 8.48–8.57 (2H, m).

EXAMPLE 133

Preparation of (4,5-Dimethyl-thiazol-2-yl)-(3-methyl-4-{3-[(pyridin-3-ylmethyl)-amino]-propoxy}-benzofuran-2-yl)-methanone oxime The compound of Example 132 (185 mg), 4,5-dimethyl-thiazol-2-yl)-(3-methyl-4-{3-[(pyridin-3-ylmethyl)-amino]-propoxy}-benzofuran-2-yl)-methanone, was heated with hydroxylamine hydrochloride (74 mg) in pyridine (5 ml) at 70° C. overnight. The reaction mixture was diluted with ethyl acetate and the solution was washed with sodium bicarbonate solution and brine. The organic layer was dried over anhydrous sodium sulfate. The organic layer was evaporated to dryness and separated by silica gel column chromatography developed by a mixture of dichloromethane and methanol. Though this chromatography gave both E and Z isomers, their stereochemistry was not determined.

The less polar isomer (Example 133-1) was obtained as a colorless solid: Rf value on silica gel TLC developed by dichloromethane-methanol (10:1)=0.31, ESI-MS: m/z 451 MH$^+$), $^1$H-NMR δ: 2.07 (2H, quintet, J=7 Hz), 2.40 (3H, s), 2.43 (3H, s), 2.47 (3H, s), 2.86 (2H, t, J=7 Hz), 3.83 (2H, s), 4.12 (2H, brs), 6.60 (1H, brd, J=8 Hz), 7.08 (1H, dd, J=8 Hz, 1 Hz), 7.19 (1H, t, J=8 Hz), 7.20 (1H, m), 7.68 (1H, m), 8.48 (1H, dd, J=5 Hz, 2Hz), 8.56 (1H, d, J=2 Hz).

The more polar isomer (Example 133-2) was obtained as a colorless solid: Rf value on silica gel TLC developed by dichloromethane-methanol (10:1)=0.23, ESI-MS: m/z 451 (MH$^+$), $^1$H-NMR δ: 2.06 (2H, quintet, J=6.5 Hz), 2.24 (3H, s), 2.31 (3H, s), 2.33 (3H, s), 2.85 (2H, t, J=6.5 Hz), 3.84 (2H, s), 4.09 (2H, t, 6 Hz), 6.55 (1H, brd, 8 Hz), 7.0–7.25 (3H, m), 7.71 (1H, m), 8.47 (1H, dd, J=5 Hz, 1.5 Hz), 8.54 (1H, d, J=1.5 Hz).

Following compounds in Example 134 to Example 137 were prepared in a similar manner to Example 133. E and Z isomers of each Example were not separated.

EXAMPLE 134

Preparation of (4,5-Dimethyl-thiazol-2-yl)-(3-methyl-4-{3-[(pyridin-3-ylmethyl)-amino]-propoxy}-benzofuran-2-yl)-methanone O-ethyl-oxime Colorless oil. ESI-MS: m/z 478 (MH$^+$), $^1$H-NMR δ: 1.34+1.46 {3H, NOCH$_2$CH$_3$,[1.34 (t, J=7 Hz), 1.46 (t, J=7 Hz)]}, 2.05 (2H, quintet, J=6.6 Hz, CH$_2$CH$_2$CH$_2$), 2.26+2.33+2.34+2.36+2.43 {9H, 3×CH$_3$[2.26 (s), 2.33 (s), 2.36 (s), 2.43 (s)]}, 2.89 (2H, t, J=6.5 Hz, NCH$_2$), 3.84 (2H, s, NCH$_2$), 4.15 (2H, t, J=6 Hz, OCH$_2$), 4.35+4.39 {2H, NOCH$_2$, [4.35 (q, J=7 Hz), 4.49 (q, J=7 Hz)]}, 6.60 (1H, brd, J=8 Hz, ArH), 7.0–7.26 (3H, m, ArH), 7.67 (brd, J=8 Hz, ArH), 8.48 (1H, brd, J=4 Hz, ArH), 8.57 (1H, brs, ArH).

EXAMPLE 135

Preparation of (4,5-Dimethyl-thiazol-2-yl)-(3-methyl-4-{3-[(pyridin-3-ylmethyl)-amino]-propoxy}-benzofuran-2-yl)-methanone O-(4-nitro-benzyl)-oxime Colorless oil. ESI-MS: m/z 586 (MH$^+$), $^1$H-NMR δ: 2.04 (2H, m, CH$_2$CH$_2$CH$_2$), 2.21+2.25+2.32+2.36+2.37+2.44

{9H, 3×CH₃ [2.21 (s), 2.25 (s), 2.32 (s), 2.36 (s), 2.37 (s), 2.44 (s)]}, 2.89 (2H, t, J=6.5 Hz, NCH₂), 3.83 (2H, s, NCH₂), 4.16 (2H, m, OCH₂), 5.39+5.53 {2H, NOCH₂ [5.39 (s), 5.63 (s)]}, 6.60 (1H, m, ArH), 6.95–7.3 (3H, m, ArH), 7.5–7.7 (3H, m, ArH), 8.15–8.3 (2H, m, ArH), 8.47 (1H, brd, J=4 Hz), 8.56 (1H, brs).

EXAMPLE 136

Preparation of (4,5-Dimethyl-thiazol-2-yl)-(3-methyl-4-{3-[(pyridin-3-ylmethyl)-amino]-propoxy}-benzofuran-2-yl)-methanone O-phenyl-oxime Colorless oil. ESI-MS: m/z 527 (MH⁺), ¹H-NMR δ: 2.07 (2H, quintet, J=6.5 Hz, CH₂CH₂CH₂), 2.33+2.390+2.392+ 2.44+2.49 {9H, 3×CH₃ [2.33 (s), 2.390 (s), 2.392 (s), 2.44 (s), 2.49 (s)]}, 2.90 (2H, t, J=6.5 Hz, NCH₂), 3.85 (2H, s, NCH₂), 4.18 (2H, t, J=6 Hz, OCH₂), 6.62 (1H, m, ArH), 7.0–8.4 (8H, m, ArH), 7.67 (1H, m, ArH), 8.47 (1H, brs), 8.56 (1H, brs).

EXAMPLE 137

Preparation of (4,5-Dimethyl-thiazol-2-yl)-(3-methyl-4-{3-[(pyridin-3-ylmethyl)-amino]-propoxy}-benzofuran-2-yl)-methanone O-allyl-oxime Colorless oil. ESI-MS: m/z 491 (MH⁺), ¹H-NMR δ: 2.05 (2H, quintet, J=6.5 Hz, CH₂CH₂CH₂), 2.26+2.33+2.35+ 2.37+2.43 {9H, 3×CH₃ [2.26 (s), 2.33 (s), 2.35 (s), 2.37 (s), 2.43 (s)]}, 2.88 (2H, t, J=6.5 Hz, NCH₂), 3.84 (2H, s, NCH₂), 4.15 (2H, t, J=6 Hz, OCH₂), 4.79+4.92 {2H, CH₂—CH=CH₂ [4.79 (d, J=6 Hz), 4.92 (d, J=6 Hz)]}, 5.2–5.52 (2H, m, CH=CH₂), 5.9–6.2 (1H, m, CH=CH₂), 6.60(1H, d, J=7.5 Hz, ArH), 7.0–7.26 (3H, m), 7.67 (1H, brd, J=7.5 Hz, ArH), 8.48 (1H, dd, J=5 Hz, 1.5 Hz, ArH), 8.57 (1H, brs).

EXAMPLE 138

Preparation of {3-[2-(2-Methoxy-phenyl)-3-methyl-benzofuran-4-yloxy]-propyl}-pyridin-3-ylmethyl-amine a) Preparation of [3-(2-Bromo-3-methyl-benzofuran-4-yloxy)-propyl]-pyridin-3-ylmethyl-carbamic acid tert-butyl ester:

This compound was prepared from [3-(2-bromo-3-methyl-benzofuran-4-yloxy)-propyl]-pyridin-3-ylmethyl amine, the compound of Example 75-b, by the same method as Example 116-a. Yellow solid. FAB-MS: m/z 475 (MH⁺), 477 (MH⁺); ¹H-NMR (CDCl₃) δ: 1.45 (9H, s), 2.06 (2H, brs), 2.27 (3H, s), 3.43 (2H, brs), 4.04 (2H, t, J=5.9 Hz), 4.46 (2H, s), 6.56 (1H, d, J=7.9 Hz), 7.01 (1H, d, J=8.3 Hz), 7.12 (1H, t, J=8.3 Hz), 7.20–7.24 (1H, m), 7.55–7.64 (1H, m), 8.51–8.53 (2H, m).

b) Preparation of {3-[2-(2-methoxy-phenyl)-3-methyl-benzofuran-4-yloxy]-propyl}-pyridin-3-ylmethyl-carbamic acid tert-butyl ester:

[3-(2-Bromo-3-methyl-benzofuran-4-yloxy)-propyl]-pyridin-3-ylmethyl-carbamic acid tert-butyl ester (36 mg, 0.075 mmol) was refluxed with 2-methoxy-benzeneboronic acid (57 mg, 0.375 mmol), sodium tert-butoxide (42 mg, 0.375 mmol) and tetrakis(triphenylphosphine)palladium (9 mg, 0.0075 mmol) in DME under argon atmosphere. The mixture was filtered through celite-bed and washed with ethyl acetate. The filtrate was washed with brine and dried over anhydrous sodium sulfate. The solvent was removed under reduced pressure and the residue was purified by silica gel TLC (hexane-ethyl acetate=1:2). The product was obtained as a pale yellow oil (28 mg, 74%). FAB-MS: m/z 503 (MH⁺); ¹H-NMR (CDCl₃) δ: 1.46 (9H, s), 2.08 (2H, brs), 2.29 (3H, s), 3.44 (2H, brs), 3.85 (3H, s), 4.07 (2H, m), 4.47 (2H, s), 6.99–7.54 (8H, m), 7.56 (1H, d, J=7.6 Hz), 8.50 (2H, m).

c) Preparation of {3-[2-(2-methoxy-phenyl)-3-methyl-benzofuran-4-yloxy]-propyl}-pyridin-3-ylmethyl-amine:

{3-[2-(2-Methoxy-phenyl)-3-methyl-benzofuran-4-yloxy]-propyl}-pyridin-3-ylmethyl-carbamic acid tert-butyl ester (24 mg) was treated in 10% trifluoroacetic acid in dichloromethane at room temperature for 18 hours. The mixture was washed with saturated sodium bicarbonate solution and the organic layer was washed with brine and dried over anhydrous sodium sulfate. The solvent was removed under reduced pressure, the residue was purified by silica gel TLC (dichloromethane-methanol=10:1) to give a pale yellow oil (17 mg, 88%). FAB-MS: m/z 402 (MH⁺); ¹H-NMR (CDCl₃) δ: 2.07 (2H, tt, J=6.6 Hz, 5.9 Hz), 2.28 (3H, s), 2.90 (2H, t, 6.6 Hz), 3.84 (3H, s), 3.85 (2H, s), 4.17 (2H, t, J=5.9 Hz), 6.61 (1H, d, J=7.6 Hz), 6.95–7.23 (5H, m), 7.40 (1H, dt, J=7.6 Hz, 1.7 Hz), 7.46 (1H, dd, J=7.6, 1.7 Hz), 7.67 (1H, d, J=7.4 Hz), 8.48 (1H, d, J=3.0 Hz), 8.56 (1H, s).

EXAMPLE 139

Preparation of 3-Methyl-4-{3-[(pyridin-3-ylmethyl)-amino]-propoxy}-benzofuran-2-carboxylic acid N'-(4-fluoro-phenyl)-hydrazide (Example 139-1) and 3-methyl-4-{3-[(pyridin-3-ylmethyl)-amino]-propoxy}-benzofuran-2-carboxylic acid N-(4-fluoro-phenyl)-hydrazide (Example 139-2)

a) Preparation of 4-[3-(tert-butoxycarbonyl-pyridin-3-ylmethyl-amino)-propoxy]-3-methyl-benzofuran-2-carboxylic acid 4-[3-(tert-Butoxycarbonyl-pyridin-3-ylmethyl-amino)-propoxy]-3-methyl-benzofuran-2-carboxylic acid ethyl ester (634 mg), the first intermediate of Example 87, was stirred with lithium hydroxide (113 mg) in tetrahydrofuran (2.7 ml) and water (2.7 ml) at 50° C. overnight. 2N HCl (1.35 ml) and ethyl acetate were added to the reaction mixture. The organic layer was separated, dried over anhydrous sodium sulfate and concentrated under reduced pressure. The product was obtained as a colorless foam (575 mg, 97%). The foam was used as a starting material in the next step without further purification. ESI-MS: m/z 441 (MH⁺); ¹H-NMR δ: 1.51 (9H, s), 2.05–2.11 (2H, m), 2.74 (3H, s), 3.44 (2H, m), 4.02 (2H, t, J=5.4 Hz), 4,51 (2H, s), 6.51 (1H, d, J=7.6 Hz), 7.14 (1H, d, J=8.3 Hz), 7.23–7.34 (2H, m), 7.79 (1H, br), 8.51 (1H, dd, J=1.3, 5.0 Hz), 8.59 (1H, m).

b) Preparation of (3-{2-[N'-(4-fluoro-phenyl)-hydrazinocarbonyl]-3-methyl-benzofuran-4-yloxy}-propyl)-pyridin-3-ylmethyl-carbamic acid tert-butyl ester (Example 139-b-1) and (3-{2-[N-(4-fluoro-phenyl)-hydrazinocarbonyl]-3-methyl-benzofuran-4-yloxy}-propyl)-pyridin-3-ylmethyl-carbamic acid tert-butyl ester (Example 139-b-2):

4-[3-(tert-Butoxycarbonyl-pyridin-3-ylmethyl-amino)-propoxy]-3-methyl-benzofuran-2-carboxylic acid obtained above (22.0 mg) was stirred with 4-fluorophenylhydrazine hydrochloride (9.8 mg), triethylamine (0.0084 ml) and water-soluble carbodiimide hydrochloride (11.5 mg) in dichloromethane (0.5 ml) at room temperature for 14 hours. Water and ethyl acetate were added to the mixture, and the organic layer was separated, dried over anhydrous sodium sulfate and concentrated under reduced pressure. The residue was purified by silica gel TLC developed by dichloromethane-methanol (20:1).

The less polar isomer obtained as a colorless oil was (3-{2-[N'-(4-fluoro-phenyl)-hydrazinocarbonyl]-3-methyl-benzofuran-4-yloxy}-propyl)-pyridin-3-ylmethyl-carbamic acid tert-butyl ester (13.1 mg, 48%): ESI-MS: m/z 549 (MH⁺); ¹H-NMR δ: 1.45 (9H, s), 2.08 (2H, m), 2.70 (3H, s), 3.44 (2H, m), 4.07 (2H, t, J=5.8 Hz), 4.46 (2H, br), 6.24 (1H, br), 7.00 (1H, d, J=8.2 Hz), 6.89–6.99 (4H, m), 7.06 (1H, d, J=8.6 Hz), 7.21–7.35 (2H, m), 7.54 (1H, m), 8.32 (1H, br), 8.49–8.52 (2H, m). The more polar isomer obtained as a colorless oil was (3-{2-[N-(4-fluoro-phenyl)-hydrazinocarbonyl]-3-methyl-benzofuran-4-yloxy}-propyl)-pyridin-3-ylmethyl-carbamic acid tert-butyl ester (4.7 mg, 17%): ESI-MS: m/z 549 (MH⁺); ¹H-NMR δ: 1.44 (9H, s), 2.07 (2H, m), 2.49 (3H, s), 3.42 (2H, m), 4.03 (2H, t, J=5.9 Hz), 4.45 (2H, br), 4.95 (2H, br), 6.51 (1H, d, J=7.8 Hz), 6.73 (1H, d, J=8.4 Hz), 6.93–7.01 (2H, m), 7.13–7.24 (4H, m), 7.54 (1H, m), 8.48–8.53 (2H, m).

c) Preparation of 3-methyl-4-{3-[(pyridin-3-ylmethyl)-amino]-propoxy}-benzofuran-2-carboxylic acid N'-(4-fluoro-phenyl)-hydrazide (Example 139-1):

The compound of Example 139-b-1 (12.1 mg) was stirred with trifluoroacetic acid (0.121 ml) in dichloromethane (1.2 ml) at room temperature for 3 hours. Saturated sodium bicarbonate aqueous solution and ethyl acetate were added to the mixture and the organic layer was separated, dried over sodium sulfate and concentrated under reduced pressure. The residue was purified by silica gel TLC developed by dichloromethane-methanol (10:1) to give 3-methyl-4-{3-[(pyridin-3-ylmethyl)-amino]-propoxy}-benzofuran-2-carboxylic acid N'-(4-fluoro-phenyl)-hydrazide as a colorless oil (8.6 mg, 87%). ESI-MS: m/z 449 (MH⁺); ¹H-NMR (CD₃OD) δ: 2.08 (2H, tt, J=5.9, 7.3 Hz), 2.62 (3H, s), 2.85 (2H, t, J=7.3 Hz), 3.85 (2H, s), 4.19 (2H, t, J=5.9 Hz), 6.75 (1H, d, J=7.9 Hz), 6.85–6.97 (4H, m), 7.12 (1H, d, J=7.9 Hz), 7.32–7.38 (2H, m), 7.83 (1H, m), 8.41 (1H, dd, J=1.6, 4.9 Hz), 8.52 (1H, m).

d) Preparation of 3-methyl-4-{3-[(pyridin-3-ylmethyl)-amino]-propoxy}-benzofuran-2-carboxylic acid N-(4-fluoro-phenyl)-hydrazide (Example 139-2):

This compound was prepared from the compound of Example 139-b-2 (3.3 mg) in a similar manner to Example 139-c. This was obtained as a colorless oil (1.4 mg, 52%). ESI-MS: m/z 449 (MH⁺); ¹H-NMR δ: 2.04 (2H, tt, J=6.1, 6.9 Hz), 2.48 (3H, s), 2.86 (2H, t, J=6.9 Hz), 3.83 (2H, s), 4.13 (2H, t, J=6.1 Hz), 4.95 (2H, br), 6.57 (1H, d, J=7.9 Hz), 6.73 (1H, d, J=8.3 Hz), 6.97 (2H, t, J=8.6 Hz), 7.14–7.26 (4H, m), 7.66 (1H, m), 8.50 (1H, m), 8.56 (1H, m).

EXAMPLE 140

Preparation of 3-methyl-4-{3-[(pyridin-3-ylmethyl)-amino]-propoxy}-benzofuran-2-carboxylic Acid N'-(3-nitro-phenyl)-hydrazide This compound was prepared from 4-[3-(tert-butoxycarbonyl-pyridin-3-ylmethyl-amino)-propoxy]-3-methyl-benzofuran-2-carboxylic acid (Example 139-a) and 3-nitrophenylhydrazine hydrochloride in a similar manner to Example 139-b and 139-c. ESI-MS: m/z 476 (MH⁺), ¹H-NMR δ: 2.07 (2H, tt, J=5.9, 6.8 Hz), 2.69 (3H, s), 2.88 (2H, t, J=6.8 Hz), 3.84 (2H, s), 4.18 (2H, t, J=5.9 Hz), 6.51 (1H, m), 6.66 (1H, d, J=7.9 Hz), 7.07 (1H, d, J=7.9 Hz), 7.20–7.42 (4H, m), 7.67 (1H, m), 7.74–7.77 (2H, m), 8.41 (1H, m), 8.49 (1H, m), 8.56 (1H, m).

EXAMPLE 141

Preparation of Isonicotinic Acid N'-(3-Methyl-4-{3-[(pyridin-3-ylmethyl)-amino]-propoxy}-benzofuran-2-carbonyl)-hydrazide This compound was prepared from 4-[3-(tert-butoxycarbonyl-pyridin-3-ylmethyl-amino)-propoxy]-3-methyl-benzofuran-2-carboxylic acid (Example 139-a) and isonicotinic acid hydrazine in a similar manner to Example 139-b and 139-c. Yellow solid. ESI-MS: m/z 460 (MH⁺), ¹H-NMR (CD₃OD) δ: 2.11 (2H, tt, J=5.8, 7.3 Hz), 2.66 (3H, s), 2.90 (2H, t, J=7.3 Hz), 3.89 (2H, s), 4.21 (2H, t, J=5.8 Hz), 6.78 (1H, d, J=7.9 Hz), 7.13 (1H, d, J=8.6 Hz), 7.37 (2H, m), 7.86 (1H, m), 7.89 (2H, dd, J=1.7, 4.5 Hz), 8.43 (1H, m), 8.54 (1H, m), 8.74 (2H, dd, J=1.7, 4.5 Hz).

Table 1 sets for the subtituents for each compound of the previously described Examples.

TABLE 1

| Example | R¹ | R² | Q¹N(Q²R⁶) (Q³R⁷) | R³ | R⁴ | R⁵ |
|---|---|---|---|---|---|---|
| 1 | —CO₂Et | 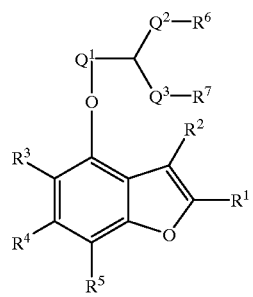 | (pyridin-3-ylmethylamino-propyl group) | H | H | H |

TABLE 1-continued

[Structure: benzofuran core with substituents O-Q¹-CH(Q²-R⁶)(Q³-R⁷) at 4-position, R² at 3-position, R¹ at 2-position, R³ at 5-position, R⁴ at 6-position, R⁵ at 7-position]

| Example | R¹ | R² | Q¹N(Q²R⁶)(Q³R⁷) | R³ | R⁴ | R⁵ |
|---|---|---|---|---|---|---|
| 2 | —CO₂Et | isopropyl | -(CH₂)₃-NH-CH₂-(3-pyridyl) | H | H | H |
| 3 | —CO₂Et | ethyl | -(CH₂)₃-NH-CH₂-(3-pyridyl) | H | H | H |
| 4 | —CO₂Et | —H | -(CH₂)₃-NH-CH₂-(3-pyridyl) | H | H | H |
| 5 | —CO₂Et | n-propyl | -(CH₂)₃-NH-tBu | H | H | H |
| 6 | —CO₂Et | n-butyl | -(CH₂)₃-NH-tBu | H | H | H |
| 7 | —CO₂Et | —CH₂NH₂ | -(CH₂)₃-NH-CH₂-(3-pyridyl) | H | H | H |
| 8 | —CO₂Me | —CH₂OH | -(CH₂)₃-NH-tBu | H | H | H |
| 9 | —CO₂Et | —CH₂OEt | -(CH₂)₃-NH-tBu | H | H | H |

TABLE 1-continued

[Structure: benzofuran with R³, R⁴, R⁵ on the benzene ring, R² at 3-position, R¹ at 2-position, and O-Q¹(Q²R⁶)(Q³R⁷) substituent at 4-position]

| Example | R¹ | R² | Q¹N(Q²R⁶)(Q³R⁷) | R³ | R⁴ | R⁵ |
|---|---|---|---|---|---|---|
| 10 | -CH₂-OH | cyclopropyl | -(CH₂)₃-NH-CH₂-(pyridin-3-yl) | H | H | H |
| 11 | -CH₂-OH | —Me | -(CH₂)₃-NH-CH₂-(pyridin-3-yl) | H | H | H |
| 12 | -CH₂-O-(2,4-difluorophenyl) | —Me | -(CH₂)₃-NH-CH₂-(pyridin-3-yl) | H | H | H |
| 13 | -CH₂-O-(3-trifluoromethylphenyl) | —Me | -(CH₂)₃-NH-CH₂-(pyridin-3-yl) | H | H | H |
| 14 | -CH₂-O-phenyl | —Me | -(CH₂)₃-NH-CH₂-(pyridin-3-yl) | H | H | H |
| 15 | -CH₂-O-(2-fluorophenyl) | —Me | -(CH₂)₃-NH-CH₂-(pyridin-3-yl) | H | H | H |
| 16 | -CH₂-O-(3-fluorophenyl) | —Me | -(CH₂)₃-NH-CH₂-(pyridin-3-yl) | H | H | H |

TABLE 1-continued

| Example | R¹ | R² | Q¹N(Q²R⁶)(Q³R⁷) | R³ | R⁴ | R⁵ |
|---|---|---|---|---|---|---|
| 17 | -CH₂-O-C₆H₄-4-F | —Me | -(CH₂)₃-NH-CH₂-(3-pyridyl) | H | H | H |
| 18 | -CH₂-O-C₆H₃-2,3-F₂ | —Me | -(CH₂)₃-NH-CH₂-(3-pyridyl) | H | H | H |
| 19 | -CH₂-O-C₆H₃-2,5-F₂ | —Me | -(CH₂)₃-NH-CH₂-(3-pyridyl) | H | H | H |
| 20 | -CH₂-O-C₆H₃-2,6-F₂ | —Me | -(CH₂)₃-NH-CH₂-(3-pyridyl) | H | H | H |
| 21 | -CH₂-O-C₆H₂-2,3,4-F₃ | —Me | -(CH₂)₃-NH-CH₂-(3-pyridyl) | H | H | H |
| 22 | -CH₂-O-C₆H₂-2,3,5-F₃ | —Me | -(CH₂)₃-NH-CH₂-(3-pyridyl) | H | H | H |
| 23 | -CH₂-O-C₆H₂-2,4,5-F₃ | —Me | -(CH₂)₃-NH-CH₂-(3-pyridyl) | H | H | H |

TABLE 1-continued
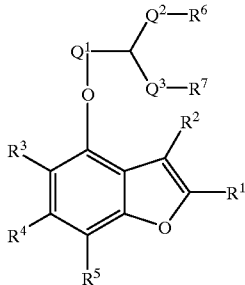
| Example | R¹ | R² | Q¹N(Q²R⁶)(Q³R⁷) | R³ | R⁴ | R⁵ |
|---|---|---|---|---|---|---|
| 24 | 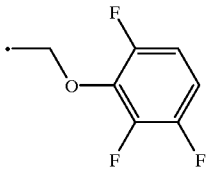 | —Me | 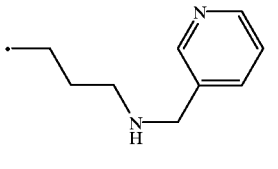 | H | H | H |
| 25 | 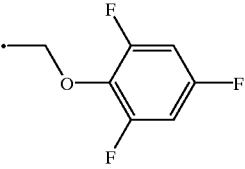 | —Me | 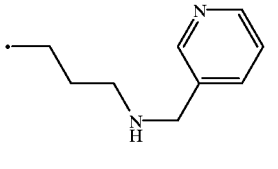 | H | H | H |
| 26 | 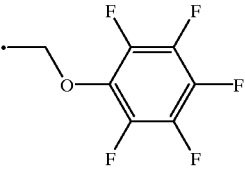 | —Me | 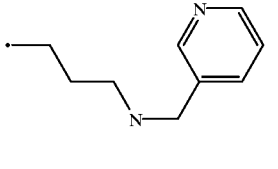 | H | H | H |
| 27 | 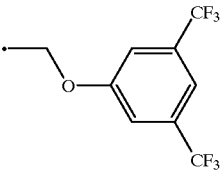 | —Me | 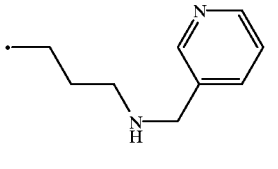 | H | H | H |
| 28 | 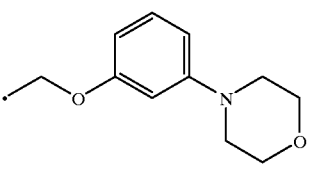 | —Me | 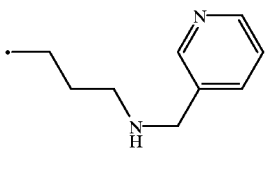 | H | H | H |
| 29 | 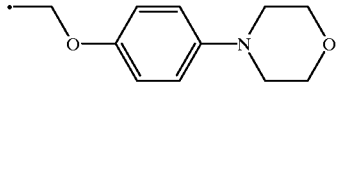 | —Me | 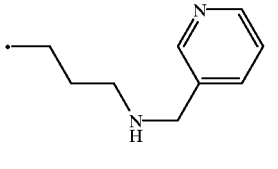 | H | H | H |

TABLE 1-continued
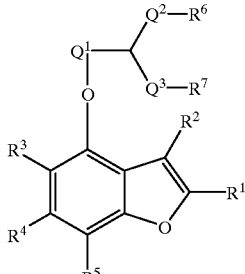
| Example | R¹ | R² | Q¹N(Q²R⁶)(Q³R⁷) | R³ | R⁴ | R⁵ |
|---|---|---|---|---|---|---|
| 30 | 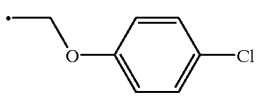 | —Me | 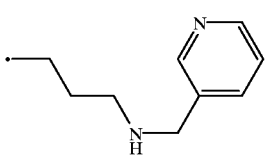 | H | H | H |
| 31 | 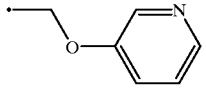 | —Me | 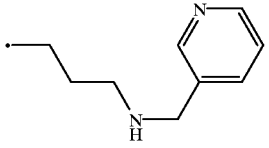 | H | H | H |
| 32 | 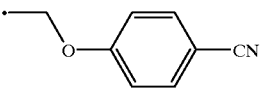 | —Me | 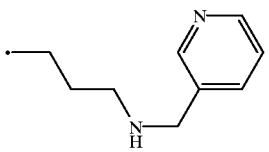 | H | H | H |
| 33 | 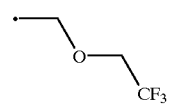 | —Me | 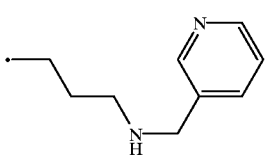 | H | H | H |
| 34 | 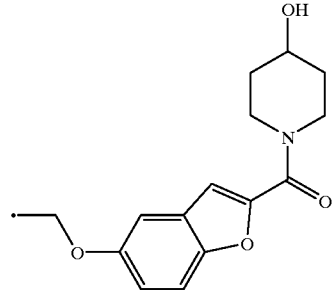 | —Me | 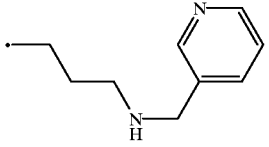 | H | H | H |

TABLE 1-continued

| Example | R¹ | R² | Q¹N(Q²R⁶)(Q³R⁷) | R³ | R⁴ | R⁵ |
|---|---|---|---|---|---|---|
| 35 | 5-(piperazine-1-carbonyl)benzofuran-2-ylmethoxy | —Me | 4-((pyridin-3-ylmethyl)amino)butyl | H | H | H |
| 36 | 5-(ethoxycarbonyl)benzofuran-2-ylmethoxy | —Me | 4-((pyridin-3-ylmethyl)amino)butyl | H | H | H |
| 37 | 2-(ethoxycarbonyl)benzofuran-7-ylmethoxy | —Me | 4-((pyridin-3-ylmethyl)amino)butyl | H | H | H |
| 38 | 5-(ethoxycarbonyl)benzofuran-2-ylmethoxy | cyclopropyl | 4-((pyridin-3-ylmethyl)amino)butyl | H | H | H |
| 39 | 5-(carbamoyl)benzofuran-2-ylmethoxy | —Me | 4-((pyridin-3-ylmethyl)amino)butyl | H | H | H |
| 40 | 5-(hydroxymethyl)benzofuran-2-ylmethoxy | —Me | 4-((pyridin-3-ylmethyl)amino)butyl | H | H | H |

TABLE 1-continued

| Example | R¹ | R² | Q¹N(Q²R⁶)(Q³R⁷) | R³ | R⁴ | R⁵ |
|---|---|---|---|---|---|---|
| 41 | 5-(aminomethyl)benzofuran-2-yl-methoxy | —Me | -(CH₂)₄-NH-CH₂-(pyridin-3-yl) | H | H | H |
| 42 | 5-(ethoxymethyl)benzofuran-2-yl-methoxy | —Me | -(CH₂)₄-NH-CH₂-(pyridin-3-yl) | H | H | H |
| 43 | 5-(2,2,2-trifluoroethoxymethyl)benzofuran-2-yl-methoxy | —Me | -(CH₂)₄-NH-CH₂-(pyridin-3-yl) | H | H | H |
| 44-1 | 5-acetylbenzofuran-2-yl-methoxy | —Me | -(CH₂)₄-NH-CH₂-(pyridin-3-yl) | H | H | H |
| 44-2 | 5-(2-hydroxypropan-2-yl)benzofuran-2-yl-methoxy | —Me | -(CH₂)₄-NH-CH₂-(pyridin-3-yl) | H | H | H |
| 45 | 5-(ethoxymethyl)benzofuran-2-yl-methoxy | —Me | -(CH₂)₃-N(CH₃)-CH₂-(pyridin-3-yl) | H | H | H |
| 46 | (2,4-difluorophenoxy)methyl | —Me | -(CH₂)₃-N(CH₃)-CH₂-(pyridin-3-yl) | H | H | H |

TABLE 1-continued

| Example | R¹ | R² | Q¹N(Q²R⁶)(Q³R⁷) | R³ | R⁴ | R⁵ |
|---|---|---|---|---|---|---|
| 47 | 5-(ethylcarbamoyl)benzofuran-2-ylmethoxy | cyclopropyl | 4-((pyridin-3-ylmethyl)amino)butyl | H | H | H |
| 48 | 5-(cyclopropylcarbamoyl)benzofuran-2-ylmethoxy | cyclopropyl | 4-((pyridin-3-ylmethyl)amino)butyl | H | H | H |
| 49 | 5-(ethoxymethyl)benzofuran-2-ylmethoxy | —Me | 1-(pyridin-3-ylmethyl)piperidin-4-yl | H | H | H |
| 50 | 5-(hydroxymethyl)benzofuran-2-ylmethoxy | —Me | (1-(pyridin-3-ylmethyl)piperidin-3-yl)methyl | H | H | H |
| 51 | 5-(acetoxymethyl)benzofuran-2-ylmethoxy | —Me | (1-(pyridin-3-ylmethyl)piperidin-3-yl)methyl | H | H | H |
| 52 | ethoxymethyl | —Me | 4-((pyridin-3-ylmethyl)amino)butyl | H | H | H |

TABLE 1-continued

[Structure: benzofuran core with substituents R¹ (at 2-position), R² (at 3-position), R³ (5-position), R⁴ (6-position), R⁵ (7-position), and at 4-position an O-Q¹-CH(Q²-R⁶)(Q³-R⁷) group]

| Example | R¹ | R² | Q¹N(Q²R⁶)(Q³R⁷) | R³ | R⁴ | R⁵ |
|---|---|---|---|---|---|---|
| 53 | —CH₂—O—CH₂CH₂—cyclohexyl | —Me | —(CH₂)₃—NH—CH₂-(pyridin-3-yl) | H | H | H |
| 54 | —CH₂—O—CH₂-(3,5-dimethoxyphenyl) | —Me | —(CH₂)₃—NH—CH₂-(pyridin-3-yl) | H | H | H |
| 55 | —CH₂—S—CH₂CH₂-phenyl | —Me | —(CH₂)₃—NH—iPr | H | H | H |
| 56 | —CH₂—S—CH₂CH₂-phenyl | —Me | —(CH₂)₃—NH—CH₂-(pyridin-3-yl) | H | H | H |
| 57 | —CH₂—S-phenyl | —Me | —(CH₂)₃—NH—CH₂-(pyridin-3-yl) | H | H | H |
| 58 | —CH₂—O-(4-chlorophenyl) | —Me | —(CH₂)₃—NH—CH₂-(pyridin-3-yl) | H | H | H |
| 59 | —CH₂—O—CH₂-(3-chlorophenyl) | —Me | —(CH₂)₃—NH—CH₂-(pyridin-3-yl) | H | H | H |

TABLE 1-continued

| Example | R¹ | R² | Q¹N(Q²R⁶)(Q³R⁷) | R³ | R⁴ | R⁵ |
|---|---|---|---|---|---|---|
| 60 | -CH₂-S-Et | —Me | -(CH₂)₃-NH-CH₂-(3-pyridyl) | H | H | H |
| 61 | -CH₂-S(=O)-CH₂CH₂-Ph | —Me | -(CH₂)₃-NH-CH₂-(3-pyridyl) | H | H | H |
| 62 | -C(=O)-NH-CH₂CH₂-cyclohexyl | —Me | -(CH₂)₃-NH-CH₂-(3-pyridyl) | H | H | H |
| 63 | -C(=O)-NH-CH₂CH₂-cyclohexyl | —Me | -(CH₂)₃-(1-pyrrolidinyl) | H | H | H |
| 64 | -C(=O)-NH-(4-CO₂Et-phenyl) | —Me | -(CH₂)₃-N(tBu) | H | H | H |
| 65 | -C(=O)-NH-(2-CO₂Et-phenyl) | —Me | -(CH₂)₃-NH-tBu | H | H | H |
| 66 | -C(=O)-NH-(2,4-difluorophenyl) | —Me | -(CH₂)₃-NH-CH₂-(3-pyridyl) | H | H | H |

TABLE 1-continued

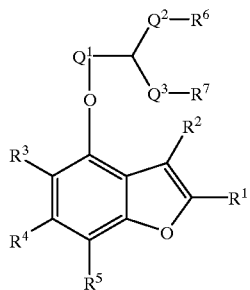

| Example | R¹ | R² | Q¹N(Q²R⁶)(Q³R⁷) | R³ | R⁴ | R⁵ |
|---|---|---|---|---|---|---|
| 67 | 2,3,4-trifluorophenyl-NHC(O)- | —Me | 3-pyridylmethyl-NH-(CH₂)₃- | H | H | H |
| 68 | 2-fluorophenyl-NHC(O)- | —Me | 3-pyridylmethyl-NH-(CH₂)₃- | H | H | H |
| 69 | 4-morpholinophenyl-NHC(O)- | —Me | 3-pyridylmethyl-NH-(CH₂)₃- | H | H | H |
| 70 | benzo[1,3]dioxol-5-yl-NHC(O)- | —Me | 3-pyridylmethyl-NH-(CH₂)₃- | H | H | H |
| 71 | 3,5-dimethoxyphenyl-NHC(O)- | —Me | 3-pyridylmethyl-NH-(CH₂)₃- | H | H | H |
| 72 | phenyl-NHC(O)- | —Me | 3-pyridylmethyl-NH-(CH₂)₃- | H | H | H |
| 73 | 4-chlorophenyl-NHC(O)- | —Me | 3-pyridylmethyl-NH-(CH₂)₃- | H | H | H |

TABLE 1-continued

| Example | R¹ | R² | Q¹N(Q²R⁶)(Q³R⁷) | R³ | R⁴ | R⁵ |
|---|---|---|---|---|---|---|
| 74 | 2-chlorophenyl-NH-C(O)- | —Me | -(CH₂)₃-NH-CH₂-(3-pyridyl) | H | H | H |
| 75 | (EtO)₂P(O)- | —Me | -(CH₂)₃-NH-CH₂-(3-pyridyl) | H | H | H |
| 76 | (iPrO)₂P(O)- | —Me | -(CH₂)₃-NH-CH₂-(3-pyridyl) | H | H | H |
| 77 | 4-(ethoxycarbonyl)oxazol-2-yl | —Me | -(CH₂)₃-NH-tBu | H | H | H |
| 78 | 4-(ethoxycarbonyl)oxazol-2-yl | —Me | -(CH₂)₃-NH-CH₂-(3-pyridyl) | H | H | H |
| 79 | 4-(4-methylpiperazin-1-ylcarbonyl)oxazol-2-yl | —Me | -(CH₂)₃-NH-CH₂-(3-pyridyl) | H | H | H |
| 80 | 4-(isopropylaminocarbonyl)oxazol-2-yl | —Me | -(CH₂)₃-NH-CH₂-(3-pyridyl) | H | H | H |

TABLE 1-continued
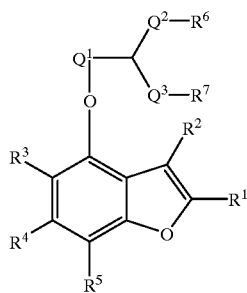
| Example | R¹ | R² | Q¹N(Q²R⁶)(Q³R⁷) | R³ | R⁴ | R⁵ |
|---|---|---|---|---|---|---|
| 81 | oxazole-CONH-CH2-(tetrahydrofuran-2-yl) | —Me | -(CH2)3-NH-CH2-(3-pyridyl) | H | H | H |
| 82 | oxazole-CO-N(piperidine-3-CO2Et) | —Me | -(CH2)3-NH-CH2-(3-pyridyl) | H | H | H |
| 83 | oxazole-CO-N(thiazolidine) | —Me | -(CH2)3-NH-CH2-(3-pyridyl) | H | H | H |
| 84 | oxazole-CONH-(3,5-difluorophenyl) | —Me | -(CH2)3-NH-CH2-(3-pyridyl) | H | H | H |
| 85 | thiazole-4-CO2Et | —Me | -(CH2)3-NH-CH2-(3-pyridyl) | H | H | H |
| 86 | oxazole-(thiazole-4-CO2Et) | —Me | -(CH2)3-NH-CH2-(3-pyridyl) | H | H | H |

TABLE 1-continued

| Example | R¹ | R² | Q¹N(Q²R⁶)(Q³R⁷) | R³ | R⁴ | R⁵ |
|---|---|---|---|---|---|---|
| 87 | (5-cyclohexylmethyl-4-ethoxycarbonyl-4,5-dihydrooxazol-2-yl) | —Me | -(CH₂)₃-NH-CH₂-(pyridin-3-yl) | H | H | H |
| 88 | (5-cyclohexylmethyl-4-(4-methylpiperazin-1-ylcarbonyl)-4,5-dihydrooxazol-2-yl) | —Me | -(CH₂)₃-NH-CH₂-(pyridin-3-yl) | H | H | H |
| 89 | (5-(2,4-difluorophenyl)-4-(4-methylpiperazin-1-ylcarbonyl)-4,5-dihydrooxazol-2-yl) | —Me | -(CH₂)₃-NH-CH₂-(pyridin-3-yl) | H | H | H |
| 90 | (5-cyclohexylmethyl-4-ethoxycarbonyloxazol-2-yl) | —Me | -(CH₂)₃-NH-CH₂-(pyridin-3-yl) | H | H | H |
| 91 | —CO₂Et | —Me | -CH₂-CH(OH)-CH₂-NH-CH₂-(pyridin-3-yl) | H | H | H |
| 92 | —C(O)NH-cyclohexyl | —Me | -CH₂-CH(OH)-CH₂-NH-iPr | H | H | H |

TABLE 1-continued
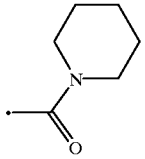
| Example | R¹ | R² | Q¹N(Q²R⁶)(Q³R⁷) | R³ | R⁴ | R⁵ |
|---|---|---|---|---|---|---|
| 93 | 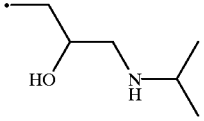 | —Me | 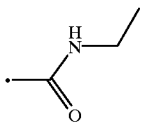 | H | H | H |
| 94 | 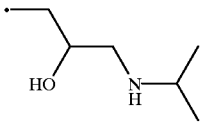 | —Me | 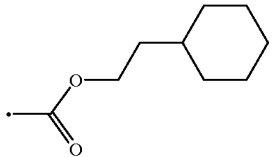 | H | H | H |
| 95 | 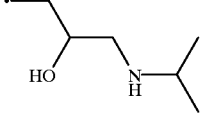 | —Me | 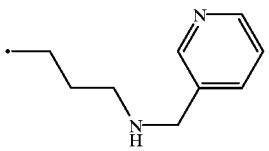 | H | H | H |
| 96 | —CO₂Et | —Me | 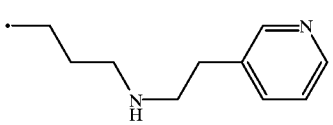 | H | H | H |
| 97 | —CO₂Et | —Me | 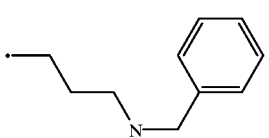 | H | H | H |
| 98 | —CO₂Et | —Me | 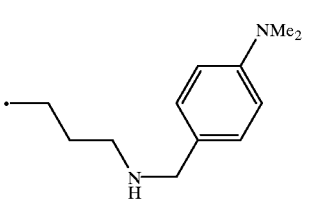 | H | H | H |
| 99 | —CO₂Et | —Me | | H | H | H |

TABLE 1-continued

| Example | R¹ | R² | Q¹N(Q²R⁶)(Q³R⁷) | R³ | R⁴ | R⁵ |
|---|---|---|---|---|---|---|
| 100 | —CO₂Et | —Me | propyl-NH-(1-benzylpiperidin-4-yl) | H | H | H |
| 101 | —CO₂Et | —Me | propyl-NH-(indan-1-yl) | H | H | H |
| 102 | —CO₂Et | —Me | propyl-NH-(1-ethylpiperidin-4-yl) | H | H | H |
| 103 | —CO₂Et | —Me | propyl-NH-(1-(pyridin-3-ylmethyl)piperidin-4-yl) | H | H | H |
| 104 | —CO₂Et | —Me | butyl-NH-tBu | H | H | H |
| 105 | —CO₂Et | —Me | pentyl-NH-tBu | H | H | H |
| 106-1 | —CO₂Et | —Me | 3-methylbutyl-NH-CH₂-(pyridin-3-yl) | H | H | H |

TABLE 1-continued
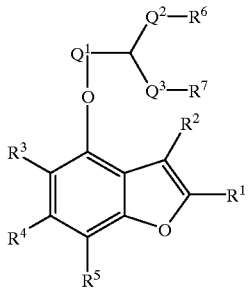
| Example | R¹ | R² | Q¹N(Q²R⁶)(Q³R⁷) | R³ | R⁴ | R⁵ |
|---|---|---|---|---|---|---|
| 106-2 | —CO₂Et | —Me | 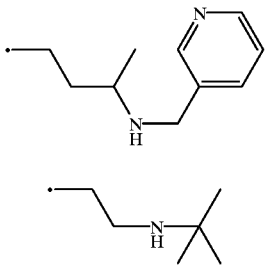 | H | H | H |
| 107 | —CO₂Et | —Me | 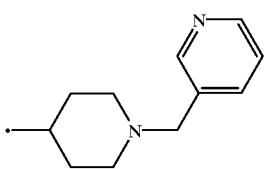 | H | H | H |
| 108 | —CO₂Et | —Me | 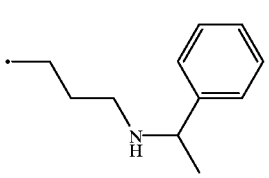 | H | H | H |
| 109 | —CO₂Et | —Me | 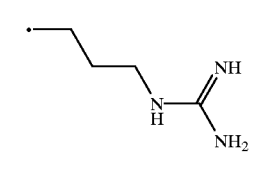 | H | H | H |
| 110 | —CO₂Et | —Me | 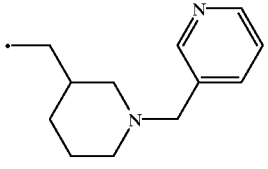 | H | H | H |
| 111 | —CO₂Et | —Me | 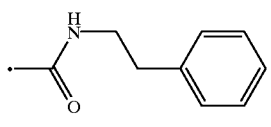 | H | H | H |
| 112 | 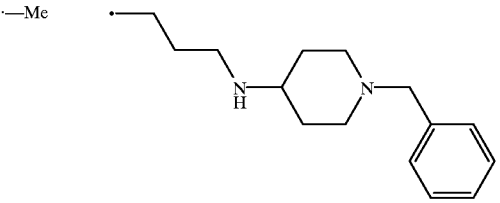 | —Me | | H | H | H |

TABLE 1-continued

| Example | R¹ | R² | Q¹N(Q²R⁶)(Q³R⁷) | R³ | R⁴ | R⁵ |
|---|---|---|---|---|---|---|
| 113 | —CO₂Et | —Me | butyl-NH-tBu | Br | H | H |
| 114 | C(=S)NH-(2,4-difluorophenyl) | —CH₃ | butyl-NH-CH₂-(3-pyridyl) | H | H | H |
| 115 | CH₂-NH-(5-methylisoxazol-3-yl) | —CH₃ | propyl-N(Me)-CH₂-(3-pyridyl) | H | H | H |
| 116 | trans-CH=CH-phenyl | —CH₃ | butyl-NH-CH₂-(3-pyridyl) | H | H | H |
| 117 | CH₂CH₂-phenyl | —CH₃ | butyl-NH-CH₂-(3-pyridyl) | H | H | H |
| 118 | C(=O)CH₂CH₂CH₃ | —CH₃ | butyl-NH-CH₂-(3-pyridyl) | H | H | H |
| 119 | CH₂CH₂CH₂-O-(3-fluorophenyl) | —CH₃ | butyl-NH-CH₂-(3-pyridyl) | H | H | H |

TABLE 1-continued

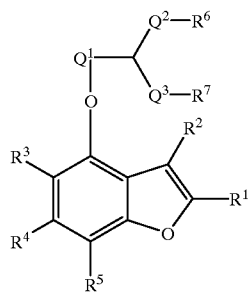

| Example | R¹ | R² | Q¹N(Q²R⁶)(Q³R⁷) | R³ | R⁴ | R⁵ |
|---|---|---|---|---|---|---|
| 120 | *-propyl-O-CH2-(3-fluorophenyl) | —CH₃ | *-butyl-NH-CH2-(pyridin-3-yl) | H | H | H |
| 121 | *-CH2-S-(4-fluorophenyl) | —CH₃ | *-butyl-NH-CH2-(pyridin-3-yl) | H | H | H |
| 122-1 | *-CH2-S(=O)-(4-fluorophenyl) | —CH₃ | *-butyl-NH-CH2-(pyridin-3-yl) | H | H | H |
| 122-2 | *-CH2-S(=O)2-(4-fluorophenyl) | —CH₃ | *-butyl-NH-CH2-(pyridin-3-yl) | H | H | H |
| 123 | *-CH=N-O-ethyl | —CH₃ | *-butyl-N(CH3)-CH2-(pyridin-3-yl) | H | H | H |
| 124 | *-CH=N-(morpholin-4-yl) | —CH₃ | *-butyl-N(CH3)-CH2-(pyridin-3-yl) | H | H | H |
| 125 | *-CH=N-(4-methylpiperazin-1-yl) | —CH₃ | *-butyl-N(CH3)-CH2-(pyridin-3-yl) | H | H | H |

TABLE 1-continued
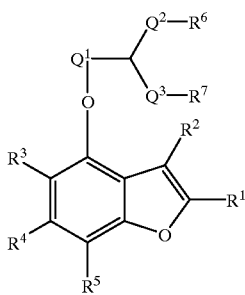
| Example | R¹ | R² | Q¹N(Q²R⁶)(Q³R⁷) | R³ | R⁴ | R⁵ |
|---|---|---|---|---|---|---|
| 126 | —COOEt | —CH₃ | 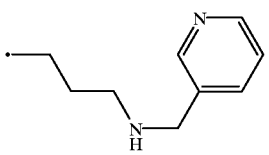 | F | H | H |
| 127 | —COOEt | —CH₃ | 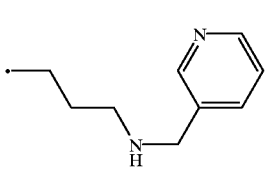 | H | H | F |
| 128 | 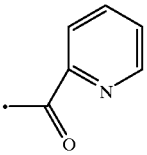 | —CH₃ | 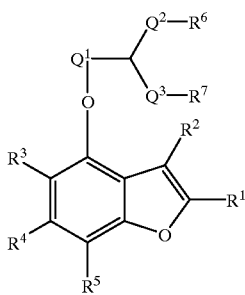 | H | H | H |
| 129 | 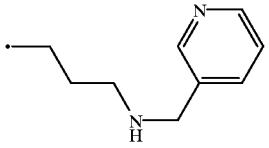 | —Me | 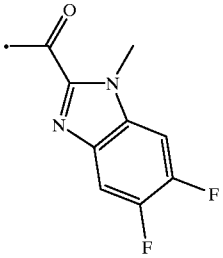 | H | H | H |
| 130 | 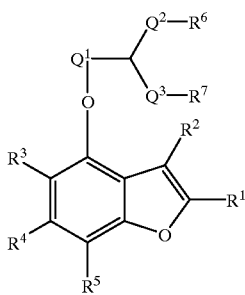 | —Me | 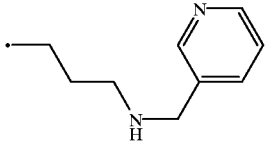 | H | H | H |
| 131 | 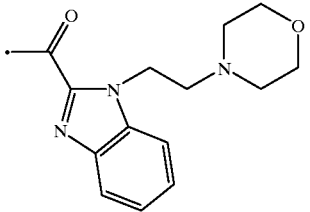 | —Me | 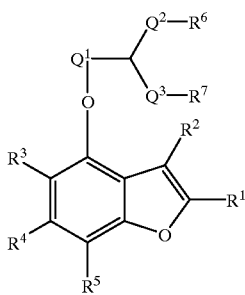 | H | H | H |

TABLE 1-continued

| Example | R¹ | R² | Q¹N(Q²R⁶)(Q³R⁷) | R³ | R⁴ | R⁵ |
|---|---|---|---|---|---|---|
| 132 | (1-oxo-ethyl)-4,5-dimethylthiazol-2-yl | —Me | -(CH₂)₃-NH-CH₂-(pyridin-3-yl) | H | H | H |
| 133-1 | (1-hydroxyimino-ethyl)-4,5-dimethylthiazol-2-yl | —Me | -(CH₂)₃-NH-CH₂-(pyridin-3-yl) | H | H | H |
| 133-2 | (1-hydroxyimino-ethyl)-4,5-dimethylthiazol-2-yl | —Me | -(CH₂)₃-NH-CH₂-(pyridin-3-yl) | H | H | H |
| 134 | (1-ethoxyimino-ethyl)-4,5-dimethylthiazol-2-yl | —Me | -(CH₂)₃-NH-CH₂-(pyridin-3-yl) | H | H | H |
| 135 | (1-(4-nitrobenzyloxyimino)-ethyl)-4,5-dimethylthiazol-2-yl | —Me | -(CH₂)₃-NH-CH₂-(pyridin-3-yl) | H | H | H |

TABLE 1-continued
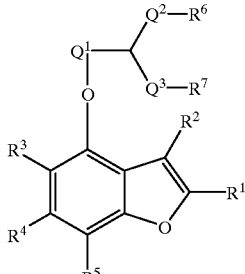
| Example | R¹ | R² | Q¹N(Q²R⁶)(Q³R⁷) | R³ | R⁴ | R⁵ |
|---|---|---|---|---|---|---|
| 136 | 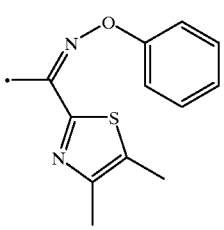 | —Me | 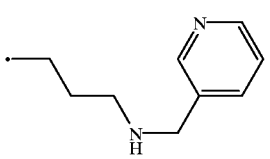 | H | H | H |
| 137 | 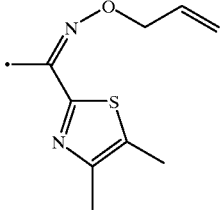 | —Me | 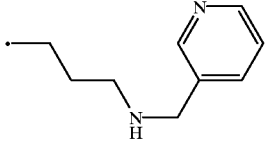 | H | H | H |
| 138 | 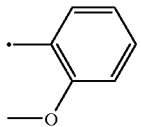 | —Me | 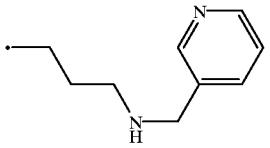 | H | H | H |
| 139-1 | 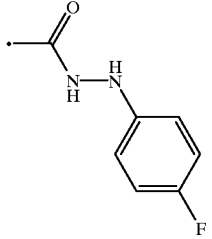 | —Me | 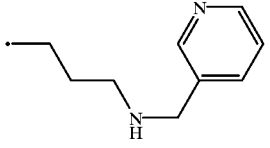 | H | H | H |
| 139-2 | 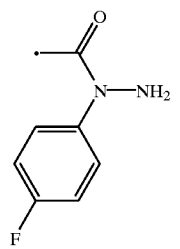 | —Me | 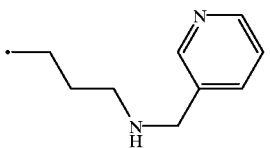 | H | H | H |

TABLE 1-continued

| Example | R¹ | R² | Q¹N(Q²R⁶)(Q³R⁷) | R³ | R⁴ | R⁵ |
|---|---|---|---|---|---|---|
| 140 | (acetyl-NH-NH-(3-nitrophenyl)) | —Me | (propyl-NH-CH₂-pyridin-3-yl) | H | H | H |
| 141 | (acetyl-NH-NH-C(O)-pyridin-3-yl) | —Me | (propyl-NH-CH₂-pyridin-3-yl) | H | H | H |

EXAMPLE A

Hard gelatin capsules each containing the following ingredients were manufactured in the conventional manner per se:

| | |
|---|---|
| {3-[2-(2-Fluoro-phenoxymethyl)-3-methyl-benzofuran-4-yloxy]-propyl}-pyridin-3-ylmethyl-amine | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

EXAMPLE B

Tablets each containing the following ingredients were manufactured in the conventional manner per se:

| | |
|---|---|
| {3-[2-(2-Fluoro-phenoxymethyl)-3-methyl-benzofuran-4-yloxy]-propyl}-pyridin-3-ylmethyl-amine | 100 mg |
| Lactose | 60 mg |
| Corn starch | 20 mg |
| Sodium Starch Glycolate | 10 mg |
| Polyvinylpyrrolidone | 6 mg |
| Talc | 3 mg |

-continued

| | |
|---|---|
| Magnesium stearate | 1 mg |
| Total | 200 mg |

What is claimed is:

1. A method for the treatment or prevention of mycosis in mammals comprising administering a therapeutically effective amount of a compound of the formula:

[I]

wherein

R¹ is hydrogen, an unsubstituted or substituted heterocyclic ring,

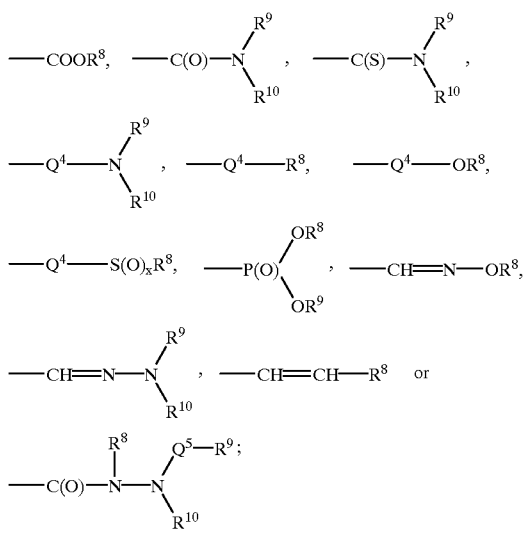

R² is hydrogen, unsubstituted or substituted lower alkyl, aralkyl, cycloalkyl or cycloalkylalkyl;

R³, R⁴ and R⁵ are independently hydrogen or halogen;

R⁶ and R⁷ are independently hydrogen, unsubstituted or substituted lower alkyl, an aromatic ring or aliphatic ring which may contain heteroatom(s); or R⁶ and R⁷ form an aliphatic ring which may contain further heteroatom(s) together with the adjacent Q², N and Q³; or Q¹ and R⁶ form an aliphatic ring which may contain further heteroatom(s) together with the adjacent N and Q²;

R⁸, R⁹ and R¹⁰ are independently hydrogen, unsubstituted or substituted lower alkyl, aralkyl, cycloalkyl, cycloalkylalkyl, an aromatic ring or aliphatic ring which may contain heteroatom(s); or R⁹ and R¹⁰ form an aliphatic ring which may contain further heteroatom(s) together with the adjacent nitrogen;

Q¹ is unsubstituted or substituted lower alkylene other than unsubstituted or substituted methylene;

Q² and Q³ are each independently a single bond, tinsubstituted or substituted lower alkylene;

Q⁴ is a single bond, carbonyl, oxime, oxime O-ether which has a substituted or unsubstituted lower alkyl, lower alkenyl, aralkyl or aryl radical on the oxygen atom, or unsubstituted or substituted lower alkylene;

Q⁵ is a single bond or carbonyl and x is an integer of 0 to 2;

with the proviso that when R¹ is —COOC₂H₅, then

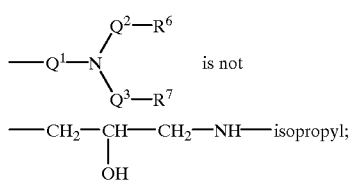 is not

—CH₂—CH—CH₂—NH—isopropyl;
        |
        OH or the pharmaceutically acceptable salts thereof.

2. The method according to claim 1, wherein R¹ is unsubstituted or substituted heterocyclic ring.

3. The method according to claim 1, wherein R¹ is —COOR⁶, and R⁸ is as defined in claim 1.

4. The method according to claim 1, wherein R¹ is

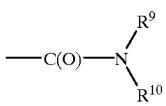

and R⁹ and R¹⁰ are as defined in claim 1.

5. The method according to claim 1, wherein R¹ is

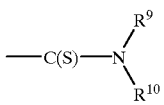

and R⁹ and R¹⁰ are as defined in claim 1.

6. The method according to claim 1, wherein R¹ is

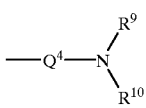

and Q⁴, R⁹ and R¹⁰ are as defined in claim 1.

7. The method according to claim 1, wherein R¹ is

and R⁸ and Q⁴ are as defined in claim 1.

8. The method according to claim 1, wherein R¹ is

and Q⁴ and R⁸ are as defined in claim 1.

9. The method according to claim 1, wherein R¹ is

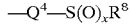

and Q⁴, R⁸ and x are as defined in claim 1.

10. The method according to claim 1, wherein R¹ is

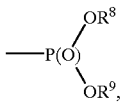

and R⁸ and R⁹ are as defined in claim 1.

11. The method according to claim 1, wherein R¹ is

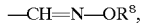

and R⁸ is as defined in claim 1.

12. The method according to claim 1, wherein R¹ is

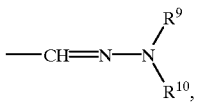

and R⁹ and R¹⁰ are as defined in claim 1.

13. The method according to claim 1, wherein R¹ is

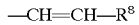

and R⁸ is as defined in claim 1.

14. The method according to claim 1, wherein $R^1$ is

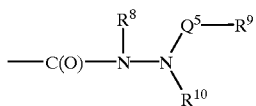

wherein $Q^5$, $R^8$, $R^9$ and $R^{10}$ are as defined in claim 1.

15. The method according to claim 1, wherein $Q^2$ is a single bond, $R^6$ is hydrogen, $Q^3$ is a single bond and $R^7$ is unsubstituted or substituted lower alkyl.

16. The method according to claim 1, wherein $Q^2$ is a single bond, $R^6$ is hydrogen, $Q^3$ is a single bond or unsubstituted or substituted lower alkylene, and $R^7$ is an aromatic ring or a 3 to 7 membered aliphatic ring which may contain heteroatom(s).

17. The method according to claim 1, wherein $Q^2$ is a single bond, $R^6$ is unsubstituted or substituted lower alkyl, $Q^3$ is a single bond and $R^7$ is unsubstituted or substituted lower alkyl.

18. The method according to claim 1, wherein $Q^2$ is a single bond, $R^6$ is unsubstituted or substituted lower alkyl, $Q^3$ is a single bond or unsubstituted or substituted lower alkylene and $R^7$ is an aromatic ring or a 3 to 7 membered aliphatic ring which may contain heteroatom(s).

19. The method according to claim 1, wherein $R^1$ is $-Q^4-R^8$; $Q^4$ is carbonyl; $R^8$ is benzoimidazolyl substituted with halogen, lower alkyl, pyridinyl-lower alkyl and/or morpholinyl-lower alkyl; $R^2$ is lower alkyl; $Q^1$ is lower alkylene; $Q^2$ is a single bond; $Q^3$ is unsubstituted lower alkylene; $R^3$, $R^4$, $R^5$ and $R^6$ are hydrogen; and $R^7$ is phenyl, pyridyl or pyrimidinyl.

20. The method according to claim 1, wherein $R^3$, $R^4$ and $R^5$ are hydrogen and the structure $Q^1N(Q^2R^6)(Q^3R^7)$ is

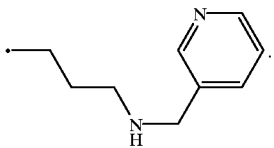

21. The method according to claim 1, wherein $R^3$, $R^4$ and $R^5$ are hydrogen, $R^2$ is methyl and the structure $Q^1N(Q^2R^6)(Q^3R^7)$ is

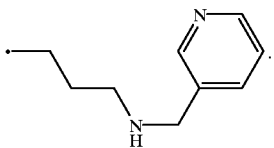

22. A bicyclic compound selected from the group consisting of: (3-methyl-4-{3-[(pyridin-3-ylmethyl)-amino]-propoxy}-benzofuran-2-yl)-methanol;
{3-[2-(2,4-difluorophenoxymethyl)-3-methyl-benzofuran-4-yloxy]-propyl}-pyridin-3-ylmethyl-amine;
{3-[2-(3-trifluoromethylphenoxymethyl)-3-methyl-benzofuran-4-yloxy]-propyl}-pyridin-ylmethyl-amine;
[3-(2-phenoxymethyl-3-methyl-benzofuran-4-yloxy-propyl]-pyridin-3-ylmethyl-amine;
{3-[2-(2-fluorophenoxymethyl)-3-methyl-benzofuran-4-yloxy]-propyl}-pyridin-3-ymethyl-amine;
{3-[2-(3-fluorophenoxymethyl)-3-methyl-benzofuran-4-yloxy]-propyl}-pyridin-3-ylmethyl-amine;
{3-[2-(4-fluorophenoxymethyl)-3-methyl-benzofuran-4-yloxy]-propyl}-pyridin-3-ylmethyl-amine;
{3-[2-(2,3-difluorophenoxymethyl)-3-methyl-benzofuran-4-yloxy]-propyl}-pyridin-3-ylmethyl-amine;
{3-[2-(2,5-difluorophenoxymethyl)-3-methyl-benzofuran-4-yloxy]-propyl}-pyridin-3-ylmethyl-amine;
{3-[2-(2,6-difluorophenoxymethyl)-3-methyl-benzofuran-4-yloxy]-propyl}-pyridin-3-ylmethyl-amine;
{3-[2-(2,3,4-trifluorophenoxymethyl)-3-methyl-benzofuran-4-yloxy]-propyl}-pyridin-3-ylmethyl-amine;
{3-[2-(2,3,5-trifluorophenoxymethyl)-3-methyl-benzofuran-4-yloxy]-propyl}-pyridin-3-ylmethyl-amine;
{3-[2-(2,4,5-trifluorophenoxymethyl)-3-methyl-benzofuran-4-yloxy]-propyl}-pyridin-3-ylmethyl-amine;
{3-[2-(2,3,6-trifluorophenoxymethyl)-3-methyl-benzofuran-4-yloxy]-propyl}-pyridin-3-ylmethyl-amine;
{3-[2-(2,4,6-trifluorophenoxymethyl)-3-methyl-benzofuran-4-yloxy]-propyl}-pyridin-3-ylmethyl-amine;
{3-[2-(2,3,4,5,6-pentafluorophenoxymethyl)-3-methyl-benzofuran-4-yloxy]-propyl}-pyridin-3-ylmethyl-amine;
{3-[2-(3,5,-bistrifluoromethylphenoxymethyl)-3-methyl-benzofuran-4-yloxy]-propyl}-pyridin-3-ylmethyl-amine;
{3-[2-(3-morpholin-phenoxymethyl)-3-methyl-benzofuran-4-yloxy]-propyl}-pyridin-3-ylmethyl-amine;
{3-[2-(4-morpholin-phenoxymethyl)-3-methyl-benzofuran-4-yloxy]-propyl}-pyridin-3-ylmethyl-amine;
{3-[2-(4-chlorophenoxymethyl)-3-methyl-benzofuran-4-yloxy]-propyl}-pyridin-3-ylmethyl-amine;
{3-[3-methyl-2-(pyridin-3-yloxymethyl)-benzofuran-4-yloxy]-propyl}-pyridin-3-ylmethyl-amine;
4-(3-methyl-4-{3-[(pyridin-3-ylmethyl)-amino]-propoxy}-benzofuran-2-ylmethoxy)-benzonitrile;
{3-[3-methyl-2-(2,2,2-trifluoro-ethoxymethyl)-benzofuran-4-yloxy]-propyl}-pyridin-3-ylmethyl-amine;
(4-hydroxy-piperidin-1-yl)-[5-(3-methyl-4-{3-[(pyridin-3-ylmethyl)-amino]-propoxy}-benzofuran-2-ylmethoxy)-benzofuran-2-yl]-methanone;
[5-(3-methyl-4-{3-[(pyridin-3-ylmethyl)-amino]-propoxy}-benzofuran-2-ylmethoxy)-benzofuran-2-yl]-piperazin-1-yl-methanone;
5-[3-methyl-4-[3-[(pyridin-3-ylmethyl)-amino]-propoxyl]-benzofuran-2-ylmethoxy]-benzofuran-2-carboxylic acid ethyl ester;
7-[3-methyl-4-[3-[(pyridin-3-ylmethyl)-amino]-propoxyl]-benzofuran-2-ylmethoxyl]-benzofuran-2-carboxylic acid ethyl ester;
5-[3-methyl-4-[3-[(pyridin-3-ylmethyl)-amino]-propoxyl]-benzofuran-2-ylmethoxyl]-benzofuran-2-carboxylic acid amide;

[5-[3-methyl-4-[3-[(pyridin-3-ylmethyl)-amino]-propoxyl]-benzofuran-2-ylmethoxyl]-benzofuran-2-yl]-methanol;

[3-[2-(2-aminomethyl-benzofuran-5-ylmethyl)-3-methyl-benzofuran-4-yloxy]-propyl]-pyridin-3-ylmethyl-amine,

[3-[2-(2-ethoxymethyl-benzofuran-5-yloxymethyl)-3-methyl-benzofuran-4-yloxy]-propyl]-pyridin-3-ylmethyl-amine;

[3-[3-methyl-2-[2-(2,2,2-trifluoro-ethoxymethyl)-benzofuran-5-yloxymethyl]-benzofuran-4-yloxy]-propyl]-pyridin-3-ylmethyl-amine;

1-[5-(3-methyl-4-{3-[(pyridin-3-ylmethyl)-amino]-propoxy}-benzofuran-2-ylmethoxy)-benzofuran-2-yl]-ethanone;

2-[5-(3-methyl-4-{3-[(pyridin-3-ylmethyl)-amino]-propoxy}-benzofuran-2-ylmethoxy)-benzofuran-2-yl]-propan-2-ol;

[3-(2-ethoxymethyl-3-methyl-benzofuran-4-yloxy)-propyl]-pyridin-3-ylmethyl-amine;

[3-[2-(2-cyclohexyl-ethoxymethyl)-3-methyl-benzofuran-4-yloxy]-propyl]-pyridin-3-ylmethyl-amine;

[3-[2-(3,5-dimethoxy-benzyloxymethyl)-3-methyl-benzofuran-4-yloxy]-propyl]-pyridin-3-ylmethyl-amine;

[3-(3-methyl-2-phenethylsulfanylmethyl-benzofuran-4-yloxy)-propyl]-pyridin-3-ylmethyl-amine;

[3-(3-methyl-2-phenylsulfanylmethyl-benzofuran-4-yloxy)-propyl]-pyridin-3-ylmethyl-amine;

{3-[2-(4-chloro-phenylsulfanylmethyl)-3-methyl-benzofuran-4-yloxy]-propyl}-pyridin-3-ylmethyl-amine;

{3-[2-(4-chloro-benzylsulfanylmethyl)-3-methyl-benzofuran-4-yloxy]-propyl}-pyridin-3-ylmethyl-amine;

[3-(2-ethylsulfanylmethyl-3-methyl-benzofuran-4-yloxy)-propyl]-pyridin-3-ylmethyl-amine;

(RS)-[3-[3-methyl-2-(2-phenyl-ethylsulfinylmethyl)-benzofuran-4-yloxy]-propyl]-pyridin-3-ylmethyl-amine;

3-methyl-4-{3-[(pyridin-3-ylmethyl)-amino]-propoxy}-benzofuran-2-carboxylic acid (2-cyclohexyl-ethyl)-amide;

3-methyl-4-{3-[(pyridin-3-ylmethyl)-amino]-propoxy}-benzofuran-2-carboxylic acid (2,4-difluorophenyl)-amide;

3-methyl-4-{3-[(pyridin-3-ylmethyl)-amino]-propoxy}-benzofuran-2-carboxylic acid (2,3,4-trifluorophenyl)-amide;

3-methyl-4-{3-[(pyridin-3-ylmethyl)-amino]-propoxy}-benzofuran-2-carboxylic acid (2-fluorophenyl)-amide;

3-methyl-4-{3-[(pyridin-3-ylmethyl)-amino]-propoxy}-benzofuran-2-carboxylic acid (4-morpholin-4-yl-phenyl)-amide;

3-methyl-4-{3-[(pyridin-3-ylmethyl)-amino]-propoxy}-benzofuran-2-carboxylic acid benzo[1,3]dioxol-5-yl amide;

3-methyl-4-{3-[(pyridin-3-ylmethyl)-amino]-propoxy}-benzofuran-2-carboxylic acid (3,5-dimethoxy-phenyl)-amide;

3-methyl-4-{3-[(pyridin-3-ylmethyl)-amino]-propoxy}-benzofuran-2-carboxylic acid phenyl-amide;

3-methyl-4-{3-[(pyridin-3-ylmethyl)-amino]-propoxy}-benzofuran-2-carboxylic acid (4-chloro-phenyl)-amide;

3-methyl-4-{3-[(pyridin-3-ylmethyl)-amino]-propoxy}-benzofuran-2-carboxylic acid (2-chloro-phenyl)-amide;

(3-methyl-4-{3-[pyridin-3-ylmethyl)-amino]-propoxy}-benzofuran-2-yl phosphonic acid diethyl ester;

(3-methyl-4-{3-[pyridin-3-ylmethyl)-amino]-propoxy}-benzofuran-2-yl phosphonic acid diisopropyl ester;

2-(3-methyl-4-{3-[(pyridin-3-ylmethyl)-amino]-propoxy}-benzofuran-2-yl)-oxazole-4-carboxylic acid ethyl ester;

(4-methyl-piperazin-1-yl)-[2-(3-methyl-4-{3-[(pyridin-3-ylmethyl)-amino]-propoxy}-benzofuran-2-yl)-oxazol-4-yl]-methanone;

2-(3-methyl-4-{3-[(pyridin-3-ylmethyl)-amino]-propoxy}-benzofuran-2-yl)-oxazole-4-carboxylic acid isopropylamide;

(RS)-2-[3-methyl-4-[3-[(pyridin-3-ylmethyl)-amino]-propoxy]-benzofuran-2-yl]-oxazole-4-carboxylic acid (tetrahydro-furan-2-ylmethyl)-amide;

(RS)-1-[2-[3-methyl-4-[3-[(pyridin-3-ylmethyl)-amino]-propoxy]-benzofuran-2-yl]-oxazole-4-carbonyl]-piperidine-3-carboxylic acid ethyl ester;

[2-(3-methyl-4-{3-[(pyridin-3-ylmethyl)-amino]-propoxy}-benzofuran-2-yl)-oxazol-4-yl]-thiazolidin-3-yl-methanone;

2-(3-methyl-4-{3-[(pyridin-3-ylmethyl)-amino]-propoxy}-benzofuran-2-yl)-oxazole-4-carboxylic acid (3,5-difluoro-phenyl)-amide;

2-(3-methyl-4-{3-[(pyridin-3-ylmethyl)-amino]-propoxy}-benzofuran-2-yl)-thiazole-4-carboxylic acid ethyl ester;

2-[2-[3-methyl-4-[3-[(pyridin-3-ylmethyl)-amino]-propoxy]-benzofuran-2-yl]-oxazol-4-yl]-thiazole-4-carboxylic acid ethyl ester;

dl-5-cyclohexylmethyl-2-(3-methyl-4-{3-[(pyridin-3-ylmethyl)-amino]-propoxy}-benzofuran-2-yl)-trans-4,5-dihydro-oxazole-4-carboxylic acid ethyl ester;

dl-[5-cyclohexylmethyl-2-(3-methyl-4-{3-[(pyridin-3-ylmethyl)-amino]-propoxy}-benzofuran-2-yl)-trans-4,5-dihydro-oxazol-4-yl]-(4-methyl-piperazin-1-yl)-methanone;

dl-[5-(2,4-difluoro-benzyl)-2-(3-methyl-4-{3-[(pyridin-3-ylmethyl)-amino]-propoxy}-benzofuran-2-yl)-trans-4,5-dihydro-oxazol-4-yl]-(4-methyl-piperazin-1-yl)-methanone;

5-cyclohexylmethyl-2-(3-methyl-4-{3-[(pyridin-3-ylmethyl)-amino]-propoxy}-benzofuran-2-yl)-oxazole-4-carboxylic acid ethyl ester;

3-methyl-4-{3-[(pyridin-3-ylmethyl)-amino]-propoxy}-benzofuran-2-carboxylic acid ethyl ester;

3-methyl-4-{3-[(pyridin-3-ylmethyl)-amino]-propoxy}-benzofuran-2-carbothioic acid (2,4-difluoro-phenyl)-amide;

(E)-[3-(3-methyl-2-styryl-benzofuran-4-yloxy)-propyl]-pyridin-3-ylmethyl-amine;

[3-(3-methyl-2-phenethyl-benzofuran-4-yloxy)-propyl]-pyridin-3-ylmethyl-amine;

1-(3-methyl-4-{3-[(pyridin-3-ylmethyl)-amino]-propoxy}-benzofuran-2-yl)-butan-1-one;

(3-{2-[3-(3-fluoro-phenoxy)-propyl]-3-methyl-benzofuran-4-yloxy}-propyl)-pyridin-3-ylmethyl-amine;

(3-{2-[3-(3-fluoro-benzyloxy)-propyl]-3-methyl-benzofuran-4-yloxy}-propyl)-pyridin-3-ylmethyl-amine;

{3-[2-(4-fluoro-phenylsulfanylmethyl)-3-methyl-benzofuran-4-yloxy]-propyl}-pyridin-3-ylmethyl-amine;

{3-[2-(4-fluoro-benzenesulfinylmethyl)-3-methyl-benzofuran-4-yloxy]-propyl}-pyridin-3-ylmethyl-amine;

{3-[2-(4-fluoro-benzenesulfonylmethyl)-3-methyl-benzofuran-4-yloxy]-propyl}-pyridin-3-ylmethyl-amine;

(3-methyl-4-{3-[(pyridin-3-ylmethyl)-amino]-propoxy}-benzofuran-2-yl-pyridin-2-yl-methanone;

(5,6-difluoro-1-methyl-1H-benzoimidazol-2-yl)-(3-methyl-4-{3-[(pyridin-3-ylmethyl)-amino]-propoxy}-benzofuran-2-yl)-methanone;

(3-methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone;

(3-methyl-4-{3-[(pyridin-3-ylmethyl)-amino]-propoxy}-benzofuran-2-yl)-[1-(2-pyridin-2-yl-ethyl)-1H-benzoimidazol-2-yl]-methanone;

(4,5-dimethyl-thiazol-2-yl)-(3-methyl-4-{3-[(pyridin-3-ylmethyl)-amino]-propoxy}-benzofuran-2-yl)-methanone;

(4,5-dimethyl-thiazol-2-yl)-(3-methyl-4-{3-[(pyridin-3-ylmethyl)-amino]-propoxy}-benzofuran-2-yl)-methanone oxime;

(4,5-dimethyl-thiazol-2-yl)-(3-methyl-4-{3-[(pyridin-3-ylmethyl)-amino]-propoxy}-benzofuran-2-yl)-methanone oxime;

(4,5-dimethyl-thiazol-2-yl)-(3-methyl-4-{3-[(pyridin-3-ylmethyl)-amino]-propoxy}-benzofuran-2-yl)-methanone O-ethyl-oxime;

(4,5-dimethyl-thiazol-2-yl)-(3-methyl-4-{3-[(pyridin-3-ylmethyl)-amino]-propoxy}-benzofuran-2-yl)-methanone O-(4-nitro-benzyl)-oxime;

(4,5-dimethyl-thiazol-2-yl)-(3-methyl-4-{3-[(pyridin-3-ylmethyl)-amino]-propoxy}-benzofuran-2-yl)-methanone O-phenyl-oxime;

(4,5-dimethyl-thiazol-2-yl)-(3-methyl-4-{3-[(pyridin-3-ylmethyl)-amino]-propoxy}-benzofuran-2-yl)-methanone O-allyl-oxime;

{3-[2-(2-methoxy-phenyl)-3-methyl-benzofuran-4-yloxy]-propyl}-pyridin-3-ylmethyl-amine;

3-methyl-4-{3-[(pyridin-3-ylmethyl)-amino]-propoxy}-benzofuran-2-carboxylic acid N'-(4-fluoro-phenyl)-hydrazide;

3-methyl-4-{3-[(pyridin-3-ylmethyl)-amino]-propoxy}-benzofuran-2-carboxylic acid N-(4-fluoro-phenyl)-hydrazide;

3-methyl-4-{3-[(pyridin-3-ylmethyl)-amino]-propoxy}-benzofuran-2-carboxylic acid N'-(3-nitro-phenyl)-hydrazide; and isonicotinic acid N'-(3-methyl-4-{3-[(pyridin-3-ylmethyl)-amino]-propoxy}-benzofuran-2-carbonyl)-hydrazide.

23. A bicyclic compound selected from the group consisting of: 3-cyclopropyl-4-{3-[(pyridin-3-ylmethyl)-amino]-propoxy}-benzofuran-2-carboxylic acid ethyl ester;

3-isopropyl-4-{3-[(pyridin-3-ylmethyl)-amino]-propoxy}-benzofuran-2-carboxylic acid ethyl ester;

3-ethyl-4-{3-[(pyridin-3-ylmethyl)-amino]-propoxy}-benzofuran-2-carboxylic acid ethyl ester;

4-{3-[(pyridin-3-ylmethyl)-amino]-propoxy}-benzofuran-2-carboxylic acid ethyl ester;

(3-cyclopropyl-4-{3-[(pyridin-3-ylmethyl)-amino]-propoxy}-benzofuran-2-yl)-methanol;

5-(3-cyclopropyl-4-{3-[(pyridin-3-ylmethyl)-amino]-propoxy}-benzofuran-2-ylmethoxy)-benzofuran-2-carboxylic acid ethyl ester;

5-(3-cyclopropyl-4-{3-[(pyridin-3-ylmethyl)-amino]-propoxy}-benzofuran-2-ylmethoxy)-benzofuran-2-carboxylic acid ethylamide; and 5-(3-cyclopropyl-4-{3-[(pyridin-3-ylmethyl)-amino]-propoxy}-benzofuran-2-ylmethoxy)-benzofuran-2-carboxylic acid cyclopropylamide.

24. A bicyclic compound selected from the group consisting of:

4-(3-tert-butylamino-propoxy)-3-propyl-benzofuran-2-carboxylic acid ethyl ester;

3-butyl-4-(3-tert-butylamino-propoxy)-benzofuran-2-carboxylic acid ethyl ester;

3-aminomethyl-4-{3-[(pyridin-3-ylmethyl)-amino]-propoxy}-benzofuran-2-carboxylic acid ethyl ester;

4-(3-tert-butylamino-propoxy)-3-hydroxymethyl-benzofuran-2-carboxylic acid methyl ester;

4-(3-tert-butylamino-propoxy)-3-ethoxymethyl-benzofuran-2-carboxylic acid ethyl ester;

{3-[2-(2-ethoxymethyl-benzofuran-5-yloxymethyl)-3-methyl-benzofuran-4-yloxy]-propyl}-methyl-pyridin-3-ylmethyl-amine;

{3-[2-(2,4-difluoro-phenoxymethyl)-3-methyl-benzofuran-4-yloxy]-propyl}-methyl-pyridin-3-ylmethyl-amine;

3-[4-[2-(2-ethoxymethyl-benzofuran-5-yloxymethyl)-3-methyl-benzofuran-4-yloxy]-piperidin-1-ylmethyl]-pyridine;

[5-[3-methyl-4-(1-pyridin-3-ylmethyl-piperidin-3-ylmethoxy)-benzofuran-2-ylmethoxy]-benzofuran-2-yl]-methanol;

acetic acid 5-[3-methyl-4-(1-pyridin-3-ylmethyl-piperidin-3-ylmethoxy)-benzofuran-2-ylmethoxy]-benzofuran-2-ylmethyl ester;

isopropyl-[3-(3-methyl-2-phenethylsulfanylmethyl-benzofuran-4-yloxy)-propyl]-amine;

3-methyl-4-(3-pyrrolidin-1-yl-propoxy)-benzofuran-2-carboxylic acid (2-cyclohexyl-ethyl)-amide;

4-[[4-(3-tert-butylamino-propoxy)-3-methyl-benzofuran-2-carbonyl]-amino]-benzoic acid ethyl ester;

2-[[4-(3-tert-butylamino-propoxy)-3-methyl-benzofuran-2-carbonyl]-amino]-benzoic acid ethyl ester;

2-{4-[3-(tert-butylamino)-propoxy]-3-methyl-benzofuran-2-yl}-oxazole-4-carboxylic acid ethyl ester;

4-[2-hydroxy-3-[(pyridin-3-ylmethyl)-amino]-propoxy]-3-methyl-benzofuran-2-carboxylic acid ethyl ester;

4-(2-hydroxy-3-isopropylamino-propoxy)-3-methyl-benzofuran-2-carboxylic acid cyclohexylamide;

[4-(2-hydroxy-3-isopropylamino-propoxy)-3-methyl-benzofuran-2-yl]-piperidin-1-yl-methanone;

4-(2-hydroxy-3-isopropylamino-propoxy)-3-methyl-benzofuran-2-carboxylic acid ethylamide;

4-(2-hydroxy-3-isopropylamino-propoxy)-3-methyl-benzofuran-2-carboxylic acid 2-cyclohexyl-ethyl ester;

3-methyl-4-(3-(2-pyridin-3-yl-ethylamino)-propoxy)-benzofuran-2-carboxylic acid ethyl ester;
4-(3-benzylamino-propoxy)-3-methyl-benzofuran-2-carboxylic acid ethyl ester;
4-(3-(4-dimethylamino-benzylamino)-propoxy)-3-methyl-benzofuran-2-carboxylic acid ethyl ester;
4-(3-(1-benzyl-piperidin-4-ylamino)-propoxy)-3-methyl-benzofuran-2-carboxylic acid ethyl ester;
4-(3-(indan-1-ylamino)-propoxy)-3-methyl-benzofuran-2-carboxylic acid ethyl ester;
4-[3-(1-ethyl-piperidin-4-ylamino)-propoxy]-3-methyl-benzofuran-2-carboxylic acid ethyl ester;
3-methyl-4-[3-(1-pyridin-3-ylmethyl-piperidin-4-ylamino)-propoxy]-benzofuran-2-carboxylic acid ethyl ester;
4-(4-tert-butylamino-butoxy)-3-methyl-benzofuran-2-carboxylic acid ethyl ester;
4-(5-tert-butylamino-pentyloxy)-3-methyl-benzofuran-2-carboxylic acid ethyl ester;
3-methyl-4-[1-methyl-3-[(pyridin-3-ylmethyl)-amino]-propoxy]-benzofuran-2-carboxylic acid ethyl ester;
3-methyl-4-[3-[(pyridin-3-ylmethyl)-amino]-butoxy]-benzofuran-2-carboxylic acid ethyl ester;
4-(2-tert-butylamino-ethoxy)-3-methyl-benzofuran-2-carboxylic acid ethyl ester;
3-methyl-4-(1-pyridin-3-ylmethyl-piperidin-4-yloxy)-benzofuran-2-carboxylic acid ethyl ester;
3-methyl-4-[3-(1-pyridin-3-yl-ethylamino)-propoxy]-benzofuran-2-carboxylic acid ethyl ester;
4-(3-guanidino-propoxy)-3-methyl-benzofuran-2-carboxylic acid ethyl ester hydrochloride;
3-methyl-4-(1-pyridin-3-ylmethyl-piperidin-3-ylmethoxy)-benzofuran-2-carboxylic acid ethyl ester;
4-[3-(1-benzyl-piperidin-4-ylamino)-propoxy]-3-methyl-benzofuran-2-carboxylic acid phenethyl-amide;
5-bromo-4-(3-tert-butylamino-propoxy)-3-methyl-benzofuran-2-carboxylic acid ethyl ester;
(5-methyl-isoxazol-3-yl)-{3-methyl-4-[3-(methyl-pyridin-3-ylmethyl-amino)-propoxy]-benzofuran-2-ylmethyl}-amine;
3-methyl-4-[3-(methyl-pyridin-3-ylmethyl-amino)-propoxy]-benzofuran-2-carbaldehyde O-ethyl-oxime;
{3-methyl-4-[3-(methyl-pyridin-3-ylmethyl-amino)-propoxy]-benzofuran-2-ylmethylene}-morpholin-4-yl-amine;
{3-methyl-4-[3-(methyl-pyridin-3-ylmethyl-amino)-propoxy]-benzofuran-2-ylmethylene}-(4-methyl-piperazin-1-yl)-amine;
5-fluoro-3-methyl-4-{3-[(pyridin-3-ylmethyl)-amino]-propoxy}-benzofuran-2-carboxylic acid ethyl ester; and
7-fluoro-3-methyl-4-{3-[(pyridin-3-ylmethyl)-amino]-propoxy}-benzofuran-2-carboxylic acid ethyl ester.

25. A bicyclic compound, (5,6-difluoro-1-methyl-1H-benzoimidazol-2-yl)-(3-methyl-4-{3-[(pyridin-3-ylmethyl)-amino]-propoxy}-benzofuran-2-yl)-methanone.

26. A bicyclic compound, (3-methyl-4-{3-[(pyridin-3-ylmethyl)-amino]-propoxy}-benzofuran-2-yl)-[1-(2-pyridin-2-yl-ethyl)-1H-benzoimidazol-2-yl]-methanone.

27. A bicyclic compound,(3-methyl-4-{3-[(pyridin-3-ylmethyl)-amino]-propoxy}-benzofuran-2-yl)-[1-(2-morpholin-4-yl-ethyl)-1H-benzoimidazol-2-yl]-methanone.

28. A method of treating or preventing mycosis in mamals comprising administering an amount of the compound according to claim 1 effective to treat or prevent mycosis in said mamal.

29. A pharmaceutical composition comprising a bicyclic compound according to claim 1 as an active ingredient and a pharmaceutically acceptable carrier.

30. A process for producing bicyclic compounds of the formula [IV],

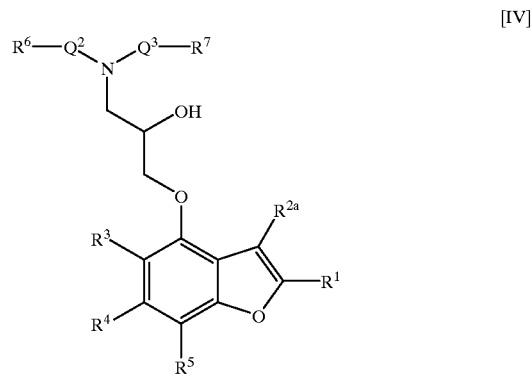

wherein $R^1$, $R^2$, $R^3$, $R^4$, $R^5$, $R^6$, $R^7$, $Q^2$ and $Q^3$ are the same as defined in claim 1, which comprises alkylating a compound of the formula [V],

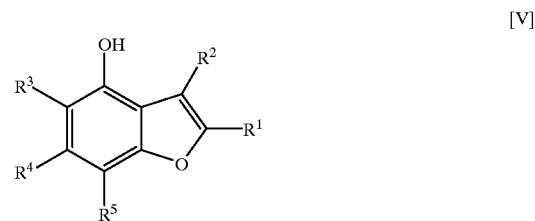

wherein $R^1$, $R^2$, $R^3$, $R^4$ and $R^5$ are the same as defined above, with an alkylating agent of the formula [VI]

wherein Y is chloro, bromo, iodo, tosyloxy or mesyloxy, and aminating the resulting compound of the formula [VII],

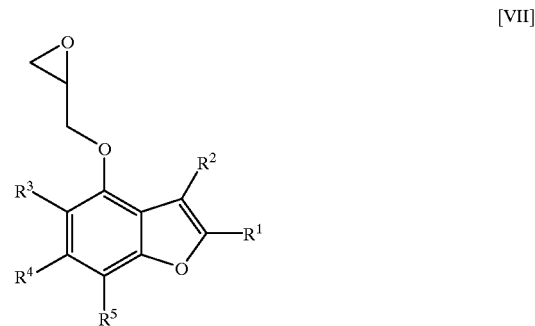

wherein $R^1$, $R^2$, $R^3$, $R^4$ and $R^5$ are the same as defined above, with an aminating agent of the formula [VIII],

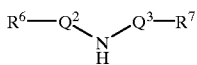
[VIII]

wherein $R^6$, $R^7$, $Q^2$ and $Q^3$ are the same as defined above.

31. A process for producing bicyclic compounds of the formula [I] in accordance with claim 1 which comprises alkylating a compound of the formula [V],

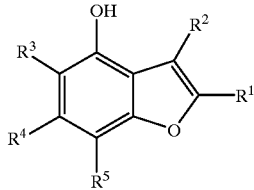
[V]

wherein $R^1$, $R^2$, $R^3$, $R^4$ and $R^5$ are the same as defined in claim 1,
with a dihalogenated alkane, and aminating the resulting compound of the formula [IX],

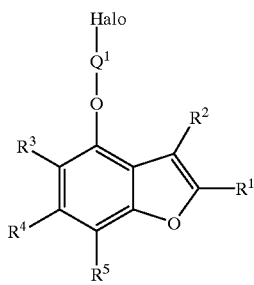
[IX]

wherein Halo is halogen, and $R^1$, $R^2$, $R^3$, $R^4$, $R^5$ and $Q^1$ are the same as defined in claim 1,
with an aminating agent of the formula [VIII]

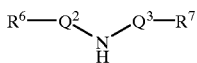
[VIII]

wherein $R^6$, $R^7$ $Q^2$ and $Q^3$ are the same as defined in claim 1.

32. A process for producing bicyclic compounds of the formula [I] in accordance with claim 1 which comprises alkylating a compound of the formula [V],

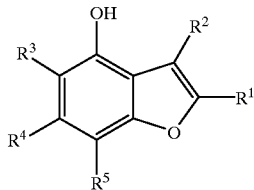
[V]

wherein $R^1$, $R^2$ $R^3$, $R^4$, and $R^5$ are the same as defined in claim 1, with an alkylating agent of the formula [X], $$HO-Q^1-{}_N{}^H-Q^2-R^6 \qquad [X]$$

wherein $Q^1$, $Q^2$ and $R^6$ are the same as defined in claim 1,
and alkylating the resulting compound of the formula [XI]

[XI]

wherein $R^1$, $R^2$, $R^3$, $R^4$, $R^5$, $R^6$ and $Q^1$ are the same as defined in claim 1,
with an alkylating agent of formula [XII],

[XII]

wherein $R^{12}$ is hydrogen or lower alkyl, and $R^7$ is the same as defined in claim 1,
or with an alkylating agent [XIII]

$$\text{Halo-}R^{92} \qquad [XIII]$$

wherein Halo is halogen and $R^{92}$ is unsubstituted or substituted lower alkyl, aralkyl, cycloalkyl or cycloalkylalkyl.

33. A compound of the formula:

[I]

wherein
$R^1$ is an unsubstituted or substituted heterocyclic ring, $$-COOR^8, \quad -C(O)-N\begin{smallmatrix}R^9\\R^{10}\end{smallmatrix}, \quad -C(S)-N\begin{smallmatrix}R^9\\R^{10}\end{smallmatrix},$$

-continued

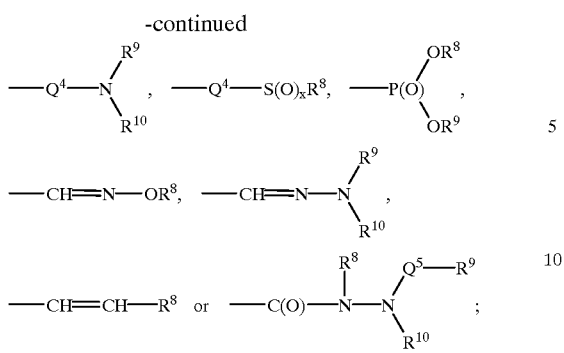

R² is hydrogen, unsubstituted or substituted lower alkyl, aralkyl, cycloalkyl or cycloalkylalkyl;

R³, R⁴ and R⁵ are independently hydrogen or halogen;

R⁶ and R⁷ are independently hydrogen, unsubstituted or substituted lower alkyl, an aromatic ring or aliphatic ring which may contain heteroatom(s); or R⁶ and R⁷ form an aliphatic ring which may contain further heteroatom(s) together with the adjacent Q², N and Q³; or Q¹ and R⁶ form an aliphatic ring which may contain further heteroatom(s) together with the adjacent N and Q²;

R⁸, R⁹ and R¹⁰ are independently hydrogen, unsubstituted or substituted lower alkyl, aralkyl, cycloalkyl, cycloalkylalkyl, an aromatic ring or aliphatic ring which may contain heteroatom(s); or R⁹ and R¹⁰ form an aliphatic ring which may contain further heteroatom(s) together with the adjacent nitrogen;

Q¹ is unsubstituted or substituted lower alkylene other than unsubstituted or substituted methylene;

Q² and Q³ are each independently a single bond, unsubstituted or substituted lower alkylene;

Q⁴ is a single bond, carbonyl, oxime, oxime O-ether which has a substituted or unsubstituted lower alkyl, lower alkenyl, aralkyl or aryl radical on the oxygen atom, or unsubstituted or substituted lower alkylene;

Q⁵ is a single bond or carbonyl and x is an integer of 0 to 2;

with the proviso that when R¹ is —COOC₂H₅, then

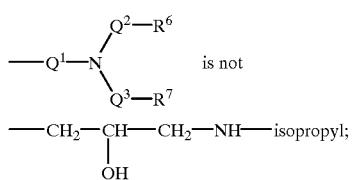 is not

—CH₂—CH(OH)—CH₂—NH—isopropyl;

or the pharmaceutically acceptable salts thereof.

34. The compound according to claim 33, wherein R¹ is unsubstituted or substituted heterocyclic ring.

35. The compound according to claim 33, wherein R¹ is

—COOR⁸.

36. The compound according to claim 33, wherein R¹ is

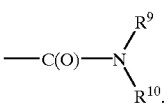

37. The compound according to claim 33, wherein R¹ is

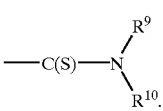

38. The compound according to claim 33, wherein R¹ is

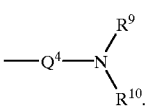

39. The compound according to claim 33, wherein R¹ is

—Q⁴—S(O)ₓR⁸.

40. The compound according to claim 33, wherein R¹ is

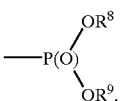

41. The compound according to claim 33, wherein R¹ is

—CH=N—OR⁸.

42. The compound according to claim 33, wherein R¹ is

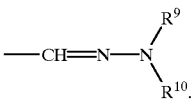

43. The compound according to claim 33, wherein R¹ is

—CH=CH—R⁸.

44. The compound according to claim 33, wherein R¹ is

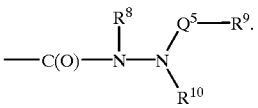

* * * * *

UNITED STATES PATENT AND TRADEMARK OFFICE
CERTIFICATE OF CORRECTION

PATENT NO. : 6,376,491 B1
DATED : April 23, 2002
INVENTOR(S) : Aoki et al.

It is certified that error appears in the above-identified patent and that said Letters Patent is hereby corrected as shown below:

Column 157,
Line 44, last word of sentence, delete "ti" and insert -- u --.

Column 159,
Line 62, after "pyridin-" insert -- 3- --.

Signed and Sealed this

Twelfth Day of November, 2002

Attest:

Attesting Officer

JAMES E. ROGAN
Director of the United States Patent and Trademark Office